United States Patent
Betageri et al.

(10) Patent No.: US 6,660,732 B2
(45) Date of Patent: Dec. 9, 2003

(54) COMPOUNDS USEFUL AS ANTI-INFLAMMATORY AGENTS

(75) Inventors: Rajashehar Betageri, Bethel, CT (US); Steffen Breitfelder, Danbury, CT (US); Pier F. Cirillo, Woodbury, CT (US); Thomas A. Gilmore, Middlebury, CT (US); Eugene R. Hickey, Danbury, CT (US); Thomas M. Kirrane, Danbury, CT (US); Monica H. Moriak, Danbury, CT (US); Neil Moss, Ridgefield, CT (US); Usha R. Patel, Brookfield, CT (US); John R. Proudfoot, Newtown, CT (US); John R. Regan, Larchmont, NY (US); Rajiv Sharma, Ridgefield, CT (US); Sanxing Sun, Danbury, CT (US); Alan D. Swinamer, Danbury, CT (US); Hidenori Takahashi, LaGrangeville, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 106 days.

(21) Appl. No.: 09/962,709

(22) Filed: Sep. 25, 2001

(65) Prior Publication Data

US 2002/0055507 A1 May 9, 2002

Related U.S. Application Data

(62) Division of application No. 09/505,582, filed on Feb. 16, 2000, now Pat. No. 6,358,945.
(60) Provisional application No. 60/124,148, filed on Mar. 12, 1999, and provisional application No. 60/165,867, filed on Nov. 16, 1999.

(51) Int. Cl.⁷ .................. A61K 31/5377; C07D 413/12
(52) U.S. Cl. .................. 514/227.8; 514/236.5; 514/236.8; 514/254.05; 514/255.05; 514/318; 514/333; 514/341; 514/371; 514/377; 514/398; 514/404; 514/406; 514/426; 514/447; 514/472; 544/58.2; 544/58.6; 544/122; 544/131; 544/140; 544/371; 544/405; 546/193; 546/256; 546/275.4; 548/196; 548/223; 548/331.5; 548/332.1; 548/364.1; 548/365.7; 548/371.7; 548/557; 548/558; 549/69; 549/480
(58) Field of Search .................. 514/227.8, 236.5, 514/236.8, 254.05, 255.05, 318, 333, 341, 406; 544/58.2, 58.6, 122, 131, 140, 371, 405; 546/193, 256, 275.4; 548/364.1, 365.7

(56) References Cited

U.S. PATENT DOCUMENTS

| 4,105,766 | A | 8/1978 | Alexander | 424/291 |
|---|---|---|---|---|
| 4,435,567 | A | 3/1984 | Lugosi et al. | 544/165 |
| 5,162,360 | A | 11/1992 | Creswell | 514/371 |
| 5,686,455 | A | 11/1997 | Adams et al. | 514/256 |
| 5,739,143 | A | 4/1998 | Adams et al. | 514/275 |
| 5,777,097 | A | 7/1998 | Lee et al. | 536/24.31 |
| 5,783,664 | A | 7/1998 | Lee et al. | 530/350 |
| 5,859,041 | A | 1/1999 | Liverton et al. | 514/396 |
| 5,869,043 | A | 2/1999 | McDonnell et al. | 424/94.1 |
| 5,871,934 | A | 2/1999 | Lee et al. | 435/7.1 |
| 5,916,760 | A | 6/1999 | Goeddel et al. | 435/15 |
| 5,948,885 | A | 9/1999 | Stein et al. | 530/324 |

FOREIGN PATENT DOCUMENTS

| DD | 293 352 | 8/1991 |
|---|---|---|
| EP | 0 272 866 | 6/1988 |
| EP | 0 395 144 | 10/1990 |
| EP | 0 418 071 | 3/1991 |
| EP | 0 692 483 | 1/1996 |
| EP | 0859054 | 8/1998 |
| EP | 0922762 | 6/1999 |
| EP | 0 955 293 | 10/1999 |
| JP | 61228444 | 10/1986 |
| WO | WO 93/24458 | 9/1993 |
| WO | WO 94/18170 | 8/1994 |
| WO | WO 94/22866 | 10/1994 |
| WO | WO 96/25157 | 8/1996 |
| WO | WO 96/40143 | 12/1996 |
| WO | WO 97/22704 | 6/1997 |
| WO | WO 97/33883 | 9/1997 |
| WO | WO 97/35855 | 10/1997 |
| WO | WO 97/35856 | 10/1997 |
| WO | WO 97/44467 | 11/1997 |
| WO | WO 97/47618 | 12/1997 |
| WO | WO 97/48697 | 12/1997 |
| WO | WO 98/07425 | 2/1998 |
| WO | WO 98/15618 | 4/1998 |
| WO | WO 98/27098 | 6/1998 |
| WO | WO 98/52558 | 11/1998 |
| WO | WO 98/52559 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/32463 | 7/1999 |
| WO | WO 99/46244 | 9/1999 |
| WO | WO 00/43384 | 7/2000 |

OTHER PUBLICATIONS

Int'l. Search Report, Boehringer Ingelheim Pharmaceuticals, Inc., Apr. 12, 2000.

*Primary Examiner*—Richard L. Raymond
(74) *Attorney, Agent, or Firm*—Robert P. Raymond; Anthony P. Bottino; Alan R. Stempel

(57) ABSTRACT

Disclosed are novel aromatic compounds which are useful for treating diseases or pathological conditions involving inflammation such as chronic inflammatory diseases. Also disclosed are pharmaceutical compositions containing and processes of making such compounds.

22 Claims, No Drawings

COMPOUNDS USEFUL AS ANTI-INFLAMMATORY AGENTS

APPLICATION DATA

This application is a divisional application of U.S. Ser. No. 09/505,582 filed Feb. 16, 2000, now U.S. Pat. No. 6,358,945, which claims benefit of U.S. provisional application No. 60/124,148 filed Mar. 12, 1999 and U.S. provisional application No. 60/165,867 filed Nov. 16, 1999.

TECHNICAL FIELD OF THE INVENTION

This invention relates to novel compounds which inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interluekin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, Lancet 349: 521–524). The monoclonal antibody is thought to function by binding to both soluble TNFα and to membrane bound TNF. A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses,* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a dis-regulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFa expression have been noted for each of the above conditions (Loffreda, et al., 1998, *FASEB J*. 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1,TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis. Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al, 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56). Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma*. 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, Springer Semin Immunopathol. 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

In view of the work cited above there is a clear need for compounds that inhibit cytokine production in order to treat various disease states.

It is therefore an object of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In one generic aspect of the invention, there is provided compounds of the formula(I):

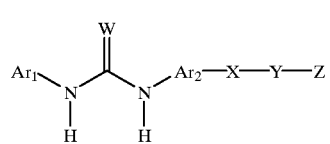

(I)

wherein:

Ar$_1$ is selected from the group consisting of:
pyrrole, pyrrolidine, pyrazole, imidazole, oxazole, thiazole, furan and thiophene; wherein Ar$_1$ may be substituted by one or more R$_1$, R$_2$ or R$_3$;

Ar$_2$ is:
phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with zero to three R$_2$ groups;

X is:
a) a C$_{5-8}$ cycloalkyl or cycloalkenyl optionally substituted with 0–2 oxo groups or 0–3 C$_{1-4}$ branched or unbranched alkyl, C$_{1-4}$ alkoxy or C$_{1-4}$ alkylamino chains; b) phenyl, furan, thiophene, pyrrole, imidazolyl, pyridine, pyrimidine, pyridinone, dihydropyridinone, maleimide, dihydromaleimide, piperdine, piperazine or pyrazine each being optionally independently substituted with 0–3 C$_{1-4}$ branched or unbranched alkyl, C$_{1-4}$alkoxy, hydroxy, nitrile, mono- or di-(C$_{1-3}$ alkyl)amino, C$_{1-6}$ alkyl-S(O)$_m$, or halogen;

Y is:
a bond or a $C_{1-4}$ saturated or unsaturated branched or unbranched carbon chain optionally partially or fully halogenated, wherein one or more methylene groups are optionally replaced by O, NH, S(O), S(O)$_2$ or S and wherein Y is optionally independently substituted with 0–2 oxo groups and one or more $C_{1-4}$ branched or unbranched alkyl which may be substituted by one or more halogen atoms;

Z is:
a) phenyl, pyridine, pyrimidine, pyridazine, imidazole, furan, thiophene, pyran, which are optionally substituted with one to three groups consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$, COOH and phenylamino wherein the phenyl ring is optionally substituted with one to two groups consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, piperidine, piperidinone, piperazine, tetrahydropyrimidone, cyclohexanone, cyclohexanol, pentamethylene sulfide, pentamethylene sulfoxide, pentamethylene sulfone, tetramethylene sulfide, tetramethylene sulfoxide or tetramethylene sulfone which are optionally substituted with one to three groups consisting of nitrile, $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;

c) $C_{1-6}$ alkoxy, secondary or tertiary amine wherein the amino nitrogen is covalently bonded to groups selected from the group consisting of $C_{1-3}$ alkyl, $C_{1-5}$alkoxyalkyl, pyridinyl-$C_{1-3}$ alkyl, imidazolyl-$C_{1-3}$ alkyl, tetrahydrofuranyl-$C_{1-3}$ alkyl, phenylamino, wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_m$, and phenyl-S(O)$_m$, wherein the phenyl ring is optionally substituted with one to two halogen, $C_{1-6}$ alkoxy, hydroxy or mono- or di-($C_{1-3}$ alkyl)amino;

R, is:
(a) $C_{3-10}$ to branched or unbranched alkyl optionally partially or fully halogenated and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described in this paragraph, and being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, nitrile, $C_{1-3}$ alkyloxy which is optionally partially or fully halogenated, $NH_2C(O)$ and di($C_{1-3}$) alkylaminocarbonyl;

(b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl each being optionally be partially or fully halogenated and optionally substituted with one to three $C_{1-3}$ alkyl groups, or an analog of such cycloalkyl group wherein one to three ring methylene groups are replaced by groups independently selected from the group consisting of O, S, CHOH, >C=O, >C=S and NH;

(c) $C_{1-3}$ branched alkenyl optionally partially or fully halogenated and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from the group consisting of halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, nitrile, $C_{1-3}$ alkoxy which is optionally partially or fully halogenated, $NH_2C(O)$ and mono- or di($C_{1-3}$)alkylaminocarbonyl;

(d) a $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

(e) nitrile; or (f) $C_{1-6}$ branched or unbranched alkoxycarbonyl, $C_{1-6}$ branched or unbranched alkylaminocarbonyl, $C_{1-6}$ branched or unbranched alkylcarbonylamino-$C_{1-3}$-alkyl;

$R_2$ is:
a $C_{1-6}$ branched or unbranched alkyl optionally partially or fully halogenated, acetyl, aroyl, $C_{1-4}$ branched or unbranched alkoxy optionally partially or fully halogenated, halogen, methoxycarbonyl or phenylsulfonyl;

$R_3$ is:
a) phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl, wherein such phenyl, naphthyl or heterocyclic group is optionally substituted with one to five groups selected from the group consisting of phenyl, naphthyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, nitrile, $C_{1-3}$ alkyloxy which may optionally be partially or fully halogenated, phenyloxy, naphthyloxy, heteraryloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$alkyl, amino-S(O)$_2$, di-($C_{1-3}$) alkylamino-S(O)$_2$, $R_4$—$C_{1-5}$ alkyl, $R_5$—$C_{1-5}$alkoxy, $R_6$—C(O)—$C_{1-5}$alkyl and $R_7$—$C_{1-5}$ alkyl($R_8$)N, carboxy-mono- or di-($C_{1-5}$)-alkyl-amino;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-($C_{1-3}$)alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl, and $R_{12}$—$C_{1-5}$ alkyl($R_{1-3}$)N;

c) cycloalkyl selected from the group consisting of cyclopentyl, cyclohexyl, cycloheptyl, bicyclopentyl, bicyclohexyl and bicycloheptyl, wherein the cycloalkyl is optionally partially or fully halogenated and optionally substituted with one to three $C_{1-3}$ alkyl groups;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) acetyl, aroyl, alkoxycarbonylalkyl or phenylsulfonyl; or f) $C_{1-6}$ branched or unbranched alkyl optionally partially or fully halogenated; or $R_1$ and $R_2$ taken together may optionally form a fused phenyl or pyridinyl ring;

each $R_1$ and $R_{13}$ is independently selected from the group consisting of: hydrogen and $C_{1-4}$ branched or unbranched alkyl optionally be partially or fully halogenated;

each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

m is 0, 1 or 2;

W is O or S and pharmaceutically acceptable derivatives thereof.

In one embodiment of the invention there are compounds of the formula(I) as provided above and wherein:

$Ar_2$ is naphthyl, tetrahydronaphthyl, indanyl or indenyl and W is O.

In another embodiment of the invention, there are the compounds of the formula (I) as provided immediately above and wherein:

$Ar_1$ is selected from thiophene and pyrazole;

X is $C_{5-7}$ cycloalkyl or $C_{5-7}$cycloalkenyl optionally substituted with 0–2 oxo groups or 0–3 $C_{1-4}$ branched or unbranched alkyl, $C_{1-4}$ alkoxy or $C_{1-4}$ alkylamino; or X is phenyl, pyridine, tetrahydropyridine, pyrimidine, furan or thiophene each being optionally independently substituted with 0–3 $C_{1-4}$ branched or unbranched alkyl, $C_{1-4}$alkoxy, hydroxy, nitrile, mono- or di-($C_{1-3}$ alkyl)amino, $C_{1-6}$ alkyl-S(O)$_m$ or halogen;

$R_1$ is $C_{1-4}$alkyl branched or unbranched, cyclopropyl or cyclohexyl optionally partially or fully halogenated and optionally substituted with one to three $C_{1-3}$ alkyl groups;

$R_3$ is $C_{1-4}$alkyl branched or unbranched, phenyl, pyrimidinyl, pyrazolyl or pyridinyl each being optionally substituted as described hereinabove in the broadest generic aspect, alkoxycarbonylalkyl or cyclopropyl or cyclopentyl optionally substituted as described hereinabove in the broadest generic aspect.

In yet another embodiment of the invention are the compounds of the formula(I) as provided immediately above and wherein:

$Ar_1$ is pyrazole;

X is cyclopentenyl, cyclohexenyl or cycloheptenyl, optionally substituted with an oxo group or 0–3 $C_{1-4}$ branched or unbranched alkyl, $C_{1-4}$alkoxy or $C_{1-4}$alkylamino; or X is phenyl, pyridine, furan or thiophene each being optionally independently substituted with 0–3 $C_{1-4}$ branched or unbranched alkyl, $C_{1-4}$alkoxy, hydroxy, nitrile, mono- or di-($C_{1-3}$ alkyl) amino, $C_{1-6}$ alkyl-S(O)$_m$ or halogen.

In yet still another embodiment of the invention there the compounds of the formula(I) as provided immediately above and wherein:

Y is —CH2—, —CH2CH2—, —CH2NH—, —CH2CH2NH— or a bond;

and

Z is phenyl, imidazole, furan, piperazine, tetrahydropyran, morpholine, thiomorpholine, thiomorpholine sulfoxide, piperidine, pyridine, secondary or tertiary amine wherein the amino nitrogen is covalently bonded to groups selected from the group consisting of $C_{1-3}$ alkyl and $C_{1-5}$ alkoxyalkyl, phenylamino wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_m$ and phenyl-S(O)$_m$ wherein the phenyl ring is optionally substituted with one to two halogen, $C_{1-6}$ alkoxy, hydroxy or mono- or di-($C_{1-3}$ alkyl)amino.

In yet a further embodiment of the invention there are the compounds of the formula(I) as provided immediately above and wherein:

$Ar_1$ is 5-tert-butyl-pyrazol-3-yl; wherein the pyrazole ring may be substituted by $R_3$;

$R_3$ is $C_{1-4}$alkyl branched or unbranched, phenyl, pyrimidinyl, pyrazolyl, pyridinyl each being optionally substituted as described hereinabove in the broadest generic aspect, alkoxycarbonylalkyl or cyclopropyl or cyclopentyl optionally substituted as described hereinabove in the broadest generic aspect.

In a still yet further embodiment of the invention there are the compounds of the formula(I) as provided immediately above and wherein X is pyridinyl.

In yet another further embodiment of the invention there are the compounds of the formula(I) as provided immediately above and wherein the pyridinyl is attached to $Ar_1$ via the 3-pyridinyl position.

The following are representative compounds of formula (I) of the invention:

1-[5-tert-butyl-2-p-tolyl-2H-pyrazol-3-yl]-3-[4-(4-(morpholin-4-yl)phenyl)naphthalen-1-yl]urea;

1-[5-tert-butyl-2-p-tolyl-2H-pyrazol-3-yl]-3-[4-(4-(morpholin-4-yl-methyl)phenyl)naphthalen-1-yl]urea;

1-[5-tert-butyl-2-p-tolyl-2H-pyrazol-3-yl]-3-[4-(4-(2-(morpholin-4-yl)ethyl)phenyl)naphthalen-1-yl]urea;

1-[5-tert-butyl-2-p-tolyl-2H-pyrazol-3-yl]-3-[4-(4-dimethylaminophenyl)naphthalen-1-yl]urea;

1-[5-tert-butyl-2-p-tolyl-2H-pyrazol-3-yl]-3-[4-(3-(morpholin-4-yl)phenyl)naphthalen-1-yl]urea;

1-[5-tert-butyl-2-p-tolyl-2H-pyrazol-3-yl]-3-[4-(3-(morpholin-4-yl-methyl)phenyl)naphthalen-1-yl]urea;

1-[5-tert-butyl-2-p-tolyl-2H-pyrazol-3-yl]-3-[4-(6-(morpholin-4-ylmethyl-pyridin-3-yl)naphthalen-1-yl]urea;

1-[5-tert-butyl-2-p-tolyl-2H-pyrazol-3-yl]-3-[4-(5-morpholin-4-ylmethyl-pyridin-2-yl)naphthalen-1-yl]urea;

1-[5-tert-butyl-2-p-tolyl-2H-pyrazol-3-yl]-3-[4-(5-morpholin-4-ylmethyl-fur-2-yl)naphthalen-1-yl]urea;

1-[5-tert-butyl-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-methyl-2H-pyrazol-3-yl]-3-[4-(6-morpholin-4-ylmethyl-pyridin-3-yl)naphthalen-1-yl]urea;

1-[5-tert-butyl-2-phenyl-2H-pyrazol-3-yl]-3-[4-(4-piperdin-1-ylmethyl-phenyl)naphthalen-1-yl]urea;

1-[5-tert-butyl-2-phenyl-2H-pyrazol-3-yl]-3-[4-(4-(4-methylpiperazin-1-yl)methylphenyl)naphthalen-1-yl]urea;

1-[5-tert-butyl-2-p-tolyl-2H-pyrazol-3-yl]-3-[4-(3,4-di(morpholin-4-yl-methyl)phenyl)naphthalen-1-yl]urea;

1-[5-tert-butyl-2-(6-methyl-pyridin-3-yl)-2H-pyrazol-3-yl]-3-[4-(6-pyridin-4-ylmethyl-pyridin-3-yl)naphthalen-1-yl]urea;

1-[5-tert-butyl-2-(6-methyl-pyridin-3-yl)-2H-pyrazol-3-yl]-3-[4-(6-(1-oxo-thiomorpholin-4-ylmethyl)pyridin-3-yl)naphthalen-1-yl]urea;

1-[5-tert-butyl-2-p-tolyl-2H-pyrazol-3-yl]-3-[4-(6-(1-oxo-thiomorpholin-4-ylmethyl)pyridin-3-yl)naphthalen-1-yl]urea;

1-[5-tert-butyl-2-(6-methyl-pyridin-3-yl)-2H-pyrazol-3-yl]-3-[4-(6-tetrahydropyran-4-ylmethyl-pyridin-3-yl)naphthalen-1-yl]urea;

1-[5-tert-butyl-2-(6-methyl-pyridin-3-yl)-2H-pyrazol-3-yl]-3-[4-(6-(1-oxo-tetrahydrothiophen-3-ylmethyl)pyridin-3-yl)naphthalen-1-yl]urea;

1-[5-tert-butyl-2-(6-methyl-pyridin-3-yl)-2H-pyrazol-3-yl]-3-[4-(6-(imidazol-1-ylmethyl)pyridin-3-yl)naphthalen-1-yl]urea;

1-[2-(3-dimethylaminomethylphenyl)-5-(1-methyl-cyclohexyl)-2H-pyrazol-3-yl]-3-[4-(6-morpholin-4-ylmethyl-pyridin-3-yl)naphthalen-1-yl]urea;

1-[2-(5-(1-methyl-cyclohexyl)-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(2-morpholin-4-ylmethyl-pyrimidin-5-yl)naphthalen-1-yl]urea;

1-[5-tert-butyl-2-(6-methyl-pyridin-3-yl)-2H-pyrazol-3-yl]-3-[4-(3-methoxy-5-(2-morpholin-4-yl-ethoxy)phenyl)naphthalen-1-yl]urea;

1-[5-tert-butyl-2-(6-methyl-pyridin-3-yl)-2H-pyrazol-3-yl]-3-[4-(3-(2-morpholin-4-yl-ethoxy)phenyl)naphthalen-1-yl]urea;

1-[5-tert-butyl-2-(6-methyl-pyridin-3-yl)-2H-pyrazol-3-yl]-3-[4-3-(dimethylamino)phenyl)naphthalen-1-yl]urea;

1-[5-tert-butyl-2-(6-methyl-pyridin-3-yl)-2H-pyrazol-3-yl]-3-[4-3-(methylsulfonyl)phenyl)naphthalen-1-yl]urea;

5-tert-butyl-3-{3-[4-(6-morpholin-4-ylmethyl-pyridin-3-yl)naphthalen-1-yl]ureido}thiophene-2-carboxylic acid methyl ester;

5-tert-butyl-3-{3-[4-(6-morpholin-4-ylmethyl-pyridin-3-yl)naphthalen-1-yl]ureido}thiophene-2-carboxylic acid methylamide;

5-tert-butyl-1-methyl-3-{3-[4-(6-morpholin-4-ylmethyl-pyridin-3-yl)naphthalen-1-yl]ureido}-1H-pyrrole-2-carboxylic acid methyl ester;

5-tert-butyl-1-methyl-3-{3-[4-(6-morpholin-4-ylmethyl-pyridin-3-yl)naphthalen-1-yl]ureido}-1H-pyrrole-2-carboxylic acid methylamide;

2-acetylamino N-(5-tert-butyl-3-{3-[4-(6-morpholin-4-ylmethyl-pyridin-3-yl)naphthalen-1-yl]ureido}thiophen-2-ylmethyl)acetamide;

1-[5-tert-butyl-2-p-tolyl-2H-pyrazol-3-yl]-3-[4-(3-morpholin-4-yl-cyclohex-1-enyl)naphthalen-1-yl]urea;

1-[5-tert-butyl-2-p-tolyl-2H-pyrazol-3-yl]-3-[4-(3-morpholin-4-yl-cylohept-1-enyl)naphthalen-1-yl]urea;

1-[5-tert-butyl-2-p-tolyl-2H-pyrazol-3-yl]-3-[4-(3-(2-morpholin-4-yl-ethylamino)cyclohex-1-enyl)naphthalen-1-yl]urea;

1-[5-tert-butyl-2-p-tolyl-2H-pyrazol-3-yl]-3-[4-(3-morpholin-4-yl-cyclohept-1-enyl)naphthalen-1-yl]urea;

1-[5-tert-butyl-2-(6-methyl-pyridin-3-yl)-2H-pyrazol-3-yl]-3-[4-(3-(pyridin-4-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(dimethylaminoethylamino)cyclohex-1-enyl)naphthalen-1-yl]urea;

1-[5-tert-butyl-2-(6-methyl-pyridin-3-yl)-2H-pyrazol-3-yl]-3-[4-(3-(pyridin-3-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(phenyl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-phenylethylamino)cyclohex-1-enyl)naphthalen-1-yl]urea;

1-[5-tert-butyl-2-(6-methyl-pyridin-3-yl)-2H-pyrazol-3-yl]-3-[4-(3-(furan-2-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-pyridin-2-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(2-piperdin-1-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(2-imidazol-4-yl-ethylamino)cyclohex-1-enyl)naphthalen-1-yl]urea;

1-[5-tert-butyl-2-(6-methyl-pyridin-3-yl)-2H-pyrazol-3-yl]-3-[4-(3-(pyridin-2-yl-methylamino)cyclohex-1-enyl)naphthalen-1-yl]urea;

1-[5-tert-butyl-2-(6-methyl-pyridin-3-yl)-2H-pyrazol-3-yl]-3-[4-(3-(2-(4-methoxyphenyl)ethylamino)cyclohex-1-enyl)naphthalen-1-yl]urea;

1-[5-tert-butyl-2-p-tolyl-2H-pyrazol-3-yl]-3-[4-(4-morpholin-4-ylmethyl-3-oxo-cyclohex-1-enyl)naphthalen-1-yl]urea;

1-[5-tert-butyl-2-p-tolyl-2H-pyrazol-3-yl]-3-[4-(4-(1-oxo-tetrahydrothiophen-3-ylmethyl)-3-oxo-cyclohex-1-enyl)naphthalen-1-yl]urea;

1-[5-tert-butyl-2-p-tolyl-2H-pyrazol-3-yl]-3-[4-(4-(1-oxo-thiomorpholin-4-ylmethyl)-3-oxo-cyclohex-1-enyl)naphthalen-1-yl]urea;

1-[5-tert-butyl-2-p-tolyl-2H-pyrazol-3-yl]-3-[4-(4-methylpiperazin-1-ylmethyl)-3-oxo-cyclohex-1-enyl)naphthalen-1-yl]urea;

1-[5-tert-butyl-2-(6-methyl-pyridin-3-yl)-2H-pyrazol-3-yl]-3-[4-{6-oxo-1-(tetrahydro-pyran-4-ylmethyl)-1,2,3,6-tetrahydro-pyridin-4-yl}naphthalen-1-yl]urea;

1-[5-tert-butyl-2-(6-methyl-pyridin-3-yl)-2H-pyrazol-3-yl]-3-[4-(2-oxo-1-pyridin-4-ylmethyl-piperdin-4-yl)naphthalen-1-yl]urea;

1-[5-tert-butyl-2-p-tolyl-2H-pyrazol-3-yl]-3-[4-(6-oxo-1-pyridin-4-yl-1,2,3,6-tetrahydro-pyridin-4-yl)naphthalen-1-yl]urea;

1-[5-tert-butyl-2-(6-methyl-pyridin-3-yl)-2H-pyrazol-3-yl]-3-[4-(6-oxo-1-pyridin-4-yl-1,2,3,6-tetrahydro-pyridin-4-yl)naphthalen-1-yl]urea;

5-tert-butyl-3-{3-[4-(6-oxo-1-pyridin-4-yl-1,2,3,6-tetrahydro-pyridin-4-yl)naphthalen-1-yl]ureido}thiophene-2-carboxylic acid methyl ester;

5-tert-butyl-1-methyl-3-{3-[4-(6-oxo-1-pyridin-4-yl-1,2,3,6-tetrahydro-pyridin-4-yl)naphthalen-1-yl]ureido}pyrrole-2-carboxylic acid methyl ester;

5-tert-butyl-1-methyl-3-{3-[4-(6-oxo-1-pyridin-4-yl-1,2,3,6-tetrahydro-pyridin-4-yl)naphthalen-1-yl]ureido}pyrrole-2-carboxylic acid methyl amide;

5-tert-butyl-3-{3-[4-(3-morpholin-4-yl-cyclohex-1-enyl)naphthalen-1-yl]ureido}thiophene-2-carboxylic acid methyl ester;

5-tert-butyl-1-methyl-3-{3-[4-(3-morpholin-4-yl-cyclohex-1-enyl)naphthalen-1-yl]ureido}pyrrole-2-carboxylic acid methyl ester; and 5-tert-butyl-1-methyl-3-{3-[4-(3-morpholin-4-yl-cyclohex-1-enyl)naphthalen-1-yl]ureido}pyrrole-2-carboxylic acid methyl amide and the pharmaceutically acceptable derivatives thereof.

In another embodiment of the invention there are provided the following compounds of formula(I):

1-[5-tert-butyl-2-p-tolyl-2H-pyrazol-3-yl]-3-[4-(4-(morpholin-4-yl-methyl)phenyl)naphthalen-1-yl]urea;

1-[5-tert-butyl-2-p-tolyl-2H-pyrazol-3-yl]-3-[4-(4-(2-(morpholin-4-yl)ethyl)phenyl)naphthalen-1-yl]urea;

1-[5-tert-butyl-2-p-tolyl-2H-pyrazol-3-yl]-3-[4-(3-(morpholin-4-yl-methyl)phenyl)naphthalen-1-yl]urea;

1-[5-tert-butyl-2-p-tolyl-2H-pyrazol-3-yl]-3-[4-(6-morpholin-4-ylmethyl-pyridin-3-yl)naphthalen-1-yl]urea;

1-[5-tert-butyl-2-p-tolyl-2H-pyrazol-3-yl]-3-[4-(5-morpholin-4-ylmethyl-pyridin-2-yl)naphthalen-1-yl]urea;

1-[5-tert-butyl-2-p-tolyl-2H-pyrazol-3-yl]-3-[4-(5-morpholin-4-ylmethyl-fir-2-yl)naphthalen-1-yl]urea;

1-[5-tert-butyl-2-(6-methyl-pyridin-3-yl)-2H-pyrazol-3-yl]-3-[4-(6-morpholin-4-ylmethyl-pyridin-3-yl)naphthalen-1-yl]urea;

1-[5-tert-butyl-2-methyl-2H-pyrazol-3-yl]-3-[4-(6-morpholin-4-ylmethyl-pyridin-3-yl)naphthalen-1-yl]urea and the pharmaceutically acceptable derivatives thereof In another generic aspect of the invention, there are provided compounds of the formula (Ia):

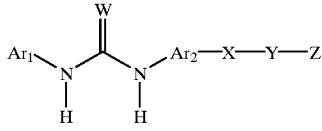

(Ia)

wherein:

Ar$_1$ is:

pyrrole, pyrrolidine, pyrazole, imidazole, oxazole, thiazole, furan and thiophene; wherein Ar$_1$ is optionally substituted by one or more R$_1$, R$_2$ or R$_3$;

Ar$_2$ is:

phenyl, naphthyl, quinoline, isoquinoline, tetrahydronaphthyl, tetrahydroquinoline, tetrahydroisoquinoline, benzimidazole, benzofuran, indanyl, indenyl and indole each being optionally substituted with zero to three R$_2$ groups;

X is:

a C$_{5-8}$ cycloalkyl or cycloalkenyl optionally substituted with one to two oxo groups or one to three C$_{1-4}$alkyl, C$_{1-4}$ alkoxy or C$_{1-4}$ alkylamino chains each being branched or unbranched;

phenyl, furanyl, thienyl, pyrrolyl, pyrazolyl, imidazolyl, pyridinyl, tetrahydropyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three C$_{1-4}$ alkyl, C$_{1-4}$alkoxy, hydroxy, nitrile, amino, mono- or di-(C$_{1-3}$ alkyl)amino, mono- or di-(C$_{1-3}$ alkylamino)carbonyl, NH$_2$C(O), C$_{1-6}$ alkyl-S(O)$_m$ or halogen;

T is:

a bond or a C$_{1-4}$ saturated or unsaturated branched or unbranched carbon chain optionally partially or fully halogenated, wherein one or more C atoms are optionally replaced by O, N, or S(O)$_m$ and wherein Y is optionally independently substituted with one to two oxo groups, nitrile, phenyl, hydroxy or one or more C$_{1-4}$ alkyl optionally substituted by one or more halogen atoms;

Z is:

aryl, indanyl, heteroaryl selected from benzimidazolyl, pyridinyl, pyrimidinyl, pyridazinyl, pyrazinyl, imidazolyl, pyrazolyl, triazolyl, tetrazolyl, furanyl, thienyl and pyranyl, heterocycle selected from piperazinyl, tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, C$_{1-6}$ alkyl, C$_{1-6}$ alkoxy, C$_{1-3}$ alkoxy-C$_{1-3}$ alkyl, C$_{1-6}$ alkoxycarbonyl, aroyl, heteroaroyl, heterocycleC$_{1-3}$acyl wherein the heteroaryl and heterocycle are as defined hereinabove in this paragraph, C$_{1-3}$acyl, oxo, hydroxy, pyridinyl-C$_{1-3}$ alkyl, imidazolyl-C$_{1-3}$ alkyl, tetrahydrofuranyl-C$_{1-3}$ alkyl, nitrile-C$_{1-3}$ alkyl, nitrile, carboxy, phenyl wherein the phenyl ring is optionally substituted with one to two halogen, C$_{1-6}$ alkoxy, hydroxy or mono- or di-(C$_{1-3}$ alkyl)amino, amino-S(O)$_m$, C$_{1-6}$ alkyl-S(O)$_m$ or phenyl-S(O)$_m$ wherein the phenyl ring is optionally substituted with one to two halogen, C$_{1-6}$ alkoxy, hydroxy, halogen or mono- or di-(C$_{1-3}$ alkyl)amino;

or Z is optionally substituted with one to three amino, aminocarbonyl or amino-C$_{1-3}$ alkyl wherein the N atom is optionally independently mono- or di-substituted by aminoC$_{1-6}$alkyl, C$_{1-3}$alkyl, arylC$_{0-3}$alkyl, C$_{1-5}$ alkoxyC$_{1-3}$ alkyl, C$_{1-5}$ alkoxy, aroyl, C$_{1-3}$acyl, C$_{1-3}$alkyl-S(O)$_m$- or arylC$_{0-3}$alkyl-S(O)$_m$— each of the aforementioned alkyl and aryl attached to the amino group is optionally substituted with one to two halogen, C$_{1-6}$ alkyl, C$_{1-6}$ alkoxy, hydroxy or mono- or di-(C$_{1-3}$ alkyl)amino; or Z is optionally substituted with one to three aryl, heterocycle or heteroaryl as hereinabove described in this paragraph each in turn is optionally substituted by halogen, C$_{1-6}$ alkyl or C$_{1-6}$ alkoxy;

or Z is hydroxy, hydroxyC$_{1-3}$alkyl, halogen, nitrile, amino wherein the N atom is optionally independently mono- or di-substituted by C$_{1-6}$alkyl, aminoC$_{1-6}$alkyl, arylC$_{0-3}$alkyl. C$_{1-5}$ alkoxyC$_{1-3}$ alkyl, C$_{1-5}$alkoxy, aroyl, C$_{1-3}$acyl, C$_{1-3}$alkyl-S(O)$_m$-, arylC$_{0-3}$alkyl-S(O)$_m$-, nitrileC$_{1-4}$alkyl or C$_{1-3}$alkoxyC$_{1-3}$alkyl, each of the aforementioned alkyl and aryl attached to the amino group is optionally substituted with one to two halogen, C$_{1-6}$ alkyl, C$_{1-6}$ alkoxy, hydroxy or mono- or di-(C$_{1-3}$ alkyl)amino, C$_{1-6}$ alkoxyheteroarylC$_{0-3}$alkyl, heteroarylC$_{0-3}$alkyl or heterocycyleC$_{0-3}$alkyl wherein the heteroaryl and heterocycle is hereinabove described in this paragraph, or Z is $C_{1-6}$ alkyl branched or unbranched, $C_{1-6}$ alkoxy, $C_{1-3}$acylamino, nitrile$C_{1-4}$alkyl, $C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;

$R_1$ is:

a) $C_{1-10}$ branched or unbranched alkyl optionally partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle, selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, nitrile, $C_{1-3}$ alkyloxy which is optionally partially or fully halogenated, $NH_2C(O)$ and di($C_{1-3}$)alkylaminocarbonyl;

b) $C_{3-7}$ cycloalkyl selected from the group consisting of cyclopropyl, cyclobutyl, cyclopentyl, cyclohexyl, cycloheptyl, bicyclopentyl, bicyclohexyl and bicycloheptyl, each optionally partially or fully halogenated and optionally substituted with one to three $C_{1-3}$ alkyl groups, or an analog of such cycloalkyl group wherein one to three ring methylene groups are replaced by groups independently selected from the group consisting of O, S, CHOH, >C=O, >C=S and NH;

c) $C_{3-10}$ branched alkenyl optionally partially or fully halogenated and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from the group consisting of halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, nitrile, $C_{1-3}$ alkoxy which is optionally partially or fully halogenated, $NH_2C(O)$ and mono- or di($C_{1-3}$)alkylaminocarbonyl;

d) a $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) nitrile; or f) $C_{1-6}$ branched or unbranched alkoxycarbonyl, $C_{1-6}$ branched or unbranched alkylaminocarbonyl, $C_{1-6}$ branched or unbranched alkylcarbonylamino-$C_{1-3}$-alkyl;

$R_2$ is:

a $C_{1-6}$ branched or unbranched alkyl optionally partially or fully halogenated and optionally substituted with nitrile, or $R_2$ is acetyl, aroyl, $C_{1-4}$ branched or unbranched alkoxy optionally partially or fully halogenated, halogen, methoxycarbonyl or phenylsulfonyl;

$R_3$ is:

a) phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl, wherein such phenyl, naphthyl or heterocyclic group is optionally substituted with one to five groups selected from the group consisting of a phenyl, naphthyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, oxo, nitrile, $C_{1-3}$ alkoxy optionally partially or fully halogenated, $C_{1-3}$ alkoxy$C_{1-5}$alkyl, $C_{1-3}$thioalkyl, $C_{1-3}$thioalkyl$C_{1-5}$alkyl, phenyloxy, naphthyloxy, heteraryloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-$C(O)$—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$alkyl, $R_5$—$C_{1-5}$ alkoxy, $R_6$—$C(O)$—$C_{1-5}$alkyl and $R_7$—$C_{1-5}$alkyl($R_8$)N, carboxy-mono- or di-($C_{1-5}$)-alkyl-amino;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$)alkylamino, phenylamino, naphthylamino, heterocyclylamino wherein the heterocyclyl moiety is selected from the group hereinabove described, $NH_2C(O)$, a mono- or di-($C_{1-3}$)alkyl aminocarbonyl, $C_{1-4}$ alkyl-$OC(O)$, $C_{1-5}$ alkyl-$C(O)$—$C_{1-4}$ branched or unbranched alkyl, an amino-$C_{1-5}$ alkyl, mono- or di-($C_{1-3}$) alkylamino-$C_{1-5}$ alkyl, $R_9$—$C_{1-5}$ alkyl, $R_{10}$—$C_{1-5}$alkoxy, $R_{11}$—$C(O)$—$C_{1-5}$ alkyl and $R_{12}$—$C_{1-5}$ alkyl($R_{13}$)N;

c) cycloalkyl selected from the group consisting of cyclopropyl, cyclobutyl, cyclopentyl, cyclohexyl, cycloheptyl, bicyclopentyl, bicyclohexyl and bicycloheptyl, wherein the cycloalkyl is optionally partially or fully halogenated and optionally substituted with one to three $C_{1-3}$ alkyl groups;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) acetyl, aroyl, $C_{1-6}$alkoxycarbonyl$C_{1-6}$ alkyl or phenylsulfonyl; or f) $C_{1-6}$ branched or unbranched alkyl optionally partially or fully halogenated; or $R_1$ and $R_2$ taken together optionally form a fused phenyl or pyridinyl ring;

each $R_8$ and $R_{13}$ is independently selected from the group consisting of: hydrogen and $C_{1-4}$ branched or unbranched alkyl optionally partially or fully halogenated;

each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

m is 0, 1 or 2;

W is O or S;

wherein X is directly attached to one or two —Y—Z, and pharmaceutically acceptable derivatives thereof.

In one embodiment of the invention there are compounds of the formula(Ia) as provided above and wherein:

$Ar_2$ is naphthyl, tetrahydronaphthyl, indanyl or indenyl and W is O.

In another embodiment of the invention are compounds of the formula (Ia) as provided immediately above and wherein:

$Ar_1$ is thiophene or pyrazole each substituted independently by one to three $R_1$, $R_2$ or $R_3$;

X is:

a $C_{5-7}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;

phenyl, indanyl, furanyl, thienyl, imidazolyl, pyridinyl, pyrazinyl, tetrahydrapyridinyl, pyrimidinyl, pyridinonyl, piperdinyl, benzimidazole or piperazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated or unsaturated branched or unbranched carbon chain optionally partially or fully halogenated, wherein one or more C atoms are optionally replaced by O or N, and wherein Y is optionally independently substituted with one to two oxo groups, nitrile, phenyl, hydroxy or one or more $C_{1-4}$ alkyl optionally substituted by one or more halogen atoms;

Z is:

phenyl, heteroaryl selected from pyridinyl, imidazolyl, furanyl and thienyl, heterocycle selected from piperazinyl, 2-oxa-5-aza-bicyclo[2.2.1]heptanyl, pentamethylene sulfidyl, pentamethylene sulfoxidyl, pentamethylene sulfonyl, tetrahydrofuranyl, morpholino, thiomorpholino and piperidinyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-$S(O)_m$, $C_{1-6}$ alkyl-$S(O)_m$ or phenyl-$S(O)_m$ wherein the phenyl ring is optionally substituted with one to two halogen, $C_{1-6}$ alkoxy, hydroxy, halogen or mono- or di-($C_{1-3}$ alkyl) amino; or Z is optionally substituted with one to three amino, aminocarbonyl or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$- or aryl$C_{0-3}$alkyl-$S(O)_m$— each of the aforementioned alkyl and aryl attached to the amino group are optionally substituted with one to two halogen, $C_{1-6}$ alkyl or $C_{1-6}$ alkoxy; or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by aroyl, $C_{1-3}$acyl, $C_{1-6}$alkyl, $C_{1-5}$ alkoxy$C_{1-3}$ alkyl, pyridinyl$C_{1-3}$alkyl, tetrahydrafuranyl$C_{1-3}$alkyl, nitrile$C_{1-4}$alkyl or phenyl wherein the phenyl ring is optionally substituted with one to two halogen, $C_{1-6}$ alkoxy, hydroxy or mono- or di-($C_{1-3}$ alkyl)amino, or Z is $C_{1-6}$alkyl branched or unbranched, $C_{1-6}$alkoxy or nitrile$C_{1-4}$alkyl;

$R_1$ is:

$C_{1-4}$ branched or unbranched alkyl optionally partially or fully halogenated;

cyclopropyl, cyclobutyl, cyclopentyl, cyclohexyl and cycloheptyl optionally partially or fully halogenated and optionally substituted with one to three $C_{1-3}$ alkyl groups, or an analog of such cycloalkyl group wherein one to three ring methylene groups are replaced by groups independently selected from the group consisting of O, S and NH;

$C_{3-10}$ branched alkenyl optionally partially or fully halogenated and optionally substituted with one to three $C_{1-5}$ branched or unbranched alkyl;

cyclopentenyl and cyclohexenyl optionally substituted with one to three $C_{1-3}$ alkyl groups;

$R_2$ is:

a $C_{1-6}$ branched or unbranched alkyl optionally partially or fully halogenated and optionally substituted with nitrile;

$R_3$ is:

phenyl or heterocyclic group selected from the group consisting of pyridinyl, pyrimidinyl, pyrazinyl, pyridazinyl and pyrazolyl, wherein such phenyl or heterocyclic group is optionally substituted with one to five groups selected from the group consisting of a phenyl, heterocycle selected from the group hereinabove described in this paragraph, $C_{1-6}$ branched or unbranched alkyl which is optionally partially or fully halogenated, cyclopropyl, cyclobutyl, cyclopentyl, cyclohexyl, cycloheptyl, bicyclopentyl, bicyclohexyl, bicycloheptyl, phenyl $C_{1-5}$ alkyl, naphthyl $C_{1-5}$ alkyl, halogen, hydroxy, oxo, nitrile, $C_{1-3}$ alkoxy optionally be partially or fully halogenated, $C_{1-3}$ alkoxy$C_{1-5}$alkyl, $C_{1-3}$thioalkyl, $C_{1-3}$thioalkyl$C_{1-5}$alkyl, phenyloxy, naphthyloxy, hetararyloxy wherein the heterocyclic moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-5}$ alkyl-$C(O)$—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$ alkyl, $R_5$—$C_{1-5}$ alkoxy, $R_6$—$C(O)$—$C_{1-5}$ alkyl and $R_7$—$C_{1-5}$ alkyl ($R_8$)N, carboxy-mono- or di-($C_{1-5}$)-alkyl-amino; a fused aryl selected from the group consisting of benzocyclobutanyl, indanyl, indenyl; wherein the fused aryl is substituted with 0 to 3 groups independently selected from the group consisting of phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halogen, nitrile, $C_{1-3}$ alkoxy which is optionally partially or fully halogenated, phenyloxy, naphthyloxy, heterocyclyloxy wherein the heterocyclyl moiety is selected from the group hereinabove described in this paragraph, nitro, amino, mono- or di-($C_{1-3}$)alkylamino, phenylamino, naphthylamino, heterocyclylamino wherein the heterocyclyl moiety is selected from the group hereinabove described in this paragraph, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-($C_{1-3}$)alkylamino-$C_{1-5}$alkyl, $R_9$—$C_{1-5}$ alkyl, $R_{10}$—$C_{1-5}$ alkoxy, $R_{11}$—C(O)—$C_{1-5}$ alkyl and $R_{12}$—$C_{1-5}$ alkyl ($R_{13}$)N; cycloalkyl selected from the group consisting of cyclopropyl, cyclobutyl, cyclopentyl, cyclohexyl, cycloheptyl, wherein the cycloalkyl is optionally partially or fully halogenated and optionally substituted with one to three $C_{1-3}$ alkyl groups;

$C_{1-6}$alkoxycarbonyl$C_{1-6}$alkyl;

or $R_1$ and $R_2$ taken together optionally form a fused phenyl or pyridinyl ring;

each $R_8$ and $R_{13}$ is independently selected from the group consisting of: hydrogen and $C_{1-4}$ branched or unbranched alkyl optionally partially or fully halogenated; and each $R_4$, $R_5$, $R_6$, $R_7$, $R_9$, $R_{10}$, $R_{11}$ and $R_{12}$ is independently selected from the group consisting of morpholine, piperidine, piperazine, imidazole and tetrazole;

wherein X is directly attached to one —Y—Z.

In yet still another embodiment of the invention there are the compounds of the formula(Ia) as provided immediately above and wherein:

$Ar_1$ is pyrazole;

X is:

cyclopentenyl, cyclohexenyl, cycloheptenyl, optionally substituted with an oxo group or one to three $C_{1-4}$ alkyl, $C_{1-4}$ alkoxy or $C_{1-4}$ alkylamino chains each being branched or unbranched; phenyl, furanyl, thienyl, pyridinyl, pyrazinyl piperidinyl or pyrimidinyl each being optionally independently substituted with one to three $C_{1-2}$ alkyl, $C_{1-2}$alkoxy, hydroxy or halogen;

Z is:

phenyl, heteroaryl selected from pyridinyl, imidazolyl and furanyl, heterocycle selected from 2-oxa-5-aza-bicyclo [2.2.1]heptanyl, pentamethylene sulfidyl, pentamethylene sulfoxidyl, pentamethylene sulfonyl, tetrahydrofuranyl, tetrahydropyranyl, piperazinyl, morpholino, thiomorpholino, thiomorpholino sulfoxide and piperidinyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-S(O)$_m$, $C_{1-6}$ alkyl-S(O)$_m$, or phenyl-S(O)$_m$ wherein the phenyl ring is optionally substituted with one to two halogen, $C_{1-6}$ alkoxy, hydroxy, halogen or mono- or di-($C_{1-3}$ alkyl)amino; or Z is optionally substituted with one to three amino, aminocarbonyl or amino-$C_{1-3}$ alkyl wherein the N atom is optionally independently mono- or di-substituted by amino$C_{1-6}$alkyl, $CH_{1-3}$alkyl, aryl$C_{0-3}$alkyl, $C_{1-5}$alkoxy$C_{1-3}$ alkyl, $C_{1-5}$ alkoxy, aroyl, $C_{1-3}$acyl, $C_{1-3}$alkyl-S(O)$_m$-, pyridinyl$C_{0-3}$alkyl, tetrahydrafuranyl$C_{0-3}$alkyl, or aryl$C_{0-3}$alkyl-S(O)$_m$— each of the aforementioned alkyl and aryl attached to the amino group is optionally substituted with one to two halogen, $C_{1-6}$ alkyl or $C_{1-6}$ alkoxy;

or Z is hydroxy, hydroxy$C_{1-3}$alkyl, halogen, nitrile, amino wherein the N atom is optionally independently mono- or di-substituted by $C_{1-6}$alkyl, pyridinyl$C_{0-3}$alkyl, tetrahydrafuranyl$C_{0-3}$alkyl, $C_{1-5}$alkoxy$C_{1-3}$ alkyl, $C_{1-3}$acyl, nitrile$C_{1-4}$alkyl or phenyl wherein the phenyl ring is optionally substituted with one to two halogen, $C_{1-6}$ alkoxy, hydroxy or mono- or di-($C_{1-3}$ alkyl)amino, or Z is $C_{1-6}$alkyl branched or unbranched, $C_{1-6}$alkoxy or nitrile$C_{1-4}$alkyl;

$R_1$ is:

$C_{1-4}$ branched or unbranched alkyl optionally partially or fully halogenated; cyclopropyl, cyclobutyl, cyclopentanyl, cyclohexanyl and cycloheptanyl optionally partially or fully halogenated and optionally substituted with one to three $C_{1-3}$ alkyl groups, or an analog of such cycloalkyl group wherein one to three ring methylene groups are replaced by groups independently selected from the group consisting of O, and NH;

$C_{3-10}$ branched alkenyl optionally partially or fully halogenated and optionally substituted with one to three $C_{1-3}$ branched or unbranched alkyl;

cyclopentenyl and cyclohexenyl optionally substituted with one to three $C_{1-3}$ alkyl groups;

$R_2$ is:

a $C_{1-6}$ branched or unbranched alkyl optionally partially or fully halogenated and optionally substituted with nitrile;

$R_3$ is:

phenyl or heterocyclic group selected from the group consisting of pyridinyl, pyrimidinyl, pyridazinyl and pyrazolyl, wherein such phenyl or heterocyclic group is optionally substituted with one to five groups selected from the group consisting of a phenyl, heterocycle selected from the group hereinabove described in this paragraph, $C_{1-6}$ branched or unbranched alkyl which is optionally partially or fully halogenated, phenyl $C_{1-5}$ alkyl, halogen, hydroxy, oxo, nitrile, $C_{1-3}$ alkoxy optionally partially or fully halogenated, $C_{1-3}$thioalkyl, $C_{1-3}$thioalkyl$C_{1-5}$alkyl, amino, mono- or di-($C_{1-3}$)akylamino, $NH_2C(O)$ or a mono- or di-($C_{1-3}$)alkyl aminocarbonyl, $C_{1-6}$alkoxycarbonyl$C_{1-6}$alkyl;

or $R_3$ is cyclopropyl or cyclopentyl each optionally partially or fully halogenated and optionally substituted with one to three $C_{1-3}$ alkyl groups or $R_1$ and $R_2$ taken together optionally form a fused phenyl or pyridinyl ring.

In yet a further embodiment of the invention there are the compounds of the formula(Ia) as provided immediately above and wherein:

Y is —$CH_2$—, —O—($CH_2$)$_{0-3}$—, —$CH_2CH_2$—, —$CH_2NH$—, —$CH_2CH_2$—NH—, NH—$CH_2CH_2$—, —$CH_2$—NH—$CH_2$—, —NH—, —NH—C(O)—, —C(O)—, —CH(OH)—, —$CH_2$($CH_2CH_3$)— or a bond;

X is:

cyclohexenyl optionally substituted with an oxo group or one to three $C_{1-4}$ alkyl $C_{1-4}$ alkoxy or $C_{1-4}$ alkylamino chains each being branched or unbranched;

phenyl, pyridinyl, pyrazinyl, piperidinyl or pyrimidinyl each being optionally independently substituted with one to three $C_{1-2}$ alkyl, $C_{1-2}$alkoxy, hydroxy or halogen;

Z is:

phenyl, heteroaryl selected from pyridinyl, imidazolyl and furanyl, heterocycle selected from 2-oxa-5-aza-bicyclo [2.2.1]heptanyl, pentamethylene sulfidyl, pentamethylene sulfoxidyl, pentamethylene sulfonyl, tetrahydrofuranyl, tetrahydropyranyl, piperazinyl, morpholino, thiomorpholino, thiomorpholino sulfoxide and piperidinyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, morpholinocarbonyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, amino-$S(O)_m$, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl)amino; or Z is optionally substituted with one to three amino or aminocarbonyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;

or Z is hydroxy, hydroxy$C_{-3}$alkyl, halogen, nitrile, amino wherein the N atom is optionally independently mono- or di-substituted by $C_{1-3}$alkyl, pyridinyl$C_{1-2}$alkyl, tetrahydrafuranyl$C_{1-2}$alkyl, $C_{1-3}$ alkoxy$C_{1-3}$ alkyl, $C_{1-3}$acyl, nitrile$C_{1-4}$alkyl, phenyl wherein the phenyl ring is optionally substituted with one to two halogen, $C_{1-6}$ alkoxy, hydroxy or mono- or di-($C_{1-3}$ alkyl)amino, or Z is $C_{1-6}$alkyl branched or unbranched, $C_{1-6}$alkoxy or nitrile$C_{1-4}$alkyl;

$R_1$ is:
$C_{1-4}$ branched or unbranched alkyl optionally partially or fully halogenated;

$R_2$ is:
a $C_{1-3}$ branched or unbranched alkyl optionally partially or fully halogenated and optionally substituted with nitrile;

$R_3$ is:
phenyl or heterocyclic group selected from the group consisting of pyridinyl, pyrimidinyl, and pyrazolyl, wherein such phenyl or heterocyclic group is optionally substituted with one to five groups selected from the group consisting of $C_{1-3}$ branched or unbranched alkyl which is optionally partially or fully halogenated, $C_{1-3}$ alkoxy which optionally partially or fully halogenated, $C_{1-3}$thioalkyl, $C_{1-3}$thioalkyl$C_{1-5}$alkyl, amino or $NH_2C(O)$;
$C_{1-3}$alkoxycarbonyl;

or $R_3$ is cyclopropyl or cyclopentyl each optionally partially or fully halogenated and optionally substituted with one to three $C_{1-3}$ alkyl groups.

In a yet still further embodiment of the invention there are the compounds of the formula(Ia) as provided immediately above and wherein:

$Ar_1$ is 5-tert-butyl-pyrazol-3-yl; wherein the pyrazole ring is substituted independently by one to two $R_2$ or $R_3$;

X is:
cyclohexenyl;
phenyl, pyridinyl, pyrazinyl, piperidinyl or pyrimidinyl each being optionally independently substituted with $C_{1-2}$alkoxy or hydroxy;

Z is:
phenyl, heteroaryl selected from pyridinyl and furanyl, heterocycle selected from 2-oxa-5-aza-bicyclo[2.2.1]heptanyl, pentamethylene sulfidyl, pentamethylene sulfoxidyl, tetrahydrofuranyl, piperazinyl, morpholino, thiomorpholino and piperidinyl, each of the aforementioned Z are optionally substituted with one to three $C_{1-3}$ alkyl, $C_{1-3}$ alkoxy, oxo, hydroxy or $NH_2C(O)$—;

or Z is hydroxy$C_{1-3}$alkyl, amino wherein the N atom is optionally independently mono- or di-substituted by pyridinylmethyl, tetrahydrofuranylmethyl, $C_{1-3}$ alkoxy$C_{1-3}$ alkyl, $C_{1-3}$acyl or nitrile$C_{1-4}$alkyl, or Z is nitrile$C_{1-4}$alkyl;

$R_3$ is:
phenyl or heterocyclic group selected from the group consisting of pyridinyl, pyrimidinyl, and pyrazolyl, wherein such phenyl or heterocyclic group is optionally substituted with one to two groups selected from the group consisting of $C_{1-2}$ alkyl which is optionally partially or fully halogenated, $C_{1-2}$ alkoxy which optionally partially or fully halogenated, $C_{1-2}$thioalkyl, $C_{1-2}$thioalkyl$C_{1-3}$alkyl, amino or $NH_2C(O)$;
$C_{1-3}$alkoxycarbonyl;

or $R_3$ is cyclopropyl or cyclopentyl each optionally partially or fully halogenated and optionally substituted with one to three $C_{1-3}$ alkyl groups.

In an even further embodiment of the invention there are the compounds of the formula(Ia) as provided immediately above and wherein X is pyridinyl.

In a yet still even further embodiment of the invention there are compounds of the formula(Ia) as provided immediately above and wherein the pyridinyl is attached to $Ar_1$ via the 3-pyridinyl position.

The following are representative compounds of formula (Ia) of the invention:

1-[5-tert-butyl-2-p-tolyl-2H-pyrazol-3-yl]-3-[4-(4-morpholin-4-yl-methylphenyl)-naphthalen-1yl]-urea;

1-[5-tert-butyl-2-p-tolyl-2H-pyrazol-3-yl]-3-[3-(4-morpholin-4-yl-methylphenyl)-naphthalen-1-yl]-urea;

1-[5-tert-butyl-2-p-tolyl-2H-pyrazol-3-yl]-3-[4-(5-morpholin-4-yl-methylfuran-2-yl)-naphthalen-1-yl]-urea;

1-[5-tert-butyl-2-p-tolyl-2H-pyrazol-3-yl]-3-[4-(3-(morpholin-4-yl-methyl)cyclohexenyl)-naphthalen-1-yl]-urea;

1-[5-tert-butyl-2-p-tolyl-2H-pyrazol-3-yl]-3-[4-(2-(4-morpholin-4-yl)ethylphenyl)-naphthalen-1-yl]-urea;

1-[5-tert-butyl-2-p-tolyl-2H-pyrazol-3-yl]-3-[4-(4-dimethylaminomethylphenyl)-naphthalen-1-yl]-urea;

1-[5-tert-butyl-2-p-tolyl-2H-pyrazol-3-yl]-3-[4-(5-(morpholin-4-yl-methyl)pyridin-2-yl)-naphthalen-1-yl]-urea;

1-[5-tert-butyl-2-p-tolyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(morpholin-4-yl-methyl)pyridin-3-yl)-naphthalen-1-yl]-urea;

1-[5-tert-butyl-2-methyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(3-(2-(morpholin-4-yl)ethylamino)cyclohexenyl)-naphthalen-1-yl]-urea;

1-[5 tert-butyl-2-p-tolyl-2H-pyrazol-3-yl]-3-[4-(3,4-(morpholin-4-yl-methyl)phenyl)-naphthalen-1-yl]-urea;

1-[5-tert-butyl-2-p-tolyl-2H-pyrazol-3-yl]-3-[4-(4-methylpiperzin-1-yl-methyl)phenyl)-naphthalen-1-yl]-urea;

1-[5-tert-butyl-2-p-tolyl-2H-pyrazol-3-yl]-3-[4-(piperdin-1-yl-methyl)phenyl)-naphthalen-1-yl]-urea;

1-[5-tert-butyl-2-(6-methyl-pyridin-3-yl)-2H-pyrazol-3-yl]-3-[4-(3-(2-(pyridin-2-yl)ethylamino)cyclohexenyl)-naphthalen-1-yl]-urea;

1-[5-tert-butyl-2-p-tolyl-2H-pyrazol-3-yl]-3-[4-(4-(2-(pyridin-4-yl)ethylaminomethyl)phenyl)naphthalen-1-yl]-urea;

1-[5-tert-butyl-2-p-tolyl-2H-pyrazol-3-yl]-3-[4-(4-(pyridin-3-yl-methylaminomethyl)phenyl)naphthalen-1-yl]-urea;

1-[5-tert-butyl-2-(6-methyl-pyridin-3-yl)-2H-pyrazol-3-yl]-3-[4-(4-(3,4-dimethoxyphenylmethyl)-3-hydroxyphenyl)naphthalen-1-yl]-urea;

1-[5-tert-butyl-2-p-tolyl-2H-pyrazol-3-yl]-3-[4-(6-oxo-1,6-dihydro-pyridin-3-yl)naphthalen-1-yl]-urea;

1-[5-tert-butyl-2-(6-methyl-pyridin-3-yl)-2H-pyrazol-3-yl]-3-[4-(4-(morpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(morpholin-4-yl-methyl)imidazol-1-yl)naphthalen-1-yl]-urea;

1-[5-tert-butyl-2-p-tolyl-2H-pyrazol-3-yl]-3-[4-(4-(morpholin-4-yl-methyl)imidazol-1-yl)naphthalen-1-yl]-urea;

1-[5-tert-butyl-2-(6-methyl-pyridin-3-yl)-2H-pyrazol-3-yl]-3-[4-(4-(furan-3-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(6-(4-hydroxybutylamino)pyridin-3-yl)-naphthalen-1-yl]-urea;

1-[5-tert-butyl-2-(6-methyl-pyridin-3-yl)-2H-pyrazol-3-yl]-3-[4-(4-(pyridin-3-yl-methyl)-3-hydroxyphenyl)naphthalen-1-yl]-urea;

1-[5-tert-butyl-2-(4-methyl-3-carbamylphenyl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(4-(imidazol-2-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(3-hydroxymorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(N-2-methoxyethy-N-methylaminomethyl)phenyl)naphthalen-1-yl]-urea;

1-[5-tert-butyl-2-(6-methyl-pyridin-3-yl)-2H-pyrazol-3-yl]-3-[4-(4-(4-hydroxymorpholin-4-yl-methyl)phenyl)naphthalen-1-yl]-urea;

1-[5-tert-butyl-2-(6-methyl-pyridin-3-yl)-2H-pyrazol-3-yl]-3-[4-(3-(morpholin-4-yl-methyl)cyclohexenyl)-naphthalen-1-yl]-urea;

1-[5-tert-butyl-2-(6-methyl-pyridin-3-yl)-2H-pyrazol-3-yl]-3-[4-(4-(tetrahydrofran-3-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(N,N-di-(2-methoxyethyl)aminomethyl)phenyl)naphthalen-1-yl]-urea;

1-[5-tert-butyl-2-(6-methyl-pyridin-3-yl)-2H-pyrazol-3-yl]-3-[4-(6-(3-cyanopropoxy)pyridin-3-yl)naphthalen-1-yl]-urea;

1-[5-tert-butyl-2-(6-methyl-pyridin-3-yl)-2H-pyrazol-3-yl]-3-[4-(4-morpholin-4-yl-methyl-piperdinyl)naphthalen-1-yl]-urea;

1-[5-tert-butyl-2-(6-methyl-pyridin-3-yl)-2H-pyrazol-3-yl]-3-[4-(4-(N,N-di-(2-cyanoethyl)aminomethyl)phenyl)naphthalen-1-yl]-urea;

1-[5-tert-butyl-2-p-tolyl-2H-pyrazol-3-yl]-3-[4-(1-morpholin-4-yl-indan-5-yl)-naphthalen-1-yl]-urea;

1-[5-tert-butyl-2-(6-methyl-pyridin-3-yl)-2H-pyrazol-3-yl]-3-[4-(4-(furan-2-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(thiomorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(3-carboxamidomorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(2-methyl-3-oxo-piperzin-1-yl-methyl)phenyl)naphthalen-1-yl]-urea;

1-[5-tert-butyl-2-(2-methylpyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(6-(4-hydroxybutyloxy)pyridin-3-yl)-naphthalen-1-yl]-urea;

1-[3-tert-butyl-1'H-[1,4']bipyrazol-5-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(4-(furan-2-yl-methyl)-3-methoxyphenyl)naphthalen-1-yl]-urea;

1-[5-tert-butyl-2-(6-methyl-pyridin-3-yl)-2H-pyrazol-3-yl]-3-[4-(5-(morpholin-4carbonyl)pyrazin-2-yl)naphthalen-1-yl]-urea;

1-[5-tert-butyl-2-(6-methyl-pyridin-3-yl)-2H-pyrazol-3-yl]-3-[4-(6-(tetrahydrothiopyran-4-yl-amino)pyridin-3-yl)-naphthalen-1-yl]-urea;

1-[5-tert-butyl-2-(2-cyanoethyl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(2,6-dimethylmorpholin-4-yl-methyl)pyridin-3-yl)-naphthalen-1-yl]-urea;

1-[5-tert-butyl-2-(2-methoxypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(2-aminoypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(6-oxo-1,6-dihydropyridin-3-yl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(morpholin-4-yl-4-carbonyl)pyridin-3-yl)-naphthalen-1-yl]-urea;

1-[5-tert-butyl-2-(6-methyl-pyridin-3-yl)-2H-pyrazol-3-yl]-3-[4-(6-(2-oxa-5-aza-bicyclo[2.2.1]hept-5-yl-methyl)pyridin-3-yl)-naphthalen-1-yl]-urea;

1-[5-tert-butyl-2-p-tolyl-2H-pyrazol-3-yl]-3-[4-(3-carbamylphenyl)naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-3-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(tetrahydrofuran-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(6-(morpholin-4-yl-methyl)-4-methoxypyridin-3-yl)-naphthalen-1-yl]-urea;

1-[5-tert-butyl-2-(6-methyl-pyridin-3-yl)-2H-pyrazol-3-yl]-3-[4-(6-(1-morpholin-4-yl-propyl)pyridin-3-yl)-naphthalen-1-yl]-urea;

1-[5-tert-butyl-2-(6-methyl-pyridin-3-yl)-2H-pyrazol-3-yl]-3-[4-(6-(N-(3-methoxypropyl)amino)pyridin-3-yl)-naphthalen-1-yl]-urea;

1-[5-tert-butyl-2-(6-methyl-pyridin-3-yl)-2H-pyrazol-3-yl]-3-[4-(6-(N-(3-methoxypropyl)-N-methylamino)pyridin-3-yl)-naphthalen-1-yl]-urea;

1-[3-tert-butyl-1'-methyl-1'H-[1,4']bipyrazol-5-yl]-3-[4-(6-(morpholin-4-yl-methyl)pyridin-3-yl)naphthalen-1-yl]-urea;

1-[5-tert-butyl-2-benzyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(4-(N-N-di-(2-cyanoethyl)aminomethyl)phenyl)-naphthalen-1-yl]-urea;

1-[5-tert-butyl-2-p-tolyl-2H-pyrazol-3-yl]-3-[4-(4-(4-carbamylphenyl)naphthalen-1-yl]-urea;

1-[5-tert-butyl-2-(6-methyl-pyridin-3-yl)-2H-pyrazol-3-yl]-3-[4-(6-(1-oxo-tetrahydrothiopyran-4yl-amino)pyridin-3-yl)-naphthalen-1-yl]-urea;

1-[5-tert-butyl-2-(6-methyl-pyridin-3-yl)-2H-pyrazol-3-yl]-3-[4-(6-(tetrahydropyran-4yl-amino)pyridin-3-yl)-naphthalen-1-yl]-urea;

1-[3-tert-butyl-1'-(3-cyanopropyl)-1'H-[1,4']bipyrazol-5-yl]-3-[4-(6-(morpholin-4-yl-methyl)pyridin-3-yl) naphthalen-1-yl]-urea;

1-[5-tert-butyl-2-p-tolyl-2H-pyrazol-3-yl]-3-[4-(3-methanesulfinylphenyl)naphthalen-1-yl]-urea;

1-[5-tert-butyl-2-p-tolyl-2H-pyrazol-3-yl]-3-[4-(3-methanesulfonylphenyl)naphthalen-1-yl]-urea;

1-[5-tert-butyl-2-p-tolyl-2H-pyrazol-3-yl]-3-[4-(3-sulfonamidophenyl)naphthalen-1-yl]-urea;

1-[5-tert-butyl-2-p-tolyl-2H-pyrazol-3-yl]-3-[4-(3-(morpholin-4-yl)carbonylphenyl)naphthalen-1-yl]-urea;

1-[5-tert-butyl-2-(6-methyl-pyridin-3-yl)-2H-pyrazol-3-y]-3-[4-(5-(tetrahydrothiopyran-4yl-amino)pyrazin-2-yl)-naphthalen-1-yl]-urea;

1-[5-tert-butyl-2-(6-methyl-pyridin-3-yl)-2H-pyrazol-3-yl]-3-[4-(6-(methylcarbonylamino)pyridin-3-yl)-naphthalen-1-yl]-urea;

1-[5-tert-butyl-2-p-tolyl-2H-pyrazol-3-yl]-3-[4-(6-(morpholin-4-yl-4-carbonyl)phenyl)-naphthalen-1-yl]-urea;

1-[3-tert-butyl-1'-(3-methylsulfanylpropyl)-1'H-[1,4']bipyrazol-5-yl]-3-[4-(6-(morpholin-4-yl-methyl)pyridin-3-yl)naphthalen-1-yl]-urea;

1-[5-tert-butyl-2-p-tolyl-2H-pyrazol-3-yl]-3-[4-(5-(morpholin-4-yl-carbonyl)pyridin-3-yl)-naphthalen-1-yl]-urea;

1-[5-tert-butyl-2-(6-methyl-pyridin-3-yl)-2H-pyrazol-3-yl]-3-[4-(5-(morpholin-4-yl-methyl)pyrazin-2-yl)-naphthalen-1-yl]-urea;

1-[5-tert-butyl-2-(6-methyl-pyridin-3-yl)-2H-pyrazol-3-yl]-3-[4-(6-aminopyridin-3-yl)naphthalen-1-yl]-urea;

1-[5-tert-butyl-2-(6-methyl-pyridin-3-yl)-2H-pyrazol-3-yl]-3-[4-(6-(1-methylpiperdin-4-yl-amino)pyridin-3-yl) naphthalen-1-yl]-urea;

1-[5-tert-butyl-2-(2-methylpyrimidin-5-yl)-2H-pyrazol-3-yl]-3-[4-(6-(2-methyl-3-oxo-piperzin-1-yl-methyl) pyridin-3-yl)naphthalen-1-yl]-urea;

1-[5-tert-butyl-2-(2-methylpyrimidin-5-yl)-2H-pyrazol-3-yl]-3-[4-(6-(morpholin-4-yl-carbonyl)pyridin-3-yl) naphthalen-1-yl]-urea;

1-[5-tert-butyl-2-(2-methylpyrimidin-5-yl)-2H-pyrazol-3-yl]-3-[4-(6-(N,N-di-(2-methoxyethyl)aminomethyl) pyridin-3-yl)naphthalen-1-yl]-urea;

1-[5-tert-butyl-2-(2-methylpyrimidin-5-yl)-2H-pyrazol-3-yl]-3-[4-(6-(1-oxo-thiomorpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(tetrahydropyran-4-yl-amino)pyridin-3-yl) naphthalen-1-yl]-urea;

1-[5-tert-butyl-2-(2-methylpyrimidin-5-yl)-2H-pyrazol-3-yl]-3-[4-(5-(morpholin-4-yl-methyl)pyrazin-2-yl) naphthalen-1-yl]-urea;

1-[5-tert-butyl-2-(2-methylthiopyrimidin-5-yl)-2H-pyrazol-3-yl]-3-[4-(6-(morpholin-4-yl-methyl)pyridin-3-yl) naphthalen-1-yl]-urea;

1-[5-tert-butyl-2-p-tolyl-2H-pyrazol-3-yl]-3-[4-(6-(2-methyl-3-oxo-piperzin-1-yl-methyl)pyridin-3-yl) naphthalen-1-yl]-urea;

1-[5-tert-butyl-2-p-tolyl-2H-pyrazol-3-yl]-3-[4-(6-(pyridin-3-yl-oxy)pyridin-3-yl)naphthalen-1-yl]-urea 1-[5-tert-butyl-2-p-tolyl-2H-pyrazol-3-yl]-3-[4-(6-(pyridin-3-yl-amino)pyridin-3-yl)naphthalen-1-yl]-urea;

1-[5-tert-butyl-2-(2-methoxypyrimidin-5-yl)-2H-pyrazol-3-yl]-3-[4-(6-(morpholin-4-yl-methyl)pyridin-3-yl) naphthalen-1-yl]-urea;

1-[5-tert-butyl-2-p-tolyl-2H-pyrazol-3-yl]-3-[4-(5-carbamylpyridin-3-yl)naphthalen-1-yl]-urea;

1-[5-tert-butyl-2-(2-aminopyrimidin-5-yl)-2H-pyrazol-3-yl]-3-[4-(6-(morpholin-4-yl-methyl)pyridin-3-yl) naphthalen-1-yl]-urea;

1-[5-tert-butyl-2-(2-methylpyrimidin-5-yl)-2H-pyrazol-3-yl]-3-[4-(4-(morpholin-4-yl-methyl)phenyl)naphthalen-1-yl]-urea;

1-[3-tert-butyl-1'-methyl-1'H-[1,4']bipyrazol-5-yl]-3-[4-(6-(morpholin-4-yl-methyl)phenyl)naphthalen-1-yl]-urea;

1-[5-tert-butyl-2-(2-cyclopropylpyrimidin-5-yl)-2H-pyrazol-3-yl]-3-[4-(6-(morpholin-4-yl-methyl)pyridin-3-yl) naphthalen-1-yl]-urea;

1-[5-tert-butyl-2-p-tolyl-2H-pyrazol-3-yl]-3-[4-(2-(pyridin-3-yl-amino)pyrimidin-5-yl)naphthalen-1-yl]-urea;

1-[5-tert-butyl-2-p-tolyl-2H-pyrazol-3-yl]-3-[4-(6-(1-oxo-tetrahydrothiopyran-4-yl-amino)pyridin-3-yl) naphthalen-1-yl]-urea;

1-[5-tert-butyl-2-p-tolyl-2H-pyrazol-3-yl]-3-[4-(6-(thiomorpholin-4-yl-methyl)pyridin-3-yl)naphthalen-1-yl]-urea;

1-[5-tert-butyl-2-p-tolyl-2H-pyrazol-3-yl]-3-[4-(3-benzyl-3H-imidazo[4,5-b]pyridin-6-yl)naphthalen-1-yl]-urea;

1-[5-tert-butyl-2-(6-methyl-pyridin-3-yl)-2H-pyrazol-3-yl]-3-[4-(6-(pyridin-3-yl-methyl)pyridin-3-yl)naphthalen-1-yl]-urea;

1-[5-tert-butyl-2-p-tolyl-2H-pyrazol-3-yl]-3-[4-(2-(morpholin-4-yl-carbonyl)pyrimidin-5-yl)naphthalen-1-yl]-urea;

1-[5-tert-butyl-2-p-tolyl-2H-pyrazol-3-yl]-3-[4-(2-(morpholin-4-yl-methyl)pyrimidin-5-yl)naphthalen-1-yl]-urea;

1-[5-tert-butyl-2-p-tolyl-2H-pyrazol-3-yl]-3-[4-(3-amino-4-carbamylphenyl)naphthalen-1-yl]-urea;

1-[5-tert-butyl-2-p-tolyl-2H-pyrazol-3-yl]-3-[4-(6-(1-oxo-thiomorpholin-4-yl-methyl)pyridin-3-yl)naphthalen-1-yl]-urea;

1-[5-tert-butyl-2-p-tolyl-2H-pyrazol-3-yl]-3-[4-(6-(pyridin-3-yl-methyl)pyridin-3-yl)naphthalen-1-yl]-urea;

1-[5-tert-butyl-2-p-tolyl-2H-pyrazol-3-yl]-3-[4-(6-(hydroxy-pyridin-3-yl-methyl)pyridin-3-yl)naphthalen-1-yl]-urea;

1-[5-tert-butyl-2-(2-methylpyrimidin-5-yl)-2H-pyrazol-3-yl]-3-[4-(2-(morpholin-4-yl-methyl)pyrimidin-5-yl) naphthalen-1-yl]-urea;

and the pharmaceutically acceptable derivatives thereof.

In another embodiment of the invention there are provided the following compounds of the formula(Ia):

1-[5-tert-butyl-2-p-tolyl-2H-pyrazol-3-yl]-3-[4-(5-(morpholin-4-yl-methyl)pyridin-2-yl)-naphthalen-1-yl]-urea;

1-[5-tert-butyl-2-p-tolyl-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(3-(2-(pyridin-2-yl)ethylamino)cyclohexenyl)-naphthalen-1-yl]-urea;

1-[5-tert-butyl-2-p-tolyl-2H-pyrazol-3-yl]-3-[4-(4-(pyridin-3-yl-methylaminomethyl)phenyl)naphthalen-1-yl]-urea;

1-[5-tert-butyl-2-(6-methyl-pyridin-3-yl)-2H-pyrazol-3-yl]-3-[4-(4-(morpholin-4-yl-methyl)phenyl)naphthalen-1-yl]-urea;

1-[5-tert-butyl-2-(6-methyl-pyridin-3-yl)-2H-pyrazol-3-yl]-3-[4-(6-(4-hydroxybutylamino)pyridin-3-yl)naphthalen-1-yl]-urea;

1-[5-tert-butyl-2-(4-methyl-3-carbamylphenyl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(4-(3-hydroxypiperidin-1-yl-methyl)phenyl)naphthalen-1-yl]-urea;

1-[5-tert-butyl-2-(6-methyl-pyridin-3-yl)-2H-pyrazol-3-yl]-3-[4-(4-(4-hydroxymorpholin-4-yl-methyl)phenyl)naphthalen-1-yl]-urea;

1-[5-tert-butyl-2-(6-methyl-pyridin-3-yl)-2H-pyrazol-3-yl]-3-[4-(3-(morpholin-4-yl-methyl)cyclohexenyl)naphthalen-1-yl]-urea;

1-[5-tert-butyl-2-(6-methyl-pyridin-3-yl)-2H-pyrazol-3-yl]-3-[4-(tetrahydrofuran-3-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(N,N-di-(2-methoxyethyl)aminomethyl)phenyl)naphthalen-1-yl]-urea;

1-[5-tert-butyl-2-(6-methyl-pyridin-3-yl)-2H-pyrazol-3-yl]-3-[4-(6-(3-cyanopropoxy)pyridin-3-yl)naphthalen-1-yl]-urea;

1-[5-tert-butyl-2-(6-methyl-pyridin-3-yl)-2H-pyrazol-3-yl]-3-[4-(4-morpholin-4-yl-methyl-piperdinyl)naphthalen-1-yl]-urea;

1-[5-tert-butyl-2-(6-methyl-pyridin-3-yl)-2H-pyrazol-3-yl]-3-[4-(4-(N,N-di-(2-cyanoethyl)aminomethyl)phenyl)naphthalen-1-yl]-urea;

1-[5-tert-butyl-2-(6-methyl-pyridin-3-yl)-2H-pyrazol-3-yl]-3-[4-(4-(furan-2-yl-methyl)-3-hydroxyphenyl)naphthalen-1-yl]-urea;

1-[5-tert-butyl-2-(6-methyl-pyridin-3-yl)-2H-pyrazol-3-yl]-3-[4-(4-(thiomorpholin-4-yl-methyl)phenyl)naphthalen-1-yl]-urea;

1-[5-tert-butyl-2-(6-methyl-pyridin-3-yl)-2H-pyrazol-3-yl]-3-[4-(4-(3-carboxamidopiperidin-1-yl-methyl)phenyl)naphthalen-1-yl]-urea;

1-[5-tert-butyl-2-(6-methyl-pyridin-3-yl)-2H-pyrazol-3-yl]-3-[4-(4-(2-methyl-3-oxo-piperzin-1-yl-methyl)phenyl)naphthalen-1-yl]-urea;

1-[5-tert-butyl-2-(2-methylpyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(6-(4-hydroxybutyloxy)pyridin-3-yl)-naphthalen-1-yl]-urea;

1-[3-tert-butyl-1'H-[1,4']bipyrazol-5-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(6-(tetrahydrothiopyran-4-yl-amino)pyridin-3-yl)naphthalen-1-yl]-urea;

1-[5-tert-butyl-2-(2-cyanoethyl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(2,6-dimethylmorpholin-4-yl-methyl)pyridin-3-yl)-naphthalen-1-yl]-urea;

1-[5-tert-butyl-2-(2-methoxypyridin-5-yl)-2H-pyrazol-3-yl]-3-[4-(6-(morpholin-4-yl-methyl)pyridin-3-yl)naphthalen-1-yl]-urea;

1-[5-tert-butyl-2-(2-aminoypyridin-5-yl)-2H-pyrazol-3-yl]-3-[4-(6-(morpholin-4-yl-methyl)pyridin-3-yl)-naphthalen-1-yl]-urea;

1-[5-tert-butyl-2-(6-methyl-pyridin-3-yl)-2H-pyrazol-3-yl]-3-[4-(6-(morpholin-4-yl-4-carbonyl)pyridin-3-yl)-naphthalen-1-yl]-urea;

1-[5-tert-butyl-2-(6-methyl-pyridin-3-yl)-2H-pyrazol-3-yl]-3-[4-(6-(2-oxa-5-aza-bicyclo[2.2.1]hept-5-yl-methyl)pyridin-3-yl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(pyridin-3-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(4-(N-(2-cyanoethyl)-N-(tetrahydrofuran-2-yl-methyl)aminomethyl)phenyl)-naphthalen-1-yl]-urea;

1-[5-tert-butyl-2-(6-methyl-pyridin-3-yl)-2H-pyrazol-3-yl]-3-[4-(6-(morpholin-4-yl-methyl)-4-methoxypyridin-3-yl)-naphthalen-1-yl]-urea;

1-[5-tert-butyl-2-(6-methyl-pyridin-3-yl)-2H-pyrazol-3-yl]-3-[4-(6-(1-morpholin-4-yl-propyl)pyridin-3-yl)-naphthalen-1-yl]-urea;

1-[3-tert-butyl-1'-methyl-1'H-[1,4']bipyrazol-5-yl]-3-[4-(6-(morpholin-4-yl-methyl)pyridin-3-yl)naphthalen-1-yl]-urea;

1-[5-tert-butyl-2-(6-methyl-pyridin-3-yl)-2H-pyrazol-3-yl]-3-[4-(6-(1-oxo-tetrahydrothiopyran-4yl-amino)pyridin-3-yl)-naphthalen-1-yl]-urea;

1-[5-tert-butyl-2-(6-methyl-pyridin-3-yl)-2H-pyrazol-3-yl]-3-[4-(6-(tetrahydropyran-4yl-amino)pyridin-3-yl)-naphthalen-1-yl]-urea;

1-[5-tert-butyl-2-(6-methyl-pyridin-3-yl)-2H-pyrazol-3-yl]-3-[4-(5-(tetrahydrothiopyran-4yl-amino)pyrazin-2-yl)-naphthalen-1-yl]-urea;

1-[5-tert-butyl-2-(6-methyl-pyridin-3-yl)-2H-pyrazol-3-yl]-3-[4-(6-(methylcarbonylamino)pyridin-3-yl)-naphthalen-1-yl]-urea;

1-[3-tert-butyl-1'-(3-methylsulfanylpropyl)-1'H-[1,4']bipyrazol-5-yl]-3-[4-(6-(morpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(1-oxo-thiomorpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(6-(tetrahydropyran-4-yl-amino)pyridin-3-yl)naphthalen-1-yl]-urea;

1-[5-tert-butyl-2-(2-methylthiopyrimidin-5-yl)-2H-pyrazol-3-yl]-3-[4-(6-(morpholin-4-yl-methyl)pyridin-3-yl)naphthalen-1-yl]-urea;

1-[5-tert-butyl-2-(2-aminopyrimidin-5-yl)-2H-pyrazol-3-yl]-3-[4-(6-(morpholin-4-yl-methyl)pyridin-3-yl)naphthalen-1-yl]-urea;

1-[3-tert-butyl-1'-methyl-1'H-[1,4']bipyrazol-5-yl]-3-[4-(6-(morpholin-4-yl-methyl)phenyl)naphthalen-1-yl]-urea;

1-[5-tert-butyl-2-p-tolyl-2H-pyrazol-3-yl]-3-[4-(6-(1-oxo-tetrahydrothiopyran-4-yl-amino)pyridin-3-yl)naphthalen-1-yl]-urea;

1-[5-tert-butyl-2-p-tolyl-2H-pyrazol-3-yl]-3-[4-(6-(thiomorpholin-4-yl-methyl)pyridin-3-yl)naphthalen-1-yl]-urea;

1-[5-tert-butyl-2-p-tolyl-2H-pyrazol-3-yl]-3-[4-(2-(morpholin-4-yl-carbonyl)pyrimidin-5-yl)naphthalen-1-yl]-urea;

1-[5-tert-butyl-2-p-tolyl-2H-pyrazol-3-yl]-3-[4-(2-(morpholin-4-yl-methyl)pyrimidin-5-yl)naphthalen-1-yl]-urea;

1-[5-tert-butyl-2-p-tolyl-2H-pyrazol-3-yl]-3-[4-(6-(1-oxo-thiomorpholin-4-yl-methyl)pyridin-3-yl)naphthalen-1-yl]-urea;

1-[5-tert-butyl-2-(2-methylpyrimidin-5-yl)-2H-pyrazol-3-yl]-3-[4-(2-(morpholin-4-yl-methyl)pyrimidin-5-yl) naphthalen-1-yl]-urea and
the pharmaceutically acceptable derivatives thereof.

In yet another generic aspect of the invention, there are provided compounds of the formula (II):

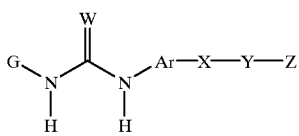

(II)

wherein:

G is:
an aromatic $C_{6-10}$ carbocycle or a nonaromatic $C_{3-10}$ carbocycle saturated or unsaturated;
a 6–10 membered heteroaryl containing 1 or more heteroatoms chosen from O, N and S;
a 5–8 membered monocyclic heterocycle containing one or more heteroatoms chosen from O,N and S; or an 8–11 membered bicyclic heterocycle, containing one or more heteroatoms chosen from O, N and S; wherein G is substituted by one or more $R_1$, $R_2$ or $R_3$;

Ar is:
phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;

X is:
a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains;
phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl;

y is: a bond or a $C_{1-4}$ saturated or unsaturated branched or unbranched carbon chain optionally partially or fully halogenated, wherein one or more methylene groups are optionally replaced by O, N, or $S(O)_m$ and wherein Y is optionally independently substituted with one to two oxo groups, phenyl or one or more $C_{1-4}$ alkyl optionally substituted by one or more halogen atoms;

Z is:
phenyl, pyridinyl, pyrimidinyl, pyridazinyl, pyrazinyl, imidazolyl, pyrazolyl, triazolyl, tetrazolyl, furanyl, thienyl, pyranyl each being optionally substituted with one to three halogen, $C_{1-6}$ alkyl, $C_{1-6}$ alkoxy, hydroxy, amino, mono- or di-($C_{1-3}$ alkyl)amino, $C_{1-6}$ alkyl-$S(O)_m$, CN, $CONH_2$, COOH or phenylamino wherein the phenyl ring is optionally substituted with one to two halogen, $C_{1-6}$ alkyl or $C_{1-6}$ alkoxy;
tetrahydropyranyl, tetrahydrofuranyl, 1,3-dioxolanonyl, 1,3-dioxanonyl, 1,4-dioxanyl, morpholinyl, thiomorpholinyl, thiomorpholino sulfoxidyl, thiomorpholino sulfonyl, piperidinyl, piperidinonyl, piperazinyl, tetrahydropyrimidonyl, cyclohexanonyl, cyclohexanolyl, pentamethylene sulfidyl, pentamethylene sulfoxidyl, pentamethylene sulfonyl, tetramethylene sulfide, tetramethylene sulfoxidyl or tetramethylene sulfonyl each being optionally substituted with one to three nitrile, $C_{1-6}$ alkyl, $C_{1-6}$ alkoxy, hydroxy, amino, mono- or di-($C_{1-3}$ alkyl)amino-$C_{1-3}$ alkyl, $CONH_2$, phenylamino-$C_{1-3}$ alkyl or $C_{1-3}$ alkoxy-$C_{1-3}$ alkyl;
halogen, $C_{1-4}$ alkyl, nitrile, amino, hydroxy, $C_{1-6}$ alkoxy, $NH_2C(O)$, mono- or di($C_{1-3}$alkyl) aminocarbonyl, mono- or di($C_{1-6}$alkyl)amino, secondary or tertiary amine wherein the amino nitrogen is covalently bonded to $C_{1-3}$ alkyl or $C_{1-5}$ alkoxyalkyl, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, carboxamide-$C_{1-3}$ alkyl, phenyl, wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$, wherein the phenyl ring is optionally substituted with one to two halogen, $C_{1-6}$ alkoxy, hydroxy, halogen or mono- or di-($C_{1-3}$ alkyl)amino;
$C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;

each $R_1$ is independently:
$C_{1-10}$ alkyl optionally be partially or fully halogenated, and optionally substituted with one to three $C_{3-10}$ cycloalkanyl, hydroxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated or $NH_2C(O)$, mono- or di($C_{1-3}$alkyl)amino, and mono- or di($C_{1-3}$alkyl) aminocarbonyl;
cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;
phenyloxy or benzyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloaryl group wherein one to two ring methyne groups are independently replaced by N;
cyclopropanyl, cyclobutanyl, cyclopentanyl, cyclohexanyl, cycloheptanyl, bicyclopentanyl, bicyclohexanyl or bicycloheptanyl, each being optionally partially or fully halogenated and optionally substituted with one to three $C_{1-3}$ alkyl groups optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;
$C_{3-10}$ branched or unbranced alkenyl each being optionally partially or fully halogenated, and optionally be substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with zero to five halogen, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, $C_{1-3}$ alkyloxy which is optionally partially or fully halogenated, $NH_2C(O)$, mono- or di($C_{1-3}$alkyl) aminocarbonyl; the $C_{3-10}$ branched or unbranced alkenyl being optionally interrupted by one or more heteroatoms chosen from O, N and $S(O)_m$;

cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

nitrile, halogen;

methoxycarbonyl, ethoxycarbonyl and propoxycarbonyl;

silyl containing three $C_{1-4}$ alkyl groups optionally partially or fully halogenated;

$C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, pyrrolidinyl, pyrrolyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

each $R_2$, $R_4$, and $R_5$ is a $C_{1-6}$ branched or unbranched alkyl optionally partially or fully halogenated, acetyl, aroyl, $C_{1-4}$ branched or unbranched alkoxy, each being optionally partially or fully halogenated, halogen, nitrile, methoxycarbonyl, $C_{1-3}$ alkyl-$S(O)_m$ optionally partially or fully halogenated, or phenylsulfonyl;

$C_{1-6}$ alkoxy, hydroxy, amino, or mono- or di-($C_{1-4}$ alkyl)amino, nitrile, halogen;

OR6;

nitro; or mono- or di-($C_{1-4}$ alkyl)amino-$S(O)_2$ optionally partially or fully halogenated, or $H_2NSO_2$;

each $R_3$ is independently:

phenyl, naphthyl, morpholinyl, pyridinyl, pyrimidinyl, pyrazinyl, pyridazinyl, pyrrolyl, pyrrolidinyl, imidazolyl, pyrazolyl, thiazolyl, oxazoyl, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkyloxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alkyl)amino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-$C(O)$—$C_{1-4}$ alkyl, amino-$C_{1-5}$ alkyl, mono- or di-($C_{1-3}$alkyl)amino-$C_{1-5}$ alkyl, amino-$S(O)_2$, di-($C_{1-3}$alkyl)amino-$S(O)_2$, $R_7$—$C_{1-5}$ alkyl, $R_8$—$C_{1-5}$ alkoxy, $R_9$—$C(O)$—$C_{1-5}$ alkyl, $R_{10}$—$C_{1-5}$ alkyl ($R_{11}$)N, carboxy-mono- or di-($C_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$alkyl)aminocarbonyl, $C_{1-4}$ alkyl-OC(O), $C_{1-5}$ alkyl-$C(O)$—$C_{1-4}$ alkyl, amino-$C_{1-5}$ alkyl, mono- or di-($C_{1-3}$) alkylamino-$C_{1-5}$ alkyl, $R_{12}$—$C_{1-5}$ alkyl, $R_{13}$—$C_{1-5}$ alkoxy, $R_{14}$—$C(O)$—$C_{1-5}$ alkyl or $R_{15}$—$C_{1-5}$ alkyl($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally partially or fully halogenated and optionally substituted with one to three $C_{1-3}$ alkyl groups, or an analog of such cycloalkyl group wherein one to three ring methylene groups are independently replaced by O, S, CHOH, >C=O, >C=S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-$S(O)_m$—$C_{1-4}$ alkyl-;

$C_{1-6}$ alkyl or $C_{1-6}$ branched or unbranched alkoxy each of which is optionally partially or fully halogenated or optionally substituted with $R_{17}$;

$OR_{18}$ or $C_{1-6}$ alkyl optionally substituted with $OR_{18}$;

amino or mono- or di-($C_{1-5}$alkyl)amino optionally substituted with $R_{19}$;

$R_{20}C(O)N(R_{21})$—, $R_{22}O$— or $R_{23}R_{24}NC(O)$—; $R_{26}(CH_2)_mC(O)N(R_{21})$— or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, $S(O)_m$ and wherein said alkynyl group is optionally independently substituted with one to two oxo groups, pyrroldinyl, pyrrolyl, morpholinyl, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$ alkyl) amino optionally substituted by one or more halogen atoms; or aroyl;

$R_6$ is a:

$C_{1-4}$ alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently: nitrile, phenyl, morpholino, piperidinyl, piperazinyl, imidazolyl, pyridinyl, tetrazolyl, amino or mono- or di-($C_{1-4}$alkyl)amino optionally partially or fully halogenated;

each $R_{11}$ and $R_{16}$ is independently:
hydrogen or $C_{1-4}$ alkyl optionally partially or fully halogenated;

$R_{1-8}$ is independently:
hydrogen or a $C_{1-4}$ alkyl optionally independently substituted with oxo or $R_{25}$;

$R_{20}$ is independently:
$C_{1-10}$ alkyl optionally partially or fully halogenated, phenyl, or pyridinyl;

$R_{21}$ is independently:
hydrogen or $C_{1-3}$ alkyl optionally partially or fully halogenated;

each $R_{22}$, $R_{23}$ and $R_{24}$ is independently:
hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-($C_{1-3}$alkyl)aminocarbonyl, phenyl, pyridinyl, amino or mono- or di-($C_{1-4}$alkyl)amino each of which is optionally partially or fully halogenated and optionally substituted with mono- or di-($C_{1-3}$alkyl)amino; or $R_{23}$ and $R_{24}$ taken together optionally form a heterocyclic or heteroaryl ring;

m=0, 1 or 2;

W is O or S and pharmaceutically acceptable derivatives thereof.

In another embodiment of the invention there is provided compounds of the formula(II) as described immediately above, and wherein G is:
phenyl, naphthyl, benzocyclobutanyl, dihydronaphthyl, tetrahydronaphthyl, benzocycloheptanyl, benzocycloheptenyl, indanyl, indenyl;

pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, indolinyl, indolonyl, indolinonyl, phthalimidyl;

oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl; wherein G is substituted by one or more $R_1$, $R_2$ or $R_3$;

In another embodiment of the invention there is provided compounds of the formula(II) as described immediately above, and wherein G is phenyl, pyridinyl, pyridonyl, naphthyl, quinolinyl, isoquinolinyl, pyrazinyl, benzimidazolyl, benzoxazolyl, benzofuranyl, benzothiophenyl, benzpyrazolyl, dihydrobenzofuranyl, dihydrobenzothiophenyl, indanyl, indenyl, indolyl, indolinyl, indolonyl or indolinonyl, wherein G is substituted by one or more $R_1$, $R_2$ or $R_3$;

Ar is:
naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:
phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl Y is:
a bond or
a $C_{1-4}$ saturated or unsaturated carbon chain wherein one of the carbon atoms is optionally replaced by O, N, or $S(O)_m$ and wherein Y is optionally independently substituted with one to two oxo groups, phenyl or one or more $C_{1-4}$ alkyl optionally substituted by one or more halogen atoms;

Z is:
phenyl, pyridinyl, pyrimidinyl, pyridazinyl, pyrazinyl, imidazolyl, furanyl, thienyl, dihydrothiazolyl, dihydrothiazolyl sulfoxidyl, pyranyl, pyrrolidinyl which are optionally substituted with one to three nitrile, $C_{1-3}$ alkyl, $C_{1-3}$ alkoxy, amino, mono- or di-($C_{1-3}$ alkyl)amino, $CONH_2$ or OH;

tetrahydropyranyl, tetrahydrofuranyl, 1,3-dioxolanonyl, 1,3-dioxanonyl, 1,4-dioxanyl, morpholinyl, thiomorpholinyl, thiomorpholino sulfoxidyl, piperidinyl, piperidinonyl, piperazinyl, tetrahydropyrimidonyl, pentamethylene sulfidyl, pentamethylene sulfoxidyl, pentamethylene sulfonyl, tetramethylene sulfidyl, tetramethylene sulfoxidyl or tetramethylene sulfonyl which are optionally substituted with one to three nitrile, $C_{1-3}$ alkyl, $C_{1-3}$ alkoxy, amino, mono- or di-($C_{1-3}$ alkyl)amino, $CONH_2$, or OH; nitrile, $C_{1-6}$ alkyl-$S(O)_m$, halogen, hydroxy, $C_{1-4}$ alkoxy, amino, mono- or di-($C_{1-6}$ alkyl)amino, mono- or di-($C_{1-3}$ alkyl)aminocarbonyl or $NH_2C(O)$;

each $R_1$ is independently:
$C_{3-6}$ alkyl optionally partially or fully halogenated, and optionally substituted with one to three $C_{3-6}$cycloalkyl, phenyl, thienyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile or $C_{1-3}$ alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, CN, hydroxy$C_{1-3}$alkyl or phenyl; or an analog of such cycloalkyl group wherein one to three ring methylene groups are independently replaced by O, S, CHOH, >C=O, >C=S or NH; or silyl containing three $C_{1-4}$ alkyl groups optionally partially or fully halogenated;

$R_2$ is independently:
halogen, $C_{1-3}$ alkoxy, $C_{1-3}$ alkyl-$S(O)_m$ optionally partially or fully halogenated, phenylsulfonyl or nitrile;

$R_3$ is independently:
phenyl, morpholino, pyridinyl, pyrimidinyl, pyrazinyl, pyrrolyl, pyrrolylidinyl, imidazolyl, pyrazolyl, each being optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, nitrile, $C_{1-3}$ alkyloxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, mono- or di-($C_{1-3}$alkyl)amino, mono- or di-($C_{1-3}$)alkylamino-$C_{1-5}$ alkyl, mono- or di-($C_{1-3}$alkyl)amino-S(O)$_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl ($R_{11}$)N, carboxy-mono- or di-($C_{1-5}$)-alkyl-amino;

$C_{1-3}$ alkyl or $C_{1-4}$ alkoxy each being optionally partially or fully halogenated or optionally substituted with $R_{17}$;

$OR_{18}$ or $C_{1-6}$ alkyl optionally substituted with $OR_{18}$;

amino or mono- or di-($C_{1-5}$ alkyl)amino optionally substituted with $R_{19}$;

$R_{20}C(O)N(R_{21})$-, $R_{22}O$—; $R_{23}R_{24}NC(O)$—; $R_{26}CH_2C(O)N(R_{21})$— or $R_{26}C(O)CH_2N(R_{21})$—; $C_{2-4}$alkenyl substituted by $R_{23}R_{24}NC(O)$—; or $C_{2-4}$ alkynyl branched or unbranched carbon chain optionally partially or fully halogenated and optionally independently substituted with one to two oxo groups, pyrroldinyl, pyrrolyl, morpholinyl, piperidinyl, piperazinyl, imidazolyl, phenyl, pyridinyl, tetrazolyl or one or more $C_{1-4}$ alkyl optionally substituted by one or more halogen atoms; and $R_{23}$ and $R_{24}$ taken together optionally form imidazolyl, piperidinyl, morpholinyl, piperazinyl or a pyridinyl ring.

In yet another embodiment of the invention there is provided compounds of the formula(II) as described immediately above, and wherein:

G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl or indolinonyl, wherein G is substituted by one or more $R_1$, $R_2$ or $R_3$;

Ar is naphthyl;

X is phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl) amino, mono- or di-($C_{1-3}$ alkylamino)carbonyl, $NH_2C(O)$, $C_{1-6}$ alkyl-S(O)$_m$ or halogen;

Y is:

a bond or a $C_{1-4}$ saturated carbon chain wherein one of the carbon atoms is optionally replaced by O, N or S and wherein Y is optionally independently substituted with an oxo group;

Z is:

phenyl, pyridinyl, pyrimidinyl, pyridazinyl, pyrazinyl, imidazolyl, dihydrothiazolyl, dihydrothiazolyl sulfoxide, pyranyl or pyrrolidinyl which are optionally substituted with one to two $C_{1-2}$ alkyl or $C_{1-2}$ alkoxy;

tetrahydropyranyl, morpholinyl, thiomorpholinyl, thiomorpholino sulfoxidyl, piperidinyl, piperidinonyl, piperazinyl or tetrahydropyrimidonyl which are optionally substituted with one to two $C_{1-2}$ alkyl or $C_{1-2}$ alkoxy; or $C_{1-3}$ alkoxy;

each $R_1$ is independently:

$C_{3-5}$ alkyl optionally partially or fully halogenated, and optionally substituted with phenyl substituted with zero to three halogen, $C_{1-3}$ alkyl which is optionally partially or fully halogenated, hydroxy, nitrile or $C_{1-3}$ alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, CN, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O; and silyl containing three $C_{1-2}$ independently alkyl groups optionally partially or fully halogenated;

each $R_2$ is independently:

bromo, chloro, fluoro, methoxy, methylsulfonyl or nitrile;

each $R_3$ is independently:

phenyl, morpholino, pyridinyl, pyrimidinyl, pyrrolylidinyl, 2,5-pyrrolidin-dionyl, imidazolyl, pyrazolyl, each of the aforementioned is optionally substituted with one to three $C_{1-3}$ alkyl which is optionally partially or fully halogenated, halogen, oxo, hydroxy, nitrile and $C_{1-3}$ alkyloxy optionally partially or fully halogenated;

$C_{1-3}$ alkyl or $C_{1-3}$ alkoxy each being optionally partially or fully halogenated or optionally substituted with $R_{17}$;

$OR_8$ or $C_{1-3}$ alkyl optionally substituted with $OR_{1-8}$; amino or mono- or di-($C_{1-3}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_2)$— or $R_{26}C(O)CH_2N(R_{21})$—;

$C_{2-4}$ alkenyl substituted by $R_{23}R_{24}NC(O)$—; or $C_{2-4}$ alkynyl substituted with pyrroldinyl or pyrrolyl; and $R_{23}$ and $R_{24}$ taken together optionally form morpholino.

In yet still another embodiment of the invention there is provided compounds of the formula(II) as described immediately above, and wherein G is phenyl, pyridinyl, pyridonyl, naphthyl, quinolinyl, isoquinolinyl, dihydrobenzofuranyl, indanyl, indolinyl, indolonyl, or indolinonyl, wherein G is substituted by one or more $R_1$, $R_2$ or $R_3$;

Ar is 1-naphthyl;

X is:

phenyl, imidazolyl, pyridinyl, pyrimidinyl, piperdinyl, piperazinyl, pyridazinyl or pyrazinyl;

Y is:

a bond or —$CH_2$—, —$CH_2CH_2$—, —C(O)—, —O—, —S—, —NH—$CH_2CH_2CH_2$—, —$N(CH_3)$—, or —NH—;

each $R_1$, is independently:

$C_{3-5}$ alkyl optionally partially or fully halogenated, and optionally substituted with phenyl;

cyclopropyl, cyclopentanyl, cyclohexanyl and bicyclopentanyl optionally substituted with one to three methyl groups optionally partially or fully halogenated, CN, hydroxymethyl or phenyl; or 2-tetrahydrofuranyl substituted by methyl; or trimethyl silyl;

each $R_3$ is independently: phenyl, morpholinyl, pyridinyl, pyrimidinyl, pyrrolylidinyl, 2,5-pyrrolidin-dionyl, imidazolyl or pyrazolyl, wherein any of the aforementioned is optionally substituted with $C_{1-2}$ alkyl which is optionally partially or fully halogenated;

$C_{1-3}$ alkyl or $C_{1-3}$ alkoxy each being optionally partially or fully halogenated or optionally substituted with diethylamino;

$OR_{18}$ or $C_{1-3}$ alkyl optionally substituted with $OR_{18}$;

amino or mono- or di-($C_{1-3}$ alkyl)amino optionally substituted with $R_{19}$;

$CH_3C(O)NH$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$alkenyl substituted by $R_{23}R_{24}NC(O)$—; or $C_{2-4}$ alkynyl substituted with pyrroldinyl or pyrrolyl;

$R_{23}$ and $R_{24}$ are H or $R_{23}$ and $R_{24}$ taken together optionally form morpholino; and $R_{26}$ is morpholino.

In another embodiment of the invention there is provided of the formula(II) as described immediately above, and wherein G is phenyl, pyridinyl or naphthyl wherein G is substituted by one or more $R_1$, $R_2$ or $R_3$;

X is:

imidazolyl or pyridinyl;

Y is:

—$CH_2$, —NH—$CH_2CH_2CH_2$— or —NH—;

Z is morpholino;

each $R_1$ is independently:

tert-butyl, sec-butyl, tert-amyl or phenyl;

$R_2$ is chloro;

$R_3$ is independently:

methyl, methoxy, methoxymethyl, hydroxypropyl, acetamide, morpholino or morpholinocarbonyl.

In yet a further embodiment of the invention there is provided of the formula(II) as described immediately above, and wherein X is pyridinyl.

In yet a further embodiment of the invention there is provided of the formula(II) as described immediately above, and wherein the pyridinyl is attached to Ar via the 3-pyridinyl position.

The following are representative compounds of the formula(II):

1-(3-Cyano-phenyl)-3-[4-(6-morpholin-4-ylmethyl-pyridin-3-yl)-naphthalen-1-yl]-urea 1-(3-Fluoro-phenyl)-3-[4-(6-morpholin-4-ylmethyl-pyridin-3-yl)-naphthalen-1-yl]-urea 1-(4-Chloro-2-trifluoromethyl-phenyl)-3-[4-(6-morpholin-4-ylmethyl-pyridin-3-yl)-naphthalen-1-yl]-urea 1-(2-Chloro-5-trifluoromethyl-phenyl)-3-[4-(6-morpholin-4-ylmethyl-pyridin-3-yl)-naphthalen-1-yl]-urea 1-(3,4-Dimethyl-phenyl)-3-[4-(6-morpholin-4-ylmethyl-pyridin-3-yl)-naphthalen-1-yl]-urea 1-(3-Iodo-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-m-tolyl-urea 1-(4-Methylsulfany-phenyl)-3-[4-(6-morpholin-4-ylmethyl-pyridin-3-yl)-naphthalen-1-yl]-urea 1-(3-Chloro-4-methyl-phenyl)-3-[4-(6-morpholin-4-ylmethyl-pyridin-3-yl)-naphthalen-1-yl]-urea 1-(4-Chloro-3-nitro-phenyl)-3-[4-(6-morpholin-4-ylmethyl-pyridin-3-yl)-naphthalen-1-yl]-urea 1-(2,5-Dichloro-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-naphthalen-2-yl-urea 1-[4-(6-Morpholin-4-ylmethyl-pyridin-3-yl)-naphthalen-1-yl]-3-phenyl-urea 1-(3-chloro-phenyl)-3-[4-(6-morpholin-4-ylmethyl-pylidin-3yl)naphthalen-1-yl]-urea 1-(4-Chloro-3-trifluoromethyl-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-(2,4,6-trichloro-phenyl)-urea 1-(2-Methyl-3-nitro-phenyl)-3-[4-(6-morpholin-4-ylmethyl-pyridin-3-yl)-naphthalen-1-yl]-urea 1-(4-Methyl-2-nitro-phenyl)-3-[4-(6-morpholin-4-ylmethyl-pyridin-3-yl)-naphthalen-1-yl]-urea 1-(2,3-Dichloro-phenyl)-3-[4-(6-morpholin-4-ylmethyl-pyridin-3-yl)-naphthalen-1-yl]-urea 1-(2-Methoxy-5-methyl-phenyl)-3-[4-(6-morpholin-4-ylmethyl-pyridin-3-yl)-naphthaten-1-yl]-urea 1-(2-Chloro-6-methyl-phenyl)-3-[4-(6-morpholin-4-ylmethyl-pyridin-3-yl)-naphthalen-1-yl]-urea 1-(2,4-Dichloro-phenyl)-3-[4-(6-morpholin-4-ylmethyl-pyridin-3-yl)-naphthalen-1-yl]-urea 1-(4-Methyl-3-nitro-phenyl)-3-[4-(6-morpholin-4-ylmethyl-pyridin-3-yl)-naphthalen-1-yl]-urea 1-(2,4-Dimethyl-phenyl)-3-[4-(6-morpholin-4-ylmethyl-pyridin-3-yl)-naphthalen-1-yl]-urea 1-(2,3-Dimethyl-phenyl)-3-[4-(6-morpholin-4-ylmethyl-pyridin-3-yl)-naphthalen-1-yl]-urea 1-(4-Cyano-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-(3,4,5-trimethoxy-phenyl)-urea 1-Biphenyl-4-yl-3-[4-(6-morpholin-4-ylmethyl-pyridin-3-yl)-naphthalen-1-yl]-urea 1-(2,5-Difluoro-phenyl)-3-[4-(6-morpholin-4-ylmethyl-pyridin-3-yl)-naphthalen-1-yl]-urea 1-(3-Chloro-2-methoxy-phenyl)-3-[4-(6-morpholin-4-ylmethyl-pyridin-3-yl)-naphthalen-1-yl]-urea 1-(2-Fluoro-3-trifluoromethyl-phenyl)-3-[4-(6-morpholin-4-ylmethyl-pyridin-3-yl)-naphthalen-1-yl]-urea 1-(4-Benzyloxy-phenyl)-3-[4-(6-morpholin-4-ylmethyl-pyridin-3-yl)-naphthalen-1-yl]-urea 1-(2-Methylsulfanyl-phenyl)-3-[4-(6-morpholin-4-ylmethyl-pyridin-3-yl)-naphthalen-1-yl]-urea 1-(2-Fluoro-6-trifluoromethyl-phenyl)-3-[4-(6-morpholin-4-ylmethyl-pyridin-3-yl)-naphthalen-1-yl]-urea 1-(4-Fluoro-3-trifluoromethyl-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-(2,4,5-trimethyl-phenyl)-urea 1-[4-(6-Morpholin-4-ylmethyl-pyridin-3-yl)-naphthalen-1-yl]-3-(4-trifluoromethyl-phenyl)-urea 1-(3-Methylsulfanyl-phenyl)-3-[4-(6-morpholin-4-ylmethyl-pyridin-3-yl)-naphthalen-1-yl]-urea 1-(2-Methoxy-phenyl)-3-[4-(6-morpholin-4-ylmethyl-pyridin-3-yl)-naphthalen-1-yl]-urea 1-(2-Fluoro-5-trifluoromethyl-phenyl)-3-[4-(6-morpholin-4-ylmethyl-pyridin-3-yl)-naphthalen-1-yl]-urea 1-(4-Methoxy-2-methyl-phenyl)-3-[4-(6-morpholin-4-ylmethyl-pyridin-3-yl)-naphthalen-1-yl]-urea 1-(2-Fluoro-5-nitro-phenyl)-3-[4-(6-morpholin-4-ylmethyl-pyridin-3-yl)-naphthalen-1-yl]-urea 1-(4-Ethoxy-phenyl)-3-[4-(6-morpholin-4-ylmethyl-pyridin-3-yl)-naphthalen-1-yl]-urea 1-(2,5-Dimethoxy-phenyl)-3-[4-(6-morpholin-4-ylmethyl-pyridin-3-yl)-naphthalen-1-yl]-urea 1-(4,5-Dimethyl-2-nitro-phenyl)-3-[4-(6-morpholin-4-ylmethyl-pyridin-3-yl)-naphthalen-1-yl]-urea 1-(5-Chloro-2-methyl-phenyl)-3-[4-(6-morpholin-4-ylmethyl-pyridin-3-yl)-naphthalen-1-yl]-urea 1-(2-Isopropyl-6-methyl-phenyl)-3-[4-(6-morpholin-4-ylmethyl-pyridin-3-yl)-naphthalen-1-yl]-urea 1-(2-Difluoromethoxy-phenyl)-3-[4-(6-morpholin-4-ylmethyl-pyridin-3-yl)-naphthalen-1-yl]-urea 1-(4-Isopropyl-phenyl)-3-[4-(6-morpholin-4-ylmethyl-pyridin-3-yl)-naphthalen-1-yl]-urea 1-(4-Methoxy-phenyl)-3-[4-(6-morpholin-4-ylmethyl-pyridin-3-yl)-naphthalen-1-yl]-urea 1-(3-Ethyl-phenyl)-3-[4-(6-morpholin-4-ylmethyl-pyridin-3-yl)-naphthalen-1-yl]-urea 1-(2-Ethoxy-phenyl)-3-[4-(6-morpholin-4-ylmethyl-pyridin-3-yl)-naphthalen-1-yl]-urea 1-(4-Butoxy-phenyl)-3-[4-(6-morpholin-4-ylmethyl-pyridin-3-yl)-naphthalen-1-yl]-urea 4-{3-[4-(6-Morpholin-4-ylmethyl-pyridin-3-yl)-naphthalen-1-yl]-ureido}-benzoic acid ethyl ester 1-(4-Butyl-2-methyl-phenyl)-3-[4-(6-morpholin-4-ylmethyl-pyridin-3-yl)-naphthalen-1-yl]-urea 1-(2,6-Dibromo-4-isopropyl-phenyl)-3-[4-(6-morpholin-4-ylmethyl-pyridin-3-yl)-naphthalen-1-yl]-urea 1-(3-Methoxy-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-(4-trifluoromethylsulfanyl-phenyl)-urea 5-{3-[4-(6-Morpholin-4-ylmethyl-pyridin-3-yl)-naphthalen-1-yl]-ureido}-isophthalic acid dimethyl ester 1-(3-Cyclopentyloxy-4-methoxy-phenyl)-3-[4-(6-morpholin-4-ylmethyl-pyridin-3-yl)-naphthalen-1-yl]-urea 3-{3-[4-(6-Morpholin-4-ylmethyl-pyridin-3-yl)-naphthalen-1-yl]-ureido}-benzoic acid ethyl ester 1-(5-tert-Butyl-2-hydroxy-phenyl)-3-[4-(6-morpholin-4-ylmethyl-pyridin-3-yl)-naphthalen-1-yl]-urea 1-(2-Hydroxymethyl-4-phenyl-cyclohexyl)-3-[4-(6-morpholin-4-ylmethyl-pyridin-3-yl)-naphthalen-1-yl]-urea 1-(2-Methylsulfanyl-5-trifluoromethyl-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-(4-pentyloxy-biphenyl-3-yl)-urea 4-Methoxy-3-{3-[4-(6-morpholin-4-ylmethyl-pyridin-3-yl)-naphthalen-1-yl]-ureido}-benzoic acid methyl ester 1-(2,5-Diethoxy-phenyl)-3-[4-(6-morpholin-4-ylmethyl-pyridin-3-yl)-naphthalen-1-yl]-urea 1-Benzothiazol-6-yl-3-[4-(6-morpholin-4-ylmethyl-pyridin-3-yl)-naphthalen-1-yl]-urea N-(2,5-Diethoxy-4-{3-[4-(6-morpholin-4-ylmethyl-pyridin-3-yl)-naphthalen-1-yl]-ureido}-phenyl)-benzamide 1-[4-(6-Morpholin-4-ylmethyl-pyridin-3-yl)-naphthalen-1-yl]-3-(3-phenoxy-phenyl)-urea 1-(5-Ethanesulfonyl-2-methoxy-phenyl)-3-[4-(6-morpholin-4-ylmethyl-pyridin-3-yl)-naphthalen-1-yl]-urea 4-Methoxy-3-{3-[4-(6-morpholin-4-ylmethyl-pyridin-3-yl)-naphthalen-1-yl]-ureido}-N-phenyl-benzamide 1-(2-Methyl-1,3-dioxo-2,3-dihydro-1H-isoindol-5-yl)-3-[4-(6-morpholin-4-ylmethyl-pyridin-3-yl)-naphthalen-1-yl]-urea 1-(2,3-Dimethyl-1H-indol-5-yl)-3-[4-(6-morpholin-4-ylmethyl-pyridin-3-yl)-naphthalen-1-yl]-urea N-Butyl-4-methoxy-3-{3-[4-(6-morpholin-4-ylmethyl-pyridin-3-yl)-naphthalen-1-yl]-ureido}-benzenesulfonamide 1-[3-(2-Methyl-[1,3]dioxolan-2-yl)-phenyl]-3-[4-(6-morpholin-4-ylmethyl-pyridin-3-yl)-naphthalen-1-yl]-urea 1-(3-Methoxy-5-trifluoromethyl-phenyl)-3-[4-(6-morpholin-4-ylmethyl-pyridin-3-yl)-naphthalen-1-yl]-urea 1-(2,4-Dimethoxy-phenyl)-3-[4-(6-morpholin-4-ylmethyl-pyridin-3-yl)-naphthalen-1-yl]-urea 1-(2-Methyl-4-nitro-phenyl)-3-[4-(6-morpholin-4-ylmethyl-pyridin-3-yl)-naphthalen-1-yl]-urea 1-(2-Methoxy-4-nitro-phenyl)-3-[4-(6-morpholin-4-ylmethyl-pyridin-3-yl)-naphthalen-1-yl]-urea 1-(4-Chloro-2-nitro-phenyl)-3-[4-(6-morpholin-4-ylmethyl-pyridin-3-yl)-naphthalen-1-yl]-urea 1-(5-Chloro-2-methoxy-phenyl)-3-[4-(6-morpholin-4-ylmethyl-pyridin-3-yl)-naphthalen-1-yl]-urea 1-(3,5-Dimethoxy-phenyl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-(4-trifluoromethoxy-phenyl)-urea 1-[4-(6-Morpholin-4-ylmethyl-pyridin-3-yl)-naphthalen-1-yl]-3-(3-trifluoromethylsulfanyl-phenyl)-urea 1-[4-(6-Morpholin-4-ylmethyl-pyridin-3-yl)-naphthalen-1-yl]-3-(2-phenoxy-phenyl)-urea 1-(2-Methoxy-5-nitro-phenyl)-3-[4-(6-morpholin-4-ylmethyl-pyridin-3-yl)-naphthalen-1-yl]-urea 1-(5-Chloro-2,4-dimethoxy-phenyl)-3-[4-(6-morpholin-4-ylmethyl-pyridin-3-yl)-naphthalen-1-yl]-urea 1-(3,5-Bis-trifluoromethyl-phenyl)-3-[4-(6-morpholin-4-ylmethyl-pyridin-3-yl)-naphthalen-1-yl]-urea 1-(2-tert-Butyl-5-methyl-pyridin-4-yl)-3-[4-(6-morpholin-4-ylmethyl-pyridin-3-yl)-naphthalen-1-yl]-urea 1-(3-Methyl-naphthalen-2-yl)-3-[4-(6-morpholin-4-ylmethyl-pyridin-3-yl)-naphthalen-1-yl]-urea 1-(3-tert-Butyl-phenyl)-3-[4-(6-morpholin-4-ylmethyl-pyridin-3-yl)-naphthalen-1-yl]-urea 1-(4-Methyl-biphenyl-3-yl)-3-[4-(6-morpholin-4-ylmethyl-pyridin-3-yl)-naphthalen-1-yl]-urea 1-(4-tert-Butyl-biphenyl-2-yl)-3-[4-(6-morpholin-4-ylmethyl-pyridin-3-yl)-naphthalen-1-yl]-urea 1-(5-Chloro-2,4-dimethoxy-phenyl)-3-[4-(6-morpholin-4-ylmethyl-pyridin-3-yl)-naphthalen-1-yl]-urea 1-(5-Isopropyl-2-methyl-phenyl)-3-[4-(6-morpholin-4-ylmethyl-pyridin-3-yl)-naphthalen-1-yl]-urea 1-(5-sec-Butyl-2-methoxy-phenyl)-3-[4-(6-morpholin-4-ylmethyl-pyridin-3-yl)-naphthalen-1-yl]-urea 1-(5-tert-Butyl-2-methoxy-3-propyl-phenyl)-3-[4-(6-morpholin-4-ylmethyl-pyridin-3-yl)-naphthalen-1-yl]-urea 1-(5-tert-Butyl-2-methoxymethyl-phenyl)-3-[4-(6-morpholin-4-ylmethyl-pyridin-3-yl)-naphthalen-1-yl]-urea 1-(5-tert-Butyl-2-methoxy-phenyl)-3-[4-(6-morpholin-4-ylmethyl-pyridin-3-yl)-naphthalen-1-yl]-urea 1-(5-tert-Butyl-2-methyl-phenyl)-3-(4-{6-[(3-methoxy-propyl)-methyl-amino]-pyridin-3-yl}-naphthalen-1-yl)-urea 1-(5-tert-Butyl-2-methyl-phenyl)-3-[4-(4-morpholin-4-ylmethyl-imidazol-1-yl)-naphthalen-1-yl]-urea 1-(5-tert-Butyl-2-methyl-phenyl)-3-[4-(6-morpholin-4-ylmethyl-pyridin-3-yl)-naphthalen-1-yl]-urea 1-(5-tert-Butyl-2-methyl-phenyl)-3-{4-[6-(3-methoxy-propylamino)-pyridin-3-yl]-naphthalen-1-yl}-urea 1-(5-tert-Butyl-2-methyl-pyridin-3-yl)-3-[4-(6-morpholin-4-ylmethyl-pyridin-3-yl)-naphthalen-1-yl]-urea 1-(5-tert-Butyl-2-morpholin-4-yl-phenyl)-3-[4-(6-morpholin-4-ylmethyl-pyridin-3-yl)-naphthalen-1-yl]-urea 1-(6-tert-Butyl-2-chloro-3-methyl-pyridin-4-yl)-3-[4-(6-morpholin-4-ylmethyl-pyridin-3-yl)-naphthalen-1-yl]-urea 1-[4-(6-Morpholin-4-ylmethyl-pyridin-3-yl)-naphthalen-1-yl]-3-(3-trifluoromethyl-phenyl)-urea 1-[4-(6-Morpholin-4-ylmethyl-pyridin-3-yl)-naphthalen-1-yl]-3-(4-trifluoromethoxy-phenyl)-urea 1-[5-(1,1-Dimethyl-propyl)-2-methoxy-phenyl]-3-[4-(6-morpholin-4-ylmethyl-pyridin-3-yl)-naphthalen-1-yl]-urea 1-[5-tert-Butyl-2-(1H-pyrazol-4-yl)-phenyl]-3-[4-(6-morpholin-4-ylmethyl-pyridin-3-yl)-naphthalen-1-yl]-urea 1-[5-tert-Butyl-2-(2-methyl-pyrimidin-5-yl)-phenyl]-3-[4-(6-morpholin-4-ylmethyl-pyridin-3-yl)-naphthalen-1-yl]-urea 1-[5-tert-Butyl-2-(3-hydroxy-propyl)-phenyl]-3-[4-(6-morpholin-4-ylmethyl-pyridin-3-yl)-naphthalen-1-yl]-urea 1-[5-tert-Butyl-2-(3-morpholin-4-yl-3-oxo-propyl)-phenyl]-3-[4-(6-morpholin-4-ylmethyl-pyridin-3-yl)-naphthalen-1-yl]-urea 1-[5-tert-Butyl-2-(morpholine-4-carbonyl)-phenyl]-3-[4-(6-morpholin-4-ylmethyl-pyridin-3-yl)-naphthalen-1-yl]-urea N-(5-tert-Butyl-2-methoxy-3-{3-[4-(6-morpholin-4-ylmethyl-pyridin-3-yl)-naphthalen-1-yl]-ureido}-phenyl)-acetamide and the pharmaceutically acceptable derivatives thereof.

In addition to the abovementioned representative compounds the following prophetic compounds of the formula (II) may be made by the general methods described hereinbelow:

1-[4-(6-{[Bis-(2-cyano-ethyl)-amino]-methyl}-pyridin-3-yl)-naphthalen-1-yl]-3-(5-tert-butyl-2-methoxy-phenyl)-urea 1-(5-tert-Butyl-2-methoxy-phenyl)-3-{4-[4-(2-methyl-3-oxo-piperazin-1-ylmethyl)-phenyl]-naphthalen-1-yl}-urea 1-[4-(6-{[Bis-(2-methoxy-ethyl)-amino]-methyl}-pyridin-3-yl)-naphthalen-1-yl]-3-(5-tert-butyl-2-methoxy-phenyl)-urea 1-(5-tert-Butyl-2-methoxy-phenyl)-3-{4-[6-(2-methyl-3-oxo-piperazin-1-ylmethyl)-pyridin-3-yl]-naphthalen-1-yl}-urea 1-(5-tert-Butyl-2-methoxy-phenyl)-3-{4-[6-(1-oxo-114-thiomorpholin-4-ylmethyl)-pyridin-3-yl]-naphthalen-1-yl}-urea 1-(5-tert-Butyl-2-methoxy-phenyl)-3-[4-(6-thiomorpholin-4-ylmethyl-pyridin-3-yl)-naphthalen-1-yl]-urea 1-(5-tert-Butyl-2-methyl-phenyl)-3-{4-[6-(1-oxo-114-thiomorpholin-4-ylmethyl)-pyridin-3-yl]-naphthalen-1-yl}-urea 1-(5-tert-Butyl-2-methyl-phenyl)-3-{4-[6-(2-methyl-3-oxo-piperazin-1-ylmethyl)-pyridin-3-yl]-naphthalen-1-yl}-urea 1-(5-tert-Butyl-2-methoxy-phenyl)-3-{4-[4-(1-oxo-11-thiomorpholin-4-ylmethyl)-phenyl]-naphthalen-1-yl}-urea 1-[4-(4-{[Bis-(2-cyano-ethyl)-amino]-methyl}-phenyl)-naphthalen-1-yl]-3-(5-tert-butyl-2-methoxy-phenyl)-urea 1-(2-Methoxy-5-pentafluoroethyl-phenyl)-3-[4-(4-morpholin-4-ylmethyl-piperidin-1-yl)-naphthalen-1-yl]-urea 1-(2-Methoxy-5-trifluoromethyl-pyridin-3-yl)-3-{4-[2-(4-oxo-piperidin-1-ylmethyl)-pyrimidin-5-yl]-naphthalen-1-yl}-urea 1-(2-Methoxy-5-trimethylsilanyl-phenyl)-3-{4-[4-(tetrahydro-pyran-4-ylamino)-phenyl]-naphthalen-1-yl}-urea 1-(3-Methoxy-naphthalen-2-yl)-3-[4-(4-morpholin-4-ylmethyl-piperidin-1-yl)-naphthalen-1-yl]-urea 1-(3-Methyl-naphthalen-2-yl)-3-[4-(4-morpholin-4-ylmethyl-phenyl)-naphthalen--yl]-urea 1-(3-tert-Butyl-5-methanesulfinyl-phenyl)-3-{4-[6-(1-methyl-piperidin-4-ylmethyl)-pyridin-3-yl]-naphthalen-1-yl}-urea 1-(3-tert-Butyl-phenyl)-3-[4-(3-pyridin-3-yl-propoxy)-naphthalen-1-yl]-urea 1-(3-tert-Butyl-phenyl)-3-[4-(4-morpholin-4-ylmethyl-phenyl)-naphthalen-1-yl]-urea 1-(4-Methoxy-biphenyl-3-yl)-3-{4-[4-(tetrahydro-pyran-4-ylmethyl)-imidazol-1-yl]-naphthalen-1-yl}-urea 1-(4-Methyl-biphenyl-3-yl)-3-{4-[4-(2-pyridin-4-yl-ethyl)-piperazin-1-yl]-naphthalen-1-yl}-urea 1-(4-tert-Butyl-biphenyl-2-yl)-3-[4-(pyridin-4-ylmethoxy)-naphthalen-1-yl]-urea 1-(4-tert-Butyl-biphenyl-2-yl)-3-{4-[2-(1-oxo-114-thiomorpholin-4-ylmethyl)-3H-imidazol-4-yl]-naphthalen-1-yl}-urea 1-(5-tert-Butyl-2-hydroxy-phenyl)-3-[4-(5-morpholin-4-ylmethyl-pyrazin-2-yl)-naphthalen-1-yl]-urea 1-(5-tert-Butyl-2-methoxy-3-propyl-phenyl)-3-{4-[4-(pyrrolidine-1-carbonyl)-phenyl]-naphthalen-1-yl}-urea 1-(5-tert-Butyl-2-methoxy-phenyl)-3-[4-(2-morpholin-4-ylmethyl-pyrimidin-5-yl)-naphthalen-1-yl]-urea 1-(5-tert-Butyl-2-methoxy-phenyl)-3-[4-(4-thiomorpholin-4-ylmethyl-phenyl)-naphthalen-1-yl]-urea 1-(5-tert-Butyl-2-methoxy-phenyl)-3-[4-(6-morpholin-4-ylmethyl-phenyl)-naphthalen-1-yl]-urea 1-(5-tert-Butyl-2-methoxy-phenyl)-3-{4-[4-(tetrahydro-pyran-4-ylamino)-phenyl]-naphthalen-1-yl}-urea 1-(5-tert-Butyl-2-methoxy-phenyl)-3-{4-[6-(4-methyl-piperazin-1-ylmethyl)-pyridin-3-yl]-naphthalen-1-yl}-urea 1-(5-tert-Butyl-2-methoxy-pyridin-3-yl)-3-{4-[6-(4-oxo-piperidin-1-ylmethyl)-pyridin-3-yl]-naphthalen-1-yl}-urea 1-(5-tert-Butyl-2-methyl-benzooxazol-7-yl)-3-[4-(6-pyridin-4-ylmethyl-pyridin-3-yl)-naphthalen-1-yl]-urea 1-(5-tert-Butyl-2-methyl-phenyl)-3-[4-(4-morpholin-4-ylmethyl-phenyl)-naphthalen-1-yl]-urea 1-(5-tert-Butyl-2-phenoxy-phenyl)-3-{4-[6-(tetrahydro-pyran-4-yloxy)-pyridin-3-yl]-naphthalen-1-yl}-urea 1-(5-tert-Butyl-2-pyrrolidin-1-yl-phenyl)-3-[4-(4-methoxy-6-morpholin-4-ylmethyl-pyridin-3-yl)-naphthalen-1-yl]-urea 1-(5-tert-Butyl-2-pyrrolidin-1-yl-phenyl)-3-[4-(6-morpholin-4-ylmethyl-pyridin-3-yl)-naphthalen-1-yl]-urea 1-(5-tert-Butyl-3-cyano-2-methoxy-phenyl)-3-{4-[2-(2,6-dimethyl-morpholin-4-ylmethyl)-pyrimidin-5-yl]-naphthalen-1-yl}-urea 1-(5-tert-Butyl-4'-dimethylamino-biphenyl-3-yl)-3-[4-(2-morpholin-4-ylmethyl-pyrimidin-5-yl)-naphthalen-1-yl]-urea 1-(6-Methoxy-3,3-dimethyl-indan-5-yl)-3-{4-[4-(morpholine-4-carbonyl)-phenyl]-naphthalen-1-yl}-urea 1-(6-tert-Butyl-2-chloro-3-methyl-pyridin-4-yl)-3-[4-(6-thiomorpholin-4-ylmethyl-pyridin-3-yl)-naphthalen-1-yl]-urea 1-(6-tert-Butyl-benzo[1,3]dioxol-4-yl)-3-{4-[6-(morpholin-4-ylamino)-pyridin-3-yl]-naphthalen-1-yl}-urea 1-(7-Methoxy-1,4,4-trimethyl-1,2,3,4-tetrahydro-quinolin-6-yl)-3-{4-[6-(tetrahydro-pyran-4-yloxy)-pyridin-3-yl]-naphthalen-1-yl}-urea 1-(7-tert-Butyl-2,4-dimethyl-benzooxazol-5-yl)-3-[4-(6-morpholin-4-ylmethyl-pyridin-3-yl)-naphthalen-1-yl]-urea 1-[2-Methoxy-5-(1-methyl-1-phenyl-ethyl)-phenyl]-3-{4-[6-(2-pyridin-4-yl-ethyl)-pyridazin-3-yl]-naphthalen-1-yl}-urea 1-[2-Methoxy-5-(1-methyl-cyclohexyl)-phenyl]-3-{4-[4-(1-methyl-piperidin-4-ylsulfanyl)-phenyl]-naphthalen-1-yl}-urea 1-[2-Methoxy-5-(1-methyl-cyclopropyl)-phenyl]-3-[4-(2-morpholin-4-ylmethyl-pyrimidin-5-yl)-naphthalen-1-yl]-urea 1-[2-Methoxy-5-(2-methyl-tetrahydro-furan-2-yl)-phenyl]-3-[4-(5-morpholin-4-ylmethyl-pyridin-2-yl)-naphthalen-1-yl]-urea 1-[2-Methoxy-5-(3-trifluoromethyl-bicyclo[1.1.1]pent-1-yl)-phenyl]-3-[4-(4-morpholin-4-ylmethyl-phenyl)-naphthalen-1-yl]-urea 1-[3-tert-Butyl-5-(1-methyl-1H-imidazol-4-yl)-phenyl]-3-[4-(5-morpholin-4-ylmethyl-pyridin-2-yl)-naphthalen-1-yl]-urea 1-[3-tert-Butyl-5-(2-pyrrolidin-1-yl-ethyl)-phenyl]-3-{4-[6-(1-methyl-piperidin-4-yloxy)-pyridin-3-yl]-naphthalen-1-yl-urea 1-[3-tert-Butyl-5-(3-pyrrolidin-1-yl-prop-1-ynyl)-phenyl]-3-[4-(6-morpholin-4-ylmethyl-pyridin-3-yl)-naphthalen-1-yl]-urea 1-[4-(6-Imidazol-1-ylmethyl-pyridin-3-yl)-naphthalen-1-yl]-3-[2-methoxy-5-(1-phenyl-cyclopropyl)-phenyl]-urea 1-[5-(1,1-Dimethyl-propyl)-2-methoxy-phenyl]-3-[4-(4-thiomorpholin-4-ylmethyl-phenyl)-naphthalen-1-yl]-urea 1-[5-(1-Cyano-cyclopropyl)-2-methoxy-phenyl]-3-[4-(2-morpholin-4-ylmethyl-pyrimidin-5-yl)-naphthalen-1-yl]-urea 1-[5-(1-Hydroxymethyl-cyclopropyl)-2-methoxy-phenyl]-3-[4-(4-morpholin-4-ylmethyl-phenyl)-naphthalen-1-yl]-urea 1-[5-tert-Butyl-1-(2-diethylamino-ethyl)-2-oxo-1,2-dihydro-pyridin-3-yl]-3-{4-[6-(1-methyl-piperidin-4-yloxy)-pyridin-3-yl]-naphthalen-1-yl}-urea 1-[5-tert-Butyl-2-(1H-pyrazol-4-yl)-phenyl]-3-[4-(2-morpholin-4-yl-ethoxy)-naphthalen-1-yl]-urea 1-[5-tert-Butyl-2-(1H-pyrazol-4-yl)-phenyl]-3-{4-[4-(4-methyl-piperazine-1-carbonyl)-phenyl]-naphthalen-1-yl}-urea 1-[5-tert-Butyl-2-(2,5-dioxo-pyrrolidin-1-yl)-phenyl]-3-{4-[6-(1H-imidazol-2-ylmethyl)-pyridin-3-yl]-naphthalen-1-yl}-urea 1-[5-tert-Butyl-2-(2-methyl-pyrimidin-5-yl)-phenyl]-3-[4-(5-pyridin-4-ylmethyl-pyridin-2-yl)-naphthalen-1-yl]-urea 1-[5-tert-Butyl-2-(2-morpholin-4-yl-2-oxo-ethoxy)-phenyl]-3-{4-[6-(2-pyridin-4-yl-ethyl)-pyridazin-3-yl]-naphthalen-1-yl}-urea 1-[5-tert-Butyl-2-(2-morpholin-4-yl-2-oxo-ethylamino)-phenyl]-3-{4-[4-(1-methyl-piperidin-4-ylamino)-piperidin-1-yl]-naphthalen-1-yl}-urea 1-[5-tert-Butyl-2-(6-methyl-pyridin-3-yl)-phenyl]-3-{4-[5-(2-pyrrolidin-1-yl-ethyl)-pyridin-2-yl]-naphthalen-1-yl}-urea 1-[5-tert-Butyl-2-methoxy-3-(3-morpholin-4-yl-3-oxo-propenyl)-phenyl]-3-[4-(6-pyrrolidin-1-ylmethyl-pyridin-3-yl)-naphthalen-1-yl]-urea 1-[5-tert-Butyl-3-(2-diethylamino-ethoxy)-2-methoxy-phenyl]-3-{4-[4-(tetrahydro-pyran-4-yloxy)-phenyl]-naphthalen-1-yl}-urea 1-[5-tert-Butyl-3-(2-pyrrolidin-1-yl-ethyl)-benzofuran-7-yl]-3-[4-(4-morpholin-4-ylmethyl-phenyl)-naphthalen-1-yl]-urea 1-[6-tert-Butyl-4-(2-dimethylamino-ethyl)-3-oxo-3,4-dihydro-2H-benzo[1,4]oxazin-8-yl]-3-{4-[6-(thiomorpholin-4-ylamino)-pyridin-3-yl]-naphthalen-1-yl}-urea 1-{5-tert-Butyl-2-methoxy-3-[2-(1-methyl-piperidin-4-yloxy)-ethyl]-phenyl}-3-[4-(4-morpholin-4-ylmethyl-phenyl)-naphthalen-1-yl]-urea 2-(4-tert-Butyl-2-{3-[4-(5-pyrrolidin-1-ylmethyl-pyridin-2-yl)-naphthalen-1-yl]-ureido}-phenoxy)-N-methyl-acetamide 2-[4-tert-Butyl-2-(3-{4-[6-(2,6-dimethyl-morpholin-4-ylmethyl)-pyridin-3-yl]-naphthalen-1-yl}-ureido)-phenoxy]-acetamide 3-(5-tert-Butyl-2-methoxy-3-{3-[4-(6-pyrrolidin-1-ylmethyl-pyridin-3-yl)-naphthalen-1-yl]-ureido}-phenyl)-acrylamide 3-{3-tert-Butyl-5-[3-(4-{4-[2-(1-oxo-1l4-thiazolidin-3-yl)-ethyl]-phenyl}-naphthalen-1-yl)-ureido]-phenyl}-N,N-dimethyl-propionamide 3-{4-[3-(5-tert-Butyl-2-methoxy-phenyl)-ureido]-naphthalen-1-yl }-benzamide 4-tert-Butyl-2-{3-[4-(2-chloro-4-morpholin-4-ylmethyl-phenyl)-naphthalen-1-yl]-ureido}-benzamide N-(4-tert-Butyl-2-{3-[4-(6-oxo-1,6-dihydro-pyridin-3-yl)-naphthalen-1-yl]-ureido}-phenyl)-2-morpholin-4-yl-acetamide N-[3-tert-Butyl-5-(3-{4-[5-(tetrahydro-pyran-4-ylamino)-pyridin-2-yl]-naphthalen-1-yl}-ureido)-phenyl]-2-morpholin-4-yl-acetamide N-[4-tert-Butyl-2-(3-{4-[4-(1-methyl-piperidin-4-yloxy)-phenyl]-naphthalen-1-yl}-ureido)-phenyl]-acetamide and the pharmaceutically acceptable derivatives thereof.

In yet another embodiment of the invention, there is provided the following compounds of the formula(II):

1-(2-tert-Butyl-methyl-pyridin-4-yl)-3-[4-(6-morpholin-4-ylmethyl-pyridin-3-yl)-naphthalen-1-yl]-urea;

1-(3-Methyl-naphthalen-2-yl)-3-[4-(6-morpholin-4-ylmethyl-pyridin-3-yl)-naphthalen-1-yl]-urea;

1-(3-tert-Butyl-phenyl)-3-[4-(4-morpholin-4-ylmethyl-phenyl)-naphthalen-1-yl]-urea;

1-(3-tert-Butyl-phenyl)-3-[4-(6-morpholin-4-ylmethyl-pyridin-3-yl)-naphthalen-1-yl]-urea;

1-(4-Methyl-biphenyl-3-yl)-3-[4-(6-morpholin-4-ylmethyl-pyridin-3-yl)-naphthalen-1-yl]-urea;

1-(4-tert-Butyl-biphenyl-2-yl)-3-[4-(6-morpholin-4-ylmethyl-pyridin-3-yl)-naphthalen-1-yl]-urea;

1-(5-Chloro-2,4-dimethoxy-phenyl)-3-[4-(6-morpholin-4-ylmethyl-pyridin-3-yl)-naphthalen-1-yl]-urea;

1-(5-Isopropyl-2-methyl-phenyl)-3-[4-(6-morpholin-4-ylmethyl-pyridin-3-yl)-naphthalen-1-yl]-urea;

1-(5-sec-Butyl-2-methoxy-phenyl)-3-[4-(6-morpholin-4-ylmethyl-pyridin-3-yl)-naphthalen-1-yl]-urea;

1-(5-tert-Butyl-2-methoxy-3-propyl-phenyl)-3-[4-(6-morpholin-4-ylmethyl-pyridin-3-yl)-naphthalen-1-yl]-urea;

1-(5-tert-Butyl-2-methoxymethyl-phenyl)-3-[4-(6-morpholin-4-ylmethyl-pyridin-3-yl)-naphthalen-1-yl]-urea;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methoxy-phenyl)-3-[4-(4-thiomorpholin-4-ylmethyl-phenyl)-naphthalen-1-yl]-urea;

1-(5-tert-Butyl-2-methoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-morpholin-4-ylmethyl-phenyl)-naphthalen-1-yl]-urea;

1-(5-tert-Butyl-2-methoxy-phenyl)-3-{4-[4-(tetrahydro-pyran-4-ylamino)-phenyl]-naphthalen-1-yl}-urea;

1(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methyl-phenyl)-3-(4-{6-[(3-methoxy-propyl)-methyl-amino]-pyridin-3-yl}-naphthalen-1-yl)-urea;

1-(5-tert-Butyl-2-methyl-phenyl)-3-[4-(4-morpholin-4-ylmethyl-imidazo-1-yl)-naphthalen-1-yl]-urea;

1-(5-tert-Butyl-2-methyl-phenyl)-3-[4-(4-morpholin-4-ylmethyl-phenyl)-naphthalen-1-yl]-urea;

1-(5-tert-Butyl-2-methyl-phenyl)-3-[4-(6-morpholin-4-ylmethyl-pyridin-3-yl)-naphthalen-1-yl]-urea;

1-(5-tert-Butyl-2-methyl-phenyl)-3-{4-[6-(3-methoxy-propylamino)-pyridin-3-yl]-naphthalen-1-yl}-urea;

1-(5-tert-Butyl-2-methyl-pyridin-3-yl)-3-[4-(6-morpholin-4-ylmethyl-pyridin-3-yl)-naphthalen-1-yl]-urea;

1-(5-tert-Butyl-2-morpholin-4-yl-phenyl)-3-[4-(6-morpholin-4-ylmethyl-pyridin-3-yl)-naphthalen-1-yl]-urea;

1-(6-tert-Butyl-2-chloro-3-methyl-pyridin-4-yl)-3-[4-(6-morpholin-4-ylmethyl-pyridin-3-yl)-naphthalen-1-yl]-urea;

1-(6-tert-Butyl-2-chloro-3-methyl-pyridin-4-yl)-3-[4-(6-thiomorpholin-4-ylmethyl-pyridin-3-yl)-naphthalen-1-yl]-urea;

1-[2-Methoxy-5-(1-methyl-cyclopropyl)-phenyl]-3-[4-(2-morpholin-4-ylmethyl-pyrimidin-5-yl)-naphthalen-1-yl]-urea;

1-[4-(6-Morpholin-4-ylmethyl-pyridin-3-yl)-naphthalen-1-yl]-3-(3-trifluoromethyl-phenyl)-urea;

1-[4-(6-Morpholin-4-ylmethyl-pyridin-3-yl)-naphthalen-1-yl]-3-(4-trifluoromethoxy-phenyl)-urea;

1-[5-(1,1-Dimethyl-propyl)-2-methoxy-phenyl]-3-[4-(4-thiomorpholin-4-ylmethyl-phenyl)-naphthalen-1-yl]-urea;

1-[5-(1,1-Dimethyl-propyl)-2-methoxy-phenyl]-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(2-morpholin-4-ylmethyl-pyrimidin-5-yl)-naphthalen-1-yl]-urea;

1-[5-tert-Butyl-2-(1H-pyrazol-4-yl)-phenyl]-3-[4-(6-morpholin-4-ylmethyl-pyridin-3-yl)-naphthalen-1-yl]-urea;

1-[5-tert-Butyl-2-(2-methyl-pyrimidin-5-yl)-phenyl]-3-[4-(5-pyridin-4-ylmethyl-pyridin-2-yl)-naphthalen-1-yl]-urea;

1-[5-tert-Butyl-2-(2-methyl-pyrimidin-5-yl)-phenyl]-3-[4-(6-morpholin-4-ylmethyl-pyridin-3-yl)-naphthalen-1-yl]-urea;

1-[5-tert-Butyl-2-(3-hydroxy-propyl)-phenyl]-3-[4-(6-morpholin-4-ylmethyl-pyridin-3-yl)-naphthalen-1-yl]-urea;

1-[5-tert-Butyl-2-(3-morpholin-4-yl-3-oxo-propyl)-phenyl]-3-[4-(6-morpholin-4-ylmethyl-pyridin-3-yl)-naphthalen-1-yl]-urea;

1-[5-tert-Butyl-2-(morpholine-4-carbonyl)-phenyl]-3-[4-(6-morpholin-4-ylmethyl-pyridin-3-yl)-naphthalen-1-yl]-urea;

2-[4-tert-Butyl-2-(3-{4-[6-(2,6-dimethyl-morpholin-4-ylmethyl)-pyridin-3-yl]-naphthalen-1-yl}-ureido)-phenoxy]-acetamide;

3-{4-[3-(5-tert-Butyl-2-methoxy-phenyl)-ureido]-naphthalen-1-yl}-benzamide;

4-tert-Butyl-2-{3-[4-(2-chloro-4-morpholin-4-ylmethyl-phenyl)-naphthalen-1-yl]-ureido}-benzamide;

and the pharmaceutically acceptable derivatives thereof.

In yet a further another embodiment of the invention there is provided the following compounds of the formula(II):

1-(2-tert-Butyl-5-methyl-pyridin-4-yl)-3-[4-(6-morpholin-4-ylmethyl-pyridin-3-yl)-naphthalen-1-yl]-urea;

1-(3-tert-Butyl-phenyl)-3-[4-(6-morpholin-4-ylmethyl-pyridin-3-yl)-naphthalen-1-yl]-urea;

1-(4-Methyl-biphenyl-3-yl)-3-[4-(6-morpholin-4-ylmethyl-pyridin-3-yl)-naphthalen-1-yl]-urea;

1-(4-tert-Butyl-biphenyl-2-yl)-3-[4-(6-morpholin-4-ylmethyl-pyridin-3-yl)-naphthalen-1-yl]-urea;

1-(5-Isopropyl-2-methyl-phenyl)-3-[4-(6-morpholin-4-ylmethyl-pyridin-3-yl)-naphthalen-1-yl]-urea;

1-(5-sec-Butyl-2-methoxy-phenyl)-3-[4-(6-morpholin-4-ylmethyl-pyridin-3-yl)-naphthalen-1-yl]-urea;

1-(5-tert-Butyl-2-methoxymethyl-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-morpholin-4-ylmethyl-pyridin-3-yl)-naphthalen-1-yl]-urea;

1-(5-tert-Butyl-2-methyl-phenyl)-3-(4-{6-[(3-methoxy-propyl)-methyl-amino]-pyridin-3-yl}-naphthalen-1-yl)-urea;

1-(5-tert-Butyl-2-methyl-phenyl)-3-[4-(6-morpholin-4-ylmethyl-pyridin-3-yl)-naphthalen-1-yl]-urea;

1-(5-tert-Butyl-2-methyl-pyridin-3-yl)-3-[4-(6-morpholin-4-ylmethyl-pyridin-3-yl)-naphthalen-1-yl]-urea;

1-[5-(1,1-Dimethyl-propyl)-2-methoxy-phenyl]-3-[4-(6-morpholin-4-ylmethyl-pyridin-3-yl)-naphthalen-1-yl]-urea;

1-[5-tert-Butyl-2-(1H-pyrazol-4-yl)-phenyl]-3-[4-(6-morpholin-4-ylmethyl-pyridin-3-yl)-naphthalen-1-yl]-urea;

1-[5-tert-Butyl-2-(2-methyl-pyrimidin-5-yl)-phenyl]-3-[4-(6-morpholin-4-ylmethyl-pyridin-3-yl)-naphthalen-1-yl]-urea;

1-[5-tert-Butyl-2-(3-hydroxy-propyl)-phenyl]-3-[4-(6-morpholin-4-ylmethyl-pyridin-3-yl)-naphthalen-1-yl]-urea;

1-[5-tert-Butyl-2-(morpholine-4-carbonyl)-phenyl]-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-acetamide and the pharmaceutically acceptable derivatives thereof.

In yet still another generic aspect of the invention, there is provided compounds of the formula(III):

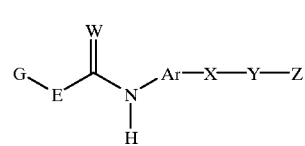

(III)

wherein:

E is carbon or a heteroatom group chosen from —O—, —NH— and —S—;

G is:

an aromatic $C_{6-10}$ carbocycle or a nonaromatic $C_{3-10}$ carbocycle saturated or unsaturated;

a 6–14 membered monocyclic, bicyclic or tricyclic heteroaryl containing 1 or more heteroatoms chosen from O, N and S;

a 6–8 membered monocyclic heterocycle containing one or more heteroatoms chosen from O, N and S; or an 8–11 membered bicyclic heterocycle, containing one or more heteroatoms chosen from O, N and S;

wherein G is optionally substituted by one or more $R_1$, $R_2$ or $R_3$;

Ar is:

phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;

X is:

a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;

aryl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated or unsaturated branched or unbranched carbon chain optionally partially or fully halogenated, wherein one or more C atoms are optionally replaced by O, N, or $S(O)_m$ and wherein Y is optionally independently substituted with one to two oxo groups, nitrile, phenyl or one or more $C_{1-4}$ alkyl optionally substituted by one or more halogen atoms;

Z is:

aryl, heteroaryl selected from pyridinyl, piperazinyl, pyrimidinyl, pyridazinyl, pyrazinyl, imidazolyl, pyrazolyl, triazolyl, tetrazolyl, furanyl, thienyl and pyranyl, heterocycle selected from tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl)amino; or Z is optionally substituted with one to three amino or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy; or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is hydroxy, halogen, nitrile, amino wherein the N atom is optionally independently mono- or di-substituted by $C_{1-3}$acyl, $C_{1-6}$alkyl or $C_{1-3}$alkoxy$C_{1-3}$ alkyl, $C_{1-6}$alkyl branched or unbranched, $C_{1-6}$alkoxy, $C_{1-3}$acylamino, nitrile$C_{1-4}$alkyl, $C_{1-6}$ alkyl-$S(O)_m$, and phenyl-$S(O)_m$, wherein the phenyl ring is optionally substituted with one to two halogen, $C_{1-6}$ alkoxy, hydroxy or mono- or di-($C_{1-3}$ alkyl)amino;

each $R_1$ is independently:

$C_{1-10}$ alkyl branched or unbranched optionally partially or fully halogenated, wherein one or more C atoms are optionally independently replaced by O, N or $S(O)_m$, and wherein said $C_{1-10}$ alkyl is optionally substituted with one to three $C_{3-10}$ cycloalkyl, hydroxy, oxo, phenyl, naphthyl, pyridinyl, pyrimidinyl, pyrazinyl, pyridazinyl, pyrrolyl, pyrrolidinyl, imidazolyl, pyrazolyl, thienyl, furyl, dioxolanyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated or $NH_2C(O)$, mono- or di-($C_{1-3}$alkyl)amino, and mono- or di-($C_{1-3}$alkyl)aminocarbonyl;

or $R_1$ is cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, nitrile, hydroxy$C_{1-3}$alkyl or aryl; or an analog of such cycloalkyl group wherein one to three ring methylene groups are independently replaced by O, $S(O)_m$, CHOH, >C=O, >C=S or NH;

phenyloxy or benzyloxy each being optionally partially or fully halogenated and optionally substituted with one to three $C_{1-3}$ alkyl groups optionally partially or fully halogenated, nitrile, hydroxy$C_{1-3}$alkyl or aryl; or an analog of such cycloaryl group wherein one to two ring methyne groups are independently replaced by N;

cyclopropyl, cyclobutyl, cyclopentyl, cyclohexyl, cycloheptyl, bicyclopentanyl, bicyclohexanyl or bicycloheptanyl, each being optionally partially or fully halogenated and optionally substituted with one to three $C_{1-3}$ alkyl optionally partially or fully halogenated, nitrile, hydroxy$C_{1-3}$alkyl or aryl; or an analog of such cycloalkyl group wherein one to three ring methylene groups are independently replaced by O, $S(O)_m$, CHOH, >C=O, >C=S or NH;

$C_{3-10}$ branched or unbranced alkenyl each being optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with one to five halogen, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, $C_{1-3}$ alkyloxy which is optionally partially or fully halogenated, $NH_2C(O)$, mono- or di-($C_{1-3}$alkyl) aminocarbonyl; the $C_{3-10}$ branched or unbranced alkenyl being optionally interrupted by one or more heteroatoms chosen from O, N and $S(O)_m$;

cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;

oxo, nitrile, halogen;

silyl containing three $C_{1-4}$ alkyl groups optionally partially or fully halogenated; or $C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di-($C_{1-3}$alkyl) amino optionally substituted by one or more halogen atoms;

each $R_2$, $R_4$, and $R_5$ is a $C_{1-6}$ branched or unbranched alkyl optionally partially or fully halogenated, $C_{1-6}$ acyl, aroyl, $C_{1-4}$ branched or unbranched alkoxy, each being optionally partially or fully halogenated, halogen, methoxycarbonyl, $C_{1-3}$ alkyl-$S(O)_m$ optionally partially or fully halogenated, or phenyl-$S(O)_m$;

$OR_6$, $C_{1-6}$ alkoxy, hydroxy, nitrile, nitro, halogen;

or amino-$S(O)_m$— wherein the N atom is optionally independently mono- or di-substituted by $C_{1-6}$alkyl or aryl$C_{0-3}$alkyl, or amino wherein the N atom is optionally independently mono- or di-substituted by $C_{1-3}$alkyl, aryl$C_{0-3}$alkyl, $C_{1-6}$acyl, $C_{1-6}$ alkyl-$(S(O)_m$- or aryl$C_{0-3}$alkyl-$(S(O)_m$-, each of the aforementioned alkyl and aryl in this subparagraph are optionally partially or fully halogenated and optionally substituted with one to two $C_{1-6}$ alkyl or $C_{1-6}$ alkoxy;

each $R_3$ is independently:

phenyl, naphthyl, morpholino, pyridinyl, pyrimidinyl, pyrazinyl, pyridazinyl, pyrrolyl, pyrrolidinyl, imidazolyl, pyrazolyl, thiazolyl, oxazoyl, [1,3,4]oxadiazol, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di-($C_{1-3}$alkyl)amino-$C_{1-5}$ alkyl, amino-$S(O)_2$, di-($C_{1-3}$alkyl)amino-$S(O)_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N, carboxy- mono- or di-($C_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$alkyl)aminocarbonyl, $C_{1-4}$ alkyl-OC(O), $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl or $R_{15}$—$C_{1-5}$ alkyl($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally be partially or fully halogenated and optionally substituted with one to three $C_{1-3}$ alkyl groups, or an analog of such cycloalkyl group wherein one to three ring methylene groups are independently replaced by O, S, CHOH, >C=O, >C=S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-$S(O)_m$—$C_{1-4}$ alkyl-;

$C_{1-6}$ alkyl or $C_{1-6}$ branched or unbranched alkoxy each of which is optionally partially or fully halogenated or optionally substituted with $R_{17}$;

$OR_{18}$ or $C_{1-6}$ alkyl optionally substituted with $OR_{18}$;

amino or mono- or di-($C_{1-5}$alkyl)amino optionally substituted with $R_{19}$;

$R_{20}C(O)N(R_{21})$—, $R_{22}O$—, or $R_{23}R_{24}NC(O)$—; $R_{26}(CH_2)_mC(O)N(R_{21})$—, $R_{23}R_{24}NC(O)$—$C_{1-3}$alkoxy or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, $S(O)_m$ and wherein said alkynyl group is optionally independently substituted with one to two oxo groups, pyrroldinyl, pyrrolyl, morpholino, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$ alkyl) amino optionally substituted by one or more halogen atoms;

$C_{1-6}$acyl or aroyl;

$R_6$ is a:

$C_{1-4}$ alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently: nitrile, phenyl, morpholino, piperidinyl, piperazinyl, imidazolyl, pyridinyl, tetrazolyl, amino or mono- or di-($C_{1-4}$alkyl)amino optionally partially or fully halogenated;

each $R_{11}$ and $R_{16}$ is independently:

hydrogen or $C_{1-4}$ alkyl optionally partially or fully halogenated;

$R_{18}$ is independently: hydrogen or a $C_{1-4}$ alkyl optionally independently substituted with oxo or $R_{25}$;

$R_{20}$ is independently:

$C_{1-10}$ alkyl optionally partially or fully halogenated, phenyl, or pyridinyl;

$R_2$, is independently:

hydrogen or $C_{1-3}$alkyl optionally partially or fully halogenated;

each $R_{22}$, $R_{23}$ and $R_{24}$ is independently: hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-($C_{1-3}$alkyl)aminocarbonyl, phenyl, pyridinyl, amino or mono- or di-($C_{1-4}$alkyl) amino each of which is optionally partially or fully halogenated and optionally substituted with mono- or di-($C_{1-3}$alkyl)amino;

or $R_{23}$ and $R_{24}$ taken together optionally form a heterocyclic or heteroaryl ring;

m=0, 1 or 2;

W is O or S and pharmaceutically acceptable derivatives thereof.

In another embodiment of the invention there is provided compounds of the formula(III) as described above and wherein:

E is —$CH_2$—, —NH— or —O—;

W is O; and

G is:

phenyl, naphthyl, benzocyclobutanyl, dihydronaphthyl, tetrahydronaphthyl, benzocycloheptanyl, benzocycloheptenyl, indanyl, indenyl; pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzooxazolyl, benzofuranyl, benzothiophenyl, benzpyrazolyl, dihydrobenzofuranyl, dibenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, 2,3-dihydro-1H-indolyl, indolinyl, indolonyl, indolinonyl, phthalimidyl, chromoyl;

oxetanyl, pyrrolidinyl, tetrahydrofuranyl, tetrahydrothiophenyl, piperidinyl, piperazinyl, morpholino, tetrahydropyranyl, dioxanyl, tetramethylene sulfonyl, tetramethylene sulfoxidyl, oxazolinyl, 3,4-dihydro-2H-benzo[1,4]oxazinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholino, thiazolidinyl, dihydrooxazinyl, dihydropyranyl, oxocanyl, heptacanyl, thioxanyl or dithianyl; wherein G is optionally substituted by one or more $R_1$, $R_2$ or $R_3$.

In yet another embodiment there are provided compounds of the formula(III) as described immediately above and wherein:

E is —NH—;

G is phenyl, pyridinyl, pyridonyl, naphthyl, quinolinyl, isoquinolinyl, pyrazinyl, benzimidazolyl, benzooxazolyl, benzooxazolonyl, benzofuranyl, benzothiophenyl, benzpyrazolyl, dihydrobenzofuranyl, dihydrobenzothiophenyl, 3,4-dihydro-2H-benzo[1,4]oxazinyl, indanyl, indenyl, indolyl, indolinyl, indolonyl, 2,3-dihydro-1H-indolyl or indolinonyl, wherein G is optionally substituted by one or more $R_1$, $R_2$ or $R_3$;

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl; each being optionally independently substituted with one to three $C_{1-4}$ alkyl, $C_{1-4}$ alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated or unsaturated carbon chain wherein one or more of the C atoms is optionally replaced by O, N, or $S(O)_m$ and wherein Y is optionally independently substituted with one to two oxo groups, nitrile, phenyl or one or more $C_{1-4}$ alkyl optionally substituted by one or more halogen atoms;

Z is:

phenyl, heteroaryl selected from pyridinyl, piperazinyl, pyrimidinyl, pyridazinyl, pyrazinyl, imidazolyl, furanyl, thienyl and pyranyl, heterocycle selected from 2-oxa-5-azabicyclo[2.2.1]heptanyl, tetrahydropyrimidonyl, pentamethylene sulfidyl, pentamethylene sulfoxidyl, pentamethylene sulfonyl, tetramethylene sulfidyl, tetramethylene sulfoxidyl tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, piperidinyl, piperidinonyl, dihydrothiazolyl, dihydrothiazolyl sulfoxidyl, pyrrolidinyl and dioxolanyl which are optionally substituted with one to three nitrile, $C_{1-3}$ alkyl, $C_{1-3}$ alkoxy, amino, mono- or di-($C_{1-3}$ alkyl)amino, $CONH_2$ or OH; or Z is optionally substituted by phenyl, heterocycle or heteroaryl as hereinabove described in this paragraph each in turn is optionally substituted by halogen, $C_{1-3}$ alkyl or $C_{1-3}$ alkoxy;

or Z is nitrile, nitrile$C_{1-3}$ alkyl, $C_{1-6}$ alkyl-$S(O)_m$, halogen, hydroxy, $C_{1-3}$ alkyl, $C_{1-3}$ acylamino, $C_{1-4}$ alkoxy, amino, mono- or di-($C_{1-3}$ alkyl)aminocarbonyl, or amino mono or di-substituted by amino$C_{1-6}$ alkyl or $C_{1-3}$alkoxy$C_{1-3}$alkyl;

each $R_1$ is independently:

$C_{1-6}$ alkyl branched or unbranched optionally partially or fully halogenated, wherein one or more C atoms are optionally independently replaced by O, N or $S(O)_m$, and wherein said $C_{1-6}$ alkyl is optionally substituted with one to three $C_{3-6}$cycloalkyl, oxo, phenyl, dioxolanyl, pyrrolidinyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile and $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; or an analog of such cycloalkyl group wherein one to three ring methylene groups are independently replaced by O, S, CHOH, >C=O, >C=S or NH;

oxo;

$C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

or silyl containing three $C_{1-4}$ alkyl groups optionally partially or fully halogenated;

$R_2$ is independently:

a $C_{1-5}$ branched or unbranched alkyl optionally partially or fully halogenated, acetyl, aroyl, $C_{1-4}$ branched or unbranched alkoxy, each being optionally partially or fully halogenated, halogen, methoxycarbonyl, $C_{1-2}$ alkyl-$S(O)_m$ optionally partially or fully halogenated, or phenyl-$S(O)_m$;

$C_{1-3}$ alkoxy, hydroxy, nitrile, nitro, halogen;

or amino-$S(O)_m$— wherein the N atom is optionally independently mono- or di-substituted by $C_{1-3}$alkyl or aryl$C_{0-3}$alkyl, or amino wherein the N atom is optionally independently mono- or di-substituted by $C_{1-3}$alkyl, aryl$C_{0-3}$alkyl, $C_{1-3}$acyl, $C_{1-4}$alkyl-$(S(O)_m$— or aryl$C_{0-3}$alkyl-$(S(O)_m$—, each of the aforementioned alkyl and aryl in this subparagraph are optionally partially or fully halogenated and optionally substituted with one to two $C_{1-3}$ alkyl or $C_{1-3}$ alkoxy;

$R_3$ is independently:

phenyl, morpholino, pyridinyl, pyrimidinyl, pyrazinyl, pyrrolyl, pyrrolidinyl, imidazolyl, [1,3,4]oxadiazol, pyrazolyl, each is optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, nitrile, $C_{1-3}$ alkoxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl) aminocarbonyl, $C_{1-5}$ alkyl-$C(O)$—$C_{1-4}$ alkyl, mono- or di-($C_{1-3}$alkyl)amino, mono- or di-($C_{1-3}$)alkylamino-$C_{1-5}$alkyl, mono- or di-($C_{1-3}$alkyl)amino-S(O)$_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl ($R_{11}$)N, carboxy-mono- or di-($C_{1-5}$)-alkyl-amino;

$C_{1-3}$ alkyl or $C_{1-4}$ alkoxy each being optionally partially or fully halogenated or optionally substituted with $R_{17}$;

$OR_{18}$ or $C_{1-6}$ alkyl optionally substituted with $OR_{18}$;

amino or mono- or di-($C_{1-5}$ alkyl)amino optionally substituted with $R_{19}$;

$R_{20}$C(O)N($R_{21}$)—, $R_{22}$O—; $R_{23}R_{24}$NC(O)—; $R_{26}$CH$_2$C(O)N($R_{21}$)—, $R_{23}R_{24}$NC(O)—$C_{1-2}$alkoxy or $R_{26}$C(O)CH$_2$N($R_{21}$)—;

$C_{2-4}$alkenyl substituted by $R_{23}R_{24}$NC(O)—; or $C_{2-4}$ alkynyl branched or unbranched carbon chain optionally partially or fully halogenated wherein one of the methylene groups is optionally replaced by O, and optionally independently substituted with one to two oxo groups, pyrroldinyl, pyrrolyl, morpholino, piperidinyl, piperazinyl, imidazolyl, phenyl, pyridinyl, tetrazolyl or one or more $C_{1-4}$ alkyl optionally substituted by one or more halogen atoms; $C_{1-3}$acyl; and $R_{23}$ and $R_{24}$ taken together optionally form imidazolyl, piperidinyl, morpholino, piperazinyl or a pyridinyl ring.

In yet still another embodiment of the invention there is provided compounds of the formula(III) as described immediately above and wherein:

G is phenyl, pyridinyl, pyridonyl, naphthyl, quinolinyl, isoquinolinyl, pyrazinyl, 3,4-dihydro-2H-benzo[1,4] oxazinyl, benzothiophenyl, dihydrobenzofuranyl, dihydrobenzothiophenyl, benzooxazolyl, indanyl, indolyl, indolinyl, indolonyl or indolinonyl, wherein G is optionally substituted by one or more $R_1$, $R_2$ or $R_3$;

Ar is naphthyl;

X is phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl) amino, mono- or di-($C_{1-3}$alkylamino)carbonyl, NH$_2$C(O), $C_{1-6}$ alkyl-S(O)$_m$ or halogen;

Y is:

a bond or a $C_{1-4}$ saturated carbon chain wherein one or more of the C atoms is optionally replaced by O, N or S and wherein Y is optionally independently substituted with nitrile or oxo;

Z is:

phenyl, pyridinyl, pyrimidinyl, pyridazinyl, pyrazinyl, imidazolyl, dihydrothiazolyl, dihydrothiazolyl sulfoxide, pyranyl, pyrrolidinyl, phenylpiperazinyl, tetrahydropyranyl, tetrahydrofuranyl, dioxolanyl, 2-oxa-5-aza-bicyclo[2.2.1] heptanyl, morpholino, thiomorpholino, thiomorpholino sulfoxidyl, piperidinyl, piperidinonyl, piperazinyl or tetrahydropyrimidonyl each of which are optionally substituted with one to two $C_{1-2}$ alkyl or $C_{1-2}$ alkoxy; or Z is hydroxy, $C_{1-3}$ alkyl, $C_{1-3}$ alkoxy, $C_{1-3}$ acylamino, $C_{1-3}$ alkylsulfonyl, nitrile $C_{1-3}$ alkyl or amino mono or di-substituted by $C_{1-3}$ alkoxy$C_{1-3}$ alkyl;

each $R_1$ is independently:

$C_{1-5}$ alkyl branched or unbranched optionally partially or fully halogenated, wherein one or more C atoms are optionally independently replaced by O, N or S(O)$_m$, and wherein said $C_{1-5}$ alkyl is optionally substituted with oxo, dioxolanyl, pyrrolidinyl, furyl or phenyl each optionally substituted with one to three halogen, $C_{1-3}$ alkyl which is optionally partially or fully halogenated, hydroxy, nitrile and $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O;

oxo;

$C_{2-4}$ alkynyl optionally partially or fully halogenated wherein one or more methylene groups are optionally replaced by O, and optionally independently substituted with one to two oxo groups, hydroxy, pyrrolidinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

or silyl containing three $C_{1-2}$ alkyl groups optionally partially or fully halogenated;

each $R_2$ is independently:

a $C_{1-4}$ alkyl optionally partially or fully halogenated, $C_{1-4}$ alkoxy optionally partially or fully halogenated, bromo, chloro, fluoro, methoxycarbonyl, methyl-S(O)$_m$, ethyl-S(O)$_m$ each optionally partially or fully halogenated or phenyl-S(O)$_m$; or $R_2$ is mono- or di-$C_{1-3}$acylamino, amino-S(O)$_m$ or S(O)$_m$amino wherein the N atom is mono- or di-substituted by $C_{1-3}$alkyl or phenyl, nitrile, nitro or amino;

each $R_3$ is independently:

phenyl, morpholino, pyridinyl, pyrimidinyl, pyrrolidinyl, 2,5-pyrrolidin-dionyl, imidazolyl, [1,3,4]oxadiazol, pyrazolyl, each of the aforementioned is optionally substituted with one to three $C_{1-3}$ alkyl which is optionally partially or fully halogenated, halogen, oxo, hydroxy, nitrile and $C_{1-3}$ alkoxy optionally partially or fully halogenated;

$C_{1-3}$ alkyl or $C_{1-3}$ alkoxy optionally partially or fully halogenated or optionally substituted with $R_{17}$;

$OR_{18}$ or $C_{1-3}$ alkyl optionally substituted with $OR_{18}$;

amino or mono- or di-($C_{1-3}$ alkyl)amino optionally substituted with $R_{19}$;

$R_{20}$C(O)N($R_2$,)—, $R_{22}$O—; $R_{23}R_{24}$NC(O)—; $R_{26}$CH$_2$C(O)N($R_{21}$)—, NH$_2$C(O)methoxy or $R_{26}$C(O)CH$_2$N($R_{21}$)—;

$C_{2-4}$ alkenyl substituted by $R_{23}R_{24}$NC(O)—; or $C_{2-4}$ alkynyl substituted with pyrroldinyl or pyrrolyl;

$C_{1-3}$acyl and $R_{23}$ and $R_{24}$ taken together optionally form morpholino.

In yet a further embodiment of the invention there is provided compounds of the formula(III) as described immediately above and wherein:

G is phenyl, pyridinyl, pyridonyl, 2-naphthyl, quinolinyl, isoquinolinyl, dihydrobenzofuranyl, indanyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro-1H-indol-5-yl, indolinyl, indolonyl, or indolinonyl, wherein G is optionally substituted by one or more $R_1$, $R_2$ or $R_3$;

Ar is 1-naphthyl;

X is:

phenyl, imidazolyl, pyridinyl, pyrimidinyl, piperdinyl, piperazinyl, pyridazinyl or pyrazinyl;

Y is:

a bond or

—CH$_2$—, —CH$_2$CH$_2$—, —C(O)—, —O—, —S—, —NH—CH$_2$CH$_2$CH$_2$—, —N(CH$_3$)—, CH$_2$(CN)CH$_2$—NH—CH$_2$ or —NH—;

Z is
morpholino, dioxolanyl, tetrahydrofuranyl, pyridinyl, 2-oxa-5-aza-bicyclo[2.2.1]heptanyl, $C_{1-3}$alkoxyphenylpiperazinyl, hydroxy, $C_{1-3}$alkyl, N,N-di$C_{1-3}$alkoxy$C_{1-3}$alkylamino, $C_{1-3}$acylamino, $C_{1-3}$alkylsulfonyl or nitrile$C_{1-3}$alkyl;

each $R_1$ is independently:
$C_{1-5}$ alkyl optionally partially or fully halogenated wherein one or more C atoms are optionally independently replaced by O or N, and wherein said $C_{1-5}$ alkyl is optionally substituted with oxo, dioxolanyl, pyrrolidinyl, furyl or phenyl optionally substituted by $C_{1-3}$alkoxy;

cyclopropyl, cyclopentanyl, cyclohexanyl and bicyclopentanyl optionally substituted with one to three methyl groups optionally partially or fully halogenated, nitrile, hydroxymethyl or phenyl; or 2-tetrahydrofuranyl substituted by methyl; or trimethyl silyl;

propynyl substituted hydroxy or tetrahydropyran-2-yloxy;

$R_2$ is
is mono- or di-$C_{1-3}$acylamino, amino-S(O)$_m$ or S(O)$_m$ amino wherein the N atom is mono- or di-substituted by $C_{1-3}$ alkyl or phenyl, bromo, chloro, fluoro, nitrile, nitro, amino, methylsulfonyl optionally partially or fully halogenated or phenylsulfonyl;

each $R_3$ is independently:
phenyl, morpholino, pyridinyl, pyrimidinyl, pyrrolidinyl, 2,5-pyrrolidin-dionyl, imidazolyl, [1,3,4]oxadiazol or pyrazolyl, each is optionally substituted with $Cl_2$ alkyl which is optionally partially or fully halogenated;

$C_{1-3}$ alkyl or $C_{1-3}$ alkoxy each being optionally partially or fully halogenated or optionally substituted with diethylamino;

$OR_{18}$ or $C_{1-3}$ alkyl optionally substituted with $OR_{18}$;

amino or mono- or di-($C_{1-3}$ alkyl)amino optionally substituted with $R_{19}$;

$CH_3C(O)NH$—, $R_{22}O$—; $R_{23}R_{24}NC(O)$—; $R_{26}CH_2C(O)N(R_{21})$—, $NH_2C(O)$methoxy or $R_{26}C(O)CH_2N(R_{21})$—;

$C_{2-4}$alkenyl substituted by $R_{23}R_{24}NC(O)$—; or
$C_{2-4}$ alkynyl substituted with pyrroldinyl or pyrrolyl;
$C_{1-2}$acyl; and
$R_{23}$ and $R_{24}$ are H or $R_{23}$ and $R_{24}$ taken together optionally form morpholino; and
$R_{26}$ is morpholino.

In yet still a further embodiment of the invention there are provided compounds of the formula(III) as described immediately above and wherein:

G is
phenyl, pyridinyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro-1H-indol-5-yl or 2-naphthyl wherein G is optionally substituted by one or more $R_1$, $R_2$ or $R_3$;

X is:
imidazolyl, pyridinyl, pyrimidinyl or pyrazinyl;
Y is:
a bond, $CH_2(CN)CH_2$—NH—$CH_2$, —$CH_2$—, —NH—$CH_2CH_2CH_2$— or —NH—;

Z is morpholin-4yl, dioxolan-2yl, tetrahydrofuranyl, pyridinyl, 2-oxa-5-aza-bicyclo[2.2.1]hept-5yl, methoxyphenylpiperazinyl, hydroxy, methyl, N,N-dimethoxyethylamino, acetylamino, methylsulfonyl or cyanoethyl;

each $R_1$ is independently:
tert-butyl, sec-butyl, tert-amyl, phenyl, tetrahydropyran-2-yloxypropynyl, hydroxypropynyl, trihalomethyl, 2,2-diethylpropionyl or cyclohexanyl;

$R_2$ is chloro, nitro, amino, nitrile, methylsulfonylamino, diacetylamino, phenylsulfonylamino, N,N-di(methylsulfonyl)amino, methylsulfonyl or trihalomethylsulfonyl;

$R_3$ is independently:
methyl, $C_{1-3}$ alkoxy, methoxymethyl, hydroxypropyl, dimethylamino, $C_{1-4}$alkylamino, $NH_2C(O)$methoxy, acetyl, pyrrolidinyl, imidazolyl, pyrazolyl, morpholino or morpholinocarbonyl.

In yet still even a further embodiment of the invention there is provided compounds of the formula(III) as described immediately above and wherein:

X is pyridinyl.

In still even a further embodiment of the invention there is provided compounds of the formula(III) as provided immediately above and wherein:

the pyridinyl is attached to Ar via the 3-pyridinyl position.

The following are representative compounds of the formula(III):

1-(4-tert-Butyl-phenyl)-3-[4-(6-morpholin-4-ylmethyl-pyridin-3-yl)-naphthalen-1-yl]-urea;

1-(5-tert-Butyl-2-methyl-phenyl)-3-[4-(4-morpholin-4-ylmethyl-piperidin-1-yl)-naphthalen-1-yl]-urea;

1-(6-Chloro-4-trifluoromethyl-pyridin-2-yl)-3-[4-(6-morpholin-4-ylmethyl-pyridin-3-yl)-naphthalen-1-yl]-urea;

1-(4-Difluoromethoxy-phenyl)-3-[4-(6-morpholin-4-ylmethyl-pyridin-3-y)-naphthalen-1-yl]-urea;

1-(3-Methyl-naphthalen-2-yl)-3-[4-(6-morpholin-4-ylmethyl-pyridin-3-yl)-naphthalen--yl]-urea;

1-[2-Methoxy-5-(1-methyl-1-phenyl-ethyl)-phenyl]-3-[4-(6-morpholin-4-ylmethyl-pyridin-3-yl)-naphthalen-1-yl]-urea;

(5-tert-Butyl-2-methyl-phenyl)-carbamic acid 3-(5-{[3-(5-tert-butyl-2-methyl-phenyl)-ureido]-naphthalen-1-yl}-pyridin-2-ylamino)-propyl ester;

1-(6-tert-Butyl-benzo[1,3]dioxol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-acetamide;

1,3-Bis-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-hydroxy-phenyl]-3-[4-(6-morpholin-4-ylmethyl-pyridin-3-yl)-naphthalen-1-yl]-urea;

1-[5-tert-Butyl-2-(2-pyrrolidin-1-yl-ethoxy)-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;

1-(2,3-Dimethyl-1H-indol-5-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(2-p-tolyloxy-5-trifluoromethyl-phenyl)-urea;

1-[2-(2-Methoxy-phenoxy)-5-trifluoromethyl-phenyl]-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-naphthalen-1-yl-urea;

1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-{5-tert-Butyl-2-[3-(tetrahydro-pyran-2-yloxy)-prop-1-ynyl]-phenyl}-3-[4-(6-morpholin-4-ylmethyl-pyridin-3-yl)-naphthalen-1-yl]-urea;

1-(5-Hydroxymethyl-2-methyl-phenyl)-3-[4-(6-morpholin-4-ylmethyl-pyridin-3-yl)-naphthalen-1-yl]-urea;

1-(2-Methoxy-dibenzofuran-3-yl)-3-[4-(6-morpholin-4-ylmethyl-pyridin-3-yl)-naphthalen-1-yl]-urea;

1-(2,5-Di-tert-butyl-phenyl)-3-[4-(6-morpholin-4-ylmethyl-pyridin-3-yl)-naphthalen-yl]-urea;

1-[3-(4-Bromo-1-methyl-1H-pyrazol-3-yl)-phenyl]-3-[4-(6-morpholin-4-ylmethyl-pyridin-3-yl)-naphthalen-1-yl]-urea;

1-(3-Hydroxy-5,6,7,8-tetrahydro-naphthalen-2-yl)-3-[4-(6-morpholin-4-ylmethyl-pyridin-3-yl)-naphthalen-1-yl]-urea;

1-(1-Acetyl-2,3-dihydro-1H-indol-5-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-oxazol-5-yl-phenyl)-urea;

1-[4-(6-Morpholin-4-ylmethyl-pyridin-3-yl)-naphthalen-1-yl]-3-(3-[1,3,4]oxadiazol-2-yl-phenyl)-urea;

1-(2-Methoxy-5-trifluoromethyl-phenyl)-3-[4-(6-morpholin-4-ylmethyl-pyridin-3-yl)-naphthalen-1-yl]-urea;

Furan-2-carboxylic acid (4-tert-butyl-2-{3-[4-(6-morpholin-4-ylmethyl-pyridin-3-yl)-naphthalen-1-yl]-ureido}-phenyl)-amide;

1-(2-Methoxy-4-phenylamino-phenyl)-3-[4-(6-morpholin-4-ylmethyl-pyridin-3-yl)-naphthalen-1-yl]-urea;

1-(5-Methoxy-2-methyl-phenyl)-3-[4-(6-morpholin-4-ylmethyl-pyridin-3-yl)-naphthalen-1-yl]-urea;

1-(3-Hydroxy-naphthalen-2-yl)-3-[4-(6-morpholin-4-ylmethyl-pyridin-3-yl)-naphthalen-1-yl]-urea;

N,N-Diethyl-4-methoxy-3-{3-[4-(6-morpholin-4-ylmethyl-pyridin-3-yl)-naphthalen-1-yl]-ureido}-benzenesulfonamide;

1-(2,2-Difluoro-benzo[1,3]dioxol-5-yl)-3-[4-(6-morpholin-4-ylmethyl-pyridin-3-yl)-naphthalen-1-yl]-urea;

1-[5-(1,1-Dimethyl-propyl)-2-phenoxy-phenyl]-3-[4-(6-morpholin-4-ylmethyl-pyridin-3-yl)-naphthalen-1-yl]-urea;

1-[5-(2,2-Dimethyl-propionyl)-2-methyl-phenyl]-3-[4-(6-morpholin-4-ylmethyl-pyridin-3-yl)-naphthalen-1-yl]-urea;

2-Chloro-5-{3-[4-(6-morpholin-4-ylmethyl-pyridin-3-yl)-naphthalen-1-yl]-ureido}-benzoic acid isopropyl ester;

1-(4-Amino-3,5-dibromo-phenyl)-3-[4-(6-morpholin-4-ylmethyl-pyridin-3-yl)-naphthalen-1-yl]-urea;

1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;

1-[5-tert-Butyl-2-(3-hydroxy-prop-1-ynyl)-phenyl]-3-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;

1-(5-tert-Butoxy-2-methoxy-phenyl)-3-[4-(6-morpholin-4-ylmethyl-pyridin-3-yl)-naphthalen-1-yl]-urea;

1-[5-(1-Cyano-cyclopropyl)-2-methoxy-phenyl-3-[4-(6-morpholin-4-ylmethyl-pyridin-3-yl)-naphthalen-1-yl]-urea;

1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;

1-(5-tert-Butyl-2-methoxy-phenyl)-3-[4-(6-[1,3]dioxolan-2-yl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-2-dimethylamino-phenyl)-3-[4-(6-morpholin-4-ylmethyl-pyridin-3-yl)-naphthalen-1-yl]-urea;

1-(5-tert-Butyl-2-propoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-hydroxymethyl-pyridin-3-yl)-naphthalen-1-yl]-urea;

1-(5-tert-Butyl-2-methoxy-phenyl)-3-{4-[6-(2,6-dimethyl-morpholin-4-ylmethyl)-1-pyridin-3-yl]-naphthalen-1-yl}-urea;

2-(5-tert-Butyl-2-methoxy-phenyl)-N-[4-(6-morpholin-4-ylmethyl-pyridin-3-yl)-naphthalen-1-yl]-acetamide;

1-(2-Methoxy-5-phenoxy-phenyl)-3-[4-(6-morpholin4-ylmethyl-pyridin-3-yl)-naphthalen-1-yl]-urea;

1-(3,3-Dimethyl-2-oxo-2,3-dihydro-1H-indol-7-yl)-3-[4-(6-morpholin-4-ylmethyl-pyridin-3-yl)-naphthalen-1-yl]-urea;

1-(5-tert-Butyl-2-cyclopentyloxy-phenyl)-3-[4-(6-morpholin-4-ylmethyl-pyridin-3-yl)-naphthalen-1-yl]-urea;

1-(5-tert-Butyl-2-methoxy-phenyl)-3-{4-[6-(3-pyridin-3-yl-pyrrolidin-1-ylmethyl)-pyridin-3-yl]-naphthalen-1-yl}-urea;

1-(5-Cyclohexyl-2-methoxy-phenyl)-3-[4-(6-morpholin-4-ylmethyl-pyridin-3-yl)-naphthalen-1-yl]-urea;

1-(2,4-Dimethoxy-5-trifluoromethyl-phenyl)-3-[4-(6-morpholin-4-ylmethyl-pyridin-3-yl)-naphthalen-1-yl]-urea;

1-(6-tert-Butyl-3-oxo-3,4-dihydro-2H-benzo[1,4]oxazin-7-yl)-3-[4-(6-morpholin-4-ylmethyl-pyridin-3-yl)-naphthalen-1-yl]-urea;

1-(5-tert-Butyl-2-methoxy-3-nitro-phenyl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-methyl-pyridin-3-yl)-naphthalen-1-yl]-urea;

N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-[6-tert-Butyl-4-(2-morpholin-4-yl-ethyl)-3-oxo-3,4-dihydro-2H-benzo-[4]oxazin-8-yl]-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;

1-(5-tert-Butyl-2-imidazol-1-yl-phenyl)-3-[4-(6-morpholin-4-ylmethyl-pyridin-3-yl)-naphthalen-1-yl]-urea;

N-(5-tert-Butyl-2-methoxy-4-{3-[4-(6-morpholin-4-ylmethyl-pyridin-3-yl)-naphthalen-1-yl]-ureido}-phenyl)-methanesulfonamide;

1-(5-tert-Butyl-3-ethylamino-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido }-phenyl)-bis(methanesulfon)amide;

1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;

1-(2-Methanesulfinyl-5-trifluoromethyl-phenyl)-3-[4-(6-morpholin-4-ylmethyl-pyridin-3-yl)-naphthalen-1-yl]-urea;

1-(2-Ethanesulfonyl-5-trifluoromethyl-phenyl)-3-[4-(6-morpholin-4-ylmethyl-pyridin-3-yl)-naphthalen-1-yl]-urea;

1-[4-(6-{[Bis-(2-methoxy-ethyl)-amino]-methyl3-pyridin-3-yl)-naphthalen-1-yl]-3-(5-tert-butyl-2-methoxy-phenyl)-urea;

1-(5-tert-Butyl-2-methoxy-phenyl)-3-{4-[6-(3-dimethylamino-pyrrolidin-1-ylmethyl)-pyridin-3-yl]-naphthalen-1-yl}-urea;

N-[1-(5-{$^4$-[$^3$-(5-tert-Butyl-2-methoxy-phenyl)-ureido]-naphthalen-1-yl}-pyridin-2-ylmethyl)-pyrrolidin-3-yl]-acetamide;

1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;

N-(5-tert-Butyl-2-methoxy-3-{³-[⁴-(6-morpholin-4-ylmethyl-pyridin-3-yl)-naphthalen-1-yl]-ureido}-phenyl)-propionamide;

1-(5-tert-Butyl-2-methyl-benzooxazol-7-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-trifluoromethanesulfonyl-phenyl)-urea;

N-(5-tert-Butyl-2-methoxy-3-13-[4-(6-morpholin-4-ylmethyl-pyridin-3-yl)-naphthalen-1-yl]-ureido}-phenyl)-isobutyramide;

2-(4-tert-Butyl-2-{3-[⁴-(6-morpholin-4-ylmethyl-pyridin-3-yl)-naphthalen-1-yl]-ureido}-phenoxy)-acetamide;

1-(5-tert-Butyl-2-oxo-2,3-dihydro-benzooxazol-7-yl)-3-[4-(6-morpholin-4-ylmethyl-pyridin-3-yl)-naphthalen-1-yl]-urea;

1-(6-tert-Butyl-3-cyano-2-methoxymethoxy-pyridin-4-yl)-3-[4-(6-morpholin-4-ylmethyl-pyridin-3-yl)-naphthalen-1-yl]-urea;

1-(6-tert-Butyl-3-cyano-2-hydroxy-pyridin-4-yl)-3-[4-(6-morpholin-4-ylmethyl-pyridin-3-yl)-naphthalen-1-yl]-urea;

1-(5-tert-Butyl-3-cyano-2-methoxy-phenyl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(1,3,3-trimethyl-2,3-dihydro-1H-indol-5-yl)-urea;

1-(5-tert-Butyl-benzooxazol-7-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido }-phenyl)-benzenesulfonamide;

Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

1-(5-tert-Butyl-2-methoxy-phenyl)-3-[4-(4-morpholin-4-ylmethyl-piperidin-1-yl)-naphthalen-1-yl]-urea;

1-[5-tert-Butyl-2-(1-methyl-1H-pyrazol-4-yl)-phenyl]-3-[4-(4-morpholin-4-ylmethyl-piperidin-1-yl)-naphthalen-1-yl]-urea;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methylsulfanyl-phenyl)-3-[4-(6-morpholin-4-ylmethyl-pyridin-3-yl)-naphthalen-1-yl]-urea;

1-(5-tert-Butyl-2-methoxy-pyridin-3-yl)-3-[4-(6-morpholin-4-ylmethyl-pyridin-3-yl)-naphthalen-1-yl]-urea;

2,2,2-Trifluoro-ethanesulfonic acid (5-tert-butyl-2-methoxy-3-{3-[4-(6-morpholin-4-ylmethyl-pyridin-3-yl)-naphthalen-1-yl-ureido}-phenyl)-amide;

N-(5-{4-[3-(5-tert-Butyl-2-methyl-phenyl)-ureido]-naphthalen-1-yl}-pyrazin-2-yl)-methanesulfonamide;

1-[4-(6-{[Bis-(2-cyano-ethyl)-amino]-methyl }-pyridin-3-yl)-naphthalen-1-yl]-3-(5-tert-butyl-2-methoxy-phenyl)-urea;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methoxy-phenyl)-3-[4-(6-thiomorpholin-4-ylmethyl-pyridin-3-yl)-naphthalen-1-yl]-urea;

1-(5-tert-Butyl-2-methoxy-phenyl)-3-{4-[6-(2,6-dimethyl-piperidin-1-ylmethyl)-pyridin-3-yl]-naphthalen-1-yl }-urea;

1-(5-tert-Butyl-2-methoxy-phenyl)-3-{4-[6-(1-oxo-tetrahydro-thiopyran-4-ylamino)-pyridin-3-yl]-naphthalen-1-yl}-urea;

1-(5-tert-Butyl-2-methoxy-phenyl)-3-{4-[6-(tetrahydro-pyran-4-ylamino)-pyridin-3-yl]-naphthalen-1-yl}-urea;

1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;

1-(5-tert-Butyl-2-methoxy-phenyl)-3-{4-[6-(2-methoxymethyl-morpholin-4-ylmethyl)-pyridin-3-yl]-naphthalen-1-yl}-urea;

1-(5-tert-Butyl-2-methoxy-phenyl)-3-(4-{6-[(2-morpholin-4-yl-ethylamino)-methyl]-pyridin-3-yl}-naphthalen-1-yl)-urea;

1-(5-tert-Butyl-2-methoxy-phenyl)-3-{4-[6-(2-methyl-3-oxo-piperazin-1-ylmethyl)-pyridin-3-yl]-naphthalen-1-yl}-urea;

1-(5-{4-[3-(5-tert-Butyl-2-methoxy-phenyl)-ureido]-naphthalen-1-yl}-pyridin-2-ylmethyl)-piperidine-3-carboxylic acid amide;

1-(5-{4-[3-(5-tert-Butyl-2-methoxy-phenyl)-ureido]-naphthalen-1-yl }-pyridin-2-ylmethyl)-piperidine-4-carboxylic acid amide;

1-(5-tert-Butyl-2-methoxy-phenyl)-3-{4-[6-(1-oxo-114-thiomorpholin-4-ylmethyl)-pyridin-3-yl]-naphthalen-1-yl}-urea;

1-(3,3-Dimethyl-2-oxo-2,3-dihydro-1H-indol-5-yl)-3-[4-(6-morpholin-4-ylmethyl-pyridin-3-yl)-naphthalen-1-yl]-urea;

1-(5-tert-Butyl-2-methoxy-phenyl)-3-{4-[6-(3-oxo-piperazin-1-ylmethyl)-pyridin-3-yl]-naphthalen-1-yl}-urea;

1-{4-[6-(4-Acetyl-piperazin-1-ylmethyl)-pyridin-3-yl]-naphthalen-1-yl}-3-(5-tert-butyl-2-methoxy-phenyl)-urea;

4-(5-{4-[3-(5-tert-Butyl-2-methoxy-phenyl)-ureido]-naphthalen-1-yl}-pyridin-2-ylmethyl)-piperazine-1-carboxylic acid ethyl ester;

1-(5-tert-Butyl-2-methoxy-phenyl)-3-(4-{6-[(2-pyridin-3-yl-ethylamino)-methyl]-pyridin-3-yl}-naphthalen-1-yl)-urea;

1-(5-tert-Butyl-2-methoxy-phenyl)-3-(4-{6-[(tetrahydro-furan-3-ylamino)-methyl]-pyridin-3-yl}-naphthalen-1-yl)-urea;

1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;

1-(5-tert-Butyl-2-methoxy-phenyl)-3-(4-{6-[(2-methylsulfanyl-ethylamino)-methyl]-pyridin-3-yl }-naphthalen-1-yl)-urea;

1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-tert-Butyl-2-methoxy-phenyl)-3-(4-{6-[(2-piperazin-1-yl-ethylamino)-methyl]-pyridin-3-yl}-naphthalen-1-yl)-urea;

1-(5-tert-Butyl-2-methoxy-phenyl)-3-{4-[6-(4-pyrimidin-2-yl-piperazin-1-ylmethyl)-pyridin-3-yl]-naphthalen-1-yl}-urea;

1-(5-tert-Butyl-2-methoxy-phenyl)-3-{4-[6-(4-pyridin-2-yl-piperazin-1-ylmethyl)-pyridin-3-yl]-naphthalen-1-yl}-urea;

1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;

1-(5-tert-Butyl-2-methoxy-phenyl)-3-{4-[6-(morpholine-4-carbonyl)-pyridin-3-yl]-naphthalen-1-yl}-urea;

1-(5-tert-Butyl-2-methoxy-phenyl)-3-{4-[6-(2-thia-5-aza-bicyclo[2.2.1 ]hept-5-ylmethyl)-pyridin-3-yl]-naphthalen-1-yl}-urea;

1-(5-tert-Butyl-2-methoxy-phenyl)-3-[4-(5-morpholin-4-ylmethyl-pyrazin-2-yl)-naphthalen-1-yl]-urea;

1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-morpholin-4-ylmethyl-pyridin-3-yl)-naphthalen-1-yl]-urea;

N-(5-{4-[3-(5-tert-Butyl-2-methoxy-phenyl)-ureido]-naphthalen-1-yl}-pyridin-2-yl)-acetamide;

N-(5-tert-Butyl-2-methoxy-3-{3-[4-(6-morpholin-4-ylmethyl-pyridin-3-yl)-naphthalen-1-yl]-ureido}-phenyl)-N-methyl-acetamide;

N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;

1-(5-tert-Butyl-2-methoxy-phenyl)-3-{4-[6-(pyridin-3-yloxy)-pyridin-3-yl]-naphthalen-1-yl}-urea;

1-(5-tert-Butyl-2-methoxy-phenyl)-3-{4-[6-(pyridin-3-ylamino)-pyridin-3-yl]-naphthalen-1-yl}-urea;

[4-(6-Morpholin-4-ylmethyl-pyridin-3-yl)-naphthalen-1-yl]-carbamic acid 3-tert-butyl-phenyl ester;

N-(5-tert-Butyl-2-methoxy-3-{3-[4-(6-morpholin-4-ylmethyl-pyridin-3-yl)-naphthalen-1-yl]-ureido}-phenyl)-methanesulfonamide and and the pharmaceutically acceptable derivatives thereof.

In yet another embodiment of the invention there is provided the following compounds of the formula(III):

1-(3-Methyl-naphthalen-2-yl)-3-[4-(6-morpholin-4ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureidol}-phenyl)-acetamide;

1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;

1-(2,3-Dimethyl-1H-indol-5-yl)-3-[4-(6-morpholin-4-ylmethyl-pyridin-3-yl)-naphthalen-1-yl]-urea;

1-{5-tert-Butyl-2-methyl-3-[3-(tetrahydro-pyran-2-yloxy)-prop-1 ynyl]-phenyl}-3-[4-(6-morpholin-4-ylmethyl-pyridin-3-yl)-naphthalen-1-yl]-urea;

1-(2-Methoxy-5-trifluoromethyl-phenyl)-3-[4-(6-morpholin-4-ylmethyl-pyridin-3-yl)-naphthalen-1-yl]-urea;

1-[5-(2,2-Dimethyl-propionyl)-2-methyl-phenyl]-3-[4-(6-morpholin-4-ylmethyl-pyridin-3-yl)-naphthalen-1-yl]-urea;

1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;

1-[5-tert-Butyl-2-(3-hydroxy-prop-1-ynyl)-phenyl]-3-[4-(6-morpholin-4-ylmethyl-pyridin-3-yl)-naphthalen-1-yl]-urea;

1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;

1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;

1-(5-tert-Butoxy-2-methoxy-phenyl)-3-[4-(6-morpholin-4-ylmethyl-pyridin-3-yl)-naphthalen-1-yl]-urea;

1-[5-(1-Cyano-cyclopropyl)-2-methoxy-phenyl]-3-[4-(6-morpholin-4-ylmethyl-pyridin-3-yl)-naphthalen-1-yl]-urea;

1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;

1-(5-tert-Butyl-2-methoxy-phenyl)-3-[4-(6-[1,3]dioxolan-2-yl-pyridin-3-yl)-naphthalen-1-yl]-urea;

1-(5-tert-Butyl-2-pyrrolidin-1-yl-phenyl)-3-[4-(6-morpholin-4-ylmethyl-pyridin-3-yl)-naphthalen-1-yl]-urea;

1-(5-tert-Butyl-2-dimethylamino-phenyl)-3-[4-(6-morpholin-4-ylmethyl-pyridin-3-yl)-naphthalen-1-yl]-urea;

1-(5-tert-Butyl-2-propoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-hydroxymethyl-pyridin-3-yl)-naphthalen-1-yl]-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-Cyclohexyl-2-methoxy-phenyl)-3-[4-(6-morpholin-4-ylmethyl-pyridin-3-yl)-naphthalen-1-yl]-urea;

1-(2,4-Dimethoxy-5-trifluoromethyl-phenyl)-3-[4-(6-morpholin-4-ylmethyl-pyridin-3-yl)-naphthalen-1-yl]-urea;

1-(5-tert-Butyl-2-methoxy-3-nitro-phenyl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-methyl-pyridin-3-yl)-naphthalen-1-yl]-urea;

N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4dihydro-2H-benzo[1,4]oxazin-8-yl)-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;

1-(5-tert-Butyl-2-imidazol-1-yl-phenyl)-3-[4-(6-morpholin-4-ylmethyl-pyridin-3-yl)-naphthalen-1-yl]-urea;

1-(5-tert-Butyl-3-ethylamino-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido }-phenyl)-bis(methanesulfon)amide;

1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;

1-(2-Methanesulfinyl-5-trifluoromethyl-phenyl)-3-[4-(6-morpholin-4-ylmethyl-pyridin-3-yl)-naphthalen-1-yl]-urea;

1-[4-(6-{[Bis-(2-methoxy-ethyl)-amino]-methyl}-pyridin-3-yl)-naphthalen-1-yl]-3-(5-tert-butyl-2-methoxy-phenyl)-urea;

N-[1-(5-{4-[3-(5-tert-Butyl-2-methoxy-phenyl)-ureido]-naphthalen-1-yl}-pyridin-2-ylmethyl)-pyrrolidin-3-yl]-acetamide;

1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-propionamide;

1-(5-tert-Butyl-2-methyl-benzooxazol-7-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-trifluoromethanesulfonyl-phenyl)-urea;

N-(5-tert-Butyl-2-methoxy-3-{3-[4-(6-morpholin-4-ylmethyl-pyridin-3-yl)-naphthalen-1-yl]-ureido}-phenyl)-isobutyramide;

2-(4-tert-Butyl-2-{3-[4-(6-morpholin-4-ylmethyl-pyridin-3-yl)-naphthalen-1-yl]-ureido}-phenoxy)-acetamide;

1-(5-tert-Butyl-2-oxo-2,3-dihydro-benzooxazol-7-yl)-3-[4-(6-morpholin-4-ylmethyl-pyridin-3-yl)-naphthalen-1-yl]-urea;

1-(5-tert-Butyl-3-cyano-2-methoxy-phenyl)-3-[4-(6-morpholin-4-ylmethyl-pyridin-3-yl)-naphthalen-1-yl]-urea;

1-(5-tert-Butyl-benzooxazol-7-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-benzenesulfonamide;

Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methylsulfanyl-phenyl)-3-[4-(6-morpholin-4-ylmethyl-pyridin-3-yl)-naphthalen-1-yl]-urea;

1-(5-tert-Butyl-2-methoxy-pyridin-3-yl)-3-[4-(6-morpholin-4-ylmethyl-pyridin-3-yl)-naphthalen-1-yl]-urea;

2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

N-(5-{4-[3-(5-tert-Butyl-2-methyl-phenyl)-ureido]-naphthalen-1-yl}-pyrazin-2-yl)-methanesulfonamide;

1-[4-(6-{[Bis-(2-cyano-ethyl)-amino]-methyl}-pyridin-3-yl)-naphthalen-1-yl]-3-(5-tert-butyl-2-methoxy-phenyl)-urea;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methoxy-phenyl)-3-[4-(6-thiomorpholin-4-ylmethyl-pyridin-3-yl)-naphthalen-1-yl]-urea;

1-(5-tert-Butyl-2-methoxy-phenyl)-3-{4-[6-(2,6-dimethyl-piperidin-1-ylmethyl)-pyridin-3-yl]-naphthalen-1-yl}-urea;

1-(5-tert-Butyl-2-methoxy-phenyl)-3-{4-[6-(1-oxo-tetrahydro-thiopyran-4-ylamino)-pyridin-3-yl]-naphthalen-1-yl}-urea;

1-(5-tert-Butyl-2-methoxy-phenyl)-3-{4-[6-(tetrahydro-pyran-4-ylamino)-pyridin-3-yl]-naphthalen-1-yl}-urea;

1-(5-tert-Butyl-2-methoxy-phenyl)-3-[4-(6-{[(2-cyano-ethyl)-(tetrahydro-furan-2-ylmethyl)-amino]-methyl}pyridin-3-yl)-naphthalen-1-yl]-urea;

1-(5-tert-Butyl-2-methoxy-phenyl)-3-{4-[6-(2-methoxymethyl-morpholin-4-ylmethyl)-pyridin-3-yl]-naphthalen-1-yl}-urea;

1-(5-tert-Butyl-2-methoxy-phenyl)-3-4-[6-(2-methyl-3-oxo-piperazin-1-ylmethyl)-pyridin-3-yl]-naphthalen-1-yl}-urea;

1-(5-{4-[3-(5-tert-Butyl-2-methoxy-phenyl)-ureido]-naphthalen-1-yl}-pyridin-2-ylmethyl)-piperidine-3-carboxylic acid amide;

1-(5-tert-Butyl-2-methoxy-phenyl)-3-{4-[6-(1-oxo-1l4-thiomorpholin-4-ylmethyl)-pyridin-3-yl]-naphthalen-1-yl}-urea;

1-(3,3-Dimethyl-2-oxo-2,3-dihydro-1H-indol-5-yl)-3-[4-(6-morpholin-4-ylmethyl-pyridin-3-yl)-naphthalen-1-yl]-urea;

1-(5-tert-Butyl-2-methoxy-phenyl)-3-{4-[6-(3-oxo-piperazin-1-ylmethyl)-pyridin-3-yl]-naphthalen-1-yl}-urea;

1-(5-tert-Butyl-2-methoxy-phenyl)-3-(4-{6-[(tetrahydro-furan-3-ylamino)-methyl]-pyridin-3-yl}-naphthalen-1-yl)-urea;

1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;

1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;

1-(5-tert-Butyl-2-methoxy-phenyl)-3-{4-[6-(morpholine-4-carbonyl)-pyridin-3-yl]-naphthalen-1-yl}-urea;

1-(5-tert-Butyl-2-methoxy-phenyl)-3-[4-(5-morpholin-4-ylmethyl-pyrazin-2-yl)-naphthalen-1-yl]-urea;

1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-morpholin-4-ylmethyl-pyridin-3-yl)-naphthalen-1-yl]-urea;

N-(5-{4-[3-(5-tert-Butyl-2-methoxy-phenyl)-ureido]-naphthalen-1-yl}-pyridin-2-yl)-acetamide;

N-(5-tert-Butyl-2-methoxy-3-{3-[4-(6-morpholin-4-ylmethyl-pyridin-3-yl)-naphthalen-1-yl]-ureido}-phenyl)-N-methyl-acetamide;

N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;

1-(5-tert-Butyl-2-methoxy-phenyl)-3-{4-[6-(pyridin-3-yloxy)-pyridin-3-yl]-naphthalen-1-yl}-urea;

[4-(6-Morpholin-4-ylmethyl-pyridin-3-yl)-naphthalen-1-yl]-carbamic acid 3-tert-butyl-phenyl ester;

N-(5-tert-Butyl-2-methoxy-3-{3-[4-(6-morpholin-4-ylmethyl-pyridin-3-yl)-naphthalen-1-yl]-ureido}-phenyl)-methanesulfonamide and and the pharmaceutically acceptable derivatives thereof.

In addition to the abovementioned compounds the following prophetic compounds of the formula(III) may be made by the general methods described hereinbelow:

1-(5-tert-Butyl-2-methylsulfanyl-pyridin-3-yl)-3-[4-(6-morpholin-4-ylmethyl-pyridin-3-yl)-naphthalen-1-yl]-urea;

1-(5-tert-Butyl-2-chloro-pyridin-3-yl)-3-[4-(6-morpholin-4-ylmethyl-pyridin-3-yl)-naphthalen-1-yl]-urea;

1-(5-tert-Butyl-2-methylamino-pyridin-3-yl)-3-[4-(6-morpholin-4-ylmethyl-pyridin-3-yl)-naphthalen-1-yl]-urea;

N-(5-tert-Butyl-3-{3-[4-(6-morpholin-4-ylmethyl-pyridin-3-yl)-naphthalen-1-yl]-ureido}-2-oxo-2H-pyridin-1-yl)-methanesulfonamide;

5-tert-Butyl-7-{3-[4-(6-morpholin-4-ylmethyl-pyridin-3-yl)-naphthalen-1-yl]-ureido }-benzooxazole-2-carboxylic acid amide;

2-(5-tert-Butyl-7-{3-[4-(6-morpholin-4-ylmethyl-pyridin-3-yl)-naphthalen-1-yl]-ureido}-benzooxazol-2-yl)-acetamide;

5-tert-Butyl-2-methoxy-3-{3-[4-(6-morpholin-4-ylmethyl-pyridin-3-yl)-naphthalen-1-yl]-ureido}-benzamide and and the pharmaceutically acceptable derivatives thereof.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formulas (I), (Ia), (II) and (III) can exist in more than one tautomeric form. The invention includes all such tautomers.

All terms as used in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, pentoxy and hexoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms selected from nitrogen, oxygen and sulfur. The heterocycle may be attached by any atom of the cycle, which results in the creation of a stable structure. Unless otherwise stated, heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl or 2-oxa- or 2-thia-5-aza-bicyclo[2.2.1]heptanyl.

The term "heteroaryl" shall be understood to mean an aromatic 5–8 membered monocyclic or 8–11 membered bicyclic ring containing 1–4 heteroatoms such as N,O and S. Unless otherwise stated, such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo [1,3]dioxol-2-onyl, tetrahydrobenzopyranyl, indolyl, indolinyl, indolonyl, indolinonyl, phthalimidyl.

The term "heteroatom" as used herein shall be understood to mean atoms other than carbon such as O, N, S and P.

The term "aryl" as used herein shall be understood to mean aromatic carbocycle or heteroaryl as defined herein.

Terms which are analogs of the above cyclic moieties such as aryloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen.

The term "halogen" as used in the present specification shall be understood to mean bromine, chlorine, fluorine or iodine.

The compounds of the invention are only those which are contemplated to be chemically stable as will be appreciated by those skilled in the art. For example, a compound which would have a 'dangling valency', or a 'carbanion' are not compounds contemplated by the invention.

The invention includes pharmaceutically acceptable derivatives of compounds of formula (I), (Ia), (II) and (III).

A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formulas(I), (Ia), (II) or (III).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and $N\text{-}(C_1\text{—}C_4\text{ alkyl})_4^+$ salts.

In addition, the compounds of this invention include prodrugs of compounds of the formula (I), (Ia), (II) and (III). Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a compound of the invention, thereby imparting the desired pharmacological effect.

Methods of Use

In accordance with the invention, there are provided methods of using the compounds of the formulas (I), (Ia), (II) and (III). The compounds of the invention effectively block inflammatory cytokine production from cells. The inhibition of cytokine production is an attractive means for preventing and treating a variety of disorders associated with excess cytokine production, e.g., diseases and pathological conditions involving inflammation. Thus, the compounds of the invention are useful for the treatment of such conditions. These encompass chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory cytokines such as responses to various infectious agents and a number of diseases of autoimmunity such as rheumatoid arthritis, toxic shock syndrome, diabetes and inflammatory bowel diseases unrelated to those listed above are discussed in the Background of the Invention.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formulas (I), (Ia), (II) or (III) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

General Synthetic Methods

The compounds of the invention may be prepared by Method A, B, or C as illustrated in Scheme I, preferably method C. Further reference in this regard may be made to PCT application No. PCT/US99/29165, U.S. Provisional application Nos. 60/124,148 and 60/165,867, and attorney docket numbers 9/183 for Kapadia et al and 9/184 for Kapadia et al. Each of the aforementioned incorporated herein by reference in their entirety.

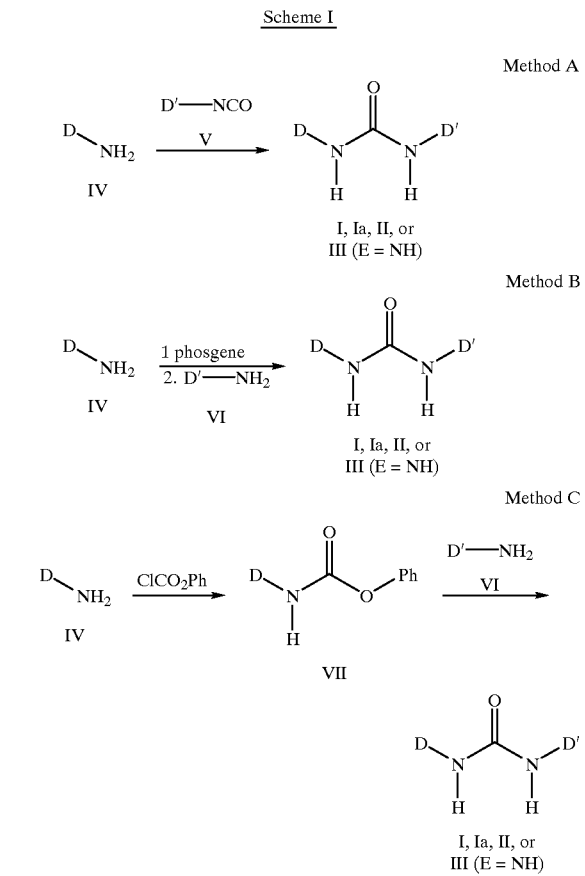

-continued

In the above Methods, D = Ar₁ (for formula I and Ia compounds) or G (for formula II or III compounds); D' = Ar₂—X—Y—Z (or its precursor) for formula I and Ia compounds or Ar—X—Y—Z (or its precursor) for formula II or III compounds In Method A, a mixture of an amine of formula IV and an isocyanate of formula V is dissolved in a non-protic, anhydrous solvent such as THF, ether, toluene, dioxane or ethyl acetate. The preferred solvent is THF. The mixture is stirred at between 0–45° C., preferably at 25° C., for 2–24 hr, and the volatiles are removed. Purification of the residue by recrystallization from an appropriate solvent such as ethyl acetate/hexanes, ethyl acetate/methanol, THF/petroleum ether, ethanol/water or by silica gel chromatography, using for example, hexanes and ethyl acetate as eluents, provides the product of formula I, Ia, II or III (E=NH).

In Method B, an amine of formula IV is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as MgSO₄ or Na₂SO₄, and the volatiles removed to provide the corresponding isocyanate, D-N=C=O. The isocyanate and amine VI are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 hr, and the volatiles are removed. Purification of the residue by recrystallization or by silica gel chromatography, as above, provides the product of formula I, Ia, II or III (E=NH).

The required isocyanate may also be prepared from the carboxylic acid D—CO₂H by reaction with a chloroformate, such as ethyl chloroformate, in the presence of a suitable base, such as triethylamine, in a suitable solvent, such as THF at about 0° C. The resulting mixed anhydride is treated with an aqueous solution of sodium azide. Heating a solution of the resulting acyl azide in a suitable solvent, such as toluene, at about reflux, results in a Curtius rearrangement, providing the isocyanate D-N=C=O in situ.

In Method C, an amine of formula IV is dissolved in a suitable solvent such as a halogenated solvent such as methylene chloride, chloroform or dichloroethane. The preferred solvent is methylene chloride. A suitable base such as triethylamine may be added, followed by phenyl chloroformate. The mixture is stirred at between 0–85° C., preferably at reflux temperature, for 2–24 hr, and the volatiles are removed providing carbamate VII. The carbamate and amine VI are mixed in a non-protic, anhydrous solvent such as THF, ether, toluene, dioxane, methylene chloride or ethyl acetate. The preferred solvent is THF. The mixture is stirred at between 0–110° C., preferably at reflux temperature, for 2–24 hr, and the volatiles are removed. Purification of the residue as above provides the product of formula I, Ia, II or III (E=NH). This Method may also be employed in the reverse sense, that is one may form the carbamate from D'NH₂ and react this carbamate with amine D-NH₂. Example 37 illustrates the synthesis of a compound of formula III in which E is —O—, and Example 38 illustrates the synthesis of a compound of formula III in which E is —CH₂—.

The method used to produce amines of formula IV will depend on the nature of the desired group D. In general, intermediates of formula IV can be made by methods known to those skilled in the art. Some general methods are illustrated in the schemes below. Compounds D'-NCO or D'-NH₂ in Scheme I may be commercially available, or may be prepared by methods known to those skilled in the art. If D' is a precursor of Ar₂—X—Y—Z or Ar—X—Y—Z, the desired final product of formula I, Ia, II or III may be constructed by methods known to those skilled in the art. Illustrative examples are contained in the Synthetic Examples section below.

Desired aminopyrazoles of formula XV, for use in preparation of compounds of formula I or Ia, can be prepared as described in Scheme II. A hydrazine of formula X, bearing substituent R₃, may be prepared by Method D or E. In Method D, an aryl bromide of formula VIII is dissolved in a non-protic, inert solvent, such as THF, 1,4-dioxane or diethyl ether, and cooled to low temperature under an inert atmosphere. The preferred temperature for the solution is −77° C. A strong base dissolved in a non-protic, inert solvent, such as hexanes, THF or ether, is added dropwise while maintaining a reaction temperature below 0° C. and preferably below −60° C. The preferred bases are alkyl lithium reagents and the most preferred is sec-butyl lithium. After the addition of the base, the reaction mixture is stirred for a period of time between thirty and ninety min or until all the starting aryl bromide has been consumed. An excess of dialkyl azodicarboxylate is added while maintaining a reaction temperature below 0° C. and preferrably below −60° C. The preferred dialkyl azodicarboxylate is di-tert-butyl azodicarboxylate. The reaction is stirred at cold temperatures and warmed to room temperature after 0.5 h to 2 hr. The reaction is quenched with the addition of water and the product extracted into a non-protic solvent, such as ethyl acetate, diethyl ether or chloroform. The organic layers are dried with agents such as MgSO₄ or Na₂SO₄ and the volatiles removed. The residue is dissolved in protic solvents, such as methanol or iso-propanol, cooled, preferably to 0–5° C. and treated with acid. Preferred acids are hydrochloric, hydrobromic, sulfuric and trifluoroacetic. The most preferred is hydrochloric acid in gaseous form. After the addition of excess acid the mixture is heated at the reflux temperature of the solvent until all starting material has been consumed. After cooling the product aryl-hydrazine salt of formula X is filtered and dried.

Scheme II

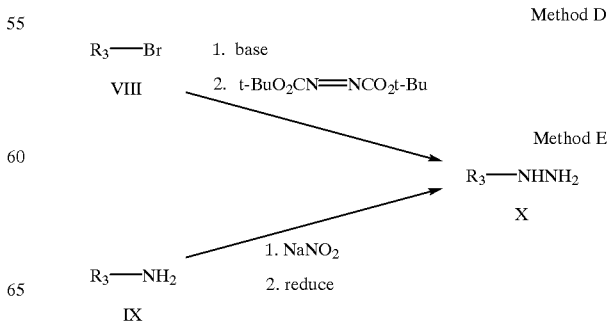

-continued

Method F

Method G

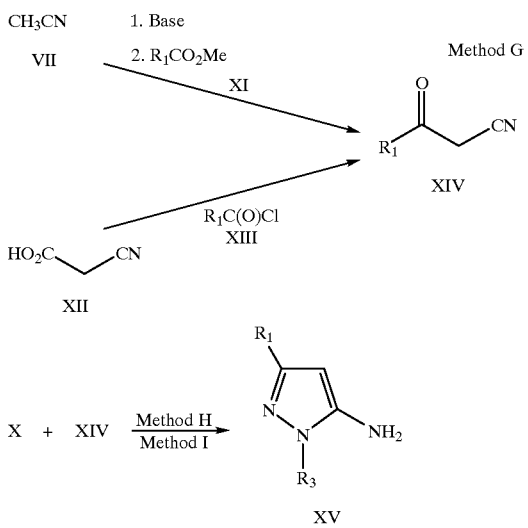

In Method E, an aryl amine bearing R$_3$ (IX) is dissolved in a concentrated aqueous acid such as hydrochloric, hydrobromic or sulfuric and cooled to ice bath temperatures. The most preferred acid is hydrochloric with concentrations between 3–8 N with the most preferred concentration of 6 N. A nitrosating reagent in water is added dropwise while maintaining a cold temperature. The preferred temperature is 0–5° C. The preferred reagent is sodium nitrite. The reaction is stirred between 10–90 min and a reducing agent is added while maintaining cold temperatures. The preferred temperature is 0–5° C.

Reducing agents include zinc, iron, samarium iodide and tin(II) chloride. The most preferred agent is tin(II) chloride dissolved in aqueous hydrochloric acid with a concentration of 3–8 N with a most preferred concentration of 6 N. The reaction is stirred between 0.5–3 h and quenched with alkali to a pH between 12–14. Alkali reagents include sodium hydroxide, potassium hydroxide, lithium hydroxide and calcium hydroxide. The most preferred alkali reagent is potassium hydroxide. The aqueous solution is extracted with a non-protic organic solvent, such as diethyl ether, chloroform, ethyl acetate and methylene chloride. The organic layers are dried with agents such as MgSO$_4$ and Na$_2$SO$_4$ and the volatiles removed to provide the aryl hydrazine (X), which can be carried forward without further purification.

A β-ketonitrile bearing R$_1$ (XIV) may be prepared by Method F or G. In Method F, a metal hydride, such as sodium hydride, potassium hydride or lithium hydride, is suspended in an anhydrous, inert, non-protic solvent, such as diethyl ether, THF and dioxane, at temperatures between 35–85° C. The most preferred metal hydride is sodium hydride and the most preferred solvent is THF at a temperature of 75° C. An alkyl ester, preferably a methyl ester (XI), and acetonitrile is dissolved in an anhydrous, inert, non-protic solvent, such as diethyl ether, THF or dioxane and added dropwise to the metal hydride suspension. The preferred solvent is THF. The mixture is kept at elevated temperatures between 3–24 h, cooled to room temperature and diluted with a non-protic solvent and aqueous acid. The organic layer is washed with water and brine, dried, with agents such as MgSO$_4$ and Na$_2$SO$_4$, and the volatiles removed to provide the β-ketonitrile (XIV), which could be used without further purification.

Alternatively, following Method G, a solution of a strong base, such as alkyl lithium reagents and metal amide reagents, such as n-butyl lithium, sec-butyl lithium, methyl lithium and lithium diisopropylamide, in an anhydrous, inert, non-protic solvent, such as diethyl ether, THF and dioxane, is cooled below 0° C. The preferred base is n-butyl lithium, the preferred solvent is THF and the preferred temperature is −77° C. A solution of cyanoacetic acid (XII) in an anhydrous, inert, non-protic solvent, such as diethyl ether, THF and dioxane, and most preferrably THF, is added dropwise while maintaining a reaction temperature below 0° C. and preferrably at −77° C. The reaction is stirred between 10–45 min while warming to 0° C. The solution of the dianion of cyanoacetic acid is cooled to temperatures below −25° C. and preferrably at −77° C. An alkyl acid chloride (XIII) dissolved in an anhydrous, inert, non-protic solvent, such as diethyl ether, THF and dioxane, and most preferrably THF, is added. The reaction mixture is warmed to 0° C. between 10–30 min and quenched with aqueous acid. The product is extracted with an organic solvent, such as chloroform, ethyl acetate, ether and methylene chloride. The combined organic extracts are dried, with agents such as MgSO$_4$ and Na$_2$SO$_4$, and the volatiles removed to provide the β-ketonitrile (XIV), which could be used without further purification.

The desired aminopyrazole (XV) may then be prepared by Method H or I. In Method H, aryl hydrazine X and β-ketonitrile XIV are mixed in an organic solvent, such as toluene, ethanol, iso-propanol or t-butanol. The preferred solvent is ethanol. An acid, such as hydrochloric acid, p-toluene sulfonic acid or sulfuric acid, is added, The preferred acid is concentrated hydrochloric acid. The mixture is heated to temperatures between 50–100° C., preferably at 80° C., for 10–24 h and cooled to room temperature. The mixture is diluted with non-protic organic solvent, such as ethyl acetate, ether, chloroform and methylene chloride, and washed with aqueous alkali, such as sodium bicarbonate and potassium carbonate. The organic layer is dried, with agents such as MgSO$_4$ and Na$_2$SO$_4$, and the volatiles removed to provide a residue which is purified by recrystallization or silica gel chromatography using hexanes and ethyl acetate as eluents. The product-rich fractions are collected and the volatiles removed to provide the desired aminopyrazole (XV).

Alternatively, using Method I, aryl hydrazine X and β-ketonitrile XIV are mixed in an organic solvent, such as toluene, ethanol, iso-propanol or t-butanol. The preferred solvent is toluene. The mixture is heated at reflux temperatures for 3–24 h with azeotropic removal of water and worked up as described above providing the aminopyrazole XV.

The synthesis of other desired aminoheterocycles that may be used in preparation of compounds of formula I or Ia can be prepared by methods known in the art and described in the literature. The examples that follow in Schemes III–XV are illustrative and, as recognized by one skilled in the art, particular reagents or conditions could be modified as needed for individual compounds. Intermediates used in the schemes below are either commercially available or easily prepared from commercially available materials by those skilled in the art.

A general synthesis for desired aminothiophenes is illustrated in Scheme III, Method J.

Scheme III

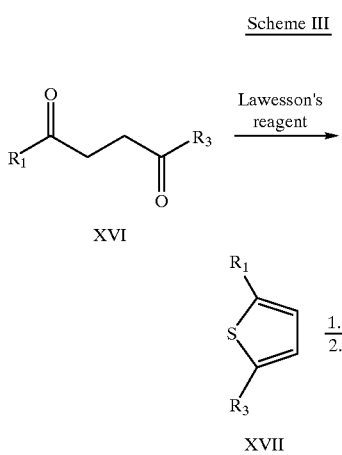

Method J

A mixture of 1-aryl-5-alkyl-butane-1,4-dione (XVI) and a sulfating reagent, such as Lawesson's reagent or phosphorous (V) sulfide, preferably Lawesson's reagent, is dissolved in a non-protic, anhydrous solvent, such as toluene, THF and dioxane. The preferred solvent is toluene. The mixture is heated at elevated temperatures and preferably at a solvent-refluxing temperature for 1–10 hr. The volatiles are removed and the residue is purified by silica gel chromatography using hexanes and ethyl acetate as eluent. The product-rich fractions are collected and the volatiles removed to provide the substituted thiophene XVII.

A mixture of substituted thiophene XVII is dissolved in a solvent such as acetic anhydride or acetic acid. The preferred solvent is acetic anhydride. The mixture is cooled to 0–30° C. and preferrably to −10° C. A solution of concentrated nitric acid in a solvent such as acetic anhydride or acetic acid, with the preferred solvent being acetic anhydride is added while cooling to 0–30° C. and preferably to −10° C. The mixture is stirred between 10–120 min, poured onto ice and extracted with a non-protic solvent such as diethyl ether, chloroform, ethyl acetate or methylene chloride. The organic extracts are washed with aqueous alkali, dried with agents such as $MgSO_4$ and $Na_2SO_4$ and the volatiles removed. The residue is purified by silica gel chromatography using hexanes and ethyl acetate as eluents. The product-rich fractions are collected and the volatiles removed to provide the 2-aryl-5-alkyl-3-nitrothiophene. The 2-aryl-5-alkyl-3-nitrothiophene is reduced by metals, such as iron, tin and zinc or catalytic hydrogenation. The preferred reduction conditions are iron in acetic acid at temperatures between 50–110° C. and preferrably at 100° C. for 5–30 min. After cooling to room temperature the reaction is diluted with water, neutralized with alkali, such as sodium hydroxide, potassium hydroxide, potassium carbonate or sodium bicarbonate, and extracted with a non-protic solvent such as diethyl ether, ethyl acetate or methylene chloride. The organic extracts are dried with agents such as $MgSO_4$ and $Na_2SO_4$ and the volatiles removed to provide the desired aminothiophene XVIII.

Scheme IV outlines a general scheme for desired aminofurans as described by Stevenson et al. (*J. Am. Chem. Soc.,* 1937, 59, 2525). An ethyl aroylacetate (XIX) is dissolved in a non-protic solvent, such as ether or THF, and treated with a strong base, such as sodium, sodium ethoxide or sodium hydride, and the anion is reacted with a bromomethyl alkylketone (XX) at low temperatures, such as 0° C. After stirring the reaction until no starting material remains, it is poured onto cold water and extracted with a non-protic solvent. The combined extracts are dried with agents such as $MgSO_4$ or $Na_2SO_4$. The diketo-ester (XXI) may be carried forward without further purification or purified by distillation or silica gel chromatography. The diketo-ester in a protic solvent, such as ethanol, is heated in the presence of a mineral acid, such as sulfuric or hydrochloric, for 5–10 h and extracted with a non-protic solvent. The combined extracts are dried with agents such as $MgSO_4$ or $Na_2SO_4$. The furan-ester (XXII) may be carried forward without further purification or purified by distillation or silica gel chromatography. The furan-ester in a protic solvent, such as ethanol, is treated with hydrazine hydrate and the mixture heated for 2–5 days. The hydrazide is isolated as above and treated with hot formic acid and the resulting furan-amine (XXIII) purified by distillation or silica gel chromatography.

Scheme IV

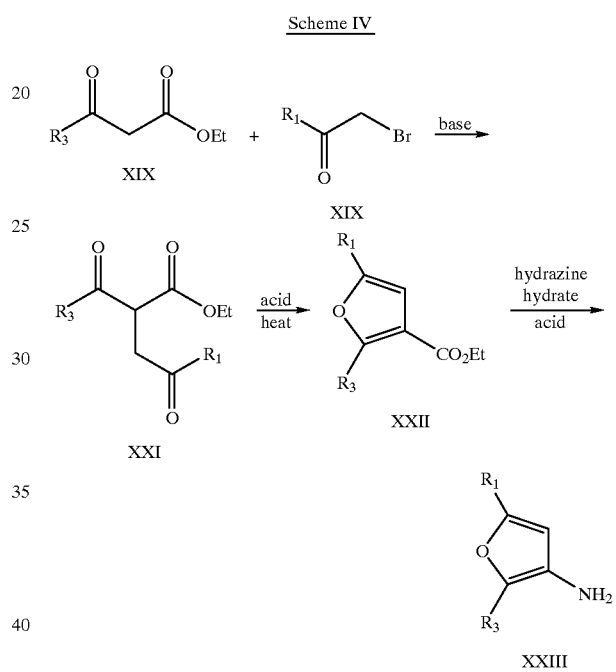

The synthesis of substituted 4-aminooxazoles may be achieved analogously to a procedure described by Lakhan et al. (*J. Het. Chem.,* 1988, 25, 1413) and illustrated in Scheme V. A mixture of aroyl cyanide (XXIV), aldehyde (XXV) and anhydrous ammonium acetate in acetic acid is heated at 100–110° C. for 3–6 hr, cooled to room temperature and quenched with water. Extraction by a non-protic solvent provides the product XXVI which can be carried forward without further purification or purified by recrystallization or silica gel chromatography.

Scheme V

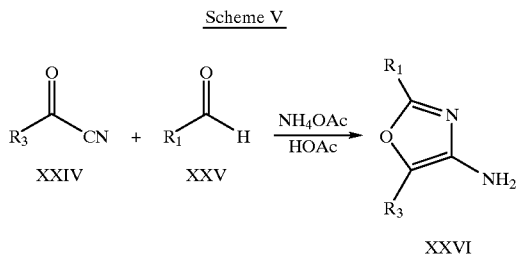

The synthesis of substituted 3-aminopyrroles (XXX) may be achieved in a manner analogous to Aiello et al., *J. Chem.*

*Soc. Perkins Trans. I*, 1981, 1. This is outlined in Scheme VI. A mixture of aryldioxoalkane (XXVII) and amine (XXVIII) in acetic acid is heated at 100–110° C. for 3–6 h and worked up in the usual manner. The product (XXIX) in acetic acid is treated with a nitrating agent, such as nitric acid and potassium nitrate in concentrated sulfuric acid. The mixture is poured onto cold water and extracted with a non-protic solvent. The combined extracts are dried with agents such as $MgSO_4$ and $Na_2SO_4$. Removal of the volatiles provides the nitro-pyrrole which which may be carried forward without further purification or purified by recrystallization or silica gel chromatography. The nitro-pyrrole is reduced to the amine with iron in acetic acid or by catalytic hydrogenation using palladium on activated carbon. The aminopyrrole (XXX) may be carried forward without further purification or purified by recrystallization or silica gel chromatography.

Scheme VI

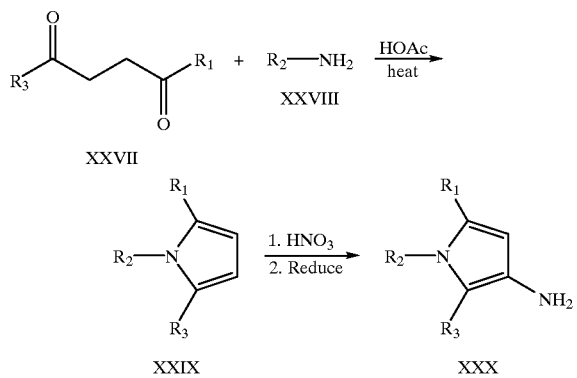

In an analogous fashion, a mixture of amine XXXI and 3-aryl-2,5-dioxoalkane (XXXII) in acetic acid is heated between 80–110° C. for 2–24 hr. The reaction is diluted with water and extracted with an organic solvent. The combined extracts are dried with agents such as $MgSO_4$ or $Na_2SO_4$ and the volatiles removed. The resulting pyrrole is treated with a nitrating agent and subsequently reduced to XXXIII as described above. The product may be carried forward without further purification or purified by recrystallization or silica gel chromatography. This process is illustrated in Scheme VII.

Scheme VII

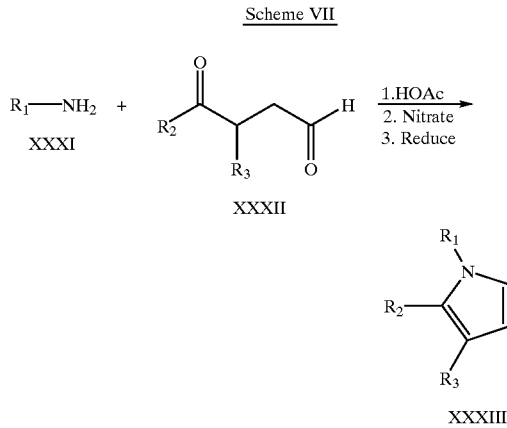

Substituted 5-aminothiazoles (XXXVII) may be prepared in a manner analogous to Gerwald et al., *J. Prakt. Chem.* 1973, 315, 539. As illustrated in Scheme VIII, to a mixture of aminocyanide XXXIV, aldehyde XXXV and sulfur in an anhydrous solvent, such as ethanol and methanol, is added dropwise a base, such as triethylamine. The mixture is heated at 50° C. for 1–3 hr. The mixture is cooled and the excess sulfur removed. Acetic acid is added to neutralize the mixture and the solid collected. The imine XXXVI is treated with acid, such as hydrochloric and toluenesulfonic acid, in water and an organic solvent. After the starting material is consumed the reaction is worked up and the product XXXVII may be carried forward without further purification or purified by recrystallization or silica gel chromatography.

Scheme VIII

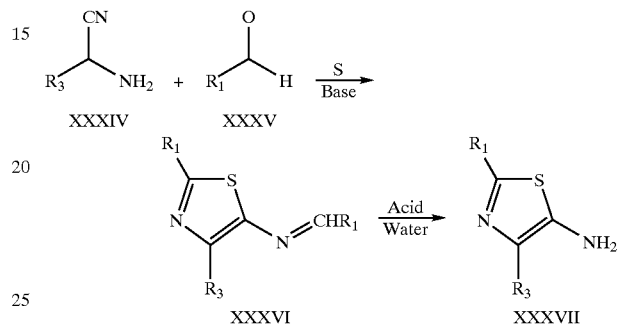

A synthesis of substituted 2-aminothiophenes (XXXIX), analogous to a procedure described by Gewald et al. (*J. Prakt. Chem.*, 1973, 315, 539) is illustrated in Scheme IX. A mixture of disubstituted thiophene-3-carboxylic acid (XXXVIII) in a protic solvent, such as acetic acid, at a temperature of 0–50° C. is treated with a nitrating agent, such as nitric acid or potassium nitrate in concentrated sulfuric acid. After the starting material has been consumed the reaction is poured onto ice and the product extracted with a non-protic solvent. The combined extracts are dried with agents such as $MgSO_4$ and $Na_2SO_4$ and the volatiles removed. The nitrothiophene is reduced to the amine with iron in acetic acid or by catalytic hydrogenation using palladium on activated carbon. The amino-thiophene may be carried forward without further purification or purified by recrystallization or silica gel chromatography.

Scheme IX

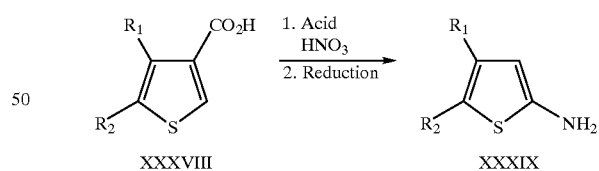

1,5-Disubstituted-3-aminopyrazoles (XLII) may be prepared as shown in Scheme X, in a fashion analogous to the procedure described by Ege et al. (*J. Het. Chem.*, 1982, 19, 1267). Potassium is added to anhydrous t-butanol and the mixture cooled to 5° C. Hydrazine XL is added, followed by cyanodibromoalkane XLI. The mixture is heated at refluxing temperatures for 3–10 hr. The mixture is cooled to room temperature and poured onto ice water. The product is extracted with an organic solvent. The combined extracts are dried with agents such as $MgSO_4$ or $Na_2SO_4$ and the volatiles removed. The product XLII may be carried forward without further purification or purified by recrystallization or silica gel chromatography.

Scheme X

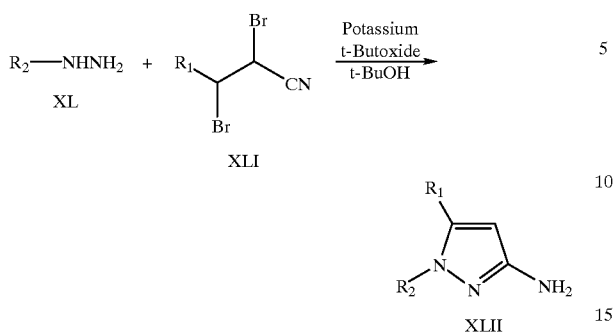

The synthesis of 2-amino-3,5-disubstituted thiophenes shown in Scheme XI, is done in a fashion analogous to Knoll et al., *J. Prakt. Chem.*, 1985, 327, 463. A mixture of substituted N-(3-aminothioacryloyl)-formamidine (XLIII) and substituted bromide (XLIV) in a protic solvent, such as methanol or ethanol, is heated, preferably at a reflux temperature, for 5–30 min and cooled below room temperature. The product thiophene-imine is filtered and dried. The thiophene-imine XLV is converted to the thiophene-amine (XLVI) by treatment with aqueous acid.

Scheme XI

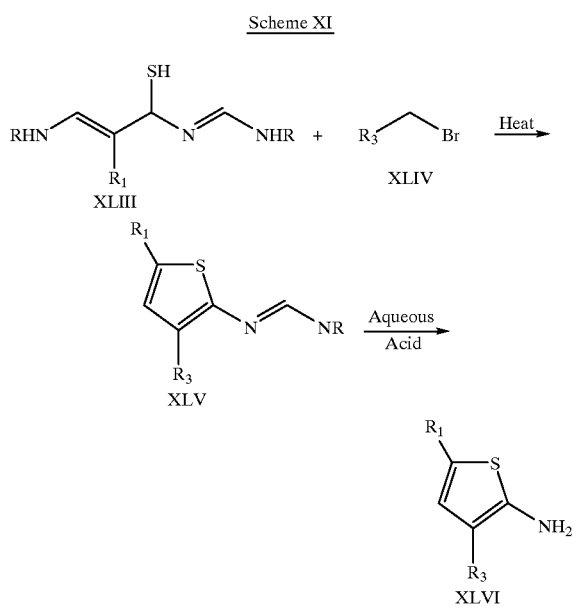

The synthesis of 1,4-disubstituted-2-aminopyrroles (L) may be accomplished in a manner analogous to Brodrick et al. (*J. Chem. Soc. Perkin Trans. I,* 1975, 1910), and as illustrated in Scheme XII. The potassium salt of formylnitrile XLVII in water is treated with amine XLVIII and acetic acid and the mixture heated at 50–90° C. for 5–30 min. The aminonitrile XLIX is collected by filtration upon cooling and then is stirred at room temperature with a base such as ethanolic potassium ethoxide for 2–5 h and the volatiles removed. The residue is diluted with water and extracted with an organic solvent. The combined extracts are dried with agents such as $MgSO_4$ and $Na_2SO_4$ and the volatiles removed. The product (L) may be carried forward without further purification or purified by recrystallization or silica gel chromatography.

Scheme XII

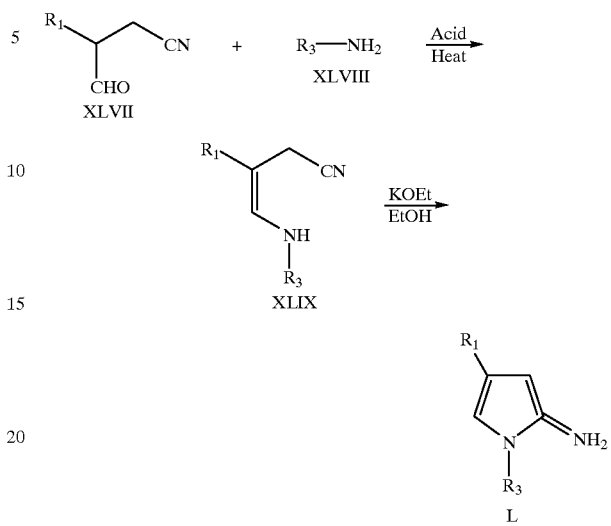

The preparation of 1,2-disubstituted-4-aminoimidazoles (LII) by reduction of the corresponding nitro compound (LI), for example with iron in acetic acid or catalytic hydrogenation may be accomplished as described by Al-Shaar et al. (*J. Chem. Soc. Perkin Trans. I,* 1992, 2779) and illustrated in Scheme XIII.

Scheme XIII

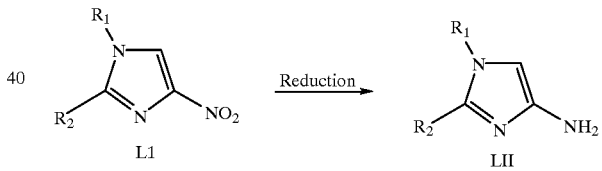

2,4-Disubstituted 5-aminooxazoles (LVII) may be prepared in a manner analogous to the procedure described by Poupaert et al. (*Synthesis,* 1972, 622) and illustrated in Scheme XIV. Acid chloride LIII is added to a cold mixture of 2-aminonitrile LIV and a base such as triethylamine in a non-protic solvent, such as THF, benzene, toluene or ether. The preferred temperature is 0° C. The mixture is stirred for 12–24 h and washed with water. The volatiles are removed and the product LV treated with ethylmercaptan and dry hydrogen chloride in dry methylene chloride for 5–30 min. The solid 5-imino-1,3-oxazole hydrochloride (LVI) is collected by filtration, dissolved in dry pyridine and the solution saturated with hydrogen sulfide during 4 h at $_0$° C. The mixture is diluted with an organic solvent and washed with water and dried. Removal of the volatiles provides the 5-amino-1,3-oxazole product (LVII) which may be carried forward without further purification or be purified by silica gel chromatography.

Scheme XIV

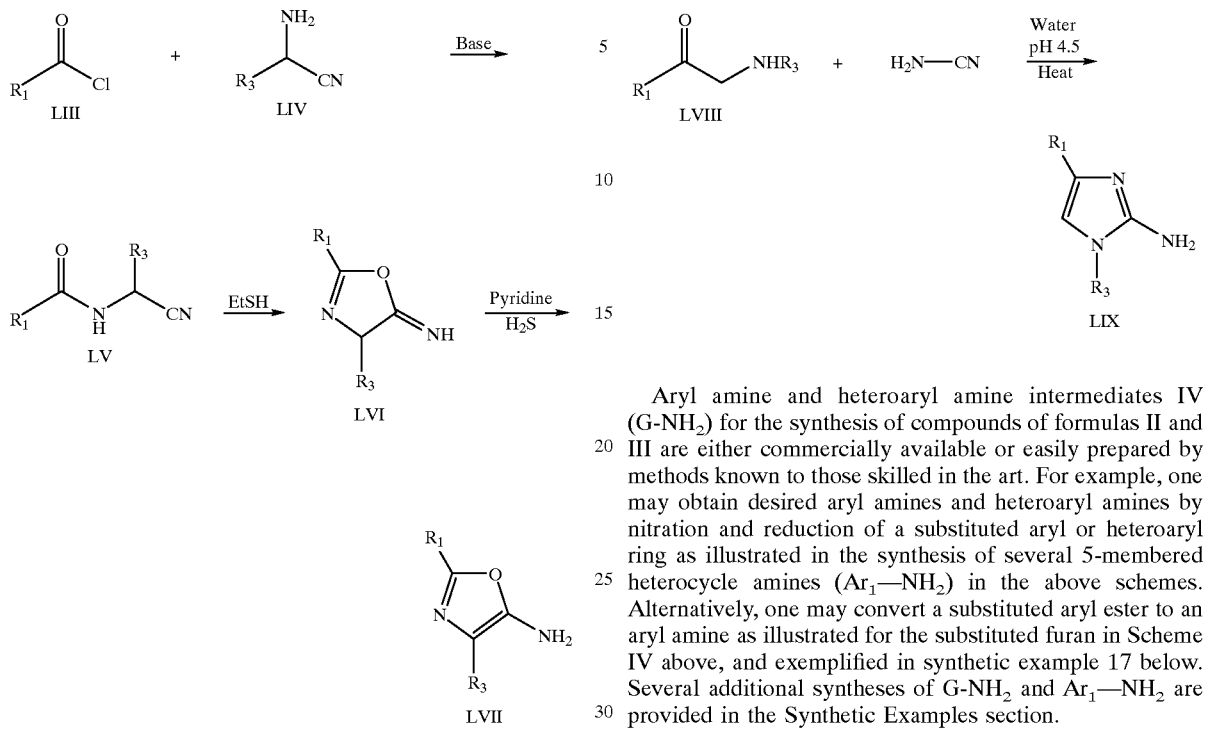

Scheme XV

The synthesis of 1,4-disubstituted-2-aminopyrazoles may be accomplished as illustrated in Scheme XV and described in Lancini et al., *J. Het. Chem.,* 1966, 3, 152. To a mixture of substituted aminoketone (LVIII) and cyanamide in water and acetic acid was added aqueous sodium hydroxide until pH 4.5 is reached. The mixture is heated at 50–90° C. for 1–5 hr, cooled and basicified with ammonium hydroxide. The product LIX is collected by filtration and dried.

Aryl amine and heteroaryl amine intermediates IV (G-NH$_2$) for the synthesis of compounds of formulas II and III are either commercially available or easily prepared by methods known to those skilled in the art. For example, one may obtain desired aryl amines and heteroaryl amines by nitration and reduction of a substituted aryl or heteroaryl ring as illustrated in the synthesis of several 5-membered heterocycle amines (Ar$_1$—NH$_2$) in the above schemes. Alternatively, one may convert a substituted aryl ester to an aryl amine as illustrated for the substituted furan in Scheme IV above, and exemplified in synthetic example 17 below. Several additional syntheses of G-NH$_2$ and Ar$_1$—NH$_2$ are provided in the Synthetic Examples section.

Methods by which intermediates V and VI (Scheme I, D'=Ar—X—Y—Z or Ar$_2$—X—Y—Z) may be prepared are described below. In Method K (Scheme XVI), a bromoarylamine LX, which may be commercially available or easily prepared by one skilled in the art, is reacted with a cycloalkenone LXI in the presence of a transition metal catalyst, for example a palladium(II) catalyst such as bis(triphenylphosphine)palladium(II) chloride, in the presence of a bis(triphenylphosphine) chelator, such as 1,2-bis(diphenylphosphino)ethane

Scheme XVI

Method K

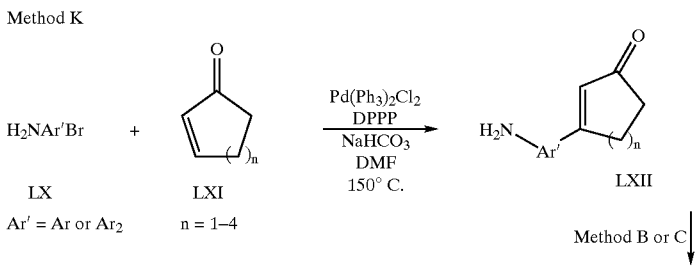

Ar' = Ar or Ar$_2$    n = 1–4

Method B or C

-continued

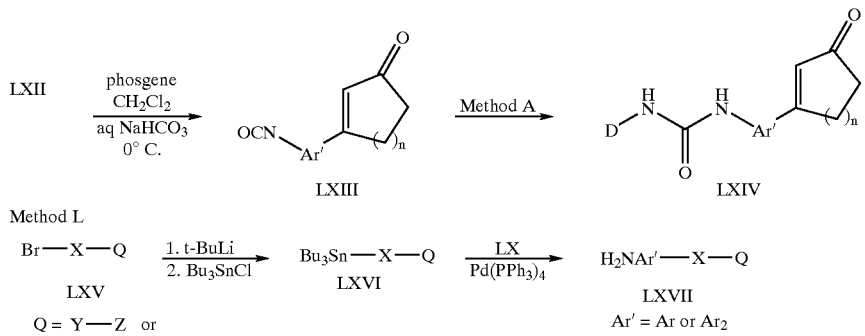

(DPPE), 1,1'-bis(diphenylphosphino)ferrocene (DPPF) and 1,3-bis(diphenylphosphino)propane (DPPP), preferably DPPP, and a base, preferably sodium bicarbonate, in a suitable solvent, preferably DMF at a temperature of about 150° C. to provide LXII. LXII may then be used (as VI) in Method B (Scheme 1), or converted to isocyanate LXIII by reaction with phosgene or a phosgene equivalent in the presence of a base, such as sodium bicarbonate in a suitable solvent such as dichloromethane, at a temperature of about 0° C., and used (as V) in Method A. The resulting product LXIV may be modified further by methods known by one skilled in the art to obtain desired compounds of formula I, as described in synthetic examples below.

In Method L, bromide LXV is reacted with a strong base, such as t-butyl lithium, in a suitable solvent, such as THF, with tributyltin chloride at a temperature of about −50° C. to −100° C., preferably about −78° C. to give LXVI. LXVI is then reacted with LX in a suitable solvent, such as THF or 1,4-dioxane, in the presence of a transition metal catalyst, preferably tetrakis(triphenylphosphine)palladium(0), at a temperature of about 50° C. to 150° C., preferably about 100° C. and in a sealed tube, providing LXVII. LXVII may then be used (as VI) in Method B or C (Scheme I), or converted to the corresponding isocyanate as described in Method K, and used (as V) in Method A.

Methods by which Y and Z may be joined to X are illustrated in Scheme XVII. As illustrated by Method M, if one desires a product in which Y includes an amino nitrogen bonded to X, an X containing a ketone may be reacted with a Y—Z containing a terminal primary or secondary amine under reductive amination conditions. For example, ketone LXIV is combined with a primary or secondary amine, in a suitable solvent such as THF. An acid, such as acetic acid, is added, followed by a suitable reducing agent, preferably sodium cyanoborohydride or sodium (triacetoxy) borohydride, to provide the desired product LXVIII.

Method N, illustrates a procedure for obtaining a methylene group for Y and a primary or secondary amine for Z. An X group bearing an aldehyde and a halogen, preferably bromine (LXIX), may be reacted with a primary or secondary amine under reductive amination conditions as described in Method M to provide LXX. This intermediate may then be used as described in Method L.

Scheme XVII

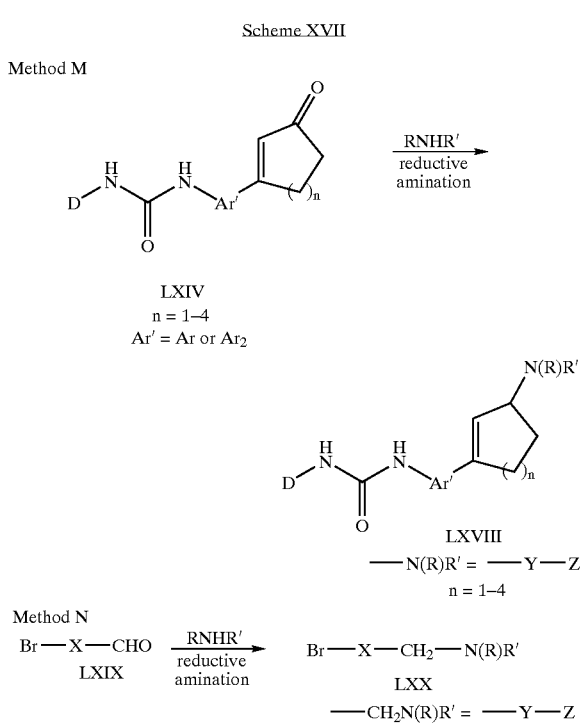

As in the cases described above, the synthesis of additional intermediates corresponding to V, VI and VII may be accomplished by methods similar to those described in the literature or known to those skilled in the art. Several examples are provided in the Synthetic Examples section below.

SYNTHETIC EXAMPLES

Example 1

1-[5-tert-Butyl-2-p-tolyl-2H-pyrazol-3-yl]-3-[4-(2-cyclohexenon-3-yl)naphthalen-1-yl]urea:

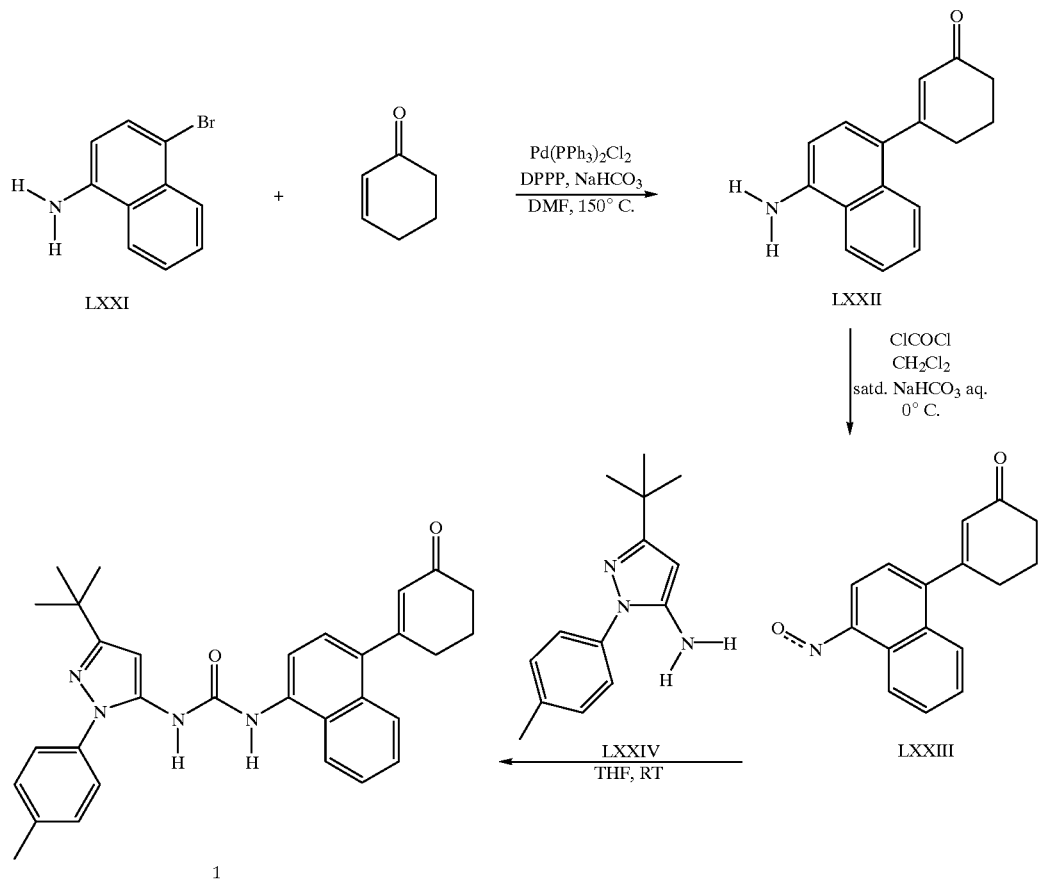

As outlined in Metheod K, a 350 mL sealed tube under inert atmosphere was charged with 4-bromo-1-naphthylamine (LXXI) (1.97 g; 8.9 mmol; 1 equiv.), 2-cyclohexenone (1.65 g; 17.2 mmol; 1.9 equiv.), sodium bicarbonate powder (2.17 g; 25.8 mmol; 2.9 equiv.), 1,3-bis(diphenylphosphino)propane (177 mg; 0.43 mmol; 0.05 equiv.), bis(triphenylphosphine)palladium(II) chloride (302 mg; 0.43 mmol; 0.05 equiv.) and DMF (degassed, 100 mL). The mixture was heated at 150° C. for 8 h. After cooling back to ambient temperature, the mixture was diluted with 100 mL EtOAc and filtered through diatomaceous earth. The solution was then transferred to a separatory funnel and washed with water (100 mL) and saturated brine (100 mL). After drylng with MgSO$_4$ the volatiles were removed in vacuo. The product was then purified by column chromatography using EtOAc (10 to 50%) in hexanes as eluent to provide 1.3 g material which was recrystallized from hot EtOAc/Hexanes to afford 800 mg LXXII (3.4 mmol; 38% yleld) as a dark brown solid. LXXII (100 mg; 0.42 mmol; 1 equiv.) was dissolved in methylene chloride (20 mL) and saturated aqueous sodium bicarbonate (20 mL) was added. The mixture was vigorously stirred at 0° C. for 15 min. The stirring was then stopped and phosgene (~2.0 M in toluene; 0.63 mL; 1.26 mmol; 3.0 equiv.) was added via syringe to the organic layer in one portion. Stirring was immediately resumed and continued at 0° C. for 20 min. The layers were then separated and the aqueous phase was extracted further with methylene chloride (1×25 mL). The combined organics were dried (Na$_2$SO$_4$), filtered and ¾ of the solvent removed in vacuo. This solution of isocyanate LXXIII was then immediately diluted with anhydrous THF (8 mL) and treated with LXXIV at room temperature (Method A). The mixture was left stirring under nitrogen overnight then MeOH (2 mL) was added and the volatiles removed in vacuo. The title compound 1 was thus obtained as an orange/red foam (200 mg; 0.41 mmol; 74%). This was recrystallized overnight from EtOAc twice to afford 49 mg of yellow crystals (mp: 168–170° C.).

Example 2

1-[5-tert-Butyl-2-p-tolyl-2H-pyrazol-3-yl]-3-{4-[3-(morpholin-4-yl)cyclohexen-1-yl]naphthalen-1-yl}urea:

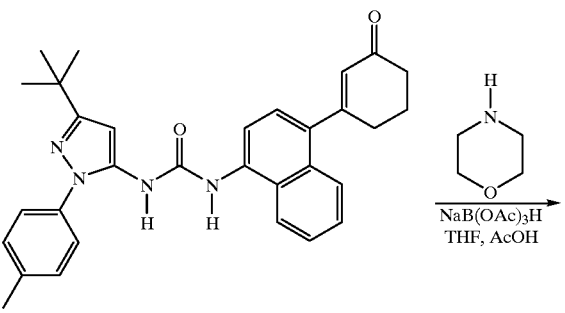

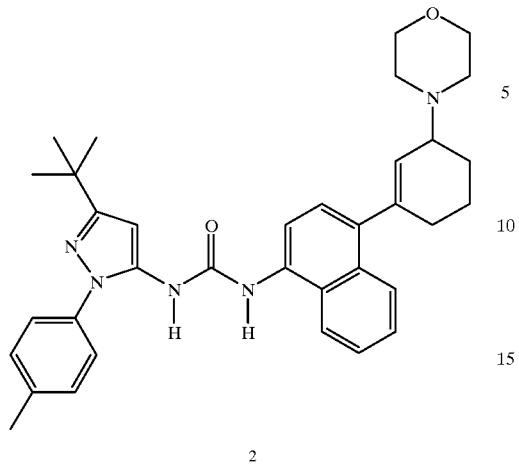

2

As described in Method M, the product from Example 1 (1) (93 mg; 0.19 mmol; 1 equiv.) and morpholine (30 uL; 0.34 mmol; 1.8 equiv.) were dissolved in 1.0 mL anhydrous THF and treated with acetic acid (16 uL; 0.28 mmol; 1.5 equiv.) and sodium (triacetoxy)borohydride (80 mg; 0.39 mmol; 2 equiv.). The reaction was stirred at room temperature for 2 days, then 5% aqueous NaOH solution (3 mL) was added and the reaction then extracted with EtOAc (3×3 mL). The combined organics were washed once with water, then brine, dried (Na$_2$SO$_4$), filtered and the solvents removed in vacuo. Column chromatography using EtOAc/hexanes as eluent afforded 64 mg of a tan foam (0.11 mmol; 60%). This was chromatographed a second time with 5% MeOH in methylene chloride to provide the title compound 2 as a light purple foam (50 mg).

Example 3

1-[5-tert-Butyl-2-p-tolyl-2H-pyrazol-3-yl]-3-{4-[5-(morpholin-4-ylmethyl)fur-2-yl]naphthalen-1-yl}urea

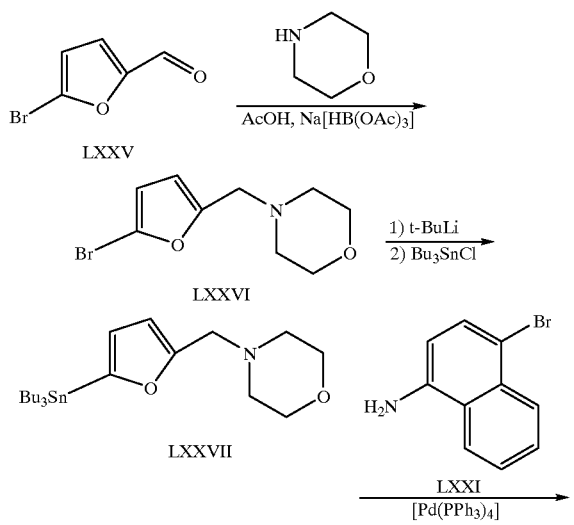

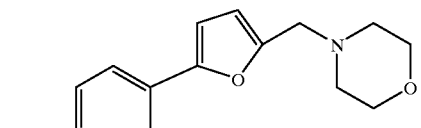

LXXVIII

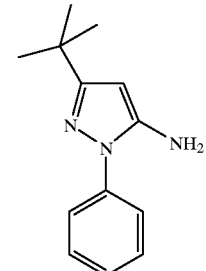

LXXIV

1) Ph(CO)Cl
2) LXXVIII
(Method C)

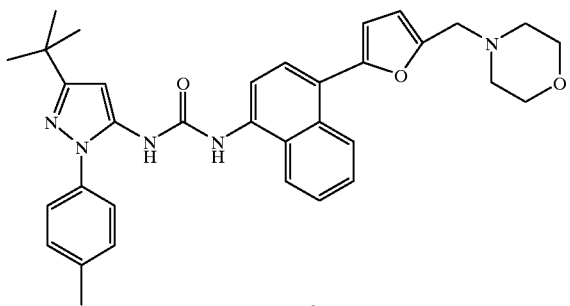

3

As described in Method N, to a mixture of 5-bromo-2-furaldehyde (LXXV) (1.76 g) and morpholine (1.00 ml) in 40 mL anhydrous THF at room temperature was added acetic acid (0.60 mL) followed by sodium triacetoxyborohydride (3.28 g). The mixture was stirred at room temperature for 3 h and then poured into a saturated solution of sodium bicarbonate (100 mL). After stirring vigorously for 5 min the layers were separated and the aqueous layer was extracted with EtOAc. The combined organic layers were washed with brine, dried (Na$_2$SO$_4$), filtered and evaporated to dryness. Purification of the residue by flash chromatography afforded 2.09 g (8.49 mmol, 84% yield) of LXXVI.

As illustrated by Method L, LXXVI (0.678 g, 2.76 mmol) was dissolved in 10 mL anhydrous THF under inert gas atmosphere and the solution was cooled to at −78° C. t-Butyllithium (4.0 mL of a 1.7 M solution in pentane) was added dropwise and the solution was stirred at −78° C. for 30 min. Tributyltinchloride (0.60 mL, 0.72 g, 2.2 mmol) was added and the solution was stirred for another 30 min at −78° C. pH7 Buffer (NaH$_2$PO$_4$/Na$_2$HPO$_4$ sat.) was added (10 mL) and the mixture was warmed to room temperature. The layers were separated and the aqueous layer was extracted with EtOAc. The combined organic layers were washed with brine, dried (Na$_2$SO$_4$), filtered and evaporated to dryness. Purification of the residue by flash chromatography afforded 0.526 g (1.15 mmol, 42% yield) of LXXVII.

As outlined in Method L, LXXVII (0.399 g, 0.874 mmol) and LXXI (0.200 g, 0.901 mmol) were dissolved in 10 mL anhydrous 1,4-dioxane in a sealable tube under inert gas atmosphere. The solution was degassed and purged with nitrogen (2×). Tetrakis(triphenylphosphine)palladium(0) (0.057 g, 0.049 mmol) was added and the solution was degassed and purged with nitrogen again (2×). The tube was sealed and heated to 100° C. for 24 h. After cooling to room temperature the mixture was diluted with EtOAc, saturated aqueous potassium carbonate solution (10 mL) was added and the mixture was stirred for 1 h at room temperature. The mixture was filtered over diatomaceous earth and the layers were separated. The aqueous layer was extracted with EtOAc. The combined organic layers were washed with brine, dried ($Na_2SO_4$), filtered an evaporated to dryness. Purification of the residue by flash chromatography afforded 0.314 g of a yellow oil, which contained LXXVIII along with tributyltin bromide. This mixture was used for the next step without further purification.

LXXVIII (0.283 g, 0.917 mmol) was reacted with the phenylcarbamate of LXXIV (0.395 g, 1.13 mmol) according to Method C. The product was purified by flash chromatography to give the title compound 3 as a yellow solid (0.338 g, 0.600 mmol, 65% yIeld) that was further purified by recrystallization to give 0.13 g of title compound 3 (mp. 144–146° C.).

Example 4

1-[5-tert-Butyl-2-p-tolyl-2H-pyrazol-3-yl]-3-{4-[6-(morpholin-4-ylmethyl)pyridin-3-yl]naphthalen-1-yl}urea:

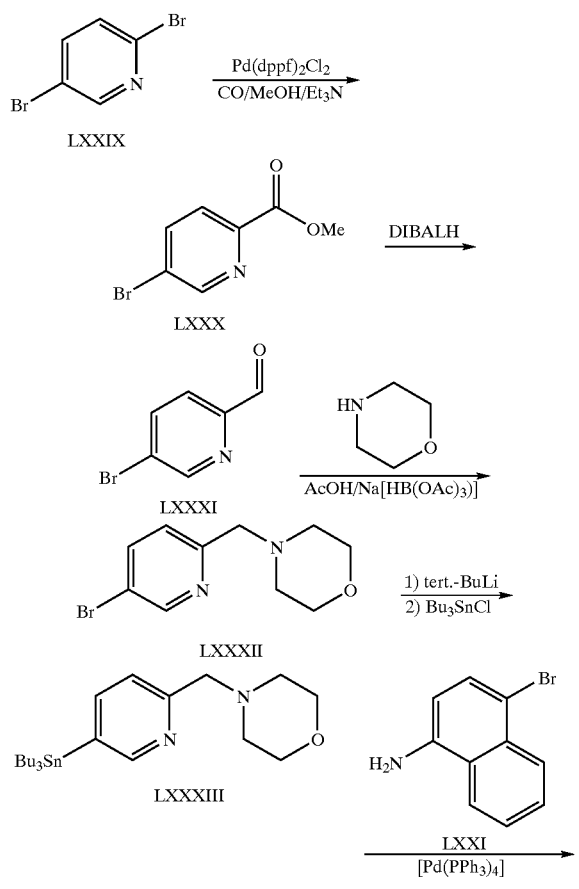

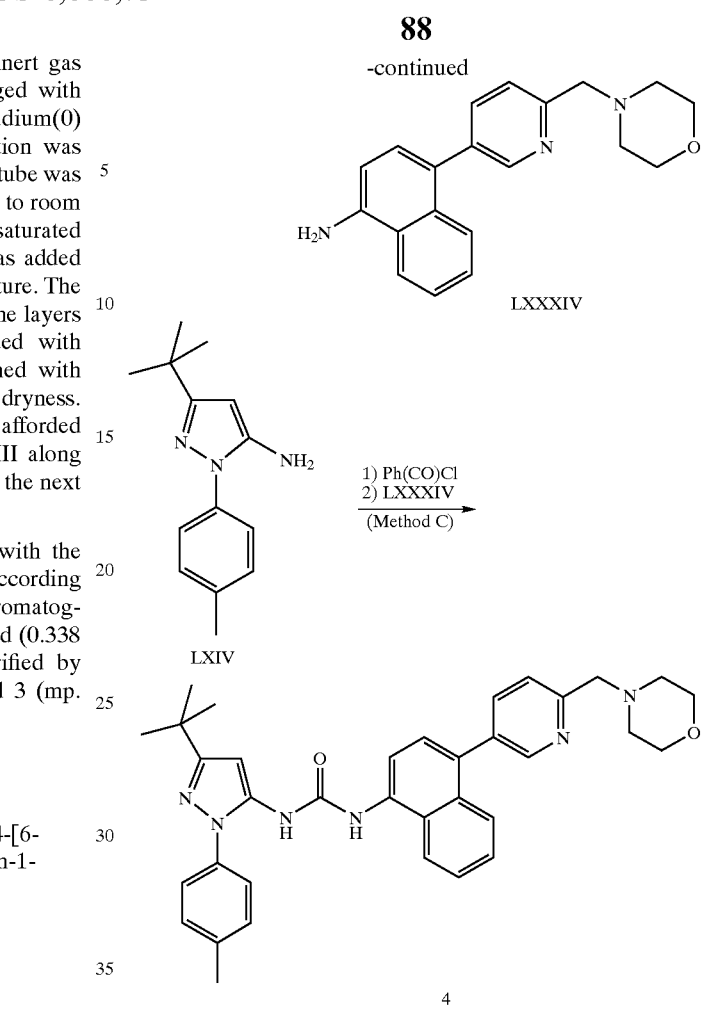

As described by R. J. Chambers and A. Marfat, (*Synthetic Communications*, 1997, 27, 515) a mixture of 2,5-dibromopyridine (LXXIX) (9.90 g, 41.78 mmol), Pd(dppf) $C_2$(1.51 g, 1.85 mmol), anhydrous MeOH (40 mL), anhydrous DMF (40 mL) and anhydrous triethylamine (12 mL) was purged in a Parr apparatus with a stream of carbon monoxide for 10 min and then stirred under 80 psi carbon monoxide at 50° C. for 4 h. The mixture was diluted with EtOAc (600 mL) and washed with water (2×100 mL) and brine (1×100 mL), dried (sodium sulfate), filtered and evaporated to dryness. The residue was purified by flash chromatography on silica gel (40% EtOAc in hexanes) to give LXXX as a light orange solid (3.733 g, 17.28 mmol, 41%).

To a solution of compound LXXX (165.9 mg, 0.7679 mmol) in anhydrous THF (10 mL) at −78° C. was added dropwise diisobutylaluminum hydride (1.0 M in THF) (2.0 mL, 2.0 mmol). The mixture was stirred at −78° C. for 2 h, then saturated potassium carbonate (0.6 mL) solution was added, the mixture was warmed to room temperature and stirred for another 30 min. Sodium sulfate was added and the mixture was stirred for 10 min. The solids were removed by filtration and the filtrate was evaporated to dryness. The residue was purified by flash chromatography on silica gel (20% EtOAc in hexanes) to give aldehyde LXXXI as a white solid (80 mg, 0.43 mmol, 56%).

To a solution of LXXXI (367.7 mg, 2.0 mmol) in anhydrous 1,2-dichloroethane (10 mL) was added morpholine (0.20 mL, 0.20 g, 2.3 mmol), followed by glacial acetic acid (0.12 mL, 0.13 g, 2.1 mmol) and sodium triacetoxyborohydride (625 mg, 2.95 mmol). The mixture was stirred at room temperature for 30 min. A saturated solution of sodium bicarbonate (10 mL) was added and the mixture was stirred vigorously for another 30 min. The layers were separated and the aqueous layer was extracted with EtOAc (3×20 mL). The combined organic layers were washed with brine, dried (sodium sulfate), filtered and evaporated to dryness. Flash chromatography (1% triethylamine in EtOAc) of the residue gave LXXXII as a light yellow oil (460.8 mg, 1.79 mmol, 91%).

To a solution of tert-butyllithium (1.42 M in pentane) (2.80 mL, 3.98 mmol) in anhydrous THF (20 mL) at −78° C. was added dropwise a solution of LXXXII (460.8 mg, 1.792 mmol) in anhydrous THF (10 mL) and the mixture was stirred at −78° C. for 10 min. Tributyltin chloride (0.49 mL, 0.59 g, 1.8 mmol) was added and the mixture was stirred at −78° C. for another 15 min. pH 7 Buffer (Na$_2$HPO$_4$/NaH$_2$PO$_4$ sat.) (10 mL) was added and the mixture was warmed to room temperature. The layers were separated and the aqueous layer was extracted with EtOAc (3×20 mL). The combined organic layers were washed with brine, dried (sodium sulfate), filtered and evaporated to dryness. Flash chromatography (EtOAc) of the residue gave LXXXIII as colorless oil (548.8 mg, 1.17 mmol, 65%).

A degassed solution of LXXXIII (302 mg, 0.646 mmol), LXXI (177 mg, 0.797 mmol) and Pd(PPh$_3$)$_4$ (55 mg, 0.48 mmol) in anhydrous 1,4-dioxane (10 mL) was heated to 100° C. in a sealed tube for 16 h. The black precipitate was removed by filtration and the tube was washed with EtOAc. The combined filtrates were stirred with potassium fluoride solution (40%) (10 mL) for 30 min. Water and brine were added, the layers were separated and the aqueous layer was extracted with EtOAc (4×50 mL). The combined organic layers were washed with brine, dried (sodium sulfate), filtered and evaporated to dryness. Flash chromatography (5% MeOH and 1% triethylamine in EtOAc) of the residue gave LXXXIV as a light brown solid (157.6 mg, 0.49 mmol, 76%).

LXXXIV and the phenyl carbamate of LXIV were reacted according to Method C. Purification by flash chromatography using 5% MeOH and 1% triethylamine in EtOAc as the eluent followed by recrystallization from EtOAc/hexanes gave the title compound 4 as a white solid (mp. 169–170° C.).

Example 5

1-[5-tert-Butyl-2-p-tolyl-2H-pyrazol-3-yl]-3-{4-[3-(morpholin-4-yl)phenyl]naphthalen-1-yl} urea

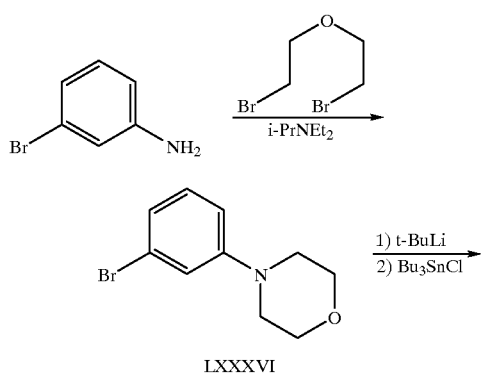

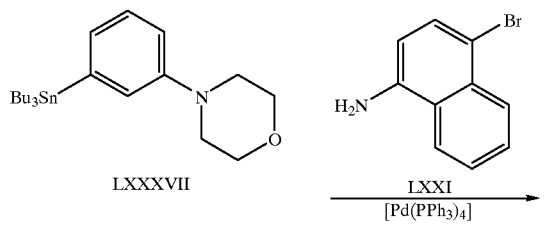

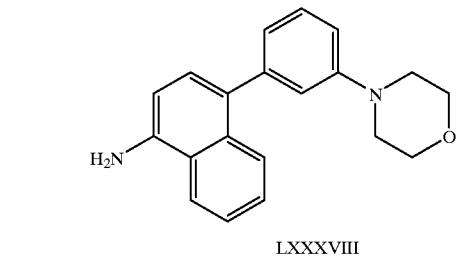

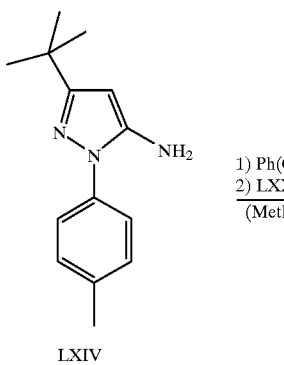

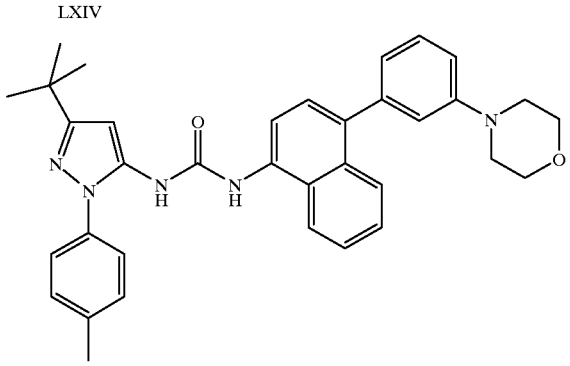

3-Bromoaniline (3.0 mL, 4.7 g, 28 mmol), 2-bromoethylether (4.2 mL, 7.7 g, 33 mmol) and diisopropylethylamine (15 mL, 11 g, 86 mmol) were dissolved in anhydrous DMF (20 mL) under inert gas atmosphere and heated to 100° C. for 6 h. After cooling to room temperature the mixture was poured into water (300 mL) and extracted with EtOAc. The combined organic layers were washed with brine, dried (Na$_2$SO$_4$), filtered and evaporated to dryness. Purification of the residue by flash chromatography afforded 2.9 g (12 mmol, 43% yleld) of LXXXVI LXXXVI (1.73 g, 7.13 mmol) was dissolved in anhydrous THF (30 mL) and cooled to −78° C. t-Butyllithium (10.0 mL of a 1.7 M solution in pentane) was added dropwise and the solution was stirred at −78° C. for 30 min. Tributyltinchloride (1.90 mL, 2.28 g, 7.00 mmol) was added and the solution was stirred for another 45 min at −78° C. pH 7 Buffer (NaH$_2$PO$_4$/Na$_2$HPO$_4$ sat.) was added (10 mL) and the mixture was warmed to room temperature. The layers were separated and the aqueous layer was extracted with EtOAc. The combined organic layers were washed with brine, dried ($Na_2SO_4$), filtered an evaporated to dryness. Purification of the residue by flash chromatography afforded 2.28 g (5.36 mmol, 77% yleld) of LXXXVII.

LXXXVII (1.49 g, 3.51 mmol) and LXXI (0.69 g, 3.11 mmol) were dissolved in 20 mL anhydrous 1,4-dioxane in a sealable tube under inert gas atmosphere. The solution was degased and purged with nitrogen (2×). Tetrakis(triphenylphosphine)palladium(0) (0.21 g, 0.18 mmol) was added and the solution was degassed and purged with nitrogen again (2×). The tube was sealed and heated to 100° C. for 17 h. After cooling to room temperature the mixture was diluted with EtOAc, saturated aqueous potassium carbonate solution (10 mL) was added and the mixture was stirred for 1 h at room temperature. The mixture was filtered over diatomaceous earth and the layers were separated. The aqueous layer was extracted with EtOAc. The combined organic layers were washed with brine, dried ($Na_2SO_4$), filtered and evaporated to dryness. Purification of the residue by flash chromatography afforded 0.363 g (1.19 mmol, 38%) of LXXXVIII.

LXXXVIII (0.360 g, 1.18 mmol) was reacted with the phenylcarbamate of LXIV (0.69 g, 1.97 mmol) according to Method C. The product was purified by flash chromatography to give a colorless solid (0.433 g, 0.77 mmol, 66% yield) that was further purified by recrystallization from EtOAc—hexanes to give 0.344 g of the title compound 5 (mp. 188–190° C.).

Table 1 illustrates additional compounds of the invention, which were prepared by methods analogous to those described above.

Example 16

1-[4-(6-{[Bis-(2-cyanoethyl)amino]methyl}pyridin-3-yl)naphthalen-1-yl]-3-(5-tert-butyl-2-methylphenyl)urea

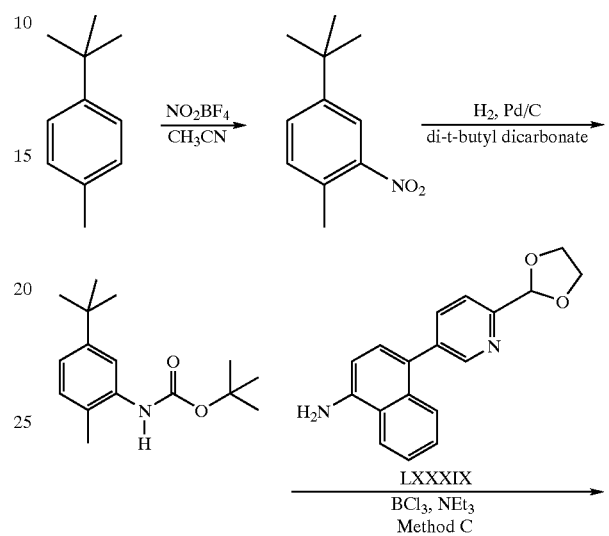

TABLE 1

| Ex. No. | $R_1$ | $R_3$ | $X^a$ | $Y^b$ | $Z^c$ | m.p. ° C. |
|---|---|---|---|---|---|---|
| 6 | t-Bu | 4-MePh | Phenyl | 4-$CH_2$ | 4-morpholinyl | 146–148 |
| 7 | t-Bu | 4-MePh | Phenyl | 3-$CH_2$ | 4-morpholinyl | 120–122 |
| 8 | t-Bu | 4-MePh | Phenyl | Bond | $4^d$-(4-morpholinyl) | >230 |
| 9 | t-Bu | 4-MePh | Phenyl | 4-$CH_2$ | 4-morpholinyl | 183–186 |
| 10 | t-Bu | 4-MePh | Phenyl | 4-$CH_2$ | $NMe_2$ | 108–114 |
| 11 | t-Bu | 4-MePh | 2-pyridyl | 5-$CH_2$ | 4-morpholinyl | foam |
| 12 | t-Bu | 4-MePh | 1-cycloheptenyl | Bond | $3^d$-(4-morpholinyl) | 133–135 |
| 13 | t-Bu | 6-Me-3-pyridyl | 3-pyridyl | 6-($CH_2$) | 4-morpholinyl | 162–165 |
| 14 | t-Bu | Me | 3-pyridyl | 6-($CH_2$) | 4-morpholinyl | foam |
| 15 | t-Bu | 6-Me-3-pyridyl | 1-cyclohexenyl | 3-[NH—($CH_2$)$_2$] | 4-morpholinyl | |

[a] number refers to position on X that is bonded to napthalene ring ($Ar_2$).
[b] number refers to position on X that Y is bonded to.
[c] number refers to position on Z that is bonded to Y (or X if Y is a bond).
[d] refers to position on X that Z is bonded to.

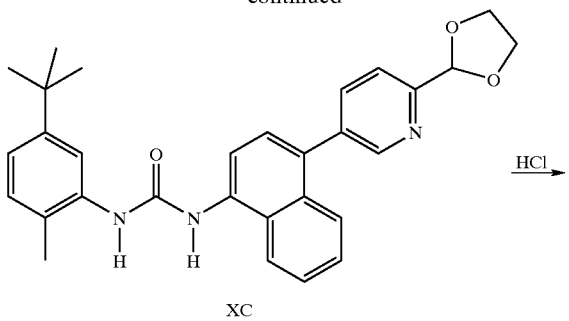

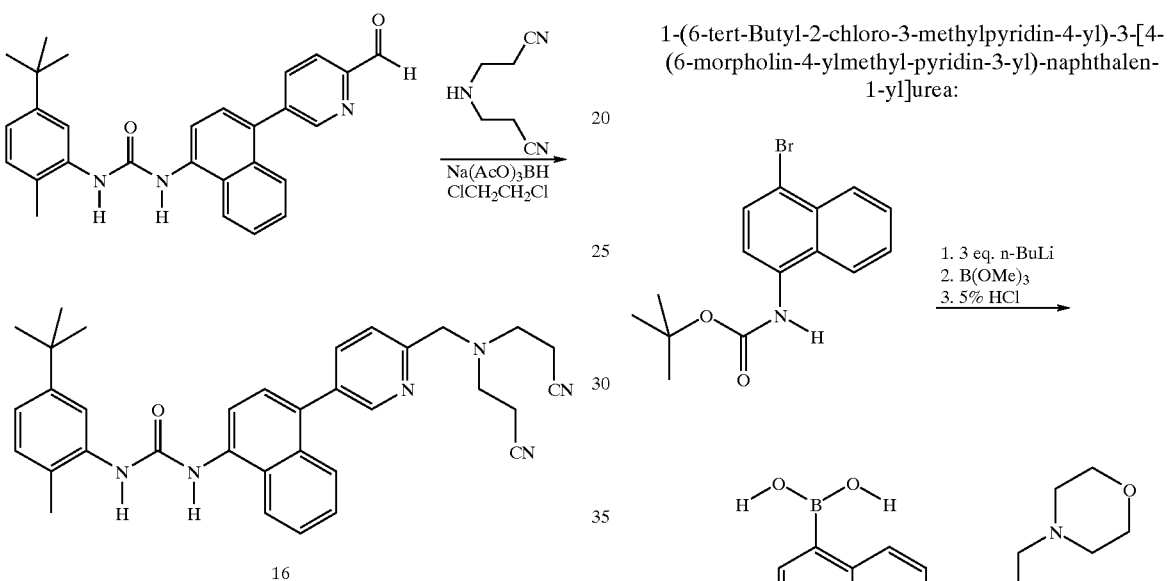

extracts were washed with brine and dried (MgSO$_4$). Removal of the volatiles in vacuo left a residue; flash chromatography using 10% MeOH/EtOAc as eluent provided 300 mg of the desired urea XC.

This urea was subjected to acidic conditions to remove the acetal which exposed the aldehyde functionality. In 1,2-dichloroethane, 1.25 equivalents of bis(2-cyanoethyl)amine were added to this aldehyde followed by the addition of sodium triacetoxyborohydride (1.5 equivalents). After column chromatography (5% MeOH/EtOAc), the title compound 16 was obtained.

Example 17

1-(6-tert-Butyl-2-chloro-3-methylpyridin-4-yl)-3-[4-(6-morpholin-4-ylmethyl-pyridin-3-yl)-naphthalen-1-yl]urea:

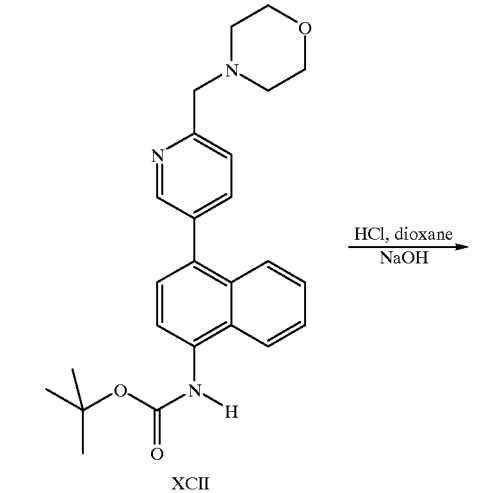

To a solution of 4-tert-butyl toluene (33.7 mmol) in acetonitrile (150 mL) at 0° C. was added nitronium tetrafluoroborate (40.5 mmol). After 30 min at room temperature, the reaction was diluted with water (50 mL) and extracted with EtOAc (3×30 mL). The combined organic extracts were washed with brine and dried (MgSO$_4$). Removal of the volatiles in vacuo left a residue; flash chromatography using 10% methylene chloride/petroleum ether as eluent provided 4-tert-butyl-2-nitrotoluene.

4-tert-Butyl-2-nitrotoluene (1.1 mmol) was dissolved in DMF (10 mL). The catalyst (10% Pd/C, 5 mg) was added followed by the addition of di-tert-butyl dicarbonate (1.4 mmol). The system was purged with argon then exposed to H$_2$ (1 atm) for 12 h. The mixture was filtered over a pad of diatomaceous earth; the filtrate was diluted with water and extracted with EtOAc (3×10 mL). The combined organic extracts were washed with brine and dried (MgSO$_4$). N-Boc-5-tert-butyl-2-methylaniline was obtained as a crystalline solid, 265 mg, after the evaporation of volatiles.

To a mixture of N-boc-5-tert-butyl-2-methylaniline (0.8 mmol) and triethylamine (0.22 mol) in benzene (10 mL) at room temperature was added via syringe boron trichloride (0.4 mmol). The resulting heterogenous mixture was stirred at 80° C. for 30 min. The heat source was removed, and aminonaphthalene LXXXIX was added (0.7 mmol). The reaction mixture was stirred at room temperature for 16 h. The reaction mixture was diluted with water (10 mL) and extracted with EtOAc (3×10 mL). The combined organic

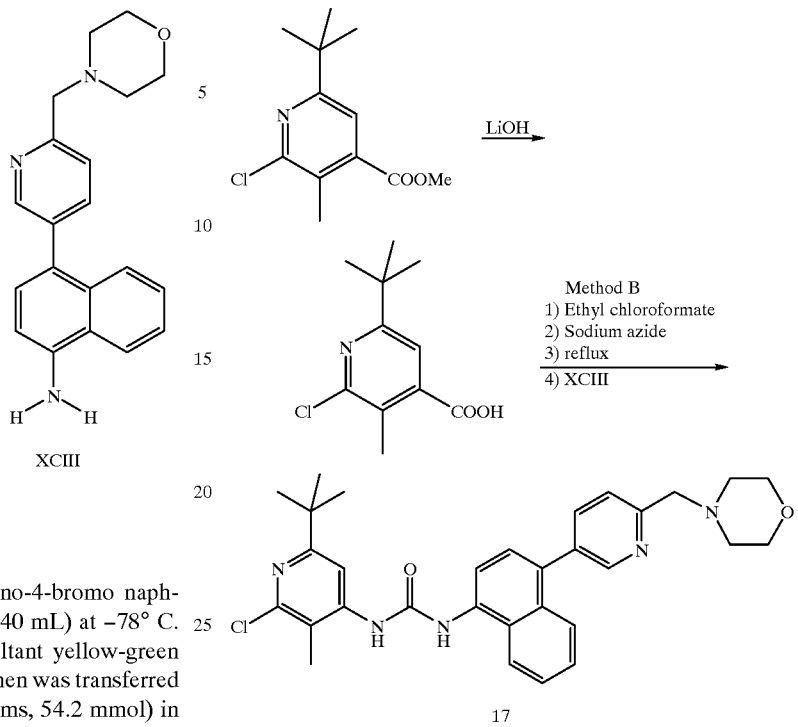

To a stirred solution of N-Boc-1-amino-4-bromo naphthalene (15.5 mmol) in anhydrous THF (40 mL) at −78° C. was added n-BuLi (47 mmol). The resultant yellow-green solution was stirred at −78° C. for two h then was transferred to a solution of trimethylborate (5.64 grams, 54.2 mmol) in anhydrous THF (25 mL) at −42° C. The reaction was allowed to warm to room temperature overnight as the bath warmed. After stirring for 16 h, 5% aqueous HCl was added (25 mL) and the mixture was stirred for 15 min. The aqueous layer was saturated with NaCl and the layers were separated. The aqueous portion was extracted with diethyl ether (3×60 mL) and the combined organics were extracted with 0.5 M NaOH (6×30 mL). The combined basic extracts were acidified to pH∼2 with 3 M HCl (∼30 mL) and the suspension was extracted with diethyl ether (3×100 mL). The combined ethereal extracts were dried (MgSO$_4$), filtered and the solvent was removed to afford the boronic acid XCI as a beige solid (2.3 g) which was used without further purification.

5-Bromo-2-(morpholin-4-ylmethyl)pyridine (0.70 mmol) and XCI (0.70 mmol) were dissolved in a biphasic mixture of dimethoxyethane (2 mL) and 2 M aq. Na$_2$CO$_3$ (1 mL). The reaction was purged with a stream of N$_2$ for 15 min, the Pd catalyst was added, and the mixture was heated at 85° C. for 16 h. The reaction was cooled to room temperature and was partitioned between water (10 mL) and EtOAc (75 mL). The layers were separated and the organic portion was washed with brine (20 mL), dried (MgSO$_4$), filtered and the solvent was removed to afford a brown solid. Column chromatography afforded the product XCII as a beige solid.

XCII (0.50 mmol) was dissolved in 2 mL anhydrous dioxane and HCl was added (2.5 mmol). The solution was stirred at room temperature for 16 h. To the resultant suspension was added diethyl ether (5 mL) and the mixture was chilled to 0° C. Neutralization with aq. NaOH and filtration afforded 4-[6-(morpholin-4-ylmethyl)pyridin-3-yl]-1-aminonaphthalene (XCIII) as a light brown solid (100 mg).

A mixture of 2-t-butyl-6-chloro-5-methylpyridine-4-carboxylic acid methyl ester (2.27 g, 9.39 mmol) and LiOH monohydrate (2.36 g, 56.3 mmol) in MeOH (30 mL) and water (10 mL) was stirred at room temperature for 24 h. The reaction was then concentrated and purified by chromatography on silica gel (eluent: 5% TFA in dichloromethane) to give the corresponding carboxylic acid (1.41 g, 66.3%).

To a stirred solution of the above carboxylic acid (0.54 g, 2.36 mmol) and triethylamine (0.66 mL, 4.75 mmol) in THF (6 mL) at −10° C. was added dropwise ethyl chloroformate (0.34 mL, 3.51 mmol). The resulting mixture was stirred at 0° C. for 1 h. A solution of sodium azide (0.40 g, 6.0 mmol) in water (2 mL) was added and stirring was continued for another 1 h. The mixture was extracted with toluene. The organic phase was separated, dried with sodium sulfate, and concentrated to 15 mL. It was then heated at reflux for 2 h forming the isocyanate in situ, before a solution of XCIII (0.39 g, 1.23 mmol) in dichloromethane (5 mL) was added. The reaction was stirred at room temperature overnight. Concentration and chromatography on silica gel (eluent: EtOAc) afforded the title compound 17 (0.60 g, 89.9%).

Example 18

1-(5-tert-Butyl-2-methylphenyl)-3-(4-{6-[(3-methoxypropyl)methylamino]pyridin-3-yl}naphthalen-1-yl)urea

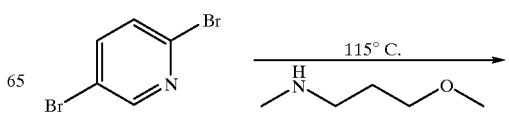

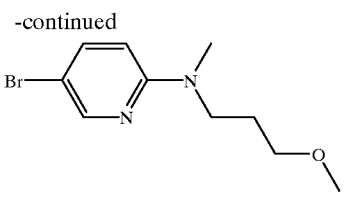
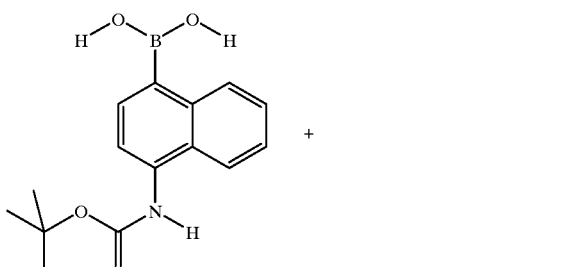
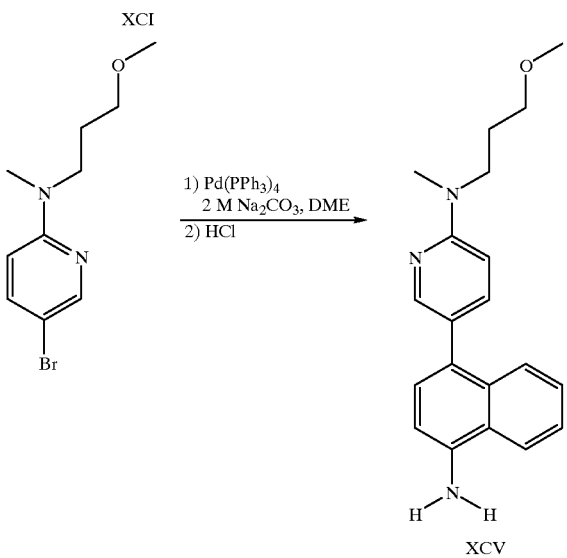
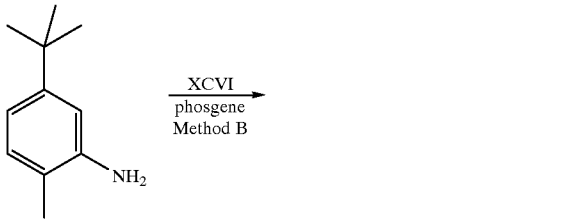
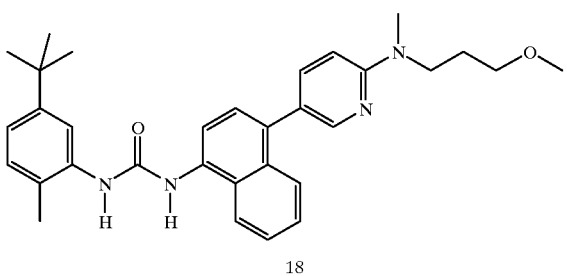

2,5-Dibromopyridine (100 mg) was heated to 115° C. in a sealed tube in the presence of 3-methoxypropyl-1-methylamine (2 mL) for 48 h to give XCIV. A Suzuki coupling of XCIV with XCI and removal of the tert-butyl carbamate (analogous to the procedures in Example 17) afforded the desired naphthylamine XCV.

5-tert-Butyl-2-methylaniline (0.56 mmol) was dissolved in dichloromethane (20 mL). An equal volume of sat. aqueous sodium bicarbonate was added, and the biphasic solution was cooled to 0° C. During the addition of phosgene (1.93 M in toluene, 0.80 mL), stirring was stopped. Immediately afterward, stirring was resumed for 15 min with the reaction mixture at 0° C. The layers were separated, the organics were dried over solid magnesium sulfate, and concentrated to approximately 5 mL of solution. The desired naphthylamine (XCVI, 0.47 mmol) in 5 mL dichloromethane was added. The reaction mixture was stirred at room temperature for 16 h. Flash chromatography using 7% MeOH/EtOAc as eluent followed with trituration with ether provided the title compound 18.

Example 19

1-[4-(6-Morpholin-4-ylmethylpyridin-3-yl)naphthalen-1-yl]-3-(3-triffuoromethyl-phenyl)urea

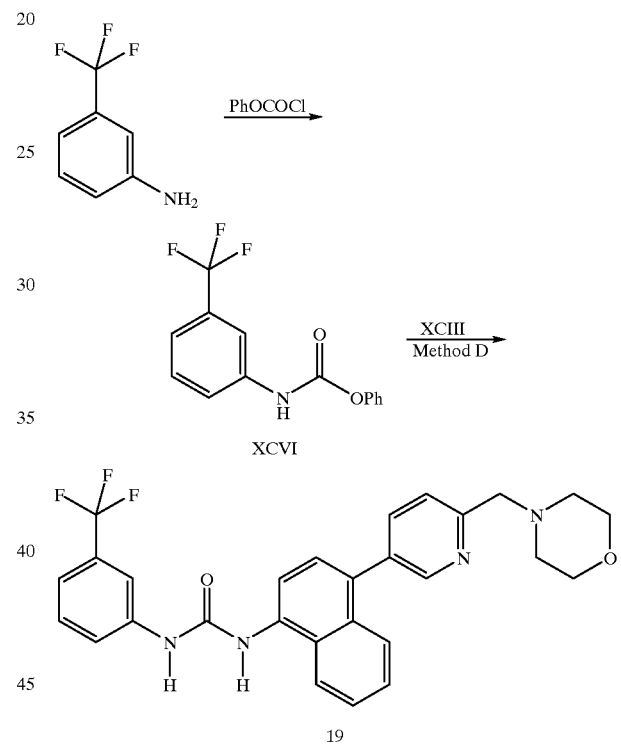

A stirred solution of 3-trifluoromethylaniline (4.7 mmol) in dry THF (30 mL) at 0° C. was treated with phenyl chloroformate (4.8 mmol). After 2 h, the reaction mixture was quenched with aqueous, saturated sodium bicarbonate solution and extracted with EtOAc. The combined organic layers were washed with aqueous, saturated sodium bicarbonate solution and brine, and were dried over solid MgSO$_4$. Concentration afforded the carbamate XCVI (97%). A mixture of XCIII (Example 17) (0.06 mmol) and the above-mentioned carbamate (0.05 mmol) was heated in a sealed tube for 2 days. The reaction mixture was cooled to room temperature. PS-trisamine (100 mg, Argonaut) and PS-isocynate resins (150 mg, Argonaut) were added, and the reaction mixture was shaken for 3 days. The reaction mixture was filtered and concentrated to provide the title compound 19.

Examples 20–25 exemplify the synthesis of aryl and heteroaryl amines which may be used as intermediate IV in Methods A–C (General Synthetic Methods) to prepare compounds of formula II or III.

Example 20

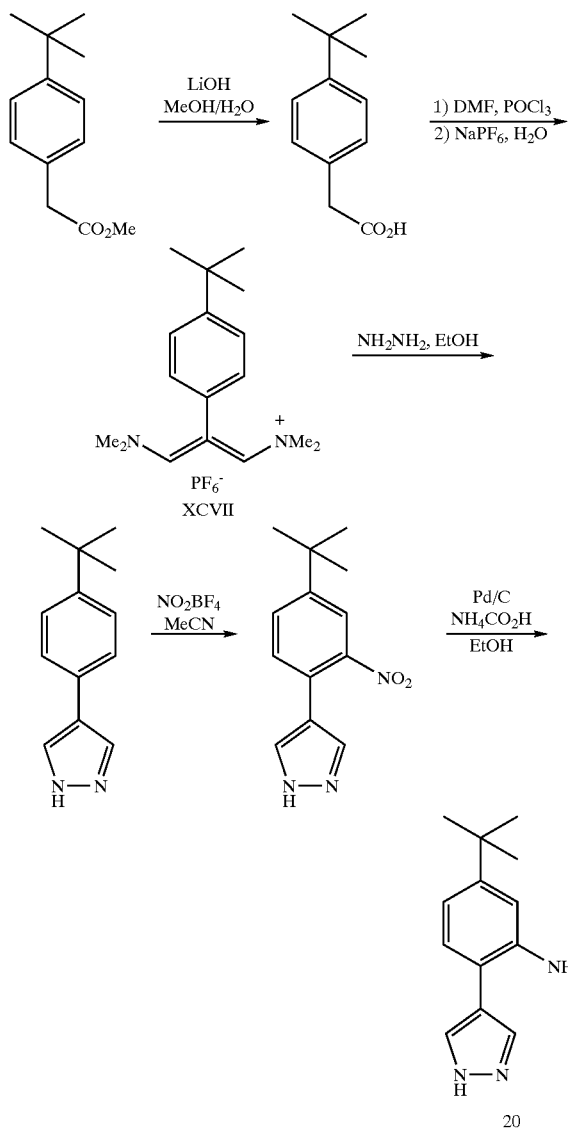

Methyl 4-t-butylphenylacetate (20 mmol) was dissolved in MeOH (160 mL) and treated with water (40 mL) and LiOH monohydrate (30 mmol). The reaction was allowed to stir at room temperature overnight. Volatiles were removed under reduced pressure; the remaining residue was diluted with water and neutralized to pH 4 with 1 N sulfuric acid. The resulting solids were filtered, washed with water and dried to leave 4-t-butylphenylacetic acid as an off-white solid (3.8 g, 99%). Anhydrous DMF (139 mmol) was cooled to 0° C. and treated with $POCl_3$ (79.6 mmol). After 5 min, 4-t-butylphenylacetic acid (19.9 mmol) was added and the reaction vessel was transferred to a 110° C. oil bath. The reaction mixture was stirred for 2 h, during which all solids dissolved. After cooling to room temperature, the reaction mixture was poured into a stirred solution of $NaPF_6$ (19.8 mmol) in water (200 mL). When precipitation of solids was complete, they were filtered, washed with water, and dried to give XCVII (7.8 g, 97%).

XCVII (5 mmol) was taken up in EtOH (50 mL), and the resulting suspension was treated with hydrazine hydrate (5 mmol). The reaction vessel was transferred to a 90° C. oil bath, and the reaction mixture was stirred at reflux for 2 h. Volatiles were removed under reduced pressure after allowing the reaction mixture to cool to room temperature. The residue was taken up in ice water, solids were filtered, washed with water and dried, giving 4-(4-t-butylphenyl)pyrazole (973 mg, 97%).

4-(4-t-butylphenyl)pyrazole (0.5 mmol) was suspended in MeCN (2 mL), cooled to 0° C., and treated with $NO_2BF_4$ (0.6 mmol). The reaction mixture was allowed to warm slowly to room temperature and was stirred at RT for 2 h. Volatiles were removed under reduced pressure after the reaction was quenched with aqueous $NaHCO_3$. The residue was taken up in water and extracted with $CH_2Cl_2$. The organics were combined, dried over $MgSO_4$, and concentrated to leave a yellow oil which was chromatographed on silica gel (eluent: $CH_2Cl_2$/EtOAc, 6:4) to give 4-(4-t-butyl-2-nitrophenyl)pyrazole as a yellow crystalline solid (71 mg, 58%).

4-(4-t-butyl-2-nitrophenyl)pyrazole (0.27 mmol) was dissolved in EtOH (3 mL) and treated with 10% Pd/C (0.2 eq by weight of nitro compound), followed by $NH_4CO_2H$ (2.7 mmol). After 30 min, the catalyst was filtered through a bed of diatomaceous earth, and the filtrate was concentrated under reduced pressure. The residue was taken up in water, the resulting solids were filtered, washed with water and dried (54 mg, 93%), giving the title compound 20.

Example 21

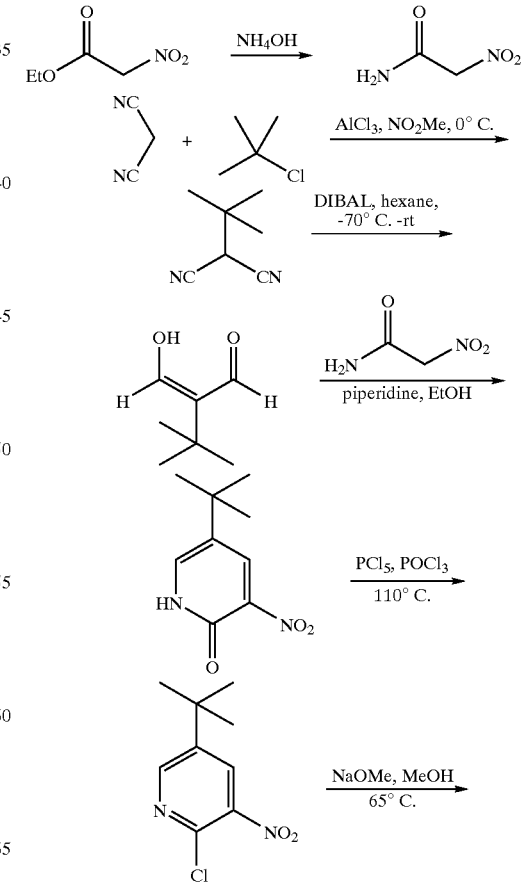

-continued

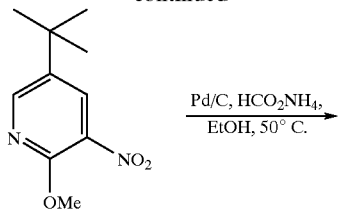

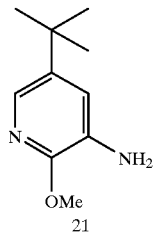
21

Ethyl nitroacetate (3.3 mL, 4.0 g, 29.7 mmol) was added to ammonium hydroxide (25 mL, 11%) and stirred overnight as described by A. V. Amet et al., *Russian Chemical Bulletin*, 1996, 45(2), 393–398. the reaction was basified with 4 N hydrochloric acid, extracted into ether (3×25 mL), then into EtOAc (3×100 mL). The combined EtOAc extracts were dried (magnesium sulfate), filtered and evaporated to dryness to afford nitroacetamide as a pale yellow solid (1.7 g, 16.3 mmol, 55%).

Trichloroaluminum (45.5 g, 341 mmol) was added slowly to 100 mL of ice cold nitromethane under nitrogen. This was followed by a solution of malononitrile (21.5 mL, 22.6 g, 341 mmol) in 50 mL of nitromethane added dropwise over one hour, keeping the temperature below 10° C. Next, a solution of tert-butyl chloride (88 mL, 74.9 g, 809 mmol) in 25 mL of nitromethane was added slowly over 2.5 h, keeping the temperature under 10° C. The reaction was capped and stored in the freezer for 60 h. The reaction was quenched by adding saturated aqueous sodium bicarbonate (500 mL) dropwise over 4 h, keeping the temperature below 10° C. The heterogeneous mixture was neutralized further with solid sodium bicarbonate (50 g). The layers were separated and the aqueous layer extracted with methylene chloride (3×250 mL). The combined organic extracts were dried (magnesium sulfate) and concentrated in vacuo to afford 42 g of a partially crystalline brown oil. The residue was vacuum distilled at 100° C. The first fraction was collected and then a solid began to form in the condenser. The cooling water was turned off and the condenser heated with a heat gun to melt the solid. This fraction was collected until no more solid formed in the condenser when cool water was run through it to afford the desired dinitrile as a low melting cream solid (19 g, 155 mmol, 46%).

A solution of the above dinitrile (961 mg, 7.9 mmol) in anhydrous hexanes (50 mL) was cooled to −70° C. in a dry ice/acetone bath under nitrogen. DIBAL-H (17.5 mL, 1.0 M in cyclohexane) was added dropwise over 20 min. The mixture was stirred at −70° C. for 45 min, then at room temperature for 5 h. The reaction was cooled to 0° C., 2 M aqueous hydrochloric acid (45 mL) was added slowly, keeping the temperature below 10° C. The mixture was stirred at room temperature for 15 h. The layers were separated and the aqueous layer extracted with ether (3×25 mL). The combined organic extracts were dried (magnesium sulfate), filtered and evaporated to dryness to afford the desired dialdehyde as a viscous yellow oil (600 mg, 4.68 mmol, 60%).

A solution of the above aldehyde (271 mg, 2.11 mmol), nitroacetamide (223 mg, 2.14 mmol), and piperidine (20% in EtOH) (250 uL, 0.51 mmol) in absolute EtOH (3 mL) was heated at 65° C. for 3 h. After cooling to room temperature, the reaction mixture was concentrated in vacuo. The residue was purified by flash chromatography on silica gel (EtOAc) to give the desired nitropyridone as a yellow solid (280 mg, 1.43 mmol, 67%).

A mixture of the nitropyridone (150 mg, 0.76 mmol), phosphorous pentachloride (199 mg, 0.96 mmol) and phosphorous oxychloride (1 drop) was heated to reflux in a sealed tube. After 2 h, the phosphorous oxychloride was removed in vacuo and the residue stirred in ice water (10 mL) for 18 h. The desired product was collected as a brown solid (95 mg, 0.44 mmol, 58%).

To a solution of 2-chloro-3-nitro-5-tert-butyl pyridine (30 mg, 0.14 mmol) in anhydrous MeOH (1.5 mL) under nitrogen was added a solution of sodium methoxide (1.57 g sodium in 40 mL anhydrous MeOH) (85 uL, 0.14 mmol). The reaction was heated in a sealed tube in an oil bath set at 80–90° C. overnight. The volatiles were removed in vacuo, the residue taken up in EtOAc (15 mL), washed with water (10 mL), brine (10 mL), dried (magnesium sulfate), filtered and evaporated to dryness. Flash chromatography of the residue on silica gel (10% EtOAc in hexanes) gave the desired 2-methoxy-3-nitro-5-tert-butyl pyridine as a glassy yellow solid (12 mg, 0.057 mmol, 41%).

To a suspension of the above intermediate (12 mg, 0.057 mmol) and Pd/C (10%, 14 mg) in absolute EtOH (1 mL) was added ammonium formate (22 mg, 0.35 mmol) and the mixture was heated to 50° C. for 1 hour. The cooled reaction mixture was filtered through diatomaceous earth and rinsed with MeOH. The filtrate was evaporated to dryness to afford the title compound 21 as a brown solid (10 mg, 0.055 mmol, 100%).

Example 22

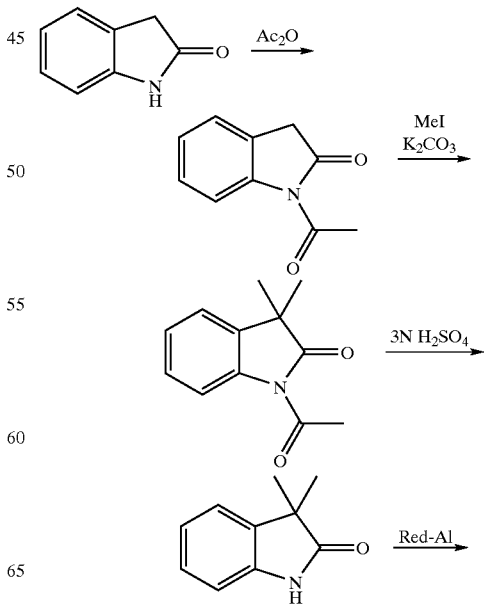

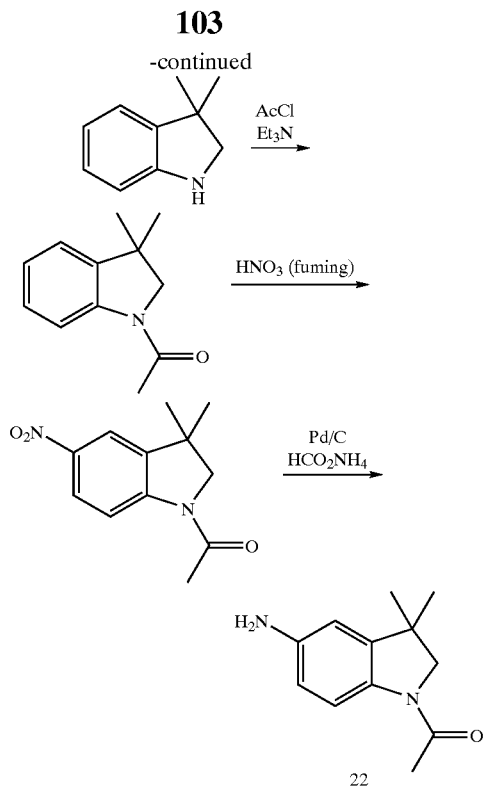

A solution of oxindole (5.0 g, 37.5 mmol) in acetic anhydride (7.1 mL, 75.1 mmol) and acetic acid (25 mL) was refluxed for 20 h. After cooling to room temperature, the reaction mixture was diluted with water (200 mL). The resulting solids were filtered, washed with water and dried to give N-acetyl oxindole as a white solid (5.2 g, 79%).

A mixture of N-acetyl oxindole (2.0 g, 11.4 mmol), iodomethane (1.56 mL, 25.1 mmol) and potassium carbonate (3.1 g, 22.8 mmol) in DMSO (20 mL) was stiffed at room temperature for 20 h. The reaction mixture was diluted with water. The resulting solids were filtered, washed with water and dried to give N-acetyl dimethyl oxindole as an orange solid (1.9 g, 84%).

A solution of N-acetyl dimethyl oxindole (500 mg, 2.5 mmol) in 3 N sulfuric acid solution (7 mL) and THF (7 mL) was refluxed for 4 h. After cooling to room temperature, the reaction mixture was diluted with ether. The ethereal layer was washed with water and brine, dried (magnesium sulfate), filtered and concentrated in vacuo. The residue was purified by flash chromatography on silica gel (eluent: 30% EtOAc in hexanes) to give dimethyl oxindole as a red solid (228 mg, 57%).

A solution of dimethyl oxindole (220 mg, 1.4 mmol) in toluene (5 mL) was treated with 65% Red-Al solution in toluene (0.64 mL, 2.05 mmol) at 80° C. After stirring at 100° C. for 4 h, the reaction mixture was quenched with 1N sodium hydroxide solution. The organic layer was separated, washed with water and brine, dried (sodium sulfate), filtered and concentrated in vacuo. The residue was purified by flash chromatography on silica gel (eluent: 25% EtOAc in hexanes) to give dimethyl indoline as a light blue oil (121 mg, 60%).

A solution of dimethyl indoline (65 mg, 0.44 mmol) and triethylamine (0.12 mL, 0.88 mmol) in dry dichloromethane (3 mL) was treated with acetyl chloride (0.05 mL, 0.66 mmol) at 0° C. The mixture was allowed to warm to room temperature and was stirred for 16 h. Then the reaction mixture was quenched with water and the product was extracted into ether. The organic layer was washed with water and brine, dried (sodium sulfate) filtered and concentrated in vacuo. The residue was purified by flash chromatography on silica gel (eluent: 30% EtOAc in hexanes) to give N-acetyl dimethyl indoline as a light yellow oil (68 mg, 82%).

A solution of N-acetyl dimethyl indoline (65 mg, 0.34 mmol) in acetic acid (2 mL) was treated with fuming nitric acid (24 L, 0.57 mmol) at room temperature and the resulting mixture was stirred for 1 h. The reaction mixture was quenched with sat. sodium bicarbonate solution and the product was extracted into EtOAc. The organic layer was washed with water and brine, dried (sodium sulfate), filtered and concentrated in vacuo. The residue was purified by flash chromatography in silica gel (eluent: 50% EtOAc in hexanes) to give the desired nitrated indoline as a light orange solid (66 mg, 67%).

A mixture of N-acetyl-3,3-dimethyl-5-nitroindoline (64 mg, 0.27 mmol), ammonium formate (86 mg, 1.36 mmol) and 10% palladium on carbon (5 mg) in MeOH (5 mL) was stirred at room temperature for 2 h. The reaction mixture was filtered through a short plug of diatomaceous earth. The filtrate was concentrated in vacuo. The residue was purified by flash chromatography on silica gel (eluent: 50% EtOAc in hexanes) to give the title compound 22 as a white solid (48 mg, 87%).

Example 23

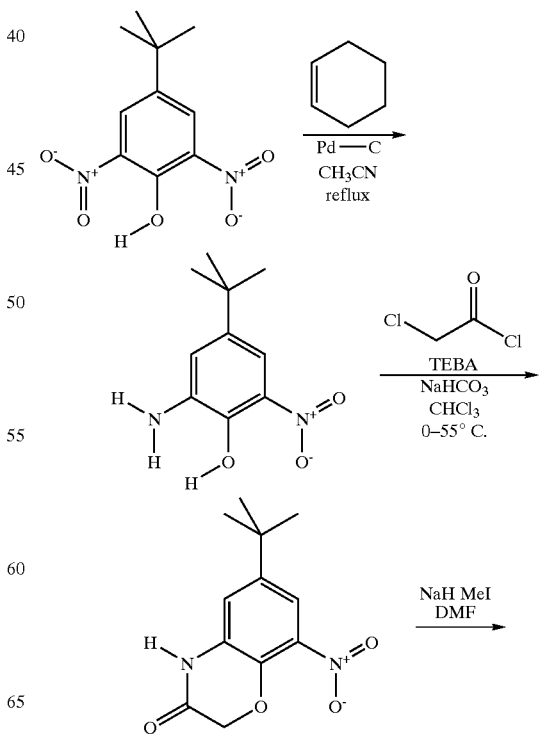

-continued

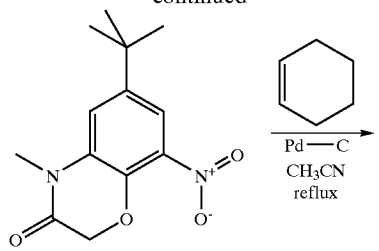

6-tert-Butyl-8-nitro-3-oxo-4-N-methyl-benzoxazine (53 mg, 0.2 mmol) was dissolved in 12.5 mL acetonitrile. Cyclohexene (0.20 mL, 2.0 mmol) and 10% palladium-on-carbon (75 mg) were added. The mixture was refluxed for 1 h, then cooled to ambient temperature and filtered through diatomaceous earth. The residues were washed with EtOAc and the combined organics were evaporated in vacuo to afford the title compound 23 (100%).

Example 24

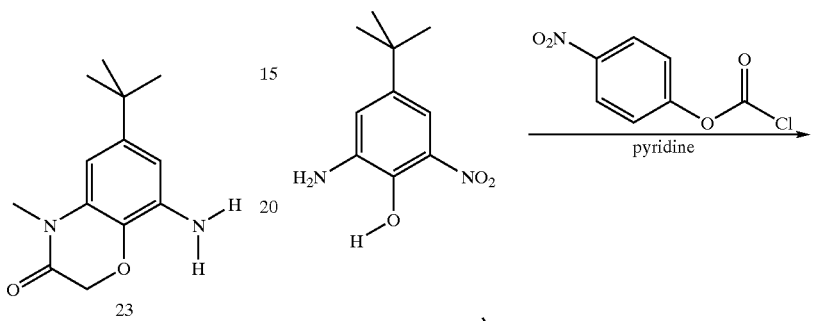

To a solution of 4-tert-butyl-2,6-dinitrophenol (3.15 g, 13.13 mmol) dissolved in 100 mL acetonitrile was added ammonium formate (5.0 g, 78.8 mmol) and 10% palladium on carbon (1.0 g). The mixture was refluxed for 20 min, then allowed to cool and filtered through diatomaceous earth. The residues were washed with EtOAc and the combined organics were evaporated in vacuo. The residue was taken up in dichloromethane and filtered through a short plug of silica gel. After removal of solvent in vacuo 2-amino-4-tert-butyl-6-nitro-phenol was obtained as a rust-red solid (4.86 mmol; 37% yield).

To a solution of 2-amino-4-tert-butyl-6-nitrophenol (258 mg, 1.23 mmol) and benzyltriethylammonium chloride (280 mg, 1.23 mmol) in 5 mL chloroform was added finely powdered NaHCO$_3$ (413 mg, 4.92 mmol). The mixture was cooled to 0° C. and -chloroacetyl chloride (0.12 mL, 1.47 mmol) in 1.5 mL chloroform was added dropwise via syringe over 15 min. Once the addition was complete, the mixture was allowed to stir at 0° C. for 1 h. It was then allowed to warm to ambient temperature and finally was gently refluxed for 6 h. The resulting crude orange mixture was allowed to cool, then was filtered through diatomaceous earth to remove a white precipitate, which was washed generously with more chloroform. After removal of the solvent in vacuo, the oily residue was treated with water (40 mL) and agitated with a spatula, whereupon a yellow precipitate formed. This pure 6-tert-butyl-8-nitro-3-oxo-benzoxazine was filtered, dried first under a stream of air, then in vacuo (1.05 mmol; 85%).

To a solution of 6-tert-butyl-8-nitro-3-oxo-benzoxazine (51 mg, 0.20 mmol) in 3.5 mL DMF at 0° C. was added sodium hydride (10 mg, 60% in mineral oil; 0.24 mmol) in one portion. After 20 min, methyl iodide (20 uL, 0.24 mmol) was added via syringe. The mixture was allowed to warm slowly to ambient temperature overnight. The crude mixture was quenched with saturated aqueous ammonium chloride solution and extracted with EtOAc (3×10 mL). The combined organics were washed with water, then brine, then dried over sodium sulfate. Filtration and removal of the solvents in vacuo afforded 6-tert-butyl-8-nitro-3-oxo-4-N-methylbenzoxazine (100%).

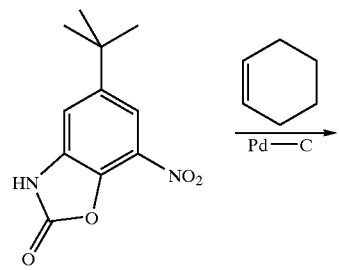

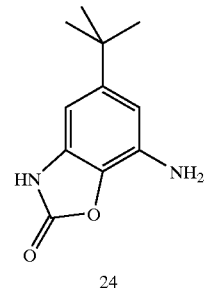

To a solution of 2-amino-4-tert-butyl-6-nitrophenol (300 mg, 1.43 mmol) and pyridine (0.30 mL) in methylene chloride (30 mL) was added 4-nitrophenylchloroformate (280 mg, 1.39 mmol). The mixture was stirred for 24 h. The resulting solution was washed with aqueous sodium bicarbonate (2×20 mL), dried over solid magnesium sulfate and concentrated to an orange solid. Column chromatography (silica gel, eluant=40% EtOAc/petroleum ether) afforded 5-tert-butyl-7-nitro-3H-benzoxazol-2-one (70%).

5-tert-Butyl-7-nitro-3H-benzoxazol-2-one (200 mg, 0.9 mmol) was dissolved in EtOH (10 mL). Cyclohexene (4 mL) and 10% palladium on carbon (50 mg) were added. The mixture was refluxed for 3 h, then cooled to ambient temperature and filtered through diatomaceous earth. Column chromatography (silica gel, eluant=25% EtOAc/petroleum ether) afforded the title compound 24 (70%).

Example 25

7-Amino-5-*tert*-butyl-2-methylbenzoxazole

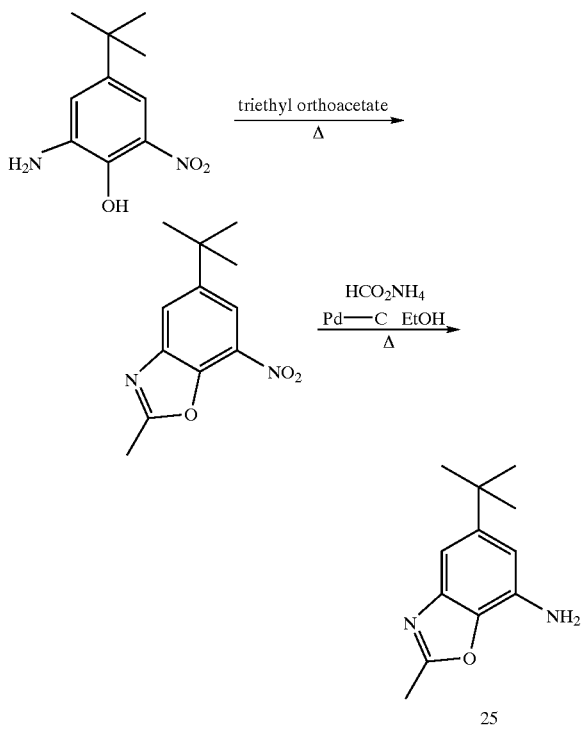

2-Amino-4-tert-butyl-6-nitrophenol was dissolved in triethyl orthoacetate (10 mL). The reaction mixture was stirred overnight at 100° C. Evaporation of volatiles in vacuo afforded 5-tert-butyl-2-methyl-7-nitrobenzoxazole (110 mg).

5-tert-Butyl-2-methyl-7-nitrobenzoxazole (100 mg, 0.4 mmol) was dissolved in EtOH (20 mL). The catalyst (10% Pd/C, 100 mg) was added followed by ammonium formate (160 mg, 0.3 mmol). The resulting heterogenous mixture was stirred at 100° C. for 1 h. Filtration followed by evaporation provided the title compound 25 (85 mg).

Examples 26–29 exemplify the synthesis of four heteroaryl amines which may be used as intermediate IV in Methods A–C (General Synthetic Methods) to prepare compounds of formula I or Ia.

Example 26

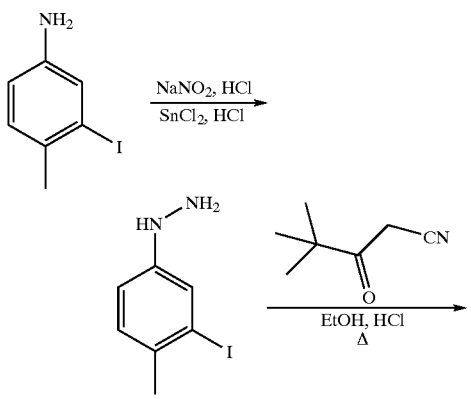

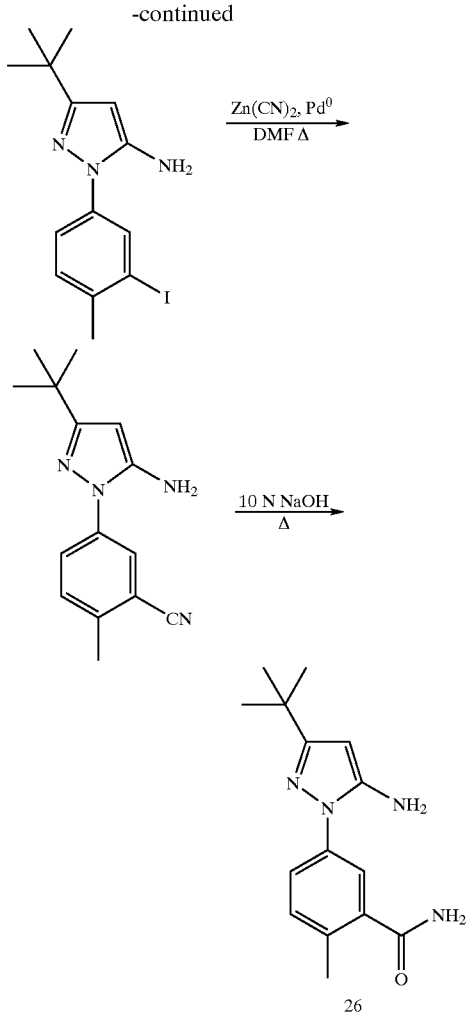

3-Iodo-4-methylphenyl amine (10 g, 43 mmol) was dissolved in 6 N HCl (40 ML), cooled to 0° C., and vigorously stirred throughout the procedure. Sodium nitrite (2.9 g, 1.03 equiv.) was dissolved in water (5 mL) and this solution was added to the reaction in a dropwise fashion. After 30 min, tin (II) chloride dihydrate (22.8 g, 1 mol) in 6 N HCl (100 mL) was added via addition funnel, and the reaction slurry was stirred at 0° C. for 3 h. The pH was adjusted to 14 with 40% aqueous sodium hydroxide solution and the aqueous mixture was extracted with EtOAc, (6×50 mL), dried (MgSO$_4$), and concentrated to give 3-iodo-4-methylphenylhydrazine (7 g, 57%). This material was used directly without further purification.

A solution of the above phenylhydrazine (5.08 g, 22 mmol) and 4,4-dimethyl-3-oxopentanenitrile (3.06 g, 1.1 equiv.) in EtOH (100 mL) containing conc. HCl (3 mL) was refluxed for 17 h, then cooled to room temperature. The pH was adjusted to 14 with 40% aqueous sodium hydroxide solution. The aqueous mixture was extracted with EtOAc, (3×50 mL), dried (MgSO$_4$), and concentrated to give 5-tert-butyl-2-(3-iodo-4-methyl-phenyl)-2H-pyrazol-3-ylamine (6.3 g, 86%). This material was used directly without further purification.

5-tert-Butyl-2-(3-iodo-4-methyl-phenyl)-2H-pyrazol-3-ylamine (2 g, 5.6 mmol) was combined with zinc cyanide (397 mg, 0.6 eq.) and tetrakis(triphenylphosphine)-palladium(0) (325 mg, 5 mol %) in deoxygenated dimethylformamide (10 mL). The resulting yellow slurry was heated at 100° C. for 4 h, cooled to room temperature, diluted with brine and 2 N HCl. The aqueous mixture was extracted with EtOAc (6×10 mL), dried (MgSO₄), and concentrated. The residue was purified by flash chromatography eluting with 20% EtOAc/petroleum ether to give 1.3 g (91%) of the desired nitrile.

The above nitrile (150 mg, 0.6 mmol) in EtOH (5 mL) was heated to 100° C. in the presence of 10 N NaOH for 2 h. The reaction was cooled to room temperature, neutralized with 50% HCl, extracted with EtOAc (6×10 mL), dried (MgSO₄) and concentrated to give the title compound 26 (130 mg, 80%).

Example 27

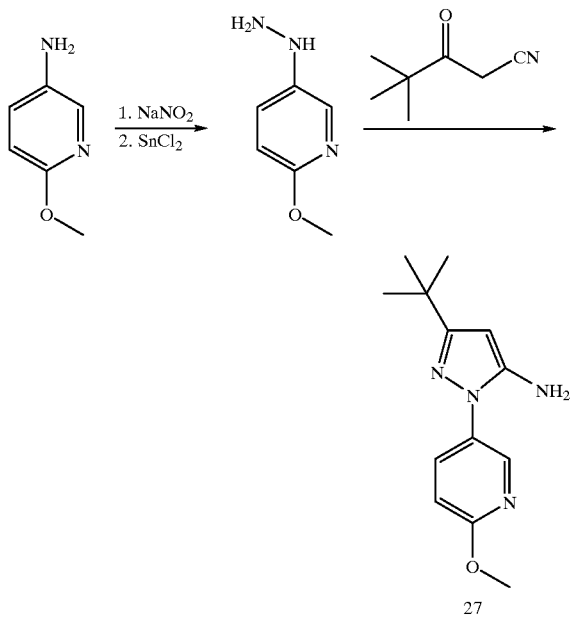

5-Amino-2-methoxypyridine (5.0 g, 40 mmol) was dissolved in 6 N HCl (10 mL), cooled to 0° C., and vigorously stirred throughout the procedure. Sodium nitrite (2.8 g, 41 mmol) was dissolved in water (10 mL) and this solution was added to the reaction solution. After 30 min, tin (II) chloride dihydrate (52 g, 230 mmol) in 6 N HCl (20 mL) was added, and the reaction slurry was stirred at 0° C. for 2.5 h. The pH was adjusted to 13 with 40% aqueous potassium hydroxide solution. Ethyl ether was added and the mixture was extracted with EtOAc (4×70 mL), dried (MgSO₄) and concentrated to give 5-hydrazino-2-methoxypyridine as an orange solid (5.1 g).

A solution of 5-hydrazino-2-methoxypyridine (2.5 g, 18 mmol) and 4,4-dimethyl-3-oxopentanenitrile (2.3 g, 18 mmol) in toluene (50 mL) was refluxed for 17 h in a flask fitted with a Dean-Stark trap, then cooled to room temperature. The reaction mixture was concentrated and the residue purified by column chromatography on silica gel, eluting with 30% EtOAc/petroleum ether to give the title compound 27 as a tan solid (3.5 g, 80%).

Example 28

5-Amino-3-*tert*-butyl-1-(2-pyridone-5-yl)pyrazole

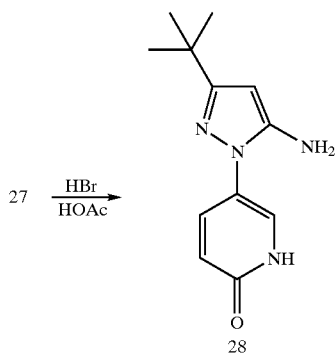

To a solution of the product of Example 27 (0.6 g, 2.4 mmol) in acetic acid (3 mL) was added 48% HBr in acetic acid (3 mL). The reaction mixture was heated to 120° C. for 15 min, cooled to room temperature, and the pH was adjusted to 7.5 with 10% aqueous sodium hydroxide solution. The aqueous mixture was extracted with EtOAc (4×15 mL), dried (MgSO₄), and concentrated to give a tan solid. The title compound 28 (0.46 g, 82%) was obtained after recrystallization from ether.

Example 29

5-Amino-3-*tert*-butyl-1-(2-cyanoethyl)pyrazole

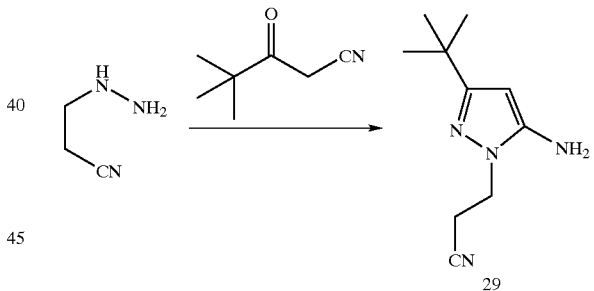

A solution of 2-cyanoethylhydrazine (3.0 g, 35 mmol) and 4,4-dimethyl-3-oxopentanenitrile (4.2 g, 34 mmol) in toluene (50 mL) was refluxed for 17 h in a flask fitted with a Dean-Stark trap, then cooled to room temperature. The slurry was filtered and the filtrate was concentrated. Column chromatography of the residue on silica gel, eluting with 50% EtOAc/petroleum ether) afforded the title compound 29 as a colorless solid (2.6 g, 40%).

Example 30

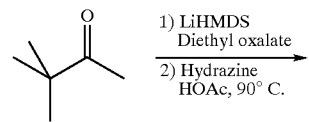

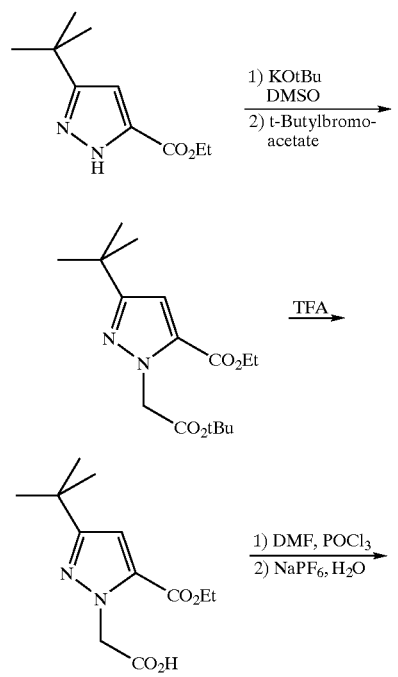

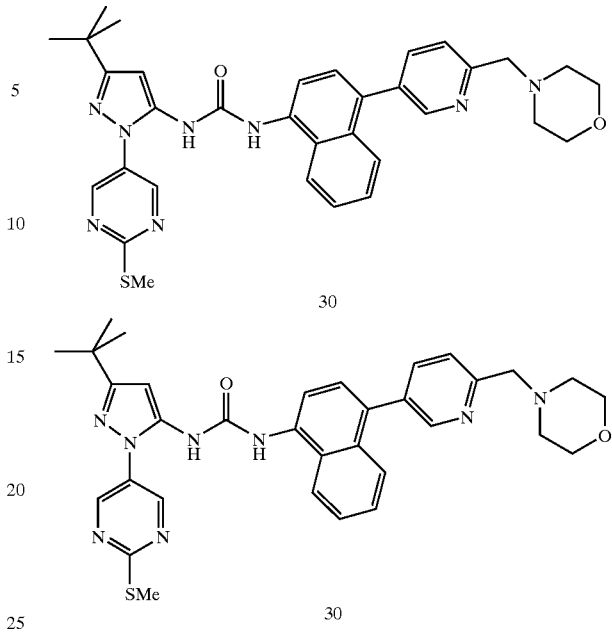

Pinacolone (100 mmol) and diethyloxalate (120 mmol) were dissolved in THF (200 mL), cooled to −78° C. and treated with LiHMDS (120 mmol, 1 M in THF). The ice bath was removed and the reaction allowed to warm to room temperature. After 2 h, volatiles were removed and the crude residue was dissolved in glacial HOAc (200 mL). Hydrazine monohydrate (110 mmol) was added and the reaction placed in a 90° C. oil bath and stirred overnight. The HOAc was removed under reduced pressure and the crude residue was taken up in aqueous $NaHCO_3$ to give a pH 6 solution. Solids were filtered, washed with water and dried to give the desired pyrazole ester (12.9 g, 66%).

KOt-Bu (67 mmol) was dissolved in DMSO (120 mL). The pyrazole ester from above (12 g, 61 mmol) was added in one portion and the reaction was stirred for 15 min. t-Butyl bromoacetate (92 mmol) was added and the reaction was stirred at room temperature for 45 min. DMSO was removed under reduced pressure and the crude residue was diluted with ice water and extracted with $CH_2Cl_2$. The organics were combined, dried over $MgSO_4$ and concentrated to leave an isomeric mixture of pyrazoles as an orange oil (21 g). The desired isomer was isolated as an oil via silica gel chromatography, eluting with $CH_2Cl_2$ (13.3 g, 70%).

The pyrazole diester (13.3 g, 43 mmol) was dissolved in neat TFA (150 mL) and stirred at room temperature for 3 h. Volatiles were removed and the crude residue was diluted with ice water and extracted with $CH_2Cl_2$. Organics were combined, washed with water, dried over $MgSO_4$ and concentrated to leave the desired carboxylic acid as a thick oil that partially crystallized (10.2 g, 94%).

Anhydrous DMF (282 mmol) was cooled to 0° C. and treated with $POCl_3$ (161 mmol). After 5 min, the above pyrazole acetic acid derivative (10.2 g, 40 mmol) was added and the suspension was transferred to a 110° C. oil bath. The reaction was stirred for 2 h, during which all solids dissolved. After cooling to room temperature, the reaction was poured into a stirred solution of NaPF$_6$, (80 mmol) in water (400 mL). When precipitation of solids was complete, they were filtered, washed with water and dried giving the desired vinamidinium salt XCVIII (14.6 g, 78%). Salt XCVIII from above (233 mg, 0.5 mmol) was taken up in DMSO (10 mL) and treated with S-methylisothiourea sulfate (0.25 mmol) and K$_2$CO$_3$ (0.25 mmol). The reaction was transferred to a 90° C. oil bath and stirred for 2 h. Volatiles were removed under reduced pressure after allowing the reaction to cool to room temperature. The residue was taken up in ice water and extracted with diethyl ether. Organics were combined, dried over MgSO$_4$ and concentrated to leave a brown tar. The desired ethyl ester was purified by chromatography on a silica gel column eluting with CH$_2$Cl$_2$/EtOAc, 1:1 to give a yellow oil that crystallized upon standing (157 mg, 98%).

The ester from above (150 mg, 0.47 mmol) was dissolved in MeOH (4 mL) and water (1 mL), treated with LiOH monohydrate (0.7 mmol) and stirred at room temperature overnight. Volatiles were removed, the residue was diluted with water, neutralized to pH 4 with 1N sulfuric acid. Solids were filtered, washed with water and dried (113 mg, 82%).

The resulting carboxylic acid (105 mg, 0.36 mmol) was suspended in benzene (4 mL) and treated with triethylamine (0.61 mmol). The resulting solution was treated with diphenylphosphoryl azide (DPPA) (0.54 mmol) and allowed to stir at room temperature for 6 h. Organics were washed with aqueous NaHCO$_3$, water, dried over MgSO$_4$ and filtered. The resulting solution was treated with LXXXIV (Example 4) (115 mg, 0.36 mmol) and the reaction was placed in a 90° C. oil bath for 1 h. Volatiles were removed and the crude residue was purified on two preparative TLC plates eluting with CH$_2$Cl$_2$/MeOH, 9:1 to give the title compound 30 as an off-white solid (61 mg, 28%).

By substituting for the S-methylisothiourea sulfate used in reaction with XCVIII, one may obtain other substituted pyrimidines corresponding to XCVIV. For example, using acetamidine hydrochloride would provide the 2-methylpyrimidine analog of XCVIV. 0-Methylisothiourea sulfate and guanidine carbonate would give the 2-methoxypyrimidine and 2-aminopyrimidine analogs respectively. By replacing S-methylisothiourea sulfate with hydrazine monohydrate or N-methylhydrazine, one may obtain a pyrazol-4-yl or 1-methylpyrazol-4-yl ring respectively in place of the substituted pyrimidine in XCVIV. Each of these analogs of XCVIV may be taken on as described above to provide the corresponding analogs of 30.

Examples 31–36 exemplify syntheses of substituted napthylamines which may be used as intermediate VI (D'-NH$_2$) as described in Methods B and C in General Synthetic Methods to produce various compounds of the invention Example 31

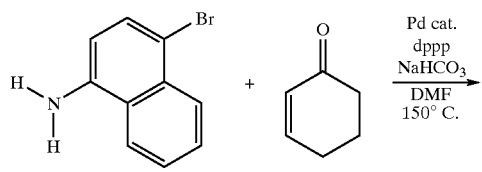

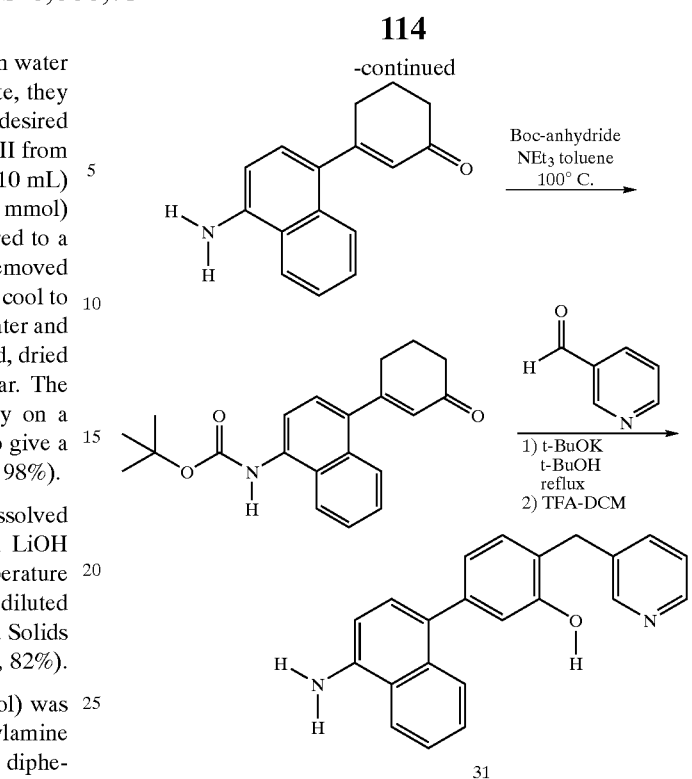

31

To a tube containing a solution of 2.0 g of 1-amino-4-bromonaphthalene (9.0 mmol; 1 equiv.) in 70 mL DMF were added 1.75 mL of 2-cyclohexen-1-one (18.0 mmol; 2.0 equiv.), 2.3 g of sodium bicarbonate (27.0 mmol; 3.0 equiv.) and 186 mg of 1,3-bis-(diphenylphosphino)propane (dppp; 0.45 mmol; 0.05 equiv.). A stream of dry nitrogen gas was bubbled through the mixture for 15 min, then 316 mg of bis-(triphenylphosphino)palladium(II) chloride (0.45 mmol; 0.05 equiv.) was added and the tube was sealed. The mixture was heated at 150° C. for 8 h, then cooled to ambient temperature, diluted with EtOAc (150 mL) and filtered through diatomaceous earth. The mixture was washed with water, then brine. The organic layer was dried (MgSO$_4$), filtered and concentrated. The crude oil was purified by column chromatography on SiO$_2$ using 10 to 50% EtOAc in hexane mixtures as eluents to give 2.0 g of a thick liquid consisting of 3-(4-aminonapthalen-1-yl)cycloxex-2-enone and DMF (molar ratio 1:2 respectively; 5.22 mmol of naphthylamine; 58% of theoretical yield).

To a solution of 4.0 g of 3-(4-aminonapthalen-1-yl) cycloxex-2-enone: DMF (1:2; 10.4 mmol; 1 equiv.) in 50 mL toluene was added 2.72 g of di-tert-butyl dicarbonate (12.5 mmol; 1.2 equiv.) and 1.5 mL triethylamine (10.4 mmol; 1 equiv.). The mixture was heated to 100° C. overnight, then cooled to ambient temperature. The reaction mixture was washed with 0.1% aqueous HCl (2×50 mL), water, brine, dried (MgSO$_4$), filtered and concentrated. The crude product precipitated and was washed with 10% EtOAc in hexane to afford, after filtration, 2.5 g of desired tert-butyl carbamate (7.4 mmol; 71% of theoretical yield).

To a solution of 186 mg of the above tert-butyl naphthyl carbamate (0.55 mmol; 1 equiv.) in 1.6 mL anhydrous tert-butanol was added 52 uL of pyridine-3-carboxaldehyde (0.55 mmol; 1 equiv.) and 1.65 mL potassium tert-butoxide solution (1.0 M; 1.32 mmol; 3 equiv.). The mixture was heated to reflux overnight, then cooled. MeOH (5 mL) and HCl solution in dioxane (4.0 M) were added until pH ~1, the reaction was then stirred for 1.5 h at ambient temperature. The mixture was then quenched with saturated NaHCO₃ aqueous solution and extracted with EtOAc (2×50 mL). The aqueous layer was treated with 4 N NaOH aqueous solution until pH~12 and extracted 2 more times. The combined organic extracts were washed with brine, dried (MgSO₄), filtered and concentrated to afford a mixture of crude products, including naphthylamine still protected as the carbamate. The residue was therefore taken up in dichloromethane (3 mL), treated with 2 mL TFA and left stirring over a weekend at ambient temperature. The mixture was quenched and neutralized with saturated aqueous NaHCO₃, extracted with dichloromethane (3×50 mL), dried (MgSO₄) and filtered. The volatiles were removed in vacuo and the crude product purified by column chromatography on SiO₂ using 50 to 100% EtOAc in hexane eluent mixtures giving 35 mg (0.11 mmol; 20% of theoretical yield) title compound 31.

Example 32

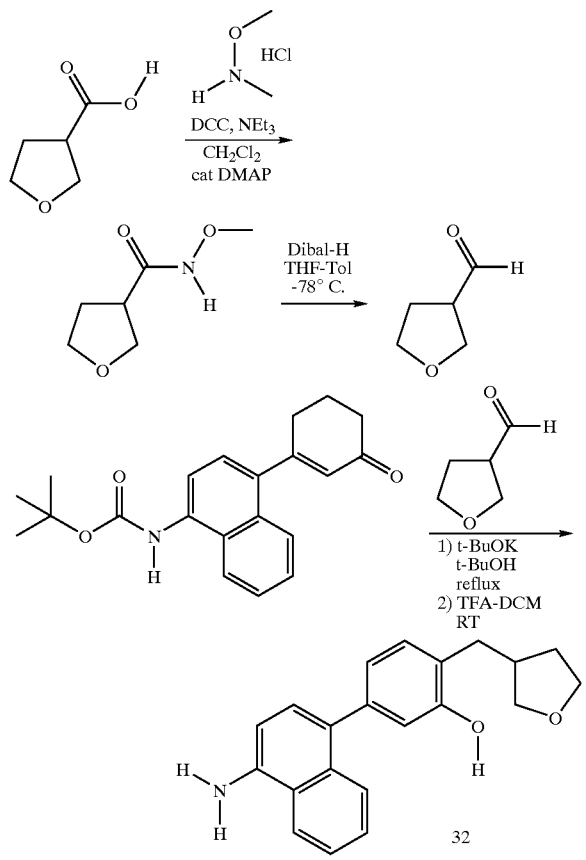

To a solution of 3.16 g of tetrahydro-3-furoic acid (27 mmol; 1 equiv.) in 25 mL anhydrous dichloromethane was added 7.85 g of dicyclohexylcarbodiimide (38 mmol; 1.4 equiv.) and 4.54 mL triethylamine (32.6 mmol; 1.2 equiv.). N-methyl-methanolamine hydrochloride was then added, followed by 60 mg of DMAP (4-dimethylamino)pyridine. An exothermic reaction ensued and a further 25 mL of dichloromethane were added. The mixture was stirred at ambient temperature overnight, then filtered through diatomaceous earth and concentrated. The residue was treated with ether and the white solid filtered off and removed. The solvent was removed from the mother liquor and the residue purified by column chromatography on SiO₂ using 15–25% EtOAc in hexanes as eluent mixtures to provide the desired amide as a colorless oil (55% of theoretical yield) that still contained 10% of dicyclohexyl urea. This was used without further purification in the next reaction.

To a solution of 1.0 g of the above amide (6.28 mmol; 1 equiv.) in 60 mL anhydrous THF at −78° C. was added 12.6 mL of 1.0 M DIBAL-H solution in toluene dropwise via syringe (12.6 mmol; 2.0 equiv.). After stirring 30 min at −78° C. the reaction mixture was quenched with 50 mL MeOH and 50 mL water. The reaction mixture was transferred to a separatory funnel and 250 mL ether were added. 1 N HCl aqueous solution was added until all the solids had dissolved. The layers were separated and the aqueous portion was extracted further with 2×100 mL ether. The combined organics were washed with saturated aqueous NaHCO₃ solution, then brine, dried over Na₂SO₄, filtered and concentrated. The crude product was purified by chromatography on silica gel using 0–5% MeOH in dichloromethane as eluent mixtures. The desired 3-tetrahydrofuroic aldehyde was obtained as a very volatile, impure colorless oil (200 mg).

To a solution of 200 mg of tert-butyl naphthyl carbamate (0.59 mmol; 1 equiv.) in 1.6 mL anhydrous tert-butanol was added 200 mg of 3-tetrahydrofuroic aldehyde from above (excess) and 1.78 mL potassium tert-butoxide solution in tert-butanol (1.0 M; 1.78 mmol; 3 equiv.). The mixture was heated to 40° C. overnight, then cooled and quenched with NH₄Cl saturated aqueous solution. The product was extracted with a dichloromethane/methanol mixture (3×100 mL). The combined extracts were washed with brine, dried over MgSO₄, and concentrated. ¹H NMR analysis revealed that only 10% of the enone was consumed. The residue (300 mg) was dissolved in 4.0 mL dichloromethane and treated with 4 mL of a 1:1 mixture dichloromethane:TFA. The mixture was stirred for 1.5 h, then neutralized with saturated NaHCO₃ aqueous solution, basified with 4 N NaOH solution and extracted with dichloromethane/methanol (3×100 mL). The combined organic extracts were washed with brine, dried (MgSO₄) and filtered and concentrated. The crude product was purified by column chromatography on silica gel using 10 to 50% EtOAc in hexane eluent mixtures to give the title compound 32 (35 mg 0.11 mmol; 19% of theoretical yield).

Example 33

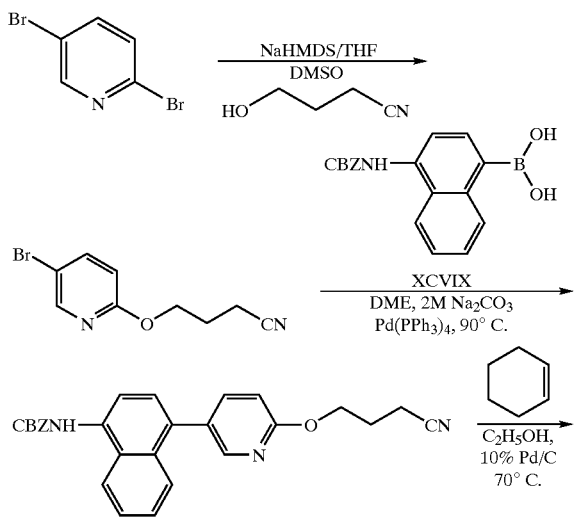

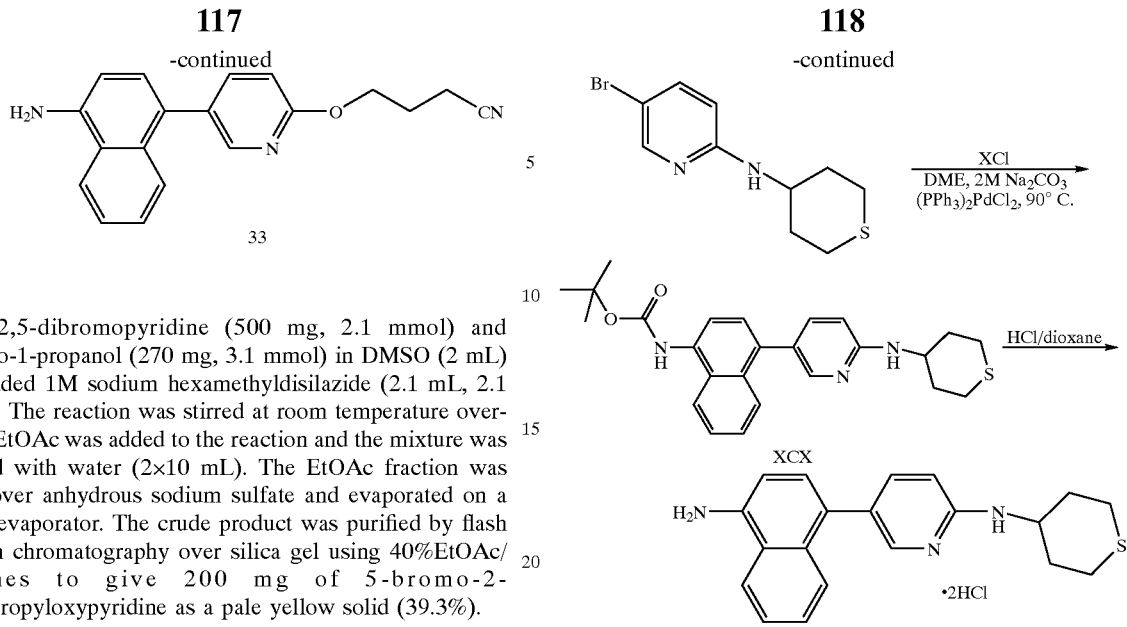

33

To 2,5-dibromopyridine (500 mg, 2.1 mmol) and 3-cyano-1-propanol (270 mg, 3.1 mmol) in DMSO (2 mL) was added 1M sodium hexamethyldisilazide (2.1 mL, 2.1 mmol). The reaction was stirred at room temperature overnight. EtOAc was added to the reaction and the mixture was washed with water (2×10 mL). The EtOAc fraction was dried over anhydrous sodium sulfate and evaporated on a rotary evaporator. The crude product was purified by flash column chromatography over silica gel using 40%EtOAc/hexanes to give 200 mg of 5-bromo-2-cyanopropyloxypyridine as a pale yellow solid (39.3%).

To the above intermediate (100 mg, 0.4 mmol) and CBZ-protected naphthylboronic acid XCVIX (prepared as described for the Boc-analog XCI in Example 17) (200 mg, 0.62 mmol) in DME (4 mL) was added 2M sodium carbonate solution (2 mL). The solution was purged with nitrogen for 10 min and to this was added palladium tetrakistriphenylphosphine (20 mg). The reaction was heated at 90° C. for 48 h and then cooled to room temperature. EtOAc was added to the reaction and the mixture was washed with water (2×10 mL). The EtOAc fraction was dried over anhydrous sodium sulfate, filtered and concentrated. The crude product was purified by flash column chromatography over silica gel eluting with 40%EtOAc/hexanes to give 70 mg of product (39%).

To the above coupled product (70 mg, 0.16 mmol) in EtOH (5 mL) was added cyclohexene (263 mg, 3.2 mmol) and 10% Pd/C (20 mg). The reaction was heated under nitrogen overnight and cooled to room temperature. The reaction was filtered over diatomaceous earth, washed with MeOH and concentrated. The crude product was purified by flash column chromatography over silica gel eluting with 50% EtOAc/hexanes to give 15 mg of the title compound 33 (31%).

Example 34

[5-(4-Aminonapthalen-1-yl)pyridin-2-yl]-(tetrahydrothiopyran-4-yl) amine dihydrochloride

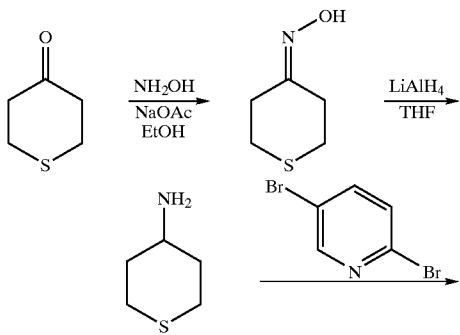

To tetrahydro-1,4-thiopyrone (2.0 g, 17.2 mmol) and hydroxylamine hydrochloride (2.0 g, 28.7 mmol) in EtOH (10 mL) was added sodium acetate trihydrate (4.0 g, 29.4 mmol) in 20 mL water. The reaction was heated at reflux for 3 h, cooled to room temperature and concentrated to 15 mL on a rotary evaporator. The residue was cooled in an ice-bath and filtered to give 2.0 g of the oxime product as a white solid m.p. 80–83° C. (88.7%).

To a dry flask containing THF (20 mL) and 1M lithium aluminium hydride in diethyl ether (19 mL) at room temperature, was added the oxime from above (500 mg, 3.82 mmol). The reaction was heated at reflux for 3 h, cooled to room temperature and the excess LAH was quenched with ice/water. Extraction with EtOAc and concentration gave 340 mg (76%) of the desired 4-aminotetrahydrothiopyran.

To the above amine (170 mg, 1.4 mmol) in dry pyridine (1 mL) was added 2,5-dibromopyridine (250 mg, 1.1 mmol) and the reaction was heated at 110–120° C. for 5 days. The reaction was extracted with EtOAc, washed with water, dried over anhydrous sodium sulfate and concentrated to give the crude product. The crude product was purified by flash column chromatography over silica gel using 30% EtOAc/hexanes as eluent to give 100 mg of pure product (33.3%).

To the above intermediate (80 mg, 0.293 mmol) and BOC-protected naphthylboronic acid XCI (Example 17) (140 mg, 0.488 mmol) in DME (4 mL) was added 2 M sodium carbonate (2 mL) and bis(triphenylphosphine) palladium chloride (15 mg). The reaction was heated at 90° C. under nitrogen for 18 h and cooled to room temperature. The reaction was extracted with EtOAc, washed with water, dried over anhydrous sodium sulfate and concentrated to give the crude product. The crude product was purified by flash column chromatography over silica gel using 30% EtOAc/hexanes as eluent to give 110 mg of pure product XCX (86.0%)

To the XCX (35 mg, 0.08 mmol) in dioxane (1 mL) was added 4 M HCl/dioxane (0.6 mL). The reaction was stirred at room temperature for 48 h. Addition of diethyl ether gave the product as the hydrochloride salt which was filtered, giving 18 mg (55%) of the title compound 34.

Example 35

[5-(4-Aminonapthalen-1-yl)pyridin-2-yl]-(tetrahydropyran-4-yl) amine dihydrochloride

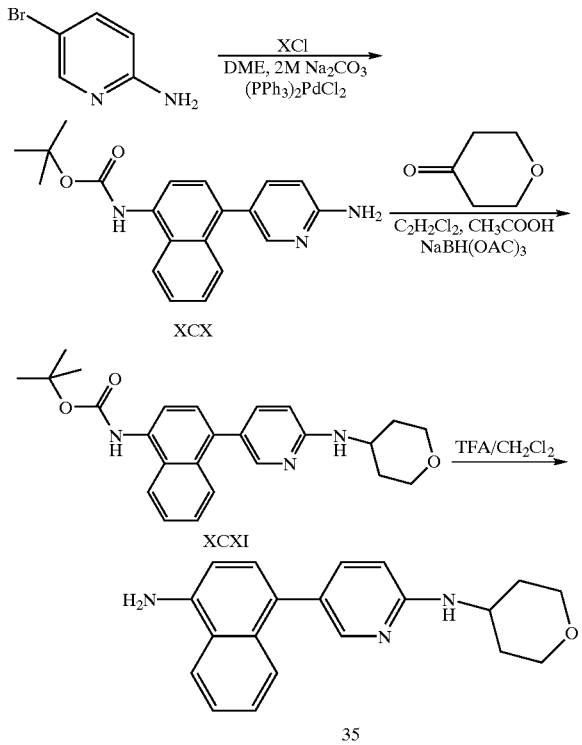

35

To 2-amino-5-bromopyridine (250 mg, 1.44 mmol) and BOC-protected naphthylboronic acid XCI (Example 17) (688 mg, 2.4 mmol) in 5 mL DME was added 2 M sodium carbonate (2.5 mL) and bis(triphenylphosphine)palladium chloride (30 mg). The reaction was heated at 90° C. under nitrogen for 18 h and cooled to room temperature. The reaction mixture was extracted with EtOAc, washed with water, dried over anhydrous sodium sulfate and concentrated. The residue was purified by flash column chromatography over silica gel eluting with 40% EtOAc/hexanes to give 370 mg coupled product XCX (76.4%).

To the above intermediate (200 mg, 0.597 mmol) and tetrahydropyranone (120 mg, 1.19 mmol) in dichloroethane (5 mL) was added glacial acetic acid (0.2 mL, 3.58 mmol) and sodium triacetoxyborohydride (380 mg, 1.79 mmol). The reaction was stirred at room temperature for 48 h and then extracted with EtOAc, washed with water, dried over anhydrous sodium sulfate and concentrated. The residue was purified by flash column chromatography over silica gel using 50% EtOAc/hexanes as eluent to give 120 mg XCXI (48.0%).

The above product, XCX, was dissolved in dichloromethane (3 mL) and treated with trifluoroacetic acid (1 mL). The reaction was stirred for 3 h and concentrated. The residue was dissolved in EtOAc (20 mL), washed with sodium bicarbonate solution, dried over anhydrous sodium sulfate concentrated to give 90 mg of the title compound 35 (98.5%).

Example 36

[5-(4-Aminonapthalen-1-yl)pyridin-2-yl]-(1-methylpiperidin-4-yl) amine

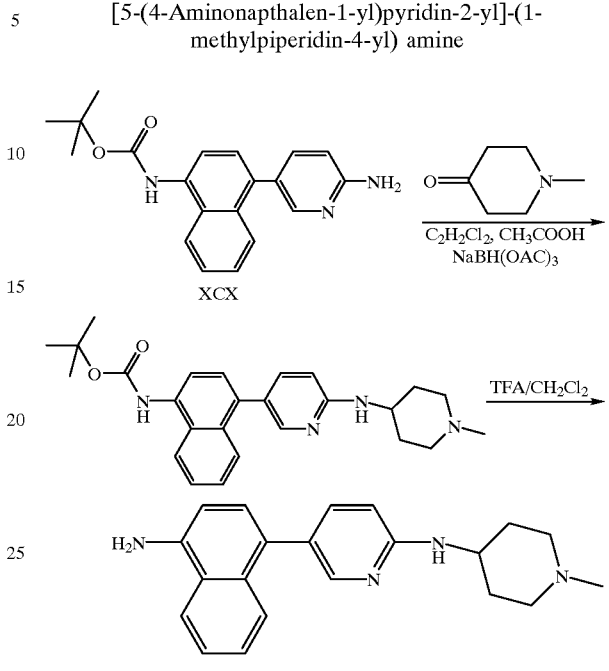

36

To a mixture of XCX (Example 35) (110 mg, 0.33 mmol) and 1-methyl-4-piperidone (80 mg, 0.7 mmol) in dichloroethane (6 mL) was added glacial acetic acid (120 mg, 2.0 mmol) and sodium triacetoxyborohydride (220 mg, 1.03 mmol). The reaction was stirred at room temperature for 96 h and then extracted with EtOAc, washed with water, dried over anhydrous sodium sulfate and concentrated. The residue was purified by flash column chromatography over silica gel using 10% MeOH/CH$_2$Cl$_2$/0.1%TEA as eluent to give 60 mg of pure product (42.0%).

The above product was dissolved in dichloromethane (3 mL) and treated with trifluoroacetic acid (1 mL). The reaction was stirred for 2.5 h and the concentrated to give 94 mg of the title compound 36 (100%).

Example 37

Example 37 illustrates the synthesis of a compound of formula III in which E is O.

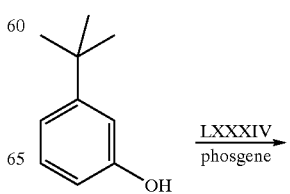

-continued

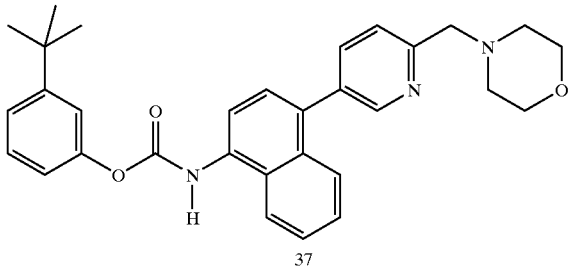

37

LXXXIV (Example 4) (100 mg, 0.31 mmol) was dissolved in dichloromethane (20 mL). An equal volume of sat. aqueous sodium bicarbonate was added, and the biphasic solution was cooled to 0° C. During the addition of phosgene (1.93 M in toluene, 0.40 mL), stirring was stopped. Immediately afterward, stirring was resumed for 15 min with the reaction mixture at 0° C. The layers were separated, the organics were dried over solid magnesium sulfate, and concentrated to approximately 5 mL of solution. 3-tert-Butylphenol (100 mg, 0.67 mmol) in dichloromethane (5 mL) was added. The reaction mixture was stirred at room temperature for 19 h. Flash chromatography using EtOAc as eluent provided 71 mg of the title compound 37.

Example 38

Example 38 illustrates the synthesis of a compound of formula III in which E is $CH_2$.

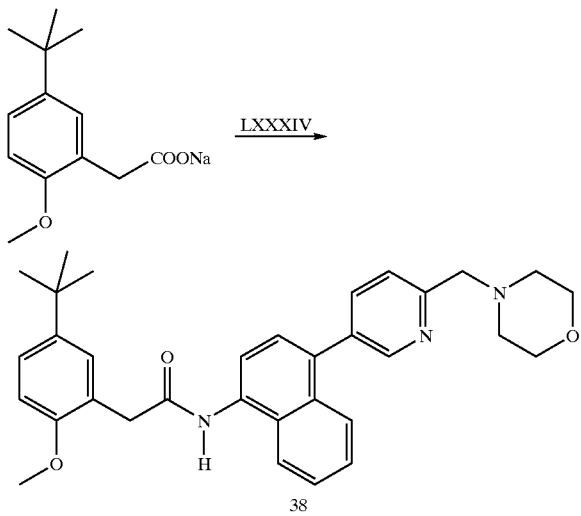

38

LXXXIV (Example 4) (100 mg, 0.4 mmol) and the sodium salt of 5-tert-butyl-2-methoxyphenylacetic acid (154 mg, 0.4 mmol) were dissolved in dichloromethane (15 mL). 1-(3-Dimethylaminopropyl)-3-ethylcarbodiimide hydrochloride (172 mg, 0.9 mmol) was added, and the reaction mixture was stirred at ambient temperature for 16 h. HPLC purification afforded 30 mg of the title compound 38.

The following additional examples were prepared by methods analogous to those described above:

1-(2-tert-Butyl-5-methyl-pyridin-4-yl)-3-[4-(6-morpholin-4-ylmethyl-pyridin-3-yl)-naphthalen-1-yl]-urea;

1-(5-tert-Butyl-2-methylphenyl]-3-{4-[6-(morpholin-4-ylmethyl)pyridin-3-yl]naphthalen-1-yl}urea:

1-(3,3-Dimethyl-2-oxo-2,3-dihydro-1H-indol-5-yl)-3-[4-(6-morpholin-4-ylmethyl-pyridin-3-yl)-naphthalen-1-yl]-urea 1-(3-Amino-5-tert-butyl-2-methoxy-phenyl)-3-[4-(6-morpholin-4-ylmethyl-pyridin-3-yl)-naphthalen-1-yl]-urea 1-(4-Methyl-biphenyl-3-yl)-3-[4-(6-morpholin-4-ylmethyl-pyridin-3-yl)-naphthalen-1-yl]-urea;

1-(4-tert-Butyl-biphenyl-2-yl)-3-[4-(6-morpholin-4-ylmethyl-pyridin-3-yl)-naphthalen-1-yl]-urea;

1-(5-{4-[3-(5-tert-Butyl-2-methoxy-phenyl)-ureido]-naphthalen-1-yl}-pyridin-2-ylmethyl)-piperidine-3-carboxylic acid amide 1-(5-Isopropyl-2-methyl-phenyl)-3-[4-(6-morpholin-4-ylmethyl-pyridin-3-yl)-naphthalen-1-yl]-urea;

1-(5-sec-Butyl-2-methoxy-phenyl)-3-[4-(6-morpholin-4-ylmethyl-pyridin-3-yl)-naphthalen-1-yl]-urea;

1-(5-tert-Butyl-2-methoxymethyl-phenyl)-3-[4-(6-morpholin-4-ylmethyl-pyridin-3-yl)-naphthalen-1-yl]-urea;

1-(5-tert-Butyl-2-methoxy-phenyl)-3-(4-{6-[(tetrahydro-furan-3-ylamino)-methyl]-pyridin-3-yl}-naphthalen-1-yl)-urea 1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea 1-(5-tert-Butyl-2-methoxy-phenyl)-3-[4-(5-morpholin-4-ylmethyl-pyrazin-2-yl)-naphthalen-1-yl]-urea 1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea 1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea 1-(5-tert-Butyl-2-methoxy-phenyl)-3-[4-(6-morpholin-4-ylmethyl-pyridin-3-yl)-naphthalen-1-yl]-urea;

1-(5-tert-Butyl-2-methoxy-phenyl)-3-[4-(6-thiomorpholin-4-ylmethyl-pyridin-3-yl)-naphthalen-1-yl]-urea 1-(5-tert-Butyl-2-methoxy-phenyl)-3-{4-[6-(1-oxo-14-thio morpholin-4-ylmethyl)-pyridin-3-yl]-naphthalen-1-yl}-urea 1-(5-tert-Butyl-2-methoxy-phenyl)-3-{4-[6-(1-oxo-tetrahydro-thiopyran-4-ylamino)-pyridin-3-yl]-naphthalen-1-yl}-urea 1-(5-tert-Butyl-2-methoxy-phenyl)-3-{4-[6-(2,6-dimethyl-morpholin-4-ylmethyl)-pyridin-3-yl]-naphthalen-1-yl}-urea 1-(5-tert-Butyl-2-methoxy-phenyl)-3-{4-[6-(2,6-dimethyl-piperidin-1-ylmethyl)-pyridin-3-yl]-naphthalen-1-yl}-urea 1-(5-tert-Butyl-2-methoxy-phenyl)-3-{4-[6-(2-methoxymethyl-morpholin-4-ylmethyl)-pyridin-3-yl]-naphthalen-1-yl}-urea 1-(5-tert-Butyl-2-methoxy-phenyl)-3-{4-[6-(2-methyl-3-oxo-piperazin-1-ylmethyl)-pyridin-3–yl]-naphthalen-1–yl}-urea 1-(5-tert-Butyl-2-methoxy-phenyl)-3-{4-[6-(2-oxa-5-aza-bicyclo[2.2.1]hept-5-ylmethyl)-pyridin-3–yl]-naphthalen-1–yl}-urea 1-(5-tert-Butyl-2-methoxy-phenyl)-3-{4-[6-(2-thia-5-aza-bicyclo[2.2.1 ]hept-5-ylmethyl)-pyridin-3–yl]-naphthalen-1–yl}-urea 1-(5-tert-Butyl-2-methoxy-phenyl)-3-{4-[6-(3-oxo-piperazin-1-ylmethyl)-pyridin-3–yl]-naphthalen-1–yl}-urea 1-(5-tert-Butyl-2-methoxy-phenyl)-3-{4-[6-(4-methyl-piperazin-1-ylmethyl)-pyridin-3–yl]-naphthalen-1–yl}-urea 1-(5-tert-Butyl-2-methoxy-phenyl)-3-{4-[6-(4-pyridin-2-yl-piperazin-1-ylmethyl)-5 pyridin-3-yl]-naphthalen-1-yl}-urea 1-(5-tert-Butyl-2-methoxy-phenyl)-3-{4-[6-(morpholine-4-carbonyl)-pyridin-3-yl]-naphthalen-1-yl}-urea 1-(5-tert-Butyl-2-methoxy-phenyl)-3-{4-[6-(pyridin-3-yoxy)-pyrdin-3-yl]-naphthalen-1-yl}-urea 1-(5-tert-Butyl-2-methoxy-phenyl)-3-{4-[6-(tetrahydro-pyran-4-ylamino)-pyridin-3-yl]-naphthalen-1-yl}-urea 1-(5-tert-Butyl-2-methyl-phenyl)-3-(4-{6-[(3-methoxy-propyl)-methyl-amino]-pyridin-3-yl}-naphthalen-1-yl)-urea;

1-(5-tert-Butyl-2-methyl-phenyl)-3-[4-(6-morpholin-4-ylmethyl-pyridin-3-yl)-naphthalen-1-yl]-urea;

1-(5-tert-Butyl-2-methyl-pyridin-3-yl)-3-[4-(6-morpholin-4-ylmethyl-pyridin-3-yl)-naphthalen-1-yl]-urea;

1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea 1-[4-(6-{[Bis-(2-cyano-ethyl)-amino]-methyl}-pyridin-3-yl)-naphthalen-1-yl]-3-(5-tert-butyl-2-methoxy-phenyl)-urea 1-[5-(1,1-Dimethyl-propyl)-2-methoxy-phenyl]-3-[4-(6-morpholin-4-ylmethyl-pyridin-3-yl)-naphthalen-1-yl]-urea;

1-[5-tert-Butyl-2-(1H-pyrazol-4-yl)-phenyl]-3-[4-(6-morpholin-4-ylmethyl-pyridin-3-yl)-naphthalen-1-yl]-urea;

1-[5-tert-Butyl-2-(2-methyl-pyrimidin-5-yl)-phenyl]-3-[4-(6-morpholin-4-ylmethyl-pyridin-3-yl)-naphthalen-1-yl]-urea;

1-[5-tert-Butyl-2-(3-hydroxy-propyl)-phenyl]-3-[4-(6-morpholin-4-ylmethyl-pyridin-3-yl)-naphthalen-1-yl]-urea;

1-[5-tert-Butyl-2-(morpholine-4-carbonyl)-phenyl]-3-[4-(6-morpholin-4-ylmethyl-pyridin-3-yl)-naphthalen-1-yl]-urea;

N-(5-{4-[3-(5-tert-Butyl-2-methoxy-phenyl)-ureido]-naphthalen-1-yl}-pyridin-2-yl)-acetamide N-(5-tert-Butyl-2-methoxy-3-{3-[4-(6-morpholin-4-ylmethyl-pyridin-3-yl)-naphthalen-1-yl]-ureido}-phenyl)-acetamide N-(5-tert-Butyl-2-methoxy-3-{3-[4-(6-morpholin-4-ylmethyl-pyridin-3-yl)-naphthalen-1-yl]-ureido}-phenyl)-N-methyl-acetamide N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide N-(5-tert-Butyl-2-methoxy-3-{3-[4-(6-morpholin-4-ylmethyl-pyridin-3-yl)-naphthalen-1-yl]-ureido}-phenyl)-methanesulfonamide.

Assessment of Biological Properties
Inhibition of TNF Production in THP Cells The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630, from *E.coli* serotype 0111.B4; stored as 1 mg/ml stock in endotoxin screened distilled $H_2O$ at −80° C.). Blanks (unstimulated) received $H_2O$ vehicle; final incubation volume was 250 μl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC50 value is the concentration of the test compound that caused a 50% decrease in the maximal TNFα production.

Preferred compounds including those from the synthetic examples above were evaluated and had $IC_{50} < 10$ M in this assay.

Inhibition of other cytokines

By similar methods using peripheral blood monocytic cells, appropriate stimuli, and commercially available ELISA kits (or other method of detection such as radioimmunoassay), for a particular cytokine, inhibition of IL-1, G M-CSF, IL-6 and IL-8 can be demonstrated (for example, see J. C. Lee et al., 1988, *Int. J Immunophannacol.*, 10, 835).

What is claimed is:
1. A compound of the formula (II):

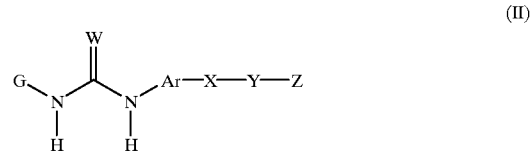

(II)

wherein:
G is:
phenyl, naphthyl, benzocyclobutanyl, dihydronaphthyl, tetrahydronaphthyl, benzocycloheptanyl, benzocycloheptenyl, indanyl, indenyl;
pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobenzopyranyl, indolyl, indolinyl, indolonyl, indolinonyl, phthalimidyl, chromoyl;
oxetanyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl;
wherein G is substituted by one or more $R_1$, $R_2$ or $R_3$;

Ar is:
  phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;

X is:
  a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains;
  phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl;

Y is:
  a bond or a $C_{1-4}$ saturated or unsaturated branched or unbranched carbon chain optionally partially or fully halogenated, wherein one or more methylene groups are optionally replaced by O, N, or $S(O)_m$ and wherein Y is optionally independently substituted with one to two oxo groups, phenyl or one or more $C_{1-4}$ alkyl optionally substituted by one or more halogen atoms;

Z is:
  phenyl, pyridinyl, pyrimidinyl, pyridazinyl, pyrazinyl, imidazolyl, pyrazolyl, triazolyl, tetrazolyl, furanyl, thienyl, pyranyl, each being optionally substituted with one to three halogen, $C_{1-6}$ alkyl, $C_{1-6}$ alkoxy, hydroxy, amino, mono- or di-($C_{1-3}$ alkyl)amino, $C_{1-6}$ alkyl-$S(O)_m$, CN, $CONH_2$, COOH or phenylamino wherein the phenyl ring is optionally substituted with one to two halogen, $C_{1-6}$ alkyl or $C_{1-6}$ alkoxy;
  tetrahydropyranyl, tetrahydrofuranyl, 1,3-dioxanyl, 1,3-dioxanonyl, 1,4-dioxanyl, morpholinyl, thiomorpholinyl, thiomorpholino sulfoxidyl, thiomorpholino sulfonyl, piperidinyl, piperidinonyl, piperazinyl, tetrahydropyrimidonyl, cyclohexanonyl, cyclohexanolyl, pentamethylene sulfidyl, pentamethylene sulfoxidyl, pentamethylene sulfonyl, tetramethylene sulfide, tetramethylene sulfoxidyl or tetramethylene sulfonyl each being optionally substituted with one to three nitrile, $C_{1-6}$ alkyl, $C_{1-6}$ alkoxy, hydroxy, amino, mono- or di-($C_{1-3}$ alkyl)amino-$C_{1-3}$ alkyl, $CONH_2$, phenylamino-$C_{1-3}$ alkyl or $C_{1-3}$ alkoxy-$C_{1-3}$ alkyl;

each $R_1$ is independently:
  $C_{1-10}$ alkyl optionally be partially or fully halogenated, and optionally substituted with one to three $C_{3-10}$ cycloalkanyl, hydroxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated or $NH_2C(O)$, mono- or di($C_{1-3}$alkyl)amino, and mono- or di($C_{1-3}$alkyl)aminocarbonyl;
  cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;
  phenyloxy or benzyloxy each being optionally partially or fully halogenated and optionally substituted with one to three $C_{1-3}$ alkyl groups optionally partially or fully halogenated, CN, hydroxy$C_{1-3}$alkyl or aryl; or an analog of such cycloaryl group wherein one to two ring methyne groups are independently replaced by N;
  cyclopropanyl, cyclobutanyl, cyclopentanyl, cyclohexanyl, cycloheptanyl, bicyclopentanyl, bicyclohexanyl or bicycloheptanyl, each being optionally partially or fully halogenated and optionally substituted with one to three $C_{1-3}$ alkyl optionally partially or fully halogenated, CN, hydroxy$C_{1-3}$alkyl or aryl; or an analog of such cycloalkyl group wherein one to three ring methylene groups are independently replaced by O, $S(O)_m$, CHOH, >C=O, >C=S or NH;
  $C_{3-10}$ branched or unbranced alkenyl each being optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with one to five halogen, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, $C_{1-3}$ alkyloxy which is optionally partially or fully halogenated, $NH_2C(O)$, mono- or di($C_{1-3}$alkyl) aminocarbonyl; the $C_{3-10}$ branched or unbranced alkenyl being optionally interrupted by one or more heteroatoms chosen from O, N and $S(O)_m$;
  cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three $C_{1-3}$ alkyl groups;
  nitrile, halogen;
  methoxycarbonyl, ethoxycarbonyl and propoxycarbonyl;
  silyl containing three $C_{1-4}$ alkyl groups optionally partially or fully halogenated;
  $C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, pyrroldinyl, pyrrolyl, one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;

each $R_2$, $R_4$, and $R_5$ is
  a $C_{1-6}$ branched or unbranched alkyl optionally partially or fully halogenated, acetyl, aroyl, $C_{1-4}$ branched or unbranched alkoxy, each being optionally partially or fully halogenated, halogen, methoxycarbonyl, $C_{1-3}$ alkyl-$S(O)_m$ optionally partially or fully halogenated, or phenylsulfonyl;

$C_{1-6}$ alkoxy, hydroxy, amino, or mono- or di-($C_{1-4}$ alkyl)amino, nitrile, halogen;

$OR_6$;

nitro; or mono- or di-($C_{1-4}$ alkyl)amino-$S(O)_2$ optionally partially or fully halogenated, or $H_2NSO_2$;

each $R_3$ is independently:

phenyl, naphthyl, morpholinyl, pyridinyl, pyrimidinyl, pyrazinyl, pyridazinyl, pyrrolyl, pyrrolidinyl, imidazolyl, pyrazolyl, thiazolyl, oxazoyl, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkyloxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-3}$alkyl)amino-$C_{1-5}$ alkyl, amino-$S(O)_2$, di-($C_{1-3}$alkyl)amino-$S(O)_2$, $R_7$—$C_{1-5}$ alkyl, $R_8$—$C_{1-5}$ alkoxy, $R_9$—$C(O)$—$C_{1-5}$ alkyl, $R_{10}$—$C_{15}$ alkyl($R_{11}$)N, carboxy-mono- or di-($C_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazolyl, pyridazinyl, pyrrolyl, imidazolyl, pyrazolyl, thienyl, furyl, isoxazolyl, isothiazolyl, $C_{1-6}$ alkyl which is optionally partially or fully halogenated, halogen, nitrile, $C_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$alkyl)aminocarbonyl, $C_{1-4}$ alkyl-OC(O), $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl or $R_{15}$—$C_{15}$ alkyl($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally be partially or fully halogenated and optionally substituted with one to three $C_{1-3}$ alkyl groups, or an analog of such cycloalkyl group wherein one to three ring methylene groups are independently replaced by O, S, CHOH, >C=O, >C=S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-$S(O)_m$—$C_{1-4}$ alkyl-;

$C_{1-6}$ alkyl or $C_{1-6}$ branched or unbranched alkoxy each of which is optionally partially or fully halogenated or optionally substituted with $R_{17}$; $OR_{18}$ or $C_{1-6}$ alkyl optionally substituted with $OR_{18}$;

amino or mono- or di-($C_{1-5}$alkyl)amino optionally substituted with $R_{19}$;

$R_{20}C(O)N(R_{21})$—, $R_{22}O$— or $R_{23}R_{24}NC(O)$—; $R_{26}(CH_2)_mC(O)N(R_{21})$— or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, $S(O)_m$ and wherein said alkynyl group is optionally independently substituted with one to two oxo groups, pyrroldinyl, pyrrolyl, morpholinyl, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$ alkyl)amino which may be substituted by one or more halogen atoms; or aroyl;

$R_6$ is a:

$C_{1-4}$ alkyl optionally partially or fully halogenated and optionally substituted with $R_{26}$;

each $R_7$, $R_8$, $R_9$, $R_{10}$, $R_{12}$, $R_{13}$, $R_{14}$, $R_{15}$, $R_{17}$, $R_{19}$, $R_{25}$ and $R_{26}$ is independently:

nitrile, phenyl, morpholino, piperidinyl, piperazinyl, imidazolyl, pyridinyl, tetrazolyl, amino or mono- or di-($C_{1-4}$alkyl)amino optionally partially or fully halogenated;

each $R_{11}$ and $R_{16}$ is independently:

hydrogen or $C_{1-4}$ alkyl optionally partially or fully halogenated;

$R_{18}$ is independently:

hydrogen or a $C_{1-4}$ alkyl optionally independently substituted with oxo or $R_{25}$;

$R_{20}$ is independently:

$C_{1-10}$ alkyl optionally partially or fully halogenated, phenyl, or pyridinyl;

$R_{21}$ is independently:

hydrogen or $C_{1-3}$ alkyl optionally partially or fully halogenated;

each $R_{22}$, $R_{23}$ and $R_{24}$ is independently:
hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-($C_{1-3}$alkyl)aminocarbonyl, phenyl, pyridinyl, amino or mono- or di-($C_{1-4}$alkyl)amino each of which is optionally partially or fully halogenated and optionally substituted with mono- or di-($C_{1-3}$alkyl)amino;
or $R_{23}$ and $R_{24}$ taken together optionally form a heterocyclic or heteroaryl ring;
m=0, 1 or 2;
W is O or S and
pharmaceutically acceptable derivatives thereof;
wherein at least one of G, Ar, X or Z is a heterocyclic or heteroaryl ring.

2. The compound according to claim 1 wherein
G is phenyl, pyridinyl, pyridonyl, naphthyl, quinolinyl, isoquinolinyl, pyrazinyl, benzimidazolyl, benzoxazolyl, benzofuranyl, benzothiophenyl, benzpyrazolyl, dihydrobenzofuranyl, dihydrobenzothiophenyl, indanyl, indenyl, indolyl, indolinyl, indolonyl or indolinonyl, wherein G is substituted by one or more $R_1$, $R_2$ or $R_3$;
Ar is:
naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;
X is:
phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl;
Y is:
a bond or
a $C_{1-4}$ saturated or unsaturated carbon chain wherein one of the carbon atoms is optionally replaced by O, N, or $S(O)_m$ and wherein Y is optionally independently substituted with one to two oxo groups, phenyl or one or more $C_{1-4}$ alkyl optionally substituted by one or more halogen atoms;
Z is:
phenyl, pyridinyl, pyrimidinyl, pyridazinyl, pyrazinyl, imidazolyl, furanyl, thienyl, dihydrothiazolyl, dihydrothiazolyl sulfoxidyl, pyranyl, pyrrolidinyl which are optionally substituted with one to three nitrile, $C_{1-3}$ alkyl, $C_{1-3}$ alkoxy, amino, mono- or di-($C_{1-3}$ alkyl)amino, $CONH_2$ or OH;
tetrahydropyranyl, tetrahydrofuranyl, 1,3-dioxolanonyl, 1,3-dioxanonyl, 1,4-dioxanyl, morpholinyl, thiomorpholinyl, thiomorpholino sulfoxidyl, piperidinyl, piperidinonyl, piperazinyl, tetrahydropyrimidonyl, pentamethylene sulfidyl, pentamethylene sulfoxidyl, pentamethylene sulfonyl, tetramethylene sulfidyl, tetramethylene sulfoxidyl or tetramethylene sulfonyl which are optionally substituted with one to three nitrile, $C_{1-3}$ alkyl, $C_{1-3}$ alkoxy, amino, mono- or di-($C_{1-3}$ alkyl)amino, $CONH_2$, or OH;
each $R_1$ is independently:
$C_{3-6}$ alkyl optionally partially or fully halogenated, and optionally substituted with one to three $C_{3-6}$cycloalkyl, phenyl, thienyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile or $C_{1-3}$alkoxy which is optionally partially or fully halogenated;
cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, CN, hydroxy$C_{1-3}$alkyl or phenyl; or an analog of such cycloalkyl group wherein one to three ring methylene groups are independently replaced by O, S, CHOH, >C=O, >C=S or NH;
or
silyl containing three $C_{1-4}$ alkyl groups optionally partially or fully halogenated;
$R_2$ is independently:
halogen, $C_{1-3}$ alkoxy, $C_{1-3}$ alkyl-$S(O)_m$ optionally partially or fully halogenated, phenylsulfonyl or nitrile;
$R_3$ is independently:
phenyl, morpholino, pyridinyl, pyrimidinyl, pyrazinyl, pyrrolyl, pyrrolylidinyl, imidazolyl, pyrazolyl, each being optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, nitrile, $C_{1-3}$ alkyloxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl)aminocarbonyl, $C_{1-5}$ alkyl-$C(O)$—$C_{1-4}$ alkyl, mono- or di-($C_{1-3}$alkyl)amino, mono- or di-($C_{1-3}$)alkylamino-$C_{1-5}$ alkyl, mono- or di-($C_{1-3}$alkyl)amino-$S(O)_2$, $R_7$—$C_{1-5}$ alkyl, $R_8$—$C_{1-5}$ alkoxy, $R_9$—$C(O)$—$C_{1-5}$ alkyl, $R_{10}$—$C_{1-5}$ alkyl ($R_{11}$)N, carboxy-mono- or di-($C_{1-5}$)-alkyl-amino;
$C_{1-3}$ alkyl or $C_{1-4}$ alkoxy each being optionally partially or fully halogenated or optionally substituted with $R_{17}$;
$OR_{18}$ or $C_{16}$ alkyl optionally substituted with $OR_{18}$;
amino or mono- or di-($C_{1-5}$ alkyl)amino optionally substituted with $R_{19}$;
$R_{20}C(O)N(R_{21})$—, $R_{22}O$—; $R_{23}R_{24}NC(O)$—; $R_{26}CH_2C(O)N(R_{21})$— or $R_{26}C(O)CH_2N(R_{21})$—; $C_{2-4}$alkenyl substituted by $R_{23}R_{24}NC(O)$—; or
$C_{2-4}$ alkynyl branched or unbranched carbon chain optionally partially or fully halogenated and optionally independently substituted with one to two oxo groups, pyrroldinyl, pyrrolyl, morpholinyl, piperidinyl, piperazinyl, imidazolyl, phenyl, pyridinyl, tetrazolyl or one or more $C_{1-4}$ alkyl optionally substituted by one or more halogen atoms; and $R_{23}$ and $R_{24}$ taken together optionally form imidazolyl, piperidinyl, morpholinyl, piperazinyl or a pyridinyl ring.

3. The compound according to claim 2 wherein:

G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl or indolinonyl, wherein G is substituted by one or more $R_1$, $R_2$ or $R_3$;

Ar is naphthyl;

X is phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;

Y is:

a bond or a $C_{1-4}$ saturated carbon chain wherein one of the carbon atoms is optionally replaced by O, N or S and wherein Y is optionally independently substituted with an oxo group;

Z is:

phenyl, pyridinyl, pyrimidinyl, pyridazinyl, pyrazinyl, imidazolyl, dihydrothiazolyl, dihydrothiazolyl sulfoxide, pyranyl or pyrrolidinyl which are optionally substituted with one to two $C_{1-2}$ alkyl or $C_{1-2}$ alkoxy;

tetrahydropyranyl, morpholinyl, thiomorpholinyl, thiomorpholino sulfoxidyl, piperidinyl, piperidinonyl, piperazinyl or tetrahydropyrimidonyl which are optionally substituted with one to two $C_{1-2}$ alkyl or $C_{1-2}$ alkoxy;

each $R_1$ is independently:

$C_{3-5}$ alkyl optionally partially or fully halogenated, and optionally substituted with phenyl substituted with zero to three halogen, $C_{1-3}$ alkyl which is optionally partially or fully halogenated, hydroxy, nitrile or $C_{1-3}$alkoxy which is optionally partially or fully halogenated;

cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, CN, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O; and silyl containing three $C_{1-2}$ independently alkyl groups optionally partially or fully halogenated;

each $R_2$ is independently:

bromo, chloro, fluoro, methoxy, methylsulfonyl or nitrile;

each $R_3$ is independently:

phenyl, morpholino, pyridinyl, pyrimidinyl, pyrrolylidinyl, 2,5-pyrrolidin-dionyl, imidazolyl, pyrazolyl, each of the aforementioned is optionally substituted with one to three $C_{1-3}$ alkyl which is optionally partially or fully halogenated, halogen, oxo, hydroxy, nitrile and $C_{1-3}$ alkyloxy optionally partially or fully halogenated;

$C_{1-3}$ alkyl or $C_{1-3}$ alkoxy optionally partially or fully halogenated or optionally substituted with $R_{17}$;

$OR_{18}$ or $C_{1-3}$ alkyl optionally substituted with $OR_{18}$;

amino or mono- or di-($C_{1-3}$ alkyl)amino optionally substituted with $R_{19}$;

$R_{20}C(O)N(R_{21})$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$ alkenyl substituted by $R_{23}R_{24}NC(O)$—; or $C_{2-4}$ alkynyl substituted with pyrroldinyl or pyrrolyl; and $R_{23}$ and $R_{24}$ taken together optionally form morpholino.

4. The compound according to claim 3 wherein

G is phenyl, pyridinyl, pyridonyl, naphthyl, quinolinyl, isoquinolinyl, dihydrobenzofuranyl, indanyl, indolinyl, indolonyl, or indolinonyl, wherein G is substituted by one or more $R_1$, $R_2$ or $R_3$;

Ar is 1-naphthyl;

X is:

phenyl, imidazolyl, pyridinyl, pyrimidinyl, piperdinyl, piperazinyl, pyridazinyl or pyrazinyl;

Y is:

a bond or

—$CH_2$—, —$CH_2CH_2$—, —$C(O)$—, —O—, —S—, —NH—$CH_2CH_2CH_2$—, —$N(CH_3)$—, or —NH—;

each $R_1$ is independently:

$C_{3-5}$ alkyl optionally partially or fully halogenated, and optionally substituted with phenyl;

cyclopropyl, cyclopentanyl, cyclohexanyl and bicyclopentanyl optionally substituted with one to three methyl groups optionally partially or fully halogenated, CN, hydroxymethyl or phenyl; or 2-tetrahydrofuranyl substituted by methyl; or trimethyl silyl;

each $R_3$ is independently:

phenyl, morpholinyl, pyridinyl, pyrimidinyl, pyrrolylidinyl, 2,5-pyrrolidin-dionyl, imidazolyl or pyrazolyl, wherein any of the aforementioned is optionally substituted with $C_{1-2}$ alkyl which is optionally partially or fully halogenated;

$C_{1-3}$ alkyl or $C_{1-3}$ alkoxy each being optionally partially or fully halogenated or optionally substituted with diethylamino;

$OR_{18}$ or $C_{1-3}$ alkyl optionally substituted with $OR_{18}$;

amino or mono- or di-($C_{1-3}$ alkyl)amino optionally substituted with $R_{19}$;

$CH_3C(O)NH$—, $R_{22}O$—; $R_{23}R_{24}NC(O)$—; $R_{26}CH_2C(O)N(R_{21})$— or $R_{26}C(O)CH_2N(R_{21})$—;

$C_{2-4}$alkenyl substituted by $R_{23}R_{24}NC(O)$—; or $C_{2-4}$ alkynyl substituted with pyrroldinyl or pyrrolyl;

$R_{23}$ and $R_{24}$ are H or $R_{23}$ and $R_{24}$ taken together optionally form morpholino; and $R_{26}$ is morpholino.

5. The compound according to claim 4 wherein

G is phenyl, pyridinyl or naphthyl wherein G is substituted by one or more $R_1$, $R_2$ or $R_3$;

X is:

imidazolyl or pyridinyl;

Y is:

—$CH_2$-, —NH—$CH_2CH_2CH_2$— or —NH—;

Z is morpholino;

each $R_1$ is independently:

tert-butyl, sec-butyl, tert-amyl or phenyl;

$R_2$ is chloro;

$R_3$ is independently:

methyl, methoxy, methoxymethyl, hydroxypropyl, acetamide, morpholino or morpholinocarbonyl.

6. The compound according to claim 5 wherein X is pyridinyl.

7. The compound according to claim 6 wherein the pyridinyl is attached to Ar via the 3-pyridinyl position.

8. A compound of the formula (III):

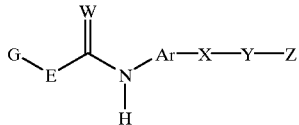

(III)

wherein:
E is —NH—;
G is:
  phenyl, naphthyl, benzocyclobutanyl, dihydronaphthyl, tetrahydronaphthyl, benzocycloheptanyl, benzocycloheptenyl, indanyl, indenyl; pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzooxazolyl, benzofuranyl, benzothiophenyl, benzpyrazolyl, dihydrobenzofuranyl, dibenzofuranyl, dihydrobenzothiophenyl, benzooxazolonyl, benzo[1,4]oxazin-3-onyl, benzodioxolyl, benzo[1,3]dioxol-2-onyl, benzofuran-3-onyl, tetrahydrobeuzopyranyl, indolyl, 2,3-dihydro-1H-indolyl, indolinyl, indolonyl, indolinonyl, phthalimidyl;
  oxetanyl, tetrahydrothiophenyl, piperidinyl, piperazinyl, morpholino, tetrahydropyranyl, dioxanyl, 3,4-dihydro-2H-benzo[1,4]oxazinyl, tertrahydropyridinyl, homopiperidinyl, pyrrolinyl, tetrahydropyrimidinyl, decahydroquinolinyl, decahydroisoquinolinyl, thiomorpholino, dihydropyranyl, oxocanyl or heptacanyl;
  wherein G is optionally substituted by one or more $R_1$, $R_2$ or $R_3$;
Ar is:
  phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl or indolyl each being optionally substituted by one or more $R_4$ or $R_5$;
X is:
  a $C_{5-8}$ cycloalkyl or cycloalkenyl optionally substituted with one to two oxo groups or one to three $C_{1-4}$ alkyl, $C_{1-4}$ alkoxy or $C_{1-4}$ alkylamino chains each being branched or unbranched;
  aryl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, benzimidazole, 3H-imidazo[4,5-b]pyridine, piperazinyl, pyridazinyl or pyrazinyl; each being optionally independently substituted with one to three $C_{1-4}$ alkyl, $C_{1-4}$alkoxy, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-$S(O)_m$ or halogen;
Y is:
  a bond or a $C_{1-4}$ saturated or unsaturated branched or unbranched carbon chain optionally partially or fully halogenated, wherein one or more C atoms are optionally replaced by O, N, or $S(O)_m$ and wherein Y is optionally independently substituted with one to two oxo groups, nitrile, phenyl or one or more $C_{1-4}$ alkyl optionally substituted by one or more halogen atoms;
Z is:
  aryl, heteroaryl selected from pyridinyl, piperazinyl, pyrimidinyl, pyridazinyl, pyrazinyl, imidazolyl, pyrazolyl, triazolyl, tetrazolyl, furanyl, thienyl and pyranyl, heterocycle selected from tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, thiomorpholino sulfonyl, piperidinyl, piperidinonyl, pyrrolidinyl and dioxolanyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, $C_{1-3}$acyl, oxo, hydroxy, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, carboxy, phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$, or phenyl-$S(O)_m$ wherein the phenyl ring is optionally substituted with one to two halogen, $C_{1-6}$ alkoxy, hydroxy, halogen or mono- or di-($C_{1-3}$ alkyl)amino;
  or Z is optionally substituted with one to three amino or amino-$C_{1-3}$ alkyl wherein the N atom is optionally independently mono- or di-substituted by amino$C_{1-6}$alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;
each $R_1$ is independently:
  $C_{1-10}$ alkyl branched or unbranched optionally partially or fully halogenated, wherein one or more C atoms are optionally independently replaced by O, N or $S(O)_m$, and wherein said $C_{1-10}$ alkyl is optionally substituted with one to three $C_{3-10}$ cycloalkyl, hydroxy, oxo, phenyl, naphthyl, pyridinyl, pyrimidinyl, pyrazinyl, pyridazinyl, pyrrolyl, pyrrolidinyl, imidazolyl, pyrazolyl, thienyl, furyl, dioxolanyl, isoxazolyl or isothiazolyl; each of the aforementioned being optionally substituted with one to five groups selected from halogen, $C_{1-6}$ alkyl which is optionally partially or fully halogenated, $C_{3-8}$ cycloalkanyl, $C_{5-8}$ cycloalkenyl, hydroxy, nitrile, $C_{1-3}$ alkoxy which is optionally partially or fully halogenated, $NH_2C(O)$, mono- or di($C_{1-3}$alkyl) amino, and mono- or di($C_{1-3}$alkyl)aminocarbonyl;
or $R_1$ is
  cyclopropyloxy, cyclobutyloxy, cyclopentyloxy, cyclohexyloxy, or cycloheptyloxy each being optionally partially or fully halogenated and optionally substituted with one to three $C_{1-3}$ alkyl groups optionally partially or fully halogenated, nitrile, hydroxy$C_{1-3}$alkyl or aryl; or an analog of such cycloalkyl group wherein one to three ring methylene groups are independently replaced by O, S(O)$_m$, CHOH, >C=O, >C=S or NH;

phenyloxy or benzyloxy each being optionally partially or fully halogenated and optionally substituted with one to three C$_{1-3}$ alkyl groups optionally partially or fully halogenated, nitrile, hydroxyC$_{1-3}$alkyl or aryl; or an analog of such cycloaryl group wherein one to two ring methyne groups are independently replaced by N;

cyclopropyl, cyclobutyl, cyclopentyl, cyclohexyl, cycloheptyl, bicyclopentanyl, bicyclohexanyl or bicycloheptanyl, each being optionally partially or fully halogenated and optionally substituted with one to three C$_{1-3}$ alkyl optionally partially or fully halogenated, nitrile, hydroxyC$_{1-3}$alkyl or aryl; or an analog of such cycloalkyl group wherein one to three ring methylene groups are independently replaced by O, S(O)$_m$, CHOH, >C=O, >C=S or NH;

C$_{3-10}$ branched or unbranced alkenyl each being optionally partially or fully halogenated, and optionally substituted with one to three C$_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned being substituted with one to five halogen, C$_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl and bicycloheptanyl, hydroxy, nitrile, C$_{1-3}$ alkyloxy which is optionally partially or fully halogenated, NH$_2$C(O), mono- or di(C$_{1-3}$alkyl) aminocarbonyl; the C$_{3-10}$ branched or unbranced alkenyl being optionally interrupted by one or more heteroatoms chosen from O, N and S(O)$_m$;

cyclopentenyl, cyclohexenyl, cyclohexadienyl, cycloheptenyl, cycloheptadienyl, bicyclohexenyl or bicycloheptenyl, wherein such cycloalkenyl group is optionally substituted with one to three C$_{1-3}$ alkyl groups;

oxo, nitrile, halogen;

silyl containing three C$_{1-4}$ alkyl groups optionally partially or fully halogenated; or C$_{3-6}$ alkynyl branched or unbranched carbon chain optionally partially or fully halogenated, wherein one or more methylene groups are optionally replaced by O, NH or S(O)$_m$ and wherein said alkynyl group is optionally independently substituted with one to two oxo groups, hydroxy, pyrroldinyl, pyrrolyl, tetrahydropyranyl, one or more C$_{1-4}$ alkyl optionally substituted by one or more halogen atoms, nitrile, morpholino, piperidinyl, piperazinyl, imidazolyl, phenyl, pyridinyl, tetrazolyl, or mono- or di(C$_{1-3}$alkyl)amino optionally substituted by one or more halogen atoms;

each R$_2$, R$_4$, and R$_5$ is
a C$_{1-6}$ branched or unbranched alkyl optionally partially or fully halogenated, C$_{1-6}$acyl, aroyl, C$_{1-4}$ branched or unbranched alkoxy, each being optionally partially or fully halogenated, halogen, methoxycarbonyl, C$_{1-3}$ alkyl-S(O)$_m$ optionally partially or fully halogenated, or phenyl-S(O)$_m$;

OR$_6$, C$_{1-6}$ alkoxy, hydroxy, nitrile, nitro, halogen;

amino-S(O)$_m$— wherein the N atom is optionally independently mono- or di-substituted by C$_{1-6}$alkyl or arylC$_{0-3}$alkyl, or amino wherein the N atom is optionally independently mono- or di-substituted by C$_{1-3}$alkyl, arylC$_{0-3}$alkyl, C$_{1-6}$acyl, C$_{1-6}$alkyl-S(O)$_m$— or arylC$_{0-3}$alkyl-S(O)$_m$—, each of the aforementioned alkyl and aryl in this subparagraph are optionally partially or fully halogenated and optionally substituted with one to two C$_{1-6}$ alkyl or C$_{1-6}$ alkoxy;

each R$_3$ is independently:
phenyl, naphthyl, morpholino, pyridinyl, pyrimidinyl, pyrazinyl, pyridazinyl, pyrrolyl, pyrrolidinyl, imidazolyl, pyrazolyl, thiazolyl, oxazoyl, [1,3,4] oxadiazol, triazolyl, tetrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, C$_{1-6}$ branched or unbranched alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl C$_{1-5}$ alkyl, naphthyl C$_{1-5}$ alkyl, halogen, hydroxy, oxo, nitrile, C$_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-(C$_{1-3}$alky)lamino, phenylamino, naphthylamino, heteroaryl or heterocyclic amino wherein the heteroaryl heterocyclic moiety is as hereinabove described in this paragraph, NH$_2$C(O), a mono- or di-(C$_{1-3}$alkyl) aminocarbonyl, C$_{1-5}$ alkyl-C(O)—C$_{1-4}$ alkyl, amino-C$_{1-5}$ alkyl, mono- or di-(C$_{1-5}$alkyl)amino, mono- or di-(C$_{1-3}$alkyl)amino-C$_{1-5}$ alkyl, amino-S(O)$_2$, di-(C$_{1-3}$alkyl)amino-S(O)$_2$, R$_7$—C$_{1-5}$ alkyl, R$_8$—C$_{1-5}$ alkoxy, R$_9$—C(O)—C$_{1-5}$ alkyl, R$_{10}$—C$_{1-5}$ alkyl (R$_{11}$)N or carboxy-mono- or di-(C$_{1-5}$alkyl)-amino;

a fused aryl selected from benzocyclobutanyl, indanyl, indenyl, dihydronaphthyl, tetrahydronaphthyl, benzocycloheptanyl and benzocycloheptenyl, or a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl; wherein the fused aryl or fused heteroaryl ring is independently substituted with zero to three phenyl, naphthyl, pyridinyl, pyrimidinyl, pyrazinyl, pyridazinyl, pyrrolyl, imidazolyl, pyrazolyl, thienyl, furyl, isoxazolyl, isothiazolyl, C$_{1-6}$ alkyl which is optionally partially or fully halogenated, halogen, nitrile, C$_{1-3}$ alkyloxy which is optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, mono- or di-($C_{1-3}$alkyl)aminocarbonyl, $C_{1-4}$ alkyl-OC(O), $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, $R_{12}$—$C_{1-5}$ alkyl, $R_{13}$—$C_{1-5}$ alkoxy, $R_{14}$—C(O)—$C_{1-5}$ alkyl or $R_{15}$—$C_{1-5}$ alkyl($R_{16}$)N;

cyclopropanyl, cyclobutanyl, cyclopentanyl, cyclohexanyl, cycloheptanyl, bicyclopentanyl, bicyclohexanyl or bicycloheptanyl, each being optionally be partially or fully halogenated and optionally substituted with one to three $C_{1-3}$ alkyl groups, or an analog of such cycloalkyl group wherein one to three ring methylene groups are independently replaced by O, S, CHOH, >C=O, >C=S or NH;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-S(O)$_m C_{1-4}$ alkyl-;

$C_{1-6}$ alkyl or $C_{1-6}$ branched or unbranched alkoxy each of which is optionally partially or fully halogenated or optionally substituted with $R_{17}$;

$OR_{18}$ or $C_{1-6}$ alkyl optionally substituted with $OR_{18}$;

amino or mono- or di-($C_{1-5}$alkyl)amino optionally substituted with $R_{19}$;

$R_{20}C(O)N(R_{21})$—, $R_{22}O$— or $R_{23}R_{24}NC(O)$—; $R_{26}(CH_2)_mC(O)N(R_{21})$, $R_{23}R_{24}NC(O)$—$C_{1-3}$alkoxy or $R_{26}C(O)(CH_2)_mN(R_{21})$—;

$C_{2-6}$alkenyl substituted by $R_{23}R_{24}NC(O)$—;

$C_{2-6}$ alkynyl branched or unbranched carbon chain, optionally partially or fully halogenated, wherein one or more methylene groups are optionally replaced by O, NH, S(O)$_m$ and wherein said alkynyl group is optionally independently substituted with one to two oxo groups, pyrroldinyl, pyrrolyl, morpholino, piperidinyl, piperazinyl, imidazolyl, phenyl, pyridinyl, tetrazolyl one or more $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-4}$ alkyl)amino optionally substituted by one or more halogen atoms;

$C_{1-6}$acyl or aroyl;

$R_6$ is a:

$C_{1-4}$ alkyl optionally partially or fully halogenated and optionally substituted with $R_{26}$;

each $R_7, R_8, R_9, R_{10}, R_{12}, R_{13}, R_{14}, R_{15}, R_{17}, R_{19}, R_{25}$ and $R_{26}$ is independently:

nitrile, phenyl, morpholino, piperidinyl, piperazinyl, imidazolyl, pyridinyl, tetrazolyl, amino or mono- or di-($C_{1-4}$alkyl)amino optionally partially or fully halogenated;

each $R_{11}$ and $R_{16}$ is independently:

hydrogen or $C_{1-4}$ alkyl optionally partially or fully halogenated;

$R_{18}$ is independently:

hydrogen or a $C_{1-4}$ alkyl optionally independently substituted with oxo or $R_{25}$;

$R_{20}$ is independently:

$C_{1-10}$ alkyl optionally partially or fully halogenated, phenyl, or pyridinyl;

$R_{21}$ is independently:

hydrogen or $C_{1-3}$ alkyl optionally partially or fully halogenated;

each $R_{22}, R_{23}$ and $R_{24}$ is independently:

hydrogen, $C_{1-6}$ alkyl optionally partially or fully halogenated, said $C_{1-6}$ alkyl is optionally interrupted by one or more O, N or S, said $C_{1-6}$ alkyl also being independently optionally substituted by mono- or di-($C_{1-3}$alkyl)aminocarbonyl, phenyl, pyridinyl, amino or mono- or di-($C_{1-4}$alkyl)amino each of which is optionally partially or fully halogenated and optionally substituted with mono- or di-($C_{1-3}$alkyl)amino;

or $R_{23}$ and $R_{24}$ taken together optionally form a heterocyclic or heteroaryl ring;

m=0, 1 or 2;

W is O or S and the pharmaceutically acceptable derivatives thereof.

9. The compound according to claim 8 wherein:

W is O.

10. The compound according to claim 9 wherein

G is phenyl, pyridinyl, pyridonyl, naphthyl, quinolinyl, isoquinolinyl, pyrazinyl, benzimidazolyl, benzooxazolyl, benzooxazolonyl, benzofuranyl, benzothiophenyl, benzpyrazolyl, dihydrobenzofuranyl, dihydrobenzothiophenyl, 3,4-dihydro-2H-benzo[1,4]oxazinyl, indanyl, indenyl, indolyl, indolinyl, indolonyl, 2,3-dihydro-1H-indolyl or indolinonyl, wherein G is optionally substituted by one or more $R_1$, $R_2$ or $R_3$;

Ar is:

naphthyl, quinolinyl, isoquinolinyl, tetrahydronaphthyl, tetrahydroquinolinyl, tetrahydroisoquinolinyl, indanyl, indenyl or indolyl each being optionally substituted by one or more $R_4$ or $R_5$ groups;

X is:

phenyl, furanyl, thienyl, pyrrolyl, pyrazolyl, imidazolyl, pyridinyl, pyrimidinyl, pyridinonyl, dihydropyridinonyl, maleimidyl, dihydromaleimidyl, piperdinyl, piperazinyl, pyridazinyl or pyrazinyl; each being optionally independently substituted with one to three $C_{1-4}$ alkyl, $C_{1-4}$alkoxy, hydroxy, nitrile, amino, mono- or alkyl)amino, mono- or di-($C_{1-3}$ alkylamino)carbonyl, $NH_2C(O)$, $C_{1-6}$ alkyl-S(O)$_m$ or halogen;

Y is:

a bond or a $C_{1-4}$ saturated or unsaturated carbon chain wherein one or more of the C atoms is optionally replaced by O, N, or S(O)$_m$ and wherein Y is optionally independently substituted with one to two oxo groups, nitrile, phenyl or one or more $C_{1-4}$ alkyl optionally substituted by one or more halogen atoms;

Z is:

phenyl, heteroaryl selected from pyridinyl, piperazinyl, pyrimidinyl, pyridazinyl, pyrazinyl, imidazolyl, furanyl, thienyl and pyranyl, heterocycle selected from 2-oxa-5-aza-bicyclo[2.2.1]heptanyl, tetrahydropyrimidonyl, pentamethylene sulfidyl, pentamethylene sulfoxidyl, pentamethylene sulfonyl, tetramethylene sulfidyl, tetramethylene sulfoxidyl tetramethylene sulfonyl, tetrahydropyranyl, tetrahydrofuranyl, 1,3-dioxolanonyl, 1,3-dioxanonyl, 1,4-dioxanyl, morpholino, thiomorpholino, thiomorpholino sulfoxidyl, piperidinyl, piperidinonyl, dihydrothiazolyl, dihydrothiazolyl sulfoxidyl, pyrrolidinyl and dioxolanyl which are optionally substituted with one to three nitrile, $C_{1-3}$ alkyl, $C_{1-3}$ alkoxy, amino, mono- or di-($C_{1-3}$ alkyl)amino, $CONH_2$ or OH;

or Z is optionally substituted by phenyl, heterocycle or heteroaryl as hereinabove described in this paragraph each in turn is optionally substituted by halogen, $C_{1-3}$ alkyl or $C_{1-3}$ alkoxy;

each $R_1$ is independently:
  $C_{1-6}$ alkyl branched or unbranched optionally partially or fully halogenated, wherein one or more C atoms are optionally independently replaced by O, N or $S(O)_m$, and wherein said $C_{1-6}$ alkyl is optionally substituted with one to three $C_{3-6}$cycloalkyl, oxo, phenyl, dioxolanyl, pyrrolidinyl, furyl, isoxazolyl or isothiazolyl; each of the aforementioned being optionally substituted with one to three groups selected from halogen, $C_{1-3}$ alkyl which is optionally partially or fully halogenated, hydroxy, nitrile and $C_{1-3}$alkoxy which is optionally partially or fully halogenated;
  cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; or an analog of such cycloalkyl group wherein one to three ring methylene groups are independently replaced by O, S, CHOH, >C=O, >C=S or NH;
  oxo;
  $C_{3-6}$ alkynyl branched or unbranched carbon chain optionally partially or fully halogenated, wherein one or more methylene groups are optionally replaced by O, NH or $S(O)_m$ and wherein said alkynyl group is optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms;
  or
  silyl containing three $C_{1-4}$ alkyl groups optionally partially or fully halogenated;
$R_2$ is independently:
  a $C_{1-5}$ branched or unbranched alkyl optionally partially or fully halogenated, acetyl, aroyl, $C_{1-4}$ branched or unbranched alkoxy, each being optionally partially or fully halogenated, halogen, methoxycarbonyl, $C_{1-2}$ alkyl-$S(O)_m$ optionally partially or fully halogenated, or phenyl-$S(O)_m$;
  $C_{1-3}$ alkoxy, hydroxy, nitrile, nitro, halogen;
  amino-$S(O)_m$— wherein the N atom is optionally independently mono- or di-substituted by $C_{1-3}$alkyl or aryl$C_{0-3}$alkyl, or amino wherein the N atom is optionally independently mono- or di-substituted by $C_{1-3}$alkyl, aryl$C_{0-3}$alkyl, $C_{1-3}$acyl, $C_{1-4}$alkyl-$S(O)_m$— or aryl$C_{0-3}$alkyl-$S(O)_m$—, each of the aforementioned alkyl and aryl in this subparagraph are optionally partially or fully halogenated and optionally substituted with one to two $C_{1-3}$ alkyl or $C_{1-3}$ alkoxy;
$R_3$ is independently:
  phenyl, morpholino, pyridinyl, pyrimidinyl, pyrazinyl, pyrrolyl, pyrrolidinyl, imidazolyl, [1,3,4]oxadiazol, pyrazolyl, each is optionally substituted with one to three phenyl, naphthyl, heterocycle or heteroaryl as hereinabove described in this paragraph, $C_{1-6}$ alkyl which is optionally partially or fully halogenated, cyclopropanyl, cyclobutanyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halogen, oxo, hydroxy, nitrile, $C_{1-3}$ alkoxy optionally partially or fully halogenated, phenyloxy, naphthyloxy, heteroaryloxy or heterocyclicoxy wherein the heteroaryl or heterocyclic moiety is as hereinabove described in this paragraph, nitro, amino, mono- or di-($C_{1-3}$alkyl)amino, phenylamino, naphthylamino, heteroaryl or heterocyclic amino wherein the heteroaryl or heterocyclic moiety is as hereinabove described in this paragraph, $NH_2C(O)$, a mono- or di-($C_{1-3}$alkyl)aminocarbonyl, $C_{1-5}$ alkyl-C(O)—$C_{1-4}$ alkyl, mono- or di-($C_{1-3}$alkyl) amino, mono- or di-($C_{1-3}$)alkylamino-$C_{1-5}$ alkyl, mono- or di-($C_{1-3}$alkyl)amino-$S(O)_2$, $R_7$—$C_{1-5}$ alkyl, $R_8$—$C_{1-5}$ alkoxy, $R_9$—C(O)—$C_{1-5}$ alkyl, $R_{10}$—$C_{1-5}$ alkyl($R_{11}$)N or carboxy-mono- or di-($C_{1-5}$)-alkyl-amino;
  $C_{1-3}$ alkyl or $C_{1-4}$ alkoxy each being optionally partially or fully halogenated or optionally substituted with $R_{17}$;
  $OR_{18}$ or $C_{1-6}$ alkyl optionally substituted with $OR_{18}$;
  amino or mono- or di-($C_{1-5}$ alkyl)amino optionally substituted with $R_{19}$;
  $R_{20}C(O)N(R_{21})$—, $R_{22}O$—; $R_{23}R_{24}NC(O)$—; $R_{26}CH_2C(O)N(R_{21})$—, $R_{23}R_{24}NC(O)$—$C_{1-2}$alkoxy or $R_{26}C(O)CH_2N(R_{21})$—;
  $C_{24}$alkenyl substituted by $R_{23}R_{24}NC(O)$—; or
  $C_{24}$ alkynyl branched or unbranched carbon chain optionally partially or fully halogenated wherein one of the methylene groups is optionally replaced by O, and optionally independently substituted with one to two oxo groups, pyrroldinyl, pyrrolyl, morpholino, piperidinyl, piperazinyl, imidazolyl, phenyl, pyridinyl, tetrazolyl or one or more $C_{1-4}$ alkyl optionally substituted by one or more halogen atoms;
  $C_{1-3}$acyl; and
  $R_{23}$ and $R_{24}$ taken together optionally form imidazolyl, piperidinyl, morpholino, piperazinyl or a pyridinyl ring.

11. The compound according to claim 10 wherein:
G is
  phenyl, pyridinyl, pyridonyl, naphthyl, quinolinyl, isoquinolinyl, pyrazinyl, 3,4-dihydro-2H-benzo[1,4] oxazinyl, benzothiophenyl, dihydrobenzofuranyl, dihydrobenzothiophenyl, benzooxazolyl, indanyl, indolyl, indolinyl, indolonyl or indolinonyl, wherein G is optionally substituted by one or more $R_1$, $R_2$ or $R_3$;
Ar is naphthyl;
X is
  phenyl, imidazolyl, pyridinyl, pyrimidinyl, piperdinyl, piperazinyl, pyridazinyl or pyrazinyl each being optionally independently substituted with one to three $C_{1-4}$ alkyl, $C_{1-4}$alkoxy, hydroxy, nitrile, amino, mono- or di-($C_{1-3}$ alkyl)amino, mono- or alkylamino)carbonyl, $NH_2C(O)$, $C_{1-6}$ alkyl-$S(O)_m$ or halogen;
Y is:
  a bond or
  a $C_{1-4}$ saturated carbon chain wherein one or more of the C atoms is optionally replaced by O, N or S and wherein Y is optionally independently substituted with nitrile or oxo;

Z is:
  phenyl, pyridinyl, pyrimidinyl, pyridazinyl, pyrazinyl, imidazolyl, dihydrothiazolyl, dihydrothiazolyl sulfoxide, pyranyl, pyrrolidinyl, phenylpiperazinyl, tetrahydropyranyl, tetrahydrofuranyl, dioxolanyl, 2-oxa-5-aza-bicyclo[2.2.1]heptanyl, morpholino, thiomorpholino, thiomorpholino sulfoxidyl, piperidinyl, piperidinonyl, piperazinyl or tetrahydropyrimidonyl each of which are optionally substituted with one to two $C_{1-2}$ alkyl or $C_{1-2}$ alkoxy;

each $R_1$ is independently:
  $C_{1-5}$ alkyl branched or unbranched optionally partially or fully halogenated, wherein one or more C atoms are optionally independently replaced by O, N or $S(O)_m$, and wherein said $C_{1-5}$ alkyl is optionally substituted with oxo, dioxolanyl, pyrrolidinyl, furyl or phenyl each optionally substituted with one to three halogen, $C_{1-3}$ alkyl which is optionally partially or fully halogenated, hydroxy, nitrile and $C_{1-3}$alkoxy which is optionally partially or fully halogenated;
  cyclopropyl, cyclobutyl, cyclopentanyl, cyclohexanyl, bicyclopentanyl or bicyclohexanyl, each being optionally partially or fully halogenated and optionally substituted with one to three $C_{1-3}$ alkyl groups optionally partially or fully halogenated, nitrile, hydroxy$C_{1-3}$alkyl or phenyl; and an analog of cyclopropyl, cyclobutyl, cyclopentanyl, cyclohexanyl, bicyclopentanyl or bicyclohexanyl wherein one ring methylene group is replaced by O;
  oxo;
  $C_{2-4}$ alkynyl optionally partially or fully halogenated wherein one or more methylene groups are optionally replaced by O, and optionally independently substituted with one to two oxo groups, hydroxy, pyrroldinyl, pyrrolyl, tetrahydropyranyl, $C_{1-4}$ alkyl optionally substituted by one or more halogen atoms, nitrile, morpholino, piperidinyl, piperazinyl, imidazolyl, phenyl, pyridinyl, tetrazolyl, or mono- or di($C_{1-3}$alkyl)amino optionally substituted by one or more halogen atoms; or
  silyl containing three $C_{1-2}$ alkyl groups optionally partially or fully halogenated;

each $R_3$ is independently:
  phenyl, morpholino, pyridinyl, pyrimidinyl, pyrrolidinyl, 2,5-pyrrolidin-dionyl, imidazolyl, [1,3,4]oxadiazol, pyrazolyl, each of the aforementioned is optionally substituted with one to three $C_{1-3}$ alkyl which is optionally partially or fully halogenated, halogen, oxo, hydroxy, nitrile or $C_{1-3}$ alkoxy optionally partially or fully halogenated;
  $C_{1-3}$ alkyl or $C_{1-3}$ alkoxy optionally partially or fully halogenated or optionally substituted with $R_{17}$;
  $OR_{18}$ or $C_{1-3}$ alkyl optionally substituted with $OR_{18}$;
  amino or mono- or di-($C_{1-3}$ alkyl)amino optionally substituted with $R_{19}$;
  $R_{20}C(O)N(R_{21})$—, $R_{22}O$—; $R_{23}R_{24}NC(O)$—; $R_{26}CH_2C(O)N(R_{21})$—, $NH_2C(O)$methoxy or $R_{26}C(O)CH_2N(R_{21})$—;
  $C_{2-4}$ alkenyl substituted by $R_{23}R_{24}NC(O)$—; or
  $C_{2-4}$ alkynyl substituted with pyrroldinyl or pyrrolyl;
  $C_{1-3}$acyl and
  $R_{23}$ and $R_{24}$ taken together optionally form morpholino.

12. The compound according to claim 11 wherein

G is phenyl, pyridinyl, pyridonyl, 2-naphthyl, quinolinyl, isoquinolinyl, dihydrobenzofuranyl, indanyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro-1H-indol-5-yl, indolinyl, indolonyl, or indolinonyl, wherein G is optionally substituted by one or more $R_1$, $R_2$ or $R_3$;

Ar is 1-naphthyl;

X is:
  phenyl, imidazolyl, pyridinyl, pyrimidinyl, piperdinyl, piperazinyl, pyridazinyl or pyrazinyl;

Y is:
  a bond or
    —$CH_2$—, —$CH_2CH_2$—, —$C(O)$—, —$O$—, —$S$—, —$NH$—$CH_2CH_2CH_2$—, $CH_2(CN)CH_2$—$NH$—$CH_2$ or —$NH$—;

Z is
  morpholino, dioxolanyl, tetrahydrofuranyl, pyridinyl, 2-oxa-5-aza-bicyclo[2.2.1]heptanyl or $C_{1-3}$alkoxyphenylpiperazinyl;

each $R_1$ is independently:
  $C_{1-5}$ alkyl optionally partially or fully halogenated wherein one or more C atoms are optionally independently replaced by O or N, and wherein said $C_{1-5}$ alkyl is optionally substituted with oxo, dioxolanyl, pyrrolidinyl, furyl or phenyl optionally substituted by $C_{1-3}$alkoxy;
  cyclopropyl, cyclopentanyl, cyclohexanyl or bicyclopentanyl optionally substituted with one to three methyl groups optionally partially or fully halogenated, nitrile, hydroxymethyl or phenyl; or 2-tetrahydrofuranyl substituted by methyl; or trimethyl silyl;
  propynyl substituted hydroxy or tetrahydropyran-2-yloxy;

each $R_3$ is independently:
  phenyl, morpholino, pyridinyl, pyrimidinyl, pyrrolidinyl, 2,5-pyrrolidin-dionyl, imidazolyl, [1,3,4]oxadiazol or pyrazolyl, each is optionally substituted with $C_{1-2}$ alkyl which is optionally partially or fully halogenated;
  $C_{1-3}$ alkyl or $C_{1-3}$ alkoxy each being optionally partially or fully halogenated or optionally substituted with diethylamino;
  $OR_{18}$ or $C_{1-3}$ alkyl optionally substituted with $OR_{18}$;
  amino or mono- or di-($C_{1-3}$ alkyl)amino optionally substituted with $R_{19}$;
  $CH_3C(O)NH$—, $R_{22}O$—; $R_{23}R_{24}NC(O)$—; $R_{26}CH_2C(O)N(R_{21})$—, $NH_2C(O)$methoxy or $R_{26}C(O)CH_2N(R_{21})$—;
  $C_{2-4}$alkenyl substituted by $R_{23}R_{24}NC(O)$—; or
  $C_{24}$ alkynyl substituted with pyrroldinyl or pyrrolyl;
  $C_{1-2}$acyl; and
  $R_{23}$ and $R_{24}$ are H or $R_{23}$ and $R_{24}$ taken together optionally form morpholino; and
  $R_{26}$ is morpholino.

13. The compound according to claim 12 wherein

G is
  phenyl, pyridinyl, 5-indolyl, 3-oxo-3,4-dihydro-2H-benzo[1,4]oxazin-8-yl, benzooxalolyl, 2,3-dihydrobenzooxazol-7-yl, 2-oxo-2,3-dihydro-1H-indol-5-yl or 2-naphthyl wherein G is optionally substituted by one or more $R_1$, $R_2$ or $R_3$;

X is:
  imidazolyl, pyridinyl, pyrimidinyl or pyrazinyl;

Y is:
  a bond, CH₂(CN)CH₂—NH—CH₂, —CH₂—, —NH—CH₂CH₂CH₂— or —NH—;
Z is morpholin-4yl, dioxolan-2yl, tetrahydrofuranyl, pyridinyl, 2-oxa-5-aza-bicyclo[2.2.1]hept-5yl or methoxyphenylpiperazinyl;
each $R_1$ is independently:
  tert-butyl, sec-butyl, tert-amyl, phenyl, tetrahydropyran-2-yloxypropynyl, hydroxypropynyl, trihalomethyl, 2,2-diethylpropionyl or cyclohexanyl;
$R_2$ is chloro, nitro, amino, nitrile, methylsulfonylamino, diacetylamino, phenylsulfonylamino, N,N-di(methylsulfonyl)amino, methylsulfonyl or trihalomethylsulfonyl;
$R_3$ is independently:
  methyl, $C_{1-3}$ alkoxy, methoxymethyl, hydroxypropyl, dimethylamino, $C_{1-4}$alkylamino, NH₂C(O)methoxy, acetyl, pyrrolidinyl, imidazolyl, pyrazolyl, morpholino or morpholinocarbonyl.

14. The compound according to claim 13 wherein X is pyridinyl.

15. The compound according to claim 14 wherein the pyridinyl is attached to Ar via the 3-pyridinyl position.

16. A compound selected from:
  1-(2-tert-Butyl-5-methyl-pyridin-4-yl)-3-[4-(6-morpholin-4-ylmethyl-pyridin-3-yl)-naphthalen-1-yl]-urea;
  1-(3-tert-Butyl-phenyl)-3-[4-(6-morpholin-4-ylmethyl-pyridin-3-yl)-naphthalen-1-yl]-urea;
  1-(4-Methyl-biphenyl-3-yl)-3-[4-(6-morpholin-4-ylmethyl-pyridin-3-yl)-naphthalen-1-yl]-urea;
  1-(4-tert-Butyl-biphenyl-2-yl)-3-[4-(6-morpholin-4-ylmethyl-pyridin-3-yl)-naphthalen-1-yl]-urea;
  1-(5-Isopropyl-2-methyl-phenyl)-3-[4-(6-morpholin-4-ylmethyl-pyridin-3-yl)-naphthalen-1-yl]-urea;
  1-(5-sec-Butyl-2-methoxy-phenyl)-3-[4-(6-morpholin-4-ylmethyl-pyridin-3-yl)-naphthalen-1-yl]-urea;
  1-(5-tert-Butyl-2-methoxymethyl-phenyl)-3-[4-(6-morpholin-4-ylmethyl-pyridin-3-yl)-naphthalen-1-yl]-urea;
  1-(5-tert-Butyl-2-methoxy-phenyl)-3-[4-(6-morpholin-4-ylmethyl-pyridin-3-yl)-naphthalen-1-yl]-urea;
  1-(5-tert-Butyl-2-methyl-phenyl)-3-[4-(6-morpholin-4-ylmethyl-pyridin-3-yl)-naphthalen-1-yl]-urea;
  1-(5-tert-Butyl-2-methyl-pyridin-3-yl)-3-[4-(6-morpholin-4-ylmethyl-pyridin-3-yl)-naphthalen-1-yl]-urea;
  1-[5-(1,1-Dimethyl-propyl)-2-methoxy-phenyl]-3-[4-(6-morpholin-4-ylmethyl-pyridin-3-yl)-naphthalen-1-yl]-urea;
  1-[5-tert-Butyl-2-(1H-pyrazol-4-yl)-phenyl]-3-[4-(6-morpholin-4-ylmethyl-pyridin-3-yl)-naphthalen-1-yl]-urea;
  1-[5-tert-Butyl-2-(2-methyl-pyrimidin-5-yl)-phenyl]-3-[4-(6-morpholin-4-ylmethyl-pyridin-3-yl)-naphthalen-1-yl]-urea;
  1-[5-tert-Butyl-2-(3-hydroxy-propyl)-phenyl]-3-[4-(6-morpholin-4-ylmethyl-pyridin-3-yl)-naphthalen-1-yl]-urea;
  1-[5-tert-Butyl-2-(morpholine-4-carbonyl)-phenyl]-3-[4-(6-morpholin-4-ylmethyl-pyridin-3-yl)-naphthalen-1-yl]-urea;
  N-(5-tert-Butyl-2-methoxy-3-{3-[4-(6-morpholin-4-ylmethyl-pyridin-3-yl)-naphthalen-1-yl]-ureido}-phenyl)-acetamide;
  1-(3-Methyl-naphthalen-2-yl)-3-[4-(6-morpholin-4-ylmethyl-pyridin-3-yl)-naphthalen-1-yl]-urea;
  N-(5-tert-Butyl-2-methoxy-3-{3-[4-(6-morpholin-4-ylmethyl-pyridin-3-yl)-naphthalen-1-yl]-ureido}-phenyl)-acetamide;
  1-[5-tert-Butyl-3-(2,3-dihydroxy-propyl)-2-hydroxy-phenyl]-3-[4-(6-morpholin-4-ylmethyl-pyridin-3-yl)-naphthalen-1-yl]-urea;
  1-(2,3-Dimethyl-1H-indol-5-yl)-3-[4-(6-morpholin-4-ylmethyl-pyridin-3-yl)-naphthalen-1-yl]-urea;
  1-{5-tert-Butyl-2-methyl-3-[3-(tetrahydro-pyran-2-yloxy)-prop-1-ynyl]-phenyl}-3-[4-(6-morpholin-4-ylmethyl-pyridin-3-yl)-naphthalen-1-yl]-urea;
  1-(2-Methoxy-5-trifluoromethyl-phenyl)-3-[4-(6-morpholin-4-ylmethyl-pyridin-3-yl)-naphthalen-1-yl]-urea;
  1-[5-(2,2-Dimethyl-propionyl)-2-methyl-phenyl]-3-[4-(6-morpholin-4-ylmethyl-pyridin-3-yl)-naphthalen-1-yl]-urea;
  1-[5-tert-Butyl-3-(3-hydroxy-prop-1-ynyl)-2-methyl-phenyl]-3-[4-(6-morpholin-4-ylmethyl-pyridin-3-yl)-naphthalen-1-yl]-urea;
  1-[5-tert-Butyl-2-(3-hydroxy-prop-1-ynyl)-phenyl]-3-[4-(6-morpholin-4-ylmethyl-pyridin-3-yl)-naphthalen-1-yl]-urea;
  1-[5-tert-Butyl-3-(2,2-dimethyl-[1,3]dioxolan-4-ylmethyl)-2-methoxy-phenyl]-3-[4-(6-morpholin-4-ylmethyl-pyridin-3-yl)-naphthalen-1-yl]-urea;
  1-[5-tert-Butyl-3-(2,3-dihydroxy-propyl)-2-methoxy-phenyl]-3-[4-(6-morpholin-4-ylmethyl-pyridin-3-yl)-naphthalen-1-yl]-urea;
  1-(5-tert-Butoxy-2-methoxy-phenyl)-3-[4-(6-morpholin-4-ylmethyl-pyridin-3-yl)-naphthalen-1-yl]-urea;
  1-[5-(1-Cyano-cyclopropyl)-2-methoxy-phenyl]-3-[4-(6-morpholin-4-ylmethyl-pyridin-3-yl)-naphthalen-1-yl]-urea;
  1-[5-tert-Butyl-3-(2-diethylamino-ethyl)-2-methoxy-phenyl]-3-[4-(6-morpholin-4-ylmethyl-pyridin-3-yl)-naphthalen-1-yl]-urea;
  1-(5-tert-Butyl-2-methoxy-phenyl)-3-[4-(6-[1,3]dioxolan-2-yl-pyridin-3-yl)-naphthalen-1-yl]-urea;
  1-(5-tert-Butyl-2-pyrrolidin-1-yl-phenyl)-3-[4-(6-morpholin-4-ylmethyl-pyridin-3-yl)-naphthalen-1-yl]-urea;
  1-(5-tert-Butyl-2-dimethylamino-phenyl)-3-[4-(6-morpholin-4-ylmethyl-pyridin-3-yl)-naphthalen-1-yl]-urea;
  1-(5-tert-Butyl-2-propoxy-phenyl)-3-[4-(6-morpholin-4-ylmethyl-pyridin-3-yl)-naphthalen-1-yl]-urea;
  1-(5-tert-Butyl-2-methoxy-phenyl)-3-{4-[6-(2,6-dimethyl-morpholin-4-ylmethyl)-pyridin-3-yl]-naphthalen-1-yl}-urea;
  1-(5-Cyclohexyl-2-methoxy-phenyl)-3-[4-(6-morpholin-4-ylmethyl-pyridin-3-yl)-naphthalen-1-yl]-urea;
  1-(2,4-Dimethoxy-5-trifluoromethyl-phenyl)-3-[4-(6-morpholin-4-ylmethyl-pyridin-3-yl)-naphthalen-1-yl]-urea;
  1-(5-tert-Butyl-2-methoxy-3-nitro-phenyl)-3-[4-(6-morpholin-4-ylmethyl-pyridin-3-yl)-naphthalen-1-yl]-urea;
  N-Acetyl-N-(5-tert-butyl-2-methoxy-3-{3-[4-(6-morpholin-4-ylmethyl-pyridin-3-yl)-naphthalen-1-yl]-ureido}-phenyl)-acetamide;

1-(6-tert-Butyl-4-methyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(5-tert-Butyl-2-ethoxy-phenyl)-3-[4-(6-morpholin-4-ylmethyl-pyridin-3-yl)-naphthalen-1-yl]-urea;

1-(5-tert-Butyl-2-isopropoxy-phenyl)-3-[4-(6-morpholin-4-ylmethyl-pyridin-3-yl)-naphthalen-1-yl]-urea;

1-(5-tert-Butyl-2-imidazol-1-yl-phenyl)-3-[4-(6-morpholin-4-ylmethyl-pyridin-3-yl)-naphthalen-1-yl]-urea;

1-(5-tert-Butyl-3-ethylamino-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-bis(methanesulfon)amide;

1-[5-tert-Butyl-2-(1-methyl-1H-pyrazol-4-yl)-phenyl]-3-[4-(6-morpholin-4-ylmethyl-pyridin-3-yl)-naphthalen-1-yl]-urea;

1-(2-Methanesulfinyl-5-trifluoromethyl-phenyl)-3-[4-(6-morpholin-4-ylmethyl-pyridin-3-yl)-naphthalen-1-yl]-urea;

N-[1-(5-{4-[3-(5-tert-Butyl-2-methoxy-phenyl)-ureido]-naphthalen-1-yl}-pyridin-2-ylmethyl)-pyrrolidin-3-yl]-acetamide;

1-(1-Acetyl-3,3-dimethyl-2,3-dihydro-1H-indol-5-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-propionamide;

1-(5-tert-Butyl-2-methyl-benzooxazol-7-yl)-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-(3-trifluoromethanesulfonyl-phenyl)-urea;

N-(5-tert-Butyl-2-methoxy-3-{3-[4-(6-morpholin-4-ylmethyl-pyridin-3-yl)-naphthalen-1-yl]-ureido}-phenyl)-isobutyramide;

2-(4-tert-Butyl-2-{3-[4-(6-morpholin-4-ylmethyl-pyridin-3-yl)-naphthalen-1-yl]-ureido}-phenoxy)-acetamide;

1-(5-tert-Butyl-2-oxo-2,3-dihydro-benzooxazol-7-yl)-3-[4-(6-morpholin-4-ylmethyl-pyridin-3-yl)-naphthalen-1-yl]-urea;

1-(5-tert-Butyl-3-cyano-2-methoxy-phenyl)-3-[4-(6-morpholin-4-ylmethyl-pyridin-3-yl)-naphthalen-1-yl]-urea;

1-(5-tert-Butyl-benzooxazol-7-yl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-benzenesulfonamide;

Ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

1-(5-tert-Butyl-2-methoxy-phenyl)-3-[4-(2-morpholin-4-ylmethyl-pyrimidin-5-yl)-naphthalen-1-yl]-urea;

1-(5-tert-Butyl-2-methylsulfanyl-phenyl)-3-[4-(6-morpholin-4-ylmethyl-pyridin-3-yl)-naphthalen-1-yl]-urea;

1-(5-tert-Butyl-2-methoxy-pyridin-3-yl)-13-[4-(6-morpholin-4-ylmethyl-pyridin-3-yl)-naphthalen-1-yl]-urea;

2,2,2-Trifluoro-ethanesulfonic acid (5-tert-butyl-2-methoxy-3-{3-[4-(6-morpholin-4-ylmethyl-pyridin-3-yl)-naphthalen-1-yl]-ureido}-phenyl)-amide;

1-(5-tert-Butyl-2-methoxy-phenyl)-3-{4-[6-(4-methyl-piperazin-1-ylmethyl)-pyridin-3-yl]-naphthalen-1-yl}-urea;

1-(5-tert-Butyl-2-methoxy-phenyl)-3-[4-(6-thiomorpholin-4-ylmethyl-pyridin-3-yl)-naphthalen-1-yl]-urea;

1-(5-tert-Butyl-2-methoxy-phenyl)-3-{4-[6-(2,6-dimethyl-piperidin-1-ylmethyl)-pyridin-3-yl]-naphthalen-1-yl}-urea;

1-(5-tert-Butyl-2-methoxy-phenyl)-3-{4-[6-(1-oxo-tetrahydro-thiopyran-4-ylamino)-pyridin-3-yl]-naphthalen-1-yl}-urea;

1-(5-tert-Butyl-2-methoxy-phenyl)-3-{4-[6-(tetrahydro-pyran-4-ylamino)-pyridin-3-yl]-naphthalen-1-yl}-urea;

1-(5-tert-Butyl-2-methoxy-phenyl)-3-[4-(6-{[(2-cyano-ethyl)-(tetrahydro-furan-2-ylmethyl)-amino]-methyl}-pyridin-3-yl)-naphthalen-1-yl]-urea;

1-(5-tert-Butyl-2-methoxy-phenyl)-3-{4-[6-(2-methoxymethyl-morpholin-4-ylmethyl)-pyridin-3-yl]-naphthalen-1-yl}-urea;

1-(5-tert-Butyl-2-methoxy-phenyl)-3-{4-[6-(2-methyl-3-oxo-piperazin-1-ylmethyl)-pyridin-3-yl]-naphthalen-1-yl}-urea;

1-(5-{4-[3-(5-tert-Butyl-2-methoxy-phenyl)-ureido]-naphthalen-1-yl}-pyridin-2-ylmethyl)-piperidine-3-carboxylic acid amide;

1-(5-tert-Butyl-2-methoxy-phenyl)-3-{4-[6-(1-oxo-1l4-thiomorpholin-4-ylmethyl)-pyridin-3-yl]-naphthalen-1-yl}-urea;

1-(3,3-Dimethyl-2-oxo-2,3-dihydro-1H-indol-5-yl)-3-[4-(6-morpholin-4-ylmethyl-pyridin-3-yl)-naphthalen-1-yl]-urea;

1-(5-tert-Butyl-2-methoxy-phenyl)-3-{4-[6-(3-oxo-piperazin-1-ylmethyl)-pyridin-3-yl]-naphthalen-1-yl}-urea;

1-(5-tert-Butyl-2-methoxy-phenyl)-3-(4-{6-[(tetrahydro-furan-3-ylamino)-methyl]-pyridin-3-yl}-naphthalen-1-yl)-urea;

1-(5-tert-Butyl-2-methoxy-phenyl)-3-[4-(6-{[(2-cyano-ethyl)-pyridin-3-ylmethyl-amino]-methyl}-pyridin-3-yl)-naphthalen-1-yl]-urea;

1-(5-tert-Butyl-2-methoxy-phenyl)-3-{4-[6-(2-oxa-5-aza-bicyclo[2.2.1]hept-5-ylmethyl)-pyridin-3-yl]-naphthalen-1-yl}-urea;

1-(5-tert-Butyl-2-methoxy-phenyl)-3-{4-[6-(2,6-dimethyl-morpholin-4-ylmethyl)-pyridin-3-yl]-naphthalen-1-yl}-urea;

1-(5-tert-Butyl-2-methoxy-phenyl)-3-(4-{6-[4-(3-methoxy-phenyl)-piperazin-1-ylmethyl]-pyridin-3-yl}-naphthalen-1-yl)-urea;

1-(5-tert-Butyl-2-methoxy-phenyl)-3-{4-[6-(morpholine-4-carbonyl)-pyridin-3-yl]-naphthalen-1-yl}-urea;

1-(5-tert-Butyl-2-methoxy-phenyl)-3-[4-(5-morpholin-4-ylmethyl-pyrazin-2-yl)-naphthalen-1-yl]-urea;

1-(6-tert-Butyl-3-oxo-3,4-dihydro-2H-benzo[1,4]oxazin-8-yl)-3-[4-(6-morpholin-4-ylmethyl-pyridin-3-yl)-naphthalen-1-yl]-urea;

1-(3-Amino-5-tert-butyl-2-methoxy-phenyl)-3-[4-(6-morpholin-4-ylmethyl-pyridin-3-yl)-naphthalen-1-yl]-urea;

N-(5-tert-Butyl-2-methoxy-3-{3-[4-(6-morpholin-4-ylmethyl-pyridin-3-yl)-naphthalen-1-yl]-ureido}-phenyl)-N-methyl-acetamide;

N-(5-tert-Butyl-2-methoxy-3-{3-[4-(6-morpholin-4-ylmethyl-pyridin-3-yl)-naphthalen-1-yl]-ureido}-phenyl)-2,2,2-trifluoro-acetamide;

1-(5-tert-Butyl-2-methoxy-phenyl)-3-{4-[6-(pyridin-3-yloxy)-pyridin-3-yl]-naphthalen-1-yl}-urea;

N-(5-tert-Butyl-2-methoxy-3-{3-[4-(6-morpholin-4-ylmethyl-pyridin-3-yl)-naphthalen-1-yl]-ureido}-phenyl)-methanesulfonamide and the pharmaceutically acceptable derivatives thereof.

17. A pharmaceutical composition comprising a pharmaceutically effective amount of a compound according to claim 1, 8 or 16.

18. A method of treating a disease mediated by cytokines which comprises administering to a patient in need of such treatment a therapeutically effective amount of a compound according to claim 1, 8 or 16.

19. The method according to claim 18 wherein the cytokine-mediated disease is selected from rheumatoid arthritis, osteoarthritis, Crohn's disease, ulcerative colitis, multiple sclerosis, Guillain-Barre syndrome, psoriasis, graft versus host disease, systemic lupus erythematosus, diabetes, toxic shock syndrome, osteoporosis, Alzheimer's disease, acute and chronic pain, contact dermatitis and atherosclerosis.

20. A method of treating a neutrophil-mediated disease selected from stroke, myocardial infarction, thermal injury, adult respiratory distress syndrome (ARDS), multiple organ injury secondary to trauma, acute glomerulonephritis, dermatoses with acute inflammatory components, acute purulent meningitis, hemodialysis, leukopherisis, granulocyte transfusion associated syndromes and necrotizing entrerocolitis, which comprises administering to a patient in need of such treatment a therapeutically effective amount of a compound according to claim 1, 8 or 16.

21. A method of making a compound of the formula(II) according to claim 1, comprising:

a) reacting an arylamine with phenyl chloroformate in a suitable halogenated solvent with a suitable base at 0–85° C. for about 2–24 hours:

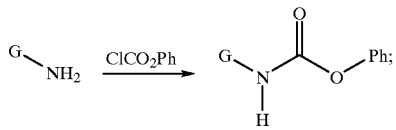

b) isolating and subsequently reacting the product of step a) with an arylamine shown below in a non-protic anhydrous solvent at 0–110° C. for about 2–24 hours, to produce a compound of the formula (II):

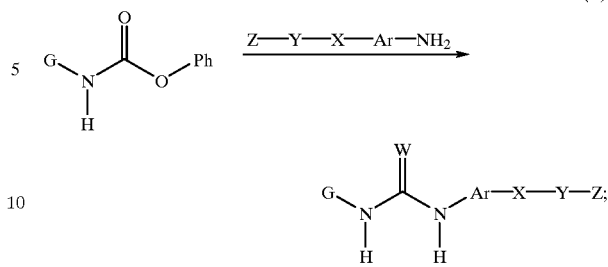

wherein W is O and G, Ar, X, Y and Z are as defined in claim 1.

22. A method of making a compound of the formula(III) according to claim 8, comprising:

a) reacting an arylamine with phenyl chloroformate in a suitable halogenated solvent with a suitable base at 0–85° C. for about 2–24 hours:

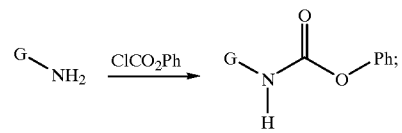

b) isolating and subsequently reacting the product of step a) with an arylamine shown below in a non-protic anhydrous solvent at 0–110° C. for about 2–24 hours, to produce a compound of the formula (III):

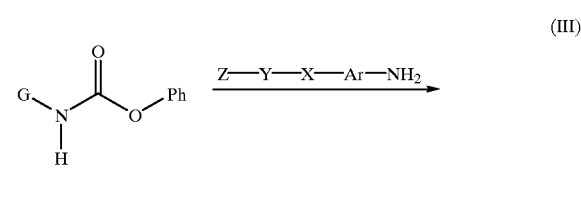

wherein B is N—H, W is O and G, Ar, X, Y and Z are as defined in claim 8.

* * * * *